US011462298B2

(12) United States Patent
Zhao et al.

(10) Patent No.: US 11,462,298 B2
(45) Date of Patent: *Oct. 4, 2022

(54) METHODS AND PROCESSES FOR NON-INVASIVE ASSESSMENT OF GENETIC VARIATIONS

(71) Applicant: SEQUENOM, INC., San Diego, CA (US)

(72) Inventors: Chen Zhao, San Diego, CA (US); Zeljko Dzakula, San Diego, CA (US); Cosmin Deciu, San Diego, CA (US); Sung Kyun Kim, San Diego, CA (US); Amin R. Mazloom, Del Mar, CA (US); Gregory Hannum, San Diego, CA (US); Mathias Ehrich, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/862,324

(22) Filed: Apr. 29, 2020

(65) Prior Publication Data

US 2020/0265921 A1  Aug. 20, 2020

Related U.S. Application Data

(63) Continuation of application No. 14/892,782, filed as application No. PCT/US2014/039389 on May 23, 2014, now Pat. No. 10,699,800.

(60) Provisional application No. 61/827,385, filed on May 24, 2013.

(51) Int. Cl.
| | |
|---|---|
| G16B 20/10 | (2019.01) |
| C12Q 1/6869 | (2018.01) |
| C12Q 1/6883 | (2018.01) |
| G16B 30/10 | (2019.01) |
| G16B 30/00 | (2019.01) |
| G16B 40/00 | (2019.01) |
| G16B 25/10 | (2019.01) |

(52) U.S. Cl.
CPC ........... *G16B 20/10* (2019.02); *C12Q 1/6869* (2013.01); *C12Q 1/6883* (2013.01); *G16B 25/10* (2019.02); *G16B 30/10* (2019.02); *G16B 30/00* (2019.02); *G16B 40/00* (2019.02)

(58) Field of Classification Search
CPC ........ G16B 20/10; G16B 25/10; G16B 30/10; G16B 30/00; G16B 40/00
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,075,212 A | 12/1991 | Rotbart |
| 5,091,652 A | 2/1992 | Mathies et al. |
| 5,432,054 A | 7/1995 | Saunders et al. |
| 5,445,934 A | 8/1995 | Fodor et al. |
| 5,670,325 A | 9/1997 | Lapidus et al. |
| 5,720,928 A | 2/1998 | Schwartz |
| 5,786,146 A | 7/1998 | Herman et al. |
| 5,928,870 A | 7/1999 | Lapidus et al. |
| 5,939,598 A | 8/1999 | Kucherlapati et al. |
| 6,015,714 A | 1/2000 | Baldarelli et al. |
| 6,090,550 A | 7/2000 | Collinge et al. |
| 6,100,029 A | 8/2000 | Lapidus et al. |
| 6,214,558 B1 | 4/2001 | Shuber et al. |
| 6,214,560 B1 | 4/2001 | Yguerabide et al. |
| 6,235,475 B1 | 5/2001 | Brenner et al. |
| 6,258,540 B1 | 7/2001 | Wainscoat et al. |
| 6,263,286 B1 | 7/2001 | Gilmanshin et al. |
| 6,403,311 B1 | 6/2002 | Chan |
| 6,566,101 B1 | 5/2003 | Shuber et al. |
| 6,617,133 B1 | 9/2003 | Noda et al. |
| 6,772,070 B2 | 8/2004 | Gilmanshin et al. |
| 6,818,395 B1 | 11/2004 | Quake et al. |
| 6,927,028 B2 | 8/2005 | Dennis et al. |
| 6,936,422 B2 | 8/2005 | El et al. |
| 7,005,264 B2 | 2/2006 | Su et al. |
| 7,169,560 B2 | 1/2007 | Lapidus et al. |
| 7,279,337 B2 | 10/2007 | Zhu |
| 7,282,337 B1 | 10/2007 | Harris |
| 7,947,454 B2 | 5/2011 | Akeson et al. |
| 7,960,105 B2 | 6/2011 | Schwartz et al. |
| 7,972,858 B2 | 7/2011 | Meller et al. |
| 8,688,388 B2 | 4/2014 | Dzakula et al. |
| 8,700,338 B2 * | 4/2014 | Oliphant .............. C12Q 1/6806 702/19 |

(Continued)

FOREIGN PATENT DOCUMENTS

| | | |
|---|---|---|
| JP | 2013-530727 A | 8/2013 |
| JP | 2014-512817 A | 5/2014 |

(Continued)

OTHER PUBLICATIONS

Love, M. CNV detection in exome sequencing data using exomeCopy. pp. 1-14, Mar. 31, 2012, printed from http://bioconductor.org/packages/2.10/bioc/vignettes/exomeCopy/inst/doc/exomeCopy.pdf. (Year: 2012).*
Miller et al. ReadDepth: A parallel R package for detecting copy number alterations from short sequencing reads. PLoS ONE, vol. 6, No. 1, e16327, Jan. 2011, printed as pp. 1-7, including Supplemental Figures S1 and S2. (Year: 2011).*
Love, M. Package 'exomeCopy.' http://citeseerx.ist.psu.edu/viewdoc/download?doi=10.1.1.367.1046&rep=rep1&type=pdf, pp. 1-18, Aug. 2, 2013. (Year: 2013).*
International Preliminary Report on Patentability dated Feb. 9, 2017 in International Application No. PCT/US2015/042701, 14 pages.
International Search Report and Written Opinion dated Aug. 8, 2011 in International Application No. PCT/US2011/024132, 14 pages.
International Search Report and Written Opinion dated May 23, 2018 in International Application No. PCT/US2018/023151, 13 pages.

(Continued)

*Primary Examiner* — Jennifer Dunston
(74) *Attorney, Agent, or Firm* — Grant IP, Inc.

(57) ABSTRACT

Provided herein are methods, processes and apparatuses for non-invasive assessment of genetic variations that make use of decision analyses. The decision analyses sometimes include segmentation analyses and/or odds ratio analyses.

16 Claims, 39 Drawing Sheets

(56) References Cited

U.S. PATENT DOCUMENTS

| | | |
|---|---|---|
| 9,260,745 B2 | 2/2016 | Rava et al. |
| 9,598,731 B2 | 3/2017 | Talasaz |
| 10,424,394 B2 | 9/2019 | Deciu et al. |
| 10,699,800 B2 | 6/2020 | Zhao et al. |
| 11,200,963 B2 | 12/2021 | Mazloom et al. |
| 2001/0014850 A1 | 8/2001 | Gilmanshin et al. |
| 2001/0049102 A1 | 12/2001 | Huang et al. |
| 2002/0006621 A1 | 1/2002 | Bianchi |
| 2002/0045176 A1 | 4/2002 | Lo et al. |
| 2002/0110818 A1 | 8/2002 | Chan |
| 2002/0119469 A1 | 8/2002 | Shuber et al. |
| 2002/0164629 A1 | 11/2002 | Quake et al. |
| 2003/0013101 A1 | 1/2003 | Balasubramanian |
| 2003/0082600 A1 | 5/2003 | Olek et al. |
| 2003/0180779 A1 | 9/2003 | Lofton-day et al. |
| 2003/0207326 A1 | 11/2003 | Su et al. |
| 2003/0232346 A1 | 12/2003 | Su |
| 2004/0081993 A1 | 4/2004 | Cantor et al. |
| 2004/0110208 A1 | 6/2004 | Chan et al. |
| 2004/0137470 A1 | 7/2004 | Dhallan |
| 2005/0019784 A1 | 1/2005 | Su et al. |
| 2005/0095599 A1 | 5/2005 | Pittaro et al. |
| 2005/0112590 A1 | 5/2005 | Boom et al. |
| 2005/0147980 A1 | 7/2005 | Berlin et al. |
| 2005/0164241 A1 | 7/2005 | Hahn et al. |
| 2005/0227278 A1 | 10/2005 | Wall |
| 2005/0287592 A1 | 12/2005 | Kless |
| 2006/0046258 A1 | 3/2006 | Lapidus et al. |
| 2006/0063171 A1 | 3/2006 | Akeson et al. |
| 2006/0068440 A1 | 3/2006 | Chan et al. |
| 2006/0252071 A1 | 11/2006 | Lo et al. |
| 2007/0026406 A1 | 2/2007 | El Ghaoui et al. |
| 2007/0065823 A1 | 3/2007 | Dressman et al. |
| 2007/0202525 A1 | 8/2007 | Quake et al. |
| 2008/0020390 A1 | 1/2008 | Mitchell et al. |
| 2008/0070792 A1 | 3/2008 | Stoughton et al. |
| 2008/0081330 A1 | 4/2008 | Kahvejian |
| 2008/0138809 A1 | 6/2008 | Kapur et al. |
| 2008/0187915 A1 | 8/2008 | Polonsky et al. |
| 2008/0233575 A1 | 9/2008 | Harris et al. |
| 2009/0026082 A1 | 1/2009 | Rothberg et al. |
| 2009/0029377 A1 | 1/2009 | Lo et al. |
| 2009/0075252 A1 | 3/2009 | Harris et al. |
| 2009/0129647 A1 | 5/2009 | Dimitrova et al. |
| 2009/0191565 A1 | 7/2009 | Lapidus et al. |
| 2009/0197257 A1 | 8/2009 | Harris |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0109197 A1 | 5/2010 | Hansen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0151471 A1 | 6/2010 | Faham et al. |
| 2010/0216151 A1 | 8/2010 | Lapidus et al. |
| 2010/0216153 A1 | 8/2010 | Lapidus et al. |
| 2010/0261285 A1 | 10/2010 | Goldstein et al. |
| 2010/0310421 A1 | 12/2010 | Oliver et al. |
| 2010/0330557 A1 | 12/2010 | Yakhini et al. |
| 2011/0086769 A1 | 4/2011 | Oliphant et al. |
| 2011/0105353 A1 | 5/2011 | Lo et al. |
| 2011/0159601 A1 | 6/2011 | Golovchenko et al. |
| 2011/0171634 A1 | 7/2011 | Xiao et al. |
| 2011/0174625 A1 | 7/2011 | Akeson et al. |
| 2011/0177498 A1 | 7/2011 | Clarke et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0288780 A1 | 11/2011 | Rabinowitz et al. |
| 2011/0294699 A1 | 12/2011 | Lee et al. |
| 2011/0312503 A1 | 12/2011 | Chuu et al. |
| 2011/0319272 A1 | 12/2011 | Fan et al. |
| 2012/0046877 A1 | 2/2012 | Hyland et al. |
| 2012/0122701 A1 | 5/2012 | Ryan et al. |
| 2012/0165203 A1 | 6/2012 | Quake et al. |
| 2012/0184449 A1 | 7/2012 | Hixson et al. |
| 2012/0191367 A1 | 7/2012 | Stuelpnagel et al. |
| 2012/0214678 A1 | 8/2012 | Rava et al. |
| 2012/0264115 A1 | 10/2012 | Rava |
| 2012/0270212 A1 | 10/2012 | Rabinowitz et al. |
| 2012/0270739 A1 | 10/2012 | Rava et al. |
| 2013/0012399 A1 | 1/2013 | Myers et al. |
| 2013/0022977 A1 | 1/2013 | Lapidus et al. |
| 2013/0029852 A1 | 1/2013 | Rava et al. |
| 2013/0034546 A1 | 2/2013 | Rava et al. |
| 2013/0085681 A1 | 4/2013 | Deciu et al. |
| 2013/0096011 A1 | 4/2013 | Rava et al. |
| 2013/0130921 A1 | 5/2013 | Gao et al. |
| 2013/0130923 A1 | 5/2013 | Ehrich et al. |
| 2013/0150253 A1 | 6/2013 | Deciu et al. |
| 2013/0196317 A1 | 8/2013 | Lapidus et al. |
| 2013/0237431 A1 | 9/2013 | Lo et al. |
| 2013/0245961 A1 | 9/2013 | Lo et al. |
| 2013/0261983 A1 | 10/2013 | Dzakula et al. |
| 2013/0288244 A1 | 10/2013 | Deciu et al. |
| 2013/0304392 A1 | 11/2013 | Deciu et al. |
| 2013/0309666 A1 | 11/2013 | Decui et al. |
| 2013/0310260 A1 | 11/2013 | Kim et al. |
| 2013/0325360 A1 | 12/2013 | Deciu et al. |
| 2013/0338933 A1 | 12/2013 | Deciu et al. |
| 2014/0038830 A1 | 2/2014 | Srinivasan et al. |
| 2014/0100792 A1 | 4/2014 | Deciu et al. |
| 2014/0180594 A1 | 6/2014 | Kim et al. |
| 2014/0235474 A1 | 8/2014 | Tang et al. |
| 2014/0242588 A1 | 8/2014 | Van Den Boom et al. |
| 2014/0274740 A1 | 9/2014 | Srinivasan et al. |
| 2014/0322709 A1 | 10/2014 | Lapidus et al. |
| 2015/0005176 A1 | 1/2015 | Kim et al. |
| 2015/0064695 A1 | 3/2015 | Katz et al. |
| 2015/0100244 A1 | 4/2015 | Hannum |
| 2015/0347676 A1 | 12/2015 | Zhao et al. |
| 2016/0034640 A1 | 2/2016 | Zhao et al. |
| 2016/0110497 A1 | 4/2016 | Dzakula et al. |
| 2016/0224724 A1 | 8/2016 | Zhao et al. |
| 2017/0351811 A1 | 12/2017 | Zhao et al. |
| 2018/0032671 A1 | 2/2018 | Mazloom et al. |
| 2021/0358565 A1 | 11/2021 | Tynan et al. |
| 2022/0093207 A1 | 3/2022 | Mazloom et al. |

FOREIGN PATENT DOCUMENTS

| | | |
|---|---|---|
| JP | 2016-526879 A | 9/2016 |
| WO | WO 00/06770 A1 | 2/2000 |
| WO | WO 01/32887 A1 | 5/2001 |
| WO | WO 02/42496 A2 | 5/2002 |
| WO | WO 03/000920 A2 | 1/2003 |
| WO | 03/070894 A2 | 8/2003 |
| WO | WO 03/106620 A2 | 12/2003 |
| WO | WO 2005/023091 A2 | 3/2005 |
| WO | WO 2006/056480 A2 | 6/2006 |
| WO | 2007/121276 A2 | 10/2007 |
| WO | WO 2007/140417 A2 | 12/2007 |
| WO | WO 2007/147063 A2 | 12/2007 |
| WO | WO 2008/045505 A2 | 4/2008 |
| WO | WO 2008/121828 A2 | 10/2008 |
| WO | WO 2009/007743 A1 | 1/2009 |
| WO | WO 2009/032779 A2 | 3/2009 |
| WO | WO 2009/032781 A2 | 3/2009 |
| WO | WO 2009/046445 A1 | 4/2009 |
| WO | WO 2010/004265 A1 | 1/2010 |
| WO | WO 2010/033578 A2 | 3/2010 |
| WO | WO 2010/033639 A2 | 3/2010 |
| WO | WO 2010/056728 A1 | 5/2010 |
| WO | WO 2010/059731 A2 | 5/2010 |
| WO | WO 2010/065470 A2 | 6/2010 |
| WO | WO 2010/115016 A2 | 10/2010 |
| WO | WO 2011/034631 A1 | 3/2011 |
| WO | WO 2011/038327 A1 | 3/2011 |
| WO | WO 2011/050147 A1 | 4/2011 |
| WO | WO 2011/057094 A1 | 5/2011 |
| WO | WO 2011/087760 A2 | 7/2011 |
| WO | WO 2011/090556 A1 | 7/2011 |
| WO | WO 2011/090558 A1 | 7/2011 |

(56) References Cited

FOREIGN PATENT DOCUMENTS

| | | | |
|---|---|---|---|
| WO | WO 2011/090559 A1 | 7/2011 | |
| WO | WO 2011/091063 A1 | 7/2011 | |
| WO | WO 2011/102998 A2 | 8/2011 | |
| WO | WO 2011/143659 A2 | 11/2011 | |
| WO | WO 2011/146632 A1 | 11/2011 | |
| WO | WO 2012/012703 A2 | 1/2012 | |
| WO | WO 2012/071621 A1 | 6/2012 | |
| WO | WO 2012/088348 A2 | 6/2012 | |
| WO | WO 2012/088456 A2 | 6/2012 | |
| WO | WO 2012/103031 A2 | 8/2012 | |
| WO | WO 2012/108920 A1 | 8/2012 | |
| WO | WO 2012/118745 A1 | 9/2012 | |
| WO | WO 2012/177792 A2 | 12/2012 | |
| WO | WO 2013/000100 A1 | 1/2013 | |
| WO | WO 2013/052907 A2 | 4/2013 | |
| WO | WO 2013/052913 A2 | 4/2013 | |
| WO | WO 2013/055817 A1 | 4/2013 | |
| WO | WO 2013/109981 A1 | 7/2013 | |
| WO | WO 2013/177086 A1 | 11/2013 | |
| WO | WO 2013/192562 A1 | 12/2013 | |
| WO | 2014/014497 A1 | 1/2014 | |
| WO | WO 2014/039556 A1 | 3/2014 | |
| WO | WO-2014039556 A1 * | 3/2014 | ........... C12Q 1/6874 |
| WO | WO 2014/055774 A1 | 4/2014 | |
| WO | WO 2014/055790 A2 | 4/2014 | |
| WO | WO 2014/116598 A2 | 7/2014 | |
| WO | WO 2014/165596 A1 | 10/2014 | |
| WO | WO 2014/190286 A2 | 11/2014 | |
| WO | WO 2014/205401 A1 | 12/2014 | |
| WO | WO 2015/028576 A1 | 3/2015 | |
| WO | WO 2015/040591 A1 | 3/2015 | |
| WO | WO 2015/051163 A2 | 4/2015 | |
| WO | WO 2015/054080 A1 | 4/2015 | |
| WO | WO 2015/067796 A1 | 5/2015 | |
| WO | WO 2015/183872 A1 | 12/2015 | |
| WO | WO 2016/019042 A1 | 2/2016 | |
| WO | WO 2018/022890 A1 | 2/2018 | |

OTHER PUBLICATIONS

International Search Report and Written Opinion dated May 7, 2018 in International Application No. PCT/US2018/015081, 11 pages.

International Search Report and Written Opinion dated Nov. 13, 2017 in International Application No. PCT/US2017/044185, 12 pages.

Beaudet, Arthur L. "Progress Toward Noninvasive Prenatal Diagnosis", Clinical Chemistry, 2011, 57(6):802-804.

Deligezer et al., "Sequence-Specific Histone Methylation is Detectable on Circulating Nucleosomes in Plasma", Clinical Chemistry, 2008, 54(7):1125-1131.

Go et al., "Non-Invasive Aneuploidy Detection Using Free Fetal DNA and RNA in Maternal Plasma: Recent Progress and Future Possibilities", Human Reproduction Update, Nov. 12, 2010, 17(3):372-382.

Liu et al., "Computational Methods for Detecting Copy Number Variations in Cancer Genome Using Next Generation Sequencing: Principles and Challenges", Oncotarget, Nov. 16, 2013, 4(11):1868-1881.

Loakes David, "Survey and Summary: The Applications of Universal DNA Base Analogues", Nucleic Acids Research, 2001, 29(12):2437-2447.

Pertile et al., "Rare Autosomal Trisomies, Revealed by Maternal Plasma DNA Sequencing, Suggest Increased Risk of Feto-Placental Disease", Science Translational Medicine, eaan1240, Aug. 30, 2017, 9:1-11.

Yu et al., "Combined Count- and Size-Based Analysis of Maternal Plasma DNA for Noninvasive Prenatal Detection of Fetal Subchromosomal Aberrations Facilitates Elucidation of the Fetal and/or Maternal Origin of the Aberrations", Clinical Chemistry, 2017, 63(2):495-502.

DNAcopy, http://bioconductor.org/packages/2.12/bioc/html/DNAcopy.html, Apr. 24, 2013, 21 pages.

"Extended European Search Report dated Dec. 2, 2015 in European Application No. EP11745050.2, filed on Feb. 9, 2011 and published as EP 2 536 852 on Dec. 26, 2012", 15 pages.

"Extended European Search Report dated Oct. 11, 2019 in Europe Patent Application No. 19169503.0, filed on May 23, 2014", 13 pages.

"International Preliminary Report on Patentability and Written Opinion dated Apr. 24, 2014 in International Application No. PCT/US2012/059592, filed on Oct. 10, 2012", 9 pages.

"International Preliminary Report on Patentability and Written Opinion dated Jan. 9, 2014 in International Application No. PCT/US2012/043388, filed on Jun. 20, 2012 and published as WO 2012/177792 on Dec. 27, 2012", 8 pages.

"International Preliminary Report on Patentability dated Apr. 14, 2016 in International Application No. PCT/US2014/058885, filed on Oct. 2, 2014 and published as WO 2015/051163 on Apr. 9, 2015", 11 pages.

"International Preliminary Report on Patentability dated Apr. 16, 2015 in International Application No. PCT/US2013/063314, filed on Oct. 3, 2013", 8 pages.

"International Preliminary Report on Patentability dated Apr. 16, 2015 in International Application No. PCT/US2013/063287, filed Oct. 3, 2013", 9 pages.

"International Preliminary Report on Patentability dated Apr. 21, 2016 in International Application No. PCT/US2014/059156, filed on Oct. 3, 2014", 8 pages.

"International Preliminary Report on Patentability dated Aug. 6, 2015 in International Application No. PCT/US2014/012369, filed on Jan. 21, 2014", 8 pages.

"International Preliminary Report on Patentability dated Dec. 3, 2015 in International Application No. PCT/US2014/039389, filed on May 23, 2014", 12 pages.

"International Preliminary Report on Patentability dated Dec. 31, 2014 in International Application No. PCT/US2013/047131, filed on Jun. 21, 2013", 9 pages.

"International Preliminary Report on Patentability dated Feb. 27, 2014 in International Application No. PCT/US2012/059123, filed on Oct. 5, 2012", 3 pages.

"International Preliminary Report on Patentability dated Jul. 31, 2014 in International Application No. PCT/US2013/022290, filed on Jan. 18, 2013", 9 pages.

"International Preliminary Report on Patentability dated Jun. 9, 2014 in International Application No. PCT/US2012/059114, filed on Oct. 5, 2012", 5 pages.

"International Preliminary Report on Patentability dated Oct. 15, 2015 in International Application No. PCT/US2014/032687, filed on Apr. 2, 2014", 10 pages.

"International Search Report and Written Opinion dated Jan. 5, 2016 in International Application No. PCT/US2015/042701, filed on Jul. 29, 2015", 20 pages.

"International Search Report and Written Opinion dated Apr. 5, 2013 in International Application No. PCT/US2012/043388 filed: Jun. 20, 2012 and published as: WO 12/177792 on Dec. 27, 2012", 9 pages.

"International Search Report and Written Opinion dated Apr. 2, 2014 in International Application No. PCT/US2013/063314, filed on Oct. 3, 2013 and published as WO 2014/055790 on Apr. 10, 2014", 9 pages.

"International Search Report and Written Opinion dated Dec. 13, 2013 in International Application No. PCT/US2013/063287, filed Oct. 3, 2013", 11 pages.

"International Search Report and Written Opinion dated Dec. 17, 2014 in International Application No. PCT/US2014/039389, filed on May 23, 2014", 19 pages.

"International Search Report and Written Opinion dated Feb. 18, 2015 in International Application No. PCT/US2014/058885, filed on Oct. 2, 2014", 11 pages.

"International Search Report and Written Opinion dated Jul. 14, 2014 in International Application No. PCT/US2014/032687, filed on Apr. 2, 2014", 13 pages.

(56) References Cited

OTHER PUBLICATIONS

"International Search Report and Written Opinion dated Jul. 4, 2013 in International Application No. PCT/US2013/022290 filed: Jan. 18, 2013, and published as: WO/2013/109981 on Jul. 25, 2013", 13 pages.
"International Search Report and Written Opinion dated Mar. 6, 2013 in International Application No. PCT/US2012/059592 filed: Oct. 10, 2012", 12 pages.
"International Search Report and Written Opinion dated May 9, 2014 in International Application No. PCT/US2014/012369, filed Jan. 21, 2014", 10 pages.
"International Search Report and Written Opinion dated Oct. 2, 2015 in International Patent Application No. PCT/US2015/032550, filed on May 27, 2015", 12 pages.
"International Search Report and Written Opinion dated Sep. 18, 2013 in International Application No. PCT/US2013/047131, filed on Jun. 21, 2013 and published as WO 2013/192562 on Dec. 27, 2013", 11 pages.
"International Search Report and Written Opinion dated Sep. 24, 2014 in International Application No. PCT/US2014/043497, filed on Jun. 20, 2014 and published as WO 2014/205401 on Dec. 24, 2014", 9 pages.
"International Search Report and Written Opinion dated Sep. 26, 2012 in International Application No. PCT/US2011/066639 filed: Dec. 21, 2011 and published as: WO 12/088348 Jun. 28, 2012", 9 pages.
"International Search Report and Written Opinion dated Sep. 9, 2013 in International Application No. PCT/US2012/059114, filed on Oct. 5, 2012 and published as WO/2013/052907 on Apr. 11, 2013", 14 pages.
"International Search Report and Written Opinion dated Sep. 9, 2013 in International Application No. PCT/US2012/059123, filed on Oct. 5, 2012 and published as WO/2013/052913 on Apr. 11, 2013", 16 pages.
International Search Report and Written Opinion of the international Searching Authority for International Application No. PCT/US11/24132, dated Aug. 8, 2011. 15 pages.
"Invitation to Pay Additional Fees and Partial International Search Report dated Oct. 14, 2015 in International Application No. PCT/US2015/042701, filed on Jul. 29, 2015".
"Invitation to Pay Additional Fees and Partial Search Report dated Jan. 18, 2013 in International Application No. PCT/US2012/059592 filed: Oct. 10, 2012", 10 pages.
"Invitation to Pay Additional Fees and Partial Search Report dated Jul. 3, 2013 in International Application No. PCT/US2012/059123 filed: Oct. 5, 2012 and published as: WO/2013/052913 on Apr. 11, 2013", 7 pages.
National Human Genome Research Institute, Retrieved form web http://www.genome.gov/26524120, on downloaded Sep. 9, 2015, 2 pages.
"Office Action dated Apr. 16, 2015 in U.S. Appl. No. 13/669,136, filed Nov. 5, 2012 and published as US 2013-0085681 on Apr. 4, 2013", 8 pages.
"Office Action dated Apr. 16, 2015 in U.S. Appl. No. 13/933,935, filed Jul. 2, 2013 and published as US 2013-0304392 on Nov. 14, 2013", 9 pages.
"Office Action dated Apr. 17, 2015 in U.S. Appl. No. 13/829,164, filed Mar. 14, 2013 and published as US 2013-0288244 on Oct. 31, 2014", 9 pages.
"Office Action dated Apr. 21, 2015 in U.S. Appl. No. 13/754,817, filed Jan. 30, 2013 and published as US 2013-0150253 on Jun. 13, 2013", 7 pages.
"Office Action dated Apr. 26, 2016 in U.S. Appl. No. 13/797,508, filed Mar. 12, 2013 and published as US 2013-0261983 on Oct. 3, 2013", 12 pages.
"Office Action dated Apr. 27, 2016 in U.S. Appl. No. 13/829,164, filed Mar. 14, 2013 and published as US 2013-0288244 on Oct. 31, 2014", 9 pages.
"Office Action dated Apr. 27, 2016 in U.S. Appl. No. 13/933,935, filed Jul. 2, 2013 and published as US 2013-0304392 on Nov. 14, 2013", 9 pages.
"Office Action dated Apr. 7, 2014 in U.S. Appl. No. 13/754,817, filed Jan. 30, 2013 and published as US 2013-0150253 on Jun. 13, 2013", 33 pages.
"Office Action dated Aug. 13, 2014 in U.S. Appl. No. 13/669,136, filed Nov. 5, 2012 and published as US 2013-0085681 on Apr. 4, 2013", 7 pages.
"Office Action dated Aug. 13, 2014 in U.S. Appl. No. 13/829,164, filed Mar. 14, 2013 and published as US 2013-0288244 on Oct. 31, 2014", 12 pages.
"Office Action dated Aug. 14, 2014 in U.S. Appl. No. 13/933,935, filed Jul. 2, 2013 and published as US 2013-0304392 on Nov. 14, 2013", 12 pages.
"Office Action dated Aug. 22, 2013 in U.S. Appl. No. 13/797,508, filed Mar. 12, 2013 and published as US 2013-0261983 on Oct. 3, 2013", 17 pages.
"Office Action dated Aug. 27, 2015 in U.S. Appl. No. 13/933,935, filed Jul. 2, 2013 and published as US 2013-0304392 on Nov. 14, 2013", 12 pages.
"Office Action dated Dec. 26, 2013 in U.S. Appl. No. 13/797,508, filed Mar. 12, 2013 and published as US 2013-0261983 on Oct. 3, 2013", 9 pages.
"Office Action dated Feb. 6, 2019 in U.S. Appl. No. 14/892,782, filed Nov. 20, 2015 and published as US 2016-0224724 on Aug. 4, 2016", 18 pages.
"Office Action dated Feb. 1, 2016 in U.S. Appl. No. 13/669,136, filed Nov. 5, 2012 and published as US 2013-0085681 on Apr. 4, 2013", 14 pages.
"Office Action dated Feb. 12, 2016 in U.S. Appl. No. 13/797,930, filed Mar. 12, 2013 and published as US 2013-0325360 on Dec. 5, 2013", 17 pages.
"Office Action dated Feb. 23, 2016 in U.S. Appl. No. 14/812,432, filed Jul. 29, 2015 and published as US 2016-0034640 on Feb. 4, 2016", 33 pages.
"Office Action dated Jan. 17, 2014 in U.S. Appl. No. 13/333,842, filed Dec. 21, 2011 and published as US 2012/0184449 on Jul. 19, 2012", 19 pages.
"Office Action dated Jan. 27, 2014 in U.S. Appl. No. 13/829,164, filed Mar. 14, 2013 and published as US 2013-0288244 on Oct. 31, 2014", 9 pages.
"Office Action dated Jan. 30, 2014 in U.S. Appl. No. 13/933,935, filed Jul. 2, 2013 and published as US 2013-0304392 on Nov. 14, 2013", 6 pages.
"Office Action dated Jul. 27, 2015 in U.S. Appl. No. 13/782,857, filed Mar. 1, 2013 and published as US 2013-0310260 on Nov. 21, 2013", 14 pages.
"Office Action dated Jul. 28, 2014 in U.S. Appl. No. 13/797,508, filed Mar. 12, 2013 and published as US 2013-0261983 on Oct. 3, 2013", 7 pages.
"Office Action dated Jul. 31, 2018 in U.S. Appl. No. 14/892,782, filed Nov. 20, 2015 and published as US 2016-0224724 on Aug. 4, 2016", 29 pages.
"Office Action dated Mar. 6, 2020 in U.S. Appl. No. 14/892,782, filed Nov. 20, 2015 and published as US 2016-0224724 on Aug. 4, 2016", 9 pages.
"Office Action dated Mar. 11, 2016 in U.S. Appl. No. 13/782,857, filed Mar. 1, 2013 and published as US 2013-0310260 on Nov. 21, 2013", 15 pages.
"Office Action dated Mar. 19, 2015 in U.S. Appl. No. 13/797,508, filed Mar. 12, 2013 and published as US 2013-0261983 on Oct. 3, 2013", 10 pages.
Office Action dated Mar. 22, 2016 in U.S. Appl. No. 12/727,824, filed Mar. 19, 2010 and published as US 2010-0216153 on Aug. 26, 2010, 68 pages.
"Office Action dated Mar. 3, 2016 in U.S. Appl. No. 13/829,373, filed Mar. 14, 2013 and published as US 2013-0338933 on Dec. 19, 2013", 13 pages.
"Office Action dated May 12, 2015 in U.S. Appl. No. 13/669,136, filed Nov. 5, 2012 and published as US 2013-0085681 on Apr. 4, 2013", 9 pages.

(56) References Cited

OTHER PUBLICATIONS

"Office Action dated May 13, 2015 in U.S. Appl. No. 13/333,842, filed Dec. 21, 2011 and published as US 2012/0184449 on Jul. 19, 2012", 20 pages.
"Office Action dated May 29, 2015 in U.S. Appl. No. 14/187,876, filed Feb. 24, 2014 and published as US 2014-0322709 on Oct. 30, 2014", 43 pages.
"Office Action dated May 3, 2013 in U.S. Appl. No. 13/333,842, filed Dec. 21, 2011 and published as 2012/0184449 on: Jul. 19, 2012", 19 pages.
"Office Action dated May 7, 2013 in U.S. Appl. No. 13/754,817, filed Jan. 30, 2013 and published as US 2013-0150253 on Jun. 13, 2013", 15 pages.
"Office Action dated Oct. 16, 2013 in U.S. Appl. No. 13/933,935, filed Jul. 2, 2013 and published as US 2013-0304392 on Nov. 14, 2013", 11 pages.
"Office Action dated Oct. 17, 2013 in U.S. Appl. No. 13/669,136, filed Nov. 5, 2012 and published as US 2013-0085681 on Apr. 4, 2013", 9 pages.
"Office Action dated Oct. 18, 2013 in U.S. Appl. No. 13/656,328, filed Oct. 19, 2012 and published as US 2013-0103320 on Apr. 25, 2013", 11 pages.
"Office Action dated Oct. 2, 2015 in U.S. Appl. No. 13/754,817, filed Jan. 30, 2013 and published as US 2013-0150253 on Jun. 13, 2013", 11 pages.
"Office Action dated Oct. 2, 2015 in U.S. Appl. No. 13/782,883, filed Mar. 1, 2013 and published as US 2014-0180594 on Jun. 26, 2014", 14 pages.
"Office Action dated Oct. 22, 2015 in U.S. Appl. No. 13/781,530, filed Feb. 28, 2013 and published as US 2014-0100792 on Apr. 10, 2014", 14 pages.
"Office Action dated Oct. 27, 2015 in U.S. Appl. No. 13/333,842, filed Dec. 21, 2011 and published as US 2012/0184449 on Jul. 19, 2012", 27 pages.
"Office Action dated Oct. 6, 2014 in U.S. Appl. No. 13/754,817, filed Jan. 30, 2013 and published as US 2013-0150253 on Jun. 13, 2013", 12 pages.
"Office Action dated Sep. 6, 2016 in U.S. Appl. No. 14/812,432, filed Jul. 29, 2015 and published as US 2016-0034640 on Feb. 4, 2016", 14 pages.
"Office Action dated Sep. 1, 2015 in U.S. Appl. No. 13/829,164, filed Mar. 14, 2013 and published as US 2013-0288244 on Oct. 31, 2014", 10 pages.
"Office Action dated Sep. 11, 2013 in U.S. Appl. No. 13/829,164, filed Mar. 14, 2013 and published as US 2013-0288244 on Oct. 31, 2013", 15 pages.
"Office Action dated Sep. 12, 2013 in U.S. Appl. No. 13/656,328, filed Oct. 19, 2012 and published as US 2013-0103320 on Apr. 25, 2013", 11 pages.
"Office Action dated Sep. 12, 2013 in U.S. Appl. No. 13/669,136, filed on Nov. 5, 2012 and published as: US 2013-0085681 on Apr. 4, 2013", 10 pages.
"Office Action dated Sep. 18, 2015 in U.S. Appl. No. 12/727,824, filed Mar. 19, 2010 and published as US 2010-0216153 on Aug. 26, 2010", 44 pages.
"Office Action dated Sep. 19, 2019 in U.S. Appl. No. 14/892,782, filed Nov. 20, 2015 and published as US 2016-0224724 on Aug. 4, 2016", 29 pages.
"Office Action dated Sep. 22, 2015 in U.S. Appl. No. 13/779,638, filed Feb. 27, 2013 and published as US 2013-0309666 on Nov. 21, 2013", 11 pages.
"Office Action dated Sep. 28, 2015 in U.S. Appl. No. 14/187,876, filed Feb. 24, 2014 and published as US 2014-0322709 on Oct. 30, 2014", 55 pages.
"Office Action dated Sep. 8, 2015 in U.S. Appl. No. 13/669,136, filed Nov. 5, 2012 and published as US 2013-0085681 on Apr. 4, 2013", 9 pages.
"Office Action dated Sep. 8, 2015 in U.S. Appl. No. 13/797,508, filed Mar. 12, 2013 and published as US 2013-0261983 on Oct. 3, 2013", 9 pages.
"Office Action dated Feb. 20, 2013 in U.S. Appl. No. 13/656,328, filed Oct. 19, 2012, not yet published", 13 pages.
"Office Action dated Aug. 22, 2013 in U.S. Appl. No. 13/619,039, filed Sep. 14, 2012 and published as: US 2013/0022977 on: Jan. 24, 2013", 13 pages.
"Office Action dated Feb. 15, 2013 in U.S. Appl. No. 13/669,136, filed Nov. 5, 2012 and published as: US 2013-0085681 on Apr. 4, 2013", 13 pages.
"Office Action dated Feb. 25, 2015 in U.S. Appl. No. 12/727,824, filed Sep. 13, 2012 and published as: US 2010/0216153 on: Aug. 26, 2010", 28 pages.
"Office Action dated Jan. 10, 2013 in U.S. Appl. No. 13/619,039, filed Sep. 14, 2012 and published as: US 2013/0022977 on: Jan. 24, 2013", 21 pages.
"Office Action dated Jul. 14, 2014 in U.S. Appl. No. 12/727,824, filed Sep. 13, 2012 and published as: US 2010/0216153 on: Aug. 26, 2010", 25 pages.
"Office Action dated May 16, 2011 in U.S. Appl. No. 12/727,824, filed Sep. 13, 2012 and published as: US 2010/0216153 on: Aug. 26, 2010", 11 pages.
"Office Action dated Oct. 18, 2011 in U.S. Appl. No. 12/727,824, filed Sep. 13, 2012 and published as: US 2010/0216153 on: Aug. 26, 2010", 11 pages.
Supplementary European Search Report dated Aug. 10, 2015 in European Application No. EP11745050.2, filed on Feb. 9, 2011, 15 pages.
Adinolfi Matteo, "Rapid Detection of Aneuploidies by Microsatellite and the Quantitative Fluorescent Polymerase Chain Reaction", Prenatal Diagnosis, 1997, 17(13):1299-1311.
Agarwal et al., "Commercial Landscape of Noninvasive Prenatal Testing in the United States", Prenatal Diagnosis, 2013, 33(6):521-531.
Akeson et al., "Microsecond Time-Scale Discrimination Among Polycytidylic Acid, Polyadenylic Acid, and Polyuridylic Acid as Homopolymers or as Segments Within Single RNA Molecules", Biophysical Journal, Dec. 1999, 77:3227-3233.
Alkan et al., "Personalized Copy-Number and Segmental Duplication Maps using Next-Generation Sequencing", Nature Genetics, Oct. 30, 2009, 41(10):1061-1067.
Amicucci et al., "Prenatal Diagnosis of Myotonic Dystrophy Using Fetal DNA Obtained from Maternal Plasma", Clinical Chemistry, 2000, 46:301-302.
Anantha et al., "Porphyrin Binding to Quadruplexed T4G4", Biochemistry, 1998, 37(9):2709-2714.
Armour et al., "Measurement of Locus Copy Number by Hybridisation with Amplifiable Probes", Nucleic Acids Research, Jan. 2000, 28(2):605-609.
Armour et al., "The Detection of Large Deletions or Duplications in Genomic DNA", Human Mutation, Nov. 2002, 20(5):325-337.
Ashkenasy et al., "Recognizing a Single Base in an Individual DNA Strand: A Step Toward Nanopore DNA Sequencing", Angewandte Chemie (International ed. in English), Feb. 18, 2005, 44(9):1401-1404.
Ashoor et al., "Chromosome-Selective Sequencing of Maternal Plasma Cell-free DNA for First-Trimester Detection of Trisomy 21 and Trisomy 18", American Journal of Obstetrics and Gynecology, Apr. 2012, 206(4):322.e1-322.e5.
Aston et al., "Optical Mapping and Its Potential for Large-Scale Sequencing Projects", Trends in Biotechnology, Jul. 1999, 17(7):297-302.
Aston et al., "Optical Mapping: An Approach for Fine Mapping", Methods in Enzymology, 1999, 303:55-73.
Avent et al., "Non-Invasive Diagnosis of Fetal Sex; Utilisation of Free Fetal DNA in Maternal Plasma and Ultrasound", Prenatal Diagnosis, Jul. 2006, 26(7):598-603.
Avent Neil D., "Refining Noninvasive Prenatal Diagnosis with Single-Molecule Next-Generation Sequencing", Clinical Chemistry, Apr. 2012, 58(4):657-658.
Beaucage et al., "Deoxynucleoside Phosphoramidites—A New Class of Key Intermediates for Deoxypolynucleotide Synthesis", Tetrahedron Letters, 1981, 22(20):1859-1862.

(56) References Cited

OTHER PUBLICATIONS

Benjamini et al., "Summarizing and Correcting the GC Content Bias in High-Throughput Sequencing", Nucleic Acids Research, XP0551 62924, ISSN: 0305-1048, DOI: 10.1093/nar/gks001, Feb. 9, 2012, 40(10):e72.
Berger et al., "Universal Bases for Hybridization, Replication, and Chain Termination", Nucleic Acids Research, 2000, 28(15):2911-2914.
Bergstrom et al., "Synthesis, Structure, and Deoxyribonucleic Acid Sequencing with a Universal Nucleoside: 1-(2"-Deoxy-β-D-Ribofuranosyl)-2-Nitropyrrole", Journal of the American Chemistry Society, 1995, 117:1201-1209.
Bianchi et al., "Isolation of Fetal DNA from Nucleated Erythrocytes in Maternal Blood", PNAS, 1990, 87(9):3279-3283.
Boeva et al., "Control-Free Calling of Copy Number Alterations in Deep-Sequencing Data Using GC-Content Normalization", Bioinformatics, 2011, 27(2):268-269.
Bollen,"Bioconductor: Microarray Versus Next-Generation Sequencing Toolsets", Utrecht University, Feb. 11, 2014, 14 pages.
Borsenberger et al., "Chemically Labeled Nucleotides and Oligonucleotides Encode DNA for Sensing with Nanopores", Journal of the American Chemical Society, 2009, 131:7530-7531.
Branton et al., "The Potential and Challenges of Nanopore Sequencing", Nature Biotechnology, 2008, 26:1146-1153.
Braslavsky et al., "Sequence Information Can Be Obtained from Single DNA Molecules", PNAS, Jan. 25, 2003, 100(7):3960-3964.
Brizot et al., "Maternal Serum hCG and Fetal Nuchal Translucency Thickness for the Prediction of Fetal Trisomies in the First Trimester of Pregnancy", British Journal of Obstetrices and Gynaecology, 1995, 102(2):127-132.
Brizot et al., "Maternal Serum Pregnancy-Associated Plasma Protein a and Fetal Nuchal Translucency Thickness for the Prediction of Fetal Trisomies in Early Pregnancy", Obstetrics & Gynecology, Dec. 1994, 84(6):918-922.
Brown et al., "Synthesis and Duplex Stability of Oligonucleotides Containing Adenine-Guanine Analogues", Carbohydrate Research, 1991, 216:129-139.
Brown et al., "Validation of QF-PCR for Prenatal Aneuploidy Screening in the United States", Prenatal Diagnosis, 2006, 26(11):1068-1074.
Brown Angus M., "A Step-by-Step Guide to Non-Linear Regression Analysis of Experimental Data Using a Microsoft Excel Spreadsheet Computer Methods and Programs in Biomedicine", Computer Methods and Programs in Biomedicine, Jun. 2001, 65(3):191-200.
Bruch et al., "Trophoblast-like Cells Sorted from Peripheral Maternal Blood Using Flow Cytometry: A Multiparametric Study Involving Transmission Electron Microscopy and Fetal DNA Amplification", Prenatal Diagnosis, 1991, 11:787-798.
Brunger Axel T., "Free R Value: A Novel Statistical Quantity for Assessing the Accuracy of Crystal Structures", Nature, Jan. 30, 1992, 355:472-475.
Budinska et al., "MSMAD: A Computationally Efficient Method for the Analysis of Noisy Array CGH Data", Bioinformatics, 2009, 25:703-713.
Bullard et al., "Evaluation of Statistical Methods for Normalization and Differential Expression in mRNA-Seq Experiments", BMC Bioinformatics, 2010, 11(94):1-13.
Burlingame A.L., "Mass Spectrometry", Analytical Chemistry, 1998, 70(16):647R-716R.
Campbell et al., "Identification of Somatically Acquired Rearrangements in Cancer Using Genome-Wide Massively Parallel Paired-End Sequencing", Nature Genetics, Jun. 2008, 40(6):722-729.
Canick et al., "A New Prenatal Blood Test for down Syndrome (RNA)", Women and Infants Hospital of Rhode Island, Apr. 6, 2009, 3 pages.
Canick et al., "DNA Sequencing of Maternal Plasma to Identify Down Syndrome and Other Trisomies in Multiple Gestations", Prenatal Diagnosis, May 14, 2012, 14:730-734.
Canick et al., "The Impact of Maternal Plasma DNA Fetal Fraction on next Generation Sequencing Tests for Common Fetal Aneuploidies", Prenatal Diagnosis, 2013, 33(7):667-674.
Cann et al., "A Heterodimeric DNA Polymerase: Evidence That Members of Euryarchaeota Possess a Distinct DNA Polymerase", PNAS, 1998, 95:14250.
Cariello et al., "Fidelity of Thermococcus Litoralis DNA Polymerase (Vent) in PCR Determined by Denaturing Gradient Gel Electrophoresis", Nucleic Acids Research, Aug. 11, 1991, 19(15):4193-4198.
Carlson et al., "Molecular Definition of 22q11 Deletions in 151 Velo-Cardio-Facial Syndrome Patients", The American Journal of Human Genetics, Sep. 1, 1997, 61(3):620-629.
Chan et al., "Size Distributions of Maternal and Fetal DNA in Maternal Plasma", Clinical Chemistry, 2004, 50(1):88-92.
Chandrananda et al., "Investigating and Correcting Plasma DNA Sequencing Coverage Bias to Enhance Aneuploidy Discovery", Plos One, Jan. 2014, 9:e86993.
Chen et al., "A Method for Noninvasive Detection of Fetal Large Deletions/Duplications by Low Coverage Massively Parallel Sequencing", Prenatal Diagnosis, Supp pp. 1-6, 2013, 33(6):584-590.
Chen et al., "Identification of Avian W-Linked Contigs by Short-Read Sequencing", BMC Genomics, 2012, 13(1):183.
Chen et al., "Noninvasive Prenatal Diagnosis of Fetal Trisomy 18 and Trisomy 13 by Maternal Plasma DNA Sequencing", PLoS ONE, Jul. 6, 2011, 6(7):1-7.
Chiang et al., "High-Resolution Mapping of Copy-Number Alterations with Massively Parallel Sequencing", Nature Methods, Jan. 2009, 6(1):99-103.
Chien et al., "Deoxyribonucleic Acid Polymerase from the Extreme Thermophile Thermus Aquaticus", Journal of Bacteriology, 1976, 127:1550-1557.
Chim et al., "Systematic Search for Placental DNA-Methylation Markers on Chromosome 21: Toward a Maternal Plasma-Based Epigenetic Test for Fetal Trisomy 21", Clinical Chemistry, 2008, 54(3):500-511.
Chiu et al., "Maternal Plasma DNA Analysis with Massively Parallel Sequencing by Ligation for Noninvasive Prenatal Diagnosis of Trisomy 21", Clinical Chemistry, 2010, 56(3):459-463.
Chiu et al., "Non-Invasive Prenatal Assessment of Trisomy 21 by Multiplexed Maternal Plasma DNA Sequencing: Large Scale Validity Study", BMJ, C7401 Web Appendices, Jan. 11, 2011, 342:1-9.
Chiu et al., "Noninvasive Prenatal Diagnosis of Fetal Chromosomal Aneuploidy by Massively Parallel Genomic Sequencing of DNA in Maternal Plasma", Proceedings of the National Academy of Sciences, Dec. 10, 2008, 105(51):20458-20463.
Chiu et al., "Prenatal Exclusion of β Thalassaemia Major by Examination of Maternal Plasma", The Lancet, 2002, 360:998-1000.
Chu et al., "Statistical Model for Whole Genome Sequencing and Its Application to Minimally Invasive Diagnosis of Fetal Genetic Disease", Bioinformatics, Mar. 23, 2009, 25(10):1244-1250.
Chung et al., "Discovering Transcription Factor Binding Sites in Highly Repetitive Regions of Genomes with Multi-Read Analysis of ChIP-Seq Data", PLoS Computational Biology, Jul. 2011, 7(7):e1002111.
Cohen et al., "GC Composition of the Human Genome: In Search of Isochores", Molecular Biological Evolution, 2005, 22(5):1260-1272.
Cooper et al., "Human Genome Mutations", BIOS Publishers, 1993, pp. i-xiii.
Costa et al., "Fetal RHD Genotyping in Maternal Serum During the First Trimester of Pregnancy", British Journal of Haematology, 2002, 119:255-260.
Costa et al., "New Strategy for Prenatal Diagnosis of X-Linked Disorders", The New England journal of medicine, 2002, 346:1502.
Cunningham et al., "Williams Obstetrics", McGraw-Hill, 2002, 1 page.
D'Alton ME, "Prenatal Diagnostic Procedures", Seminars in Perinatology, Jun. 1994, 18(3):140-162.

(56) References Cited

OTHER PUBLICATIONS

Dan et al., "Clinical Application of Massively Parallel Sequencing-Based Prenatal Noninvasive Fetal Trisomy Test for Trisomies 21 and 18 in 11, 105 Pregnancies with Mixed Risk Factors", Prenatal Diagnosis, 2012, 32:1225-1232.
Dan et al., "Prenatal Detection of Aneuploidy and Imbalanced Chromosomal Arrangements by Massively Parallel Sequencing", plos One, 2012, 7(2):e27835.
Datasheet, "Illumina Sequencing: TruSeq RNA and DNA Sample Preparation Kits v2", Publication No. 970-2009-039, Apr. 27, 2011, 4 pages.
Davanos et al., "Relative Quantitation of Cell-Free Fetal DNA in Maternal Plasma Using Autosomal DNA Markers", Clinica Chimica Acta, Aug. 2011, 412(17-18):1539-1543.
Deamer et al., "Nanopores and Nucleic Acids: Prospects for Ultrarapid Sequencing", Trends in Biotechnology, Apr. 2000, 18(4):147-151.
Derrien et al., "Fast Computation and Applications of Genome Mappability", Plos One, Jan. 19, 2012, 7(1):16 pages.
Dhallan et al., "Methods to Increase the Percentage of Free Fetal DNA Recovered from Maternal Circulation", JAMA: The Journal of the American Medical Association, Mar. 1, 2004, 291(9):1114-1119.
Diaz et al., "Accuracy of Replication in the Polymerase Chain Reaction. Comparison Between Thermotoga Maritima DNA Polymerase and Thermus Aquaticus DNA Polymerase", Brazilian Journal of Medical and Biological Research, 1998, 31:1239.
Ding et al., "A High-Throughput Gene Expression Analysis Technique Using Competitive PCR and Matrix-Assisted Laser Desorption Ionization Time-of-Flight MS", Proceedings of the National Academy of Sciences, Mar. 18, 2003, 100(6):3059-3064.
Dohm et al., "Substantial Biases in Ultra-Short Read Data Sets from High-Throughput DNA Sequencing", Nucleic Acids Research, Aug. 1, 2008, 36(16):10 pages.
Donoho et al., "WaveLab and Reproducible Research", Stanford University, Stanford CA 94305, USA, 1995, 1-27.
Drmanac et al., "Sequencing by Hybridization: Towards an Automated Sequencing of One Million M13 Clones Arrayed on Membranes", Electrophoresis, 1992, 13(8):566-573.
Edelmann et al., "A Common Molecular Basis for Rearrangement Disorders on Chromosome 22q11", Human Molecular Genetics, Jul. 1999, 8(7):1157-1167.
Egger et al., "Reverse Transcription Multiplex PCR for Differentiation Between Polio- and Enteroviruses from Clinical and Environmental Samples", Journal of Clinical Microbiology, Jun. 1995, 33(6):1442-1447.
Ehrich et al., "Noninvasive Detection of Fetal Trisomy 21 by Sequencing of DNA in Maternal Blood: A Study in a Clinical Setting", American Journal of Obstetrics and Gynecology, Mar. 2011, 204(3):205e1-205e11.
Eiben et al., "First-Trimester Screening: An Overview", Journal of Histochemistry & Cytochemistry, Mar. 2005, 53(3):281-283.
Ensenauer et al., "Microduplication 22q11.2, an Emerging Syndrome: Clinical, Cytogenetic, and Molecular Analysis of Thirteen Patients", American Journal of Human Genetics, 2003, 73(5):1027-1040.
Epicenter, "Product Sheet For: Nextera™ DNA Sample Prep Kit (Illumina®-Compatible) Cat. Nos. GA09115, GA091120, GA0911-50, GA0911-96, and GABC0950", Epicentre, an Illumina Company, Literature# 307, Jun. 2011, 12 pages.
Fan et al., "Analysis of the Size Distributions of Fetal and Maternal Cell-Free DNA by Paired-End Sequencing", Clinical Chemistry, 2010, 56(8):1279-1286.
Fan et al., "Noninvasive Diagnosis of Fetal Aneuploidy by Shotgun Sequencing DNA from Maternal Blood", Proceedings of the National Academy of Sciences, Oct. 21, 2008, 105(42):16266-16271.
Fan et al., "Sensitivity of Noninvasive Prenatal Detection of Fetal Aneuploidy from Maternal Plasma Using Shotgun Sequencing Is Limited Only by Counting Statistics", PLoS One, May 3, 2010, 5(5):7 pages.
Forabosco et al., "Incidence of Non-Age-Dependent Chromosomal Abnormalities: A Population-Based Study on 88965 Amniocenteses", European Journal of Human Genetics, Jan. 2009, 17(7):897-903.
Fromer et al., "Discovery and Statistical Genotyping of Copy-Number Variation from Whole-Exome Sequencing Depth", The American Journal of Human Genetics, 2012, 91(4):597-607.
Gebhard et al., "Genome-Wide Profiling of CpG Methylation Identifies Novel Targets of Aberrant Hypermethylation in Myeloid Leukemia", Cancer Research, Jun. 2006, 66(12):6118-6128.
Goya et al., "SNVMix: Predicting Single Nucleotide Variants From Next-Generation Sequencing of Tumors", Bioinformatics, 2010, 26(6):730-736.
Grati F. R, "Chromosomal Mosaicism in Human Feto-Placental Development: Implications for Prenatal Diagnosis", Journal of Clinical Medicine, Jul. 24, 2014, 3(3):809-837.
Haar Alfred, "On the Theory of Orthogonal Function Systems", Mathematische Annalen, 1910, 69(3):331-371.
Hahn et al., "Cell-Free Nucleic Acids as Potential Markers for Preeclampsia", Placenta, Feb. 2011, 32(1):S17-S20.
Harris et al., "Single-Molecule DNA Sequencing of a Viral Genome", Science, Apr. 4, 2008, 320(5872):106-109.
Herzenberg et al., "Fetal Cells in the Blood of Pregnant Women: Detection and Enrichment by Fluorescence-Activated Cell Sorting", PNAS, 1979, 76:1453-1455.
Hill et al., "Uses of Cell Free Fetal DNA in Maternal Circulation", Best Practice & Research Clinical Obstetrics and Gynaecology, Apr. 27, 2012, 26:639-654.
Hill Craig, "Gen-Probe Transcription-Mediated Amplification: System Principles", http://www.gen-probe.com/pdfs/tma_whiteppr.pdf, Jan. 1996, 1-4.
Hinds et al., "Whole-Genome Patterns of Common DNA Variation in Three Human Populations", Science, Feb. 18, 2005, 307(5712):1072-1079.
Hinnisdaels et al., "Direct Cloning of PCR Products Amplified with Pwo DNA Polymerase", Biotechniques, 20:186-188, 1996.
Hsu et al., "A Model-Based Circular Binary Segmentation Algorithm for the Analysis of Array CGH Data", BMC Research Notes, Article No. 394, Oct. 10, 2011, 4:1-12.
Hsu et al., "Denoising Array-Based Comparative Genomic Hybridization Data Using Wavelets", Biostatistics, Apr. 2005, 6(2):211-226.
Huber et al., "High-Resolution Liquid Chromatography of DNA Fragments on Non-Porous Poly(styrene-Divinylbenzene) Particles", Nucleic Acids Research, 1993, 21(5):1061-1066.
Hudecova et al., "Maternal Plasma Fetal DNA Fractions in Pregnancies with Low and High Risks for Fetal Chromosomal Aneuploidies", PLoS One, 2014, 9(2):e88484.
Hudson et al., "An STS-Based Map of the Human Genome", Science, Dec. 1995, 270(5244):1945-1954.
Hulten et al., "Rapid and Simple Prenatal Diagnosis of Common Chromosome Disorders: Advantages and Disadvantages of the Molecular Methods FISH and QF-PCR.", Reproduction, Sep. 2003, 126(3):279-297.
Hupe et al., "Analysis of Array CGH Data: From Signal Ratio to Gain and Loss of DNA Regions", Bioinformatics, 2004, 20(18):3413-3422.
Huse et al., "Accuracy and Quality of Massively Parallel DNA Pyrosequencing", Genome Biology, 2007, 8(7):R143.
Innis et al., "PCR Protocols: A Guide to Methods and Applications", 1990, 7 pages.
International Human Genome Sequencing Consortium, "Initial Sequencing and Analysis of the Human Genome", Nature, 2001, 409:860-921.
James James, "Mathematics Dictionary", Chapman & Hall, International Thomson Publishing, 5 Edition, 1992, 5 pages.
Jensen et al., "Detection of Microdeletion 22q11.2 in a Fetus by Next-Generation Sequencing of Maternal Plasma", Clinical Chemistry, Jul. 2012, 58(7):1148-1151.
Jensen et al., "High-Throughput Massively Parallel Sequencing for Fetal Aneuploidy Detection from Maternal Plasma", PLoS One, Mar. 6, 2013, 8(3):e57381.

(56) References Cited

OTHER PUBLICATIONS

Jiang et al., "FetalQuant: Deducing Fractional Fetal DNA Concentration from Massively Parallel Sequencing of DNA in Maternal Plasma", Bioinformatics, Nov. 15, 2012, 28(22):2883-2890.
Jiang et al., "Noninvasive Fetal Trisomy (NIFTY) Test: An Advanced Noninvasive Prenatal Diagnosis Methodology for Fetal Autosomal and Sex Chromosomal Aneuploidies", BMC Medical Genomics, 2012, 5(57):11 pages.
Jing et al., "Automated High Resolution Optical Mapping Using Arrayed, Fluid-Fixed DNA Molecules", Proceedings of the National Academy of Sciences, 1998, 95(14):8046-8051.
Johnston et al., "Autoradiography Using Storage Phosphor Technology", Electrophoresis, May 1990, 11(5):355-360.
Joos et al., "Covalent Attachment of Hybridizable Oligonucleotides to Glass Supports", Analytical Biochemistry, 1997, 247:96-101.
Jorgez et al., "Improving Enrichment of Circulating Fetal DNA for Genetic Testing: Size Fractionation Followed by Whole Gene Amplification", Fetal Diagnosis and Therapy, Karger Basel, CH, Jan. 1, 2009, 25(3):314-319.
Juncosa-Ginesta et al., "Improved Efficiency in Site-Directed Mutagenesis by PCR Using a *Pyrococcus* Sp. GB-D Polymerase", Biotechniques, 1994, 16(5):820-823.
Jurinke et al., "MALDI-TOF Mass Spectrometry: A Versatile Tool for High-Performance DNA Analysis", Molecular Biotechnology, 2004, 26:147-164.
Kalinina et al., "Nanoliter Scale PCR with TaqMan Detection", Nucleic Acids Research, May 15, 1997, 25(10):1999-2004.
Kato et al., "A New Packing for Separation of DNA Restriction Fragments by High Performance Liquid Chromatography", J. Biochem, 1984, 95(1):83-86.
Khandjian,"UV Crosslinking of RNA to Nylon Membrane Enhances Hybridization Signals", Mol. Bio. Rep., 1986, 11:107-115.
Kim et al., "Determination of Fetal DNA Fractions from the Plasma of Pregnant Women Using Sequence Read Counts", Prenatal Diagnosis, 2015, 35(8):810-815.
Kim et al., "Identification of Significant Regional Genetic Variations Using Continuous CNV Values in aCGH Data", Genomics, 2009, 94(5):317-323.
Kitzman et al., "Noninvasive Whole-Genome Sequencing of a Human Fetus", Science Translation Medicine, American Association for the Advancement of Science, US, Jun. 6, 2012, 4(137-140):115-122.
Klambauer et al., "cn.MOPS: Mixture of Poissons for Discovering Copy Number Variations in Next-Generation Sequencing Data With a Low False Discovery Rate", Nucleic Acids Research, 2012, 40(9):e69.
Kornberg et al., "DNA Replication", 2nd edition, 1991, 1 page.
Krumm et al., "Copy Number Variation Detection and Genotyping from Exome Sequence Data", Genome Research, May 14, 2012, 22(8):1525-1532.
Kulkarni et al., "Global DNA Methylation Patterns in Placenta and Its Association with Maternal Hypertension in Pre-Eclampsia", DNA and Cell Biology, Feb. 2011, 30(2):79-84.
Lai et al., "A Shotgun Optical Map of the Entire Plasmodium Falciparum Genome", Nature Genetics, 1999, 23(3):309-313.
Lai et al., "Comparative Analysis of Algorithms for Identifying Amplifications and Deletions in Array CGH Data", Bioinformatics, Oct. 1, 2005, 21(19):3763-3770.
Langmead et al., "Ultrafast and Memory-Efficient Alignment of Short DNA Sequences to the Human Genome", Genome Biology, Article R25, 2009, 10(3):1-10.
Lecomte et al., "Selective Inactivation of the 3" to 5" Exonuclease Activity of *Escherichia coli* DNA Polymerase I by Heat", Polynucleotides Res., 1983, 11:7505-7515.
Leek et al., "Tackling the Widespread and Critical Impact of Batch Effects in High-Throughput Data", Nature Reviews Genetics, 2010, 11(10):733-739.

Lefkowitz et al., "Clinical Validation of a Noninvasive Prenatal Test for Genomewide Detection of Fetal Copy Number Variants", American Journal of Obstetrics & Gynecology, Aug. 2016, 215(2): 227.e1-227.e16.
Levin Henry L., "It's Prime Time for Reverse Transcriptase", Cell, 1997, 88(1):5-8.
Li et al., "Detection of Paternally Inherited Fetal Point Mutations for β-Thalassemia Using Size-Fractionated Cell-Free DNA in Maternal Plasma", Journal of the American Medical Association, Feb. 16, 2005, 293:843-849.
Li et al., "Mapping Short DNA Sequencing Reads and Calling Variants Using Mapping Quality Scores", Genome Research, Aug. 19, 2008, 18(11):1851-1858.
Liao et al., "Noninvasive Prenatal Diagnosis of Fetal Trisomy 21 by Allelic Ratio Analysis Using Targeted Massively Parallel Sequencing of Maternal Plasma DNA", PLoS One, 2012, 7(5):1-7.
Liao et al., "Targeted Massively Parallel Sequencing of Maternal Plasma DNA Permits Efficient and Unbiased Detection of Fetal Alleles", Clinical Chemistry, 2010, 57(1):92-101.
Lin et al., "Synthesis and Duplex Stability of Oligonucleotides Containing Cytosine-Thymine Analogues", Nucleic Acids Research, 1989, 17(24):10373-10383.
Lin et al., "Synthesis of Oligodeoxyribonucleotides Containing Degenerate Bases and Their Use as Primers in the Polymerase Chain Reaction", Nucleic Acids Research, 1992, 20:5149-5152.
Liu et al., "CUSHAW: a CUDA Compatible Short Read Aligner to Large Genomes Based on the Burrows-Wheeler Transform", Bioinformatics, Jul. 15, 2012, 28(14):1830-1837.
Lo et al., "Digital PCR for the Molecular Detection of Fetal Chromosomal Aneuploidy", PNAS, 2007, 104(32):13116-13121.
Lo et al., "Fetal DNA in Maternal Plasma: Application to Non-Invasive Blood Group Genotyping of the Fetus", Transfusion Clinique et Biologique, 2001, 8:306-310.
Lo et al., "Increased Fetal DNA Concentrations in the Plasma of Pregnant Women Carrying Fetuses with Trisomy 21", Clinical Chemistry, 1999, 45:1747-1751.
Lo et al., "Maternal Plasma DNA Sequencing Reveals the Genome-Wide Genetic and Mutational Profile of the Fetus", Science Translational Medicine, Dec. 8, 2010, 2(61):61ra91.
Lo et al., "Plasma Placental RNA Allelic Ratio Permits Noninvasive Prenatal Chromosomal Aneuploidy Detection", Nature Medicine, 2007, 13(2):218-223.
Lo et al., "Prenatal Diagnosis of Fetal RhD Status by Molecular Analysis of Maternal Plasma", The New England Journal of Medicine, 1998, 339:1734-1738.
Lo et al., "Presence of Fetal DNA in Maternal Plasma and Serum", The Lancet, 1997, 350:485-487.
Lo et al., "Quantitative Abnormalities of Fetal NDA in Maternal Serum in Preeclampsia", Clinical Chemistry, 1999, 45:184-188.
Lo et al., "Quantitative Analysis of Fetal DNA in Maternal Plasma and Serum: Implications for Noninvasive Prenatal Diagnosis", American Journal of Human Genetics, Apr. 1, 1998, 62(4):768-775.
Lo et al., "Recent Advances in Fetal Nucleic Acids in Maternal Plasma", Journal of Histochemistry and Cytochemistry, Mar. 2005, 53(3):293-296.
Loakes et al., "5-Nitroindole as an Universal Base Analogue", Nucleic Acids Research, 1994, 22(20):4039-4043.
Lun et al., "Microfluidics Digital PCR Reveals a Higher than Expected Fraction of Fetal DNA in Maternal Plasma", Clinical Chemistry, Oct. 1, 54(10):1664-1672, 2008.
Lundberg et al., "High-Fidelity Amplification Using a Thermostable DNA Polymerase Isolated from Pyrococcus Furiosus", Gene, Dec. 1, 1991, 108:1-6.
Magi et al., "Read Count Approach for DNA Copy Number Variants Detection", Bioinformatics, including pp. 1/47-47/47 of Supplementary Material. (Year: 2011), Dec. 23, 2011, 28(4):470-478.
Mann et al., "Development and Implementation of a New Rapid Aneuploidy Diagnostic Service Within the UK National Health Service and Implications for the Future of Prenatal Diagnosis", Lancet, Sep. 29, 2001, 358(9287):1057-1061.
Margulies et al., "Genome Sequencing in Microfabricated High-density Picolitre Reactors", Nature, Sep. 15, 2005, 437(7057):376-380.

(56) References Cited

OTHER PUBLICATIONS

Mazloom Amin, "Gender Prediction with Bowtie Alignments Using Male Specific Regions", May 10, 2012, 13 pages.
Metzker Michael L., "Sequencing Technologies—The Next Generation", Nature Review Genetics, Jan. 1, 2010, 11 (1):31-46.
Miller et al., "Consensus Statement: Chromosomal Microarray Is a First-Tier Clinical Diagnostic Test for Individuals with Developmental Disabilities or Congenital Anomalies", American Journal of Human Genetics, 2010, 86(5):749-764.
Mitchell et al., "Chemical Tags Facilitate the Sensing of Individual DNA Strands with Nanopores", Angewandte Chemie International Edition, 2008, 47:5565-5568.
Morton, "Parameters of the Human Genome", Proceedings of the National Academy of Sciences, Sep. 1991, 88:7474-7476.
Moudrianakis et al., "Base Sequence Determination in Nucleic Acids with the Electron Microscope, III. Chemistry and Microscopy of Guanine-Labeled DNA", Proceedings of the National Academy of Sciences, 1965, 53:564-571.
Murtaza et al., "Non-Invasive Analysis of Acquired Resistance to Cancer Therapy by Sequencing of Plasma DNA", Nature, May 1, 2013, 497(7447):108-112.
Myers et al., "Reverse Transcription and DNA Amplification by a Thermus Thermophilus DNA Polymerase", Biochemistry, Aug. 6, 1991, 30(31):7661-7666.
Nakano et al., "Single-Molecule PCR Using Water-in-Oil Emulsion", Journal of Biotechnology, Apr. 24, 2003, 102(2):117-124.
Nason et al., "Wavelet Methods in Statistics", Table of contents. R. Springer, New York ISBN: 978-0-387-75960-9 (Print) 978-0-387-75961-6 (Online), 2008, 9 pages.
Needham-Vandevanter et al., "Characterization of an Adduct Between CC-1065 and a Defined Oligodeoxynucleotide Duplex", Nucleic Acids Research, Aug. 10, 1984, 12(15):6159-6168.
Nevin,"Future Direction of Medical Genetics", The Ulster Medical Journal, 2001, 70(1):1-2.
Ng et al., "mRNA of Placental Origin Is Readily Detectable in Maternal Plasma", PNAS, 2003, 100(8):4748-4753.
Ng et al., "The Concentration of Circulating Corticotropin-Releasing Hormone mRNA in Maternal Plasma Is Increased in Preeclampsia", Clinical Chemistry, 2003, 49:727-731.
Nguyen et al., "Denoising of Array-Based DNA Copy Number Data Using the Dual-Tree Complex Wavelet Transform", 2007 IEEE 7th International Symposium on BioInformatics and BioEngineering, Oct. 14, 2007, 137-144.
Nichols et al., "A Universal Nucleoside for Use at Ambiguous Sites in DNA Primers", Nature, 1994, 369(6480):492-493.
Nicolaides et al., "One-Stop Clinic for Assessment of Risk of Chromosomal Defects at 12 Weeks of Gestation", The Journal of Maternal-Fetal & Neonatal Medicine, Jul. 2002, 12(1):9-18.
Nolte Frederickvs., "Branched DNA Signal Amplification for Direct Quantitation of Nucleic Acid Sequences in Clinical Specimens", Advanced Clinical Chemistry, 1998, 33:201-235.
Nordstrom et al., "Characterization of Bacteriophage T7 DNA Polymerase Purified to Homogeneity by Antithioredoxin Immunoadsorbent Chromatography", Journal of Biological Chemistry, 1981, 256:3112-3117.
Nygren et al., "Quantification of Fetal DNA by Use of Methylation-Based DNA Discrimination", Clinical Chemistry, 2010, 56(10):1627-1635.
Oh et al., "CAM: A Web Tool for Combining Array CGH and Microarray Gene Expression Data from Multiple Samples", Computers in Biology and Medicine, Sep. 1, 2010, 40(9):781-785.
Ohno Susumu, "Sex Chromosomes and Sex-Linked Genes", Monographs on Endocrinology (Book 1), 1967, 201 pages.
Old et al., "Candidate Epigenetic Biomarkers for Non-Invasive Prenatal Diagnosis of down Syndrome", Reproductive Biomedicine Online, 2007, 15(2):227-235.
Oldridge et al., "Optimizing Copy Number Variation Analysis Using Genome-Wide Short Sequence Oligonucleotide Arrays.", Nucleic Acids Research, including pp. 1/25-25/25 of Supplementary Methods. (Year: 2010), Feb. 2010, 38(10):3275-3286.
Olshen et al., "Circular Binary Segmentation for the Analysis of Array-Based DNA Copy Number Data", Biostatistics, Oct. 2004, 5(4):557-572.
Omont et al., "Gene-Based Bin Analysis of Genome-Wide Association Studies", BMC Proceedings, 2008, 2(Suppl. 4):S6:9 pages.
Oroskar et al., "Detection of Immobilized Amplicons by ELISA-like Techniques", Clinical Chemistry, 1996, 42:1547-1555.
Oudejans et al., "Detection of Chromosome 21-Encoded mRNA of Placental Origin in Maternal Plasma", Clinical Chemistry, 2003, 49(9):1445-1449.
Palomaki et al., "DNA Sequencing of Maternal Plasma Reliably Identifies Trisomy 18 and Trisomy 13 as Well as down Syndrome: An International Collaborative Study", Genetics in Medicine, 2012, 14(3):296-305.
Palomaki et al., "DNA Sequencing of Maternal Plasma to Detect Down Syndrome: An International Clinical Validation Study", Genetics in Medicine, Nov. 2011, 13(11):913-920.
Pandya et al., "Screening for Fetal Trisomies by Maternal Age and Fetal Nuchal Translucency Thickness at 10 to 14 Weeks of Gestation", BJOG—Obstetrics and Gynecology, Dec. 1995, 102(12):957-962.
Pearson et al., "High-Performance Anion-Exchange Chromatography of Oligonucleotides", Journal of Chromatography, 1983, 255:137-149.
Pekalska et al., "Classifiers for Dissimilarity-Based Pattern Recognition", 15th International Conference on Pattern Recognition (ICPR'00), Barcelona,Spain, Sep. 3-8, 2000, 2:12-16.
Pertl et al., "Rapid Molecular Method for Prenatal Detection of Down's Syndrome", Lancet, May 14, 1994, 343(8907):1197-1198.
Peters et al., "Noninvasive Prenatal Diagnosis of a Fetal Microdeletion Syndrome", Correspondence to the Editor, New England Journal of Medicine, Nov. 10, 2011, 365(19)1847-1848.
Poon et al., "Differential DNA Methylation Between Fetus and Mother as a Strategy for Detecting Fetal DNA in Maternal Plasma", Clinical Chemistry, Jan. 2002, 48(1):35-41.
Purnell et al., "Discrimination of Single Base Substitutions in a DNA Strand Immobilized in a Biological Nanopore", ACS Nano, 2009, 3:2533-2538.
Pushkarev et al., "Single-Molecule Sequencing of an Individual Human Genome", Nature Biotechnology, 2009, 27(9):847-850.
Qu et al., "Analysis of Drug-DNA Binding Data", Methods Enzymology, 2000, 321:353-369.
Robin et al., "Defining the Clinical Spectrum of Deletion 22q11.2", The Journal of Pediatrics, 2005, 147(1):90-96.
Romero et al., "PCR Detection of the Human Enteroviruses", Diagnostic Molecular Microbiology, Principles and Applications, 1993, 401-406.
Romiguier et al., "Contrasting GC-Content Dynamics Across 33 Mammalian Genomes: Relationship with Life-History Traits and Chromosome Sizes", Genome research, 2010, 20:1001-1009.
Ross et al., "The DNA Sequence of the Human X Chromosome", Nature, Mar. 2005, 434(7031):325-337.
Roth et al., "JointSNVMix: A Probabilistic Model for Accurate Detection of Somatic Mutations in Normal/tumour Paired Next-Generation Sequencing Data", Bioinformatics, 2012, 28:907-913.
Saito et al., "Prenatal DNA Diagnosis of a Single-gene Disorder from Maternal Plasma", Lancet, Sep. 30, 2000, 356:1170.
Sambrook et al., "Molecular Cloning: A Laboratory Manual", Molecular Cloning: A Laboratory Manual, 2001, 3(10):52 pages.
Schouten et al., "Relative Quantification of 40 Nucleic Acid Sequences by Multiplex Ligation-Dependent Probe Amplification", Nucleic Acids Research, Jun. 15, 2002, 30(12):13 pages.
Schwinger et al., "Clinical Utility Gene Card For: DiGeorge Syndrome, Velocardiofacial Syndrome, Shprintzen Syndrome, Chromosome 22q11.2 Deletion Syndrome (22q11.2, TBX1)", European Journal of Human Genetics, Feb. 3, 2010, 18:3 pages.
Sehnert et al., "Optimal Detection of Fetal Chromosomal Abnormalities by Massively Parallel DNA Sequencing of Cell-Free Fetal DNA from Maternal Blood", Clinical Chemistry, 2011, 57(7):1042-1049.
Sekizawa Akihiko, "Cell-Free Fetal DNA Is Increased in Plasma of Women with Hyperemesis Gravidarum", Clinical Chemistry, 2001, 47:2164-2165.

(56) References Cited

OTHER PUBLICATIONS

Shah et al., "Mutational Evolution in a Lobular Breast Tumour Profiled at Single Nucleotide Resolution", Nature, 2009, 461:809-813.
Shen et al., "A Hidden Markov Model for Copy Number Variant Prediction from Whole Genome Resequencing Data", BMC Bioinformatics, 2011, 12(Suppl 6):1-7.
Shendure et al., "Next-Generation DNA Sequencing", Nature Biotechnology, 2008, 26:1135-1145.
Sherman et al., "Epidemiology of Down Syndrome", Mental Retardation and Developmental Disabilities Research Reviews, 2007, 13(3):221-227.
Shin et al., "Prevalence of Down Syndrome Among Children and Adolescents in 10 Regions of the United States", Pediatrics, 2009, 124(6):1565-1571.
Skaletsy et al., "The Male-Specific Region of the Human Y Chromosome Is a Mosaic of Discrete Sequence Classes", Nature, Jun. 19, 2003, 423(6942):825-837.
Slater H.R., "Rapid, High Throughput Prenatal Detection of Aneuploidy Using a Novel Quantitative Method (MLPA)", Journal of Medical Genetics, 2003, 40(12):907-912.
Smid et al., "Evaluation of Different Approaches for Fetal DNA Analysis from Maternal Plasma and Nucleated Blood Cells", Clinical Chemistry, 1999, 45(8):1570-1572.
Smith et al., "Direct Mechanical Measurements of the Elasticity of Single DNA Molecules by Using Magnetic Beads", Science, Nov. 13, 1992, 258(5085):1122-1126.
Snijders et al., "Assembly of Microarrays for Genome-Wide Measurement of DNA Copy Number", Nature Genetics, Nov. 2001, 29(3):263-264.
Snijders et al., "First-Trimester Ultrasound Screening for Chromosomal Defects", Ultrasound in Obstetrics & Gynecology, Mar. 1996, 7(3):216-226.
Snijders et al., "UK Multicentre Project on Assessment of Risk of Trisomy 21 by Maternal Age and Fetal Nuchal-Translucency Thickness at 10-14 Weeks of Gestation.", The Lancet, Fetal Medicine Foundation First Trimester Screening Group, Aug. 1, 1998, 352(9125):343-346.
Soni et al., "Progress Toward Ultrafast DNA Sequencing Using Solid-State Nanopores", Clinical Chemistry, Nov. 2007, 53(11):1996-2001.
Sparks et al., "Noninvasive Prenatal Detection and Selective Analysis of Cell-Free DNA Obtained from Maternal Blood: Evaluation for Trisomy 21 and Trisomy 18", American Journal of Obstetrics and Gynecology, Apr. 2012, 206(4):319.e1-319.e9.
Sparks et al., "Selective Analysis of Cell-Free DNA in Maternal Blood for Evaluation of Fetal Trisomy", Prenatal Diagnosis, 2012, 32(1):3-9.
Srinivasan et al., "Noninvasive Detection of Fetal Subchromosome Abnormalities via Deep Sequencing of Maternal Plasma", The American Journal of Human Genetics, Feb. 7, 2013, 92(2):167-176.
Stagi et al., "Bone Density and Metabolism in Subjects with Microdeletion of Chromosome 22q11 (del22q11)", European Journal of Endocrinol, 2010, 163(2):329-337.
Stanghellini et al., "Quantitation of Fetal DNA in Maternal Serum During the First Trimester of Pregnancy by the Use of a DAZ Repetitive Probe", Molecular Human Reproduction, 2006, 12(9):587-591.
Stenesh et al., "DNA Polymerase from Mesophilic and Thermophilic Bacteria. III. Lack of Fidelity in the Replication of Synthetic Polydeoxyribonucleotides by DNA Polymerase from Bacillus Licheniformis and Bacillus Stearothermophilus", Biochim Biophys Acta, 1977, 475:32-41.
Stoddart et al., "Single-Nucleotide Discrimination in Immobilized DNA Oligonucleotides with a Biological Nanopore", Proceedings of the National Academy of Sciences, 2009, 106(19):7702-7707.
Strachan T., "The Human Genome", BIOS Scientific Publishers, 1992, 160 pages.
Strauss William M., "Current Protocols in Molecular Biology", John Wiley & Sons, N.Y., 1993, 6.3.1-6.3.6.
Tabor et al., "Randomised Controlled Trial of Genetic Amniocentesis in 4606 Low-Risk Women", Lancet, 1996, 1(8493):1287-1293.
Takagi et al., "Characterization of DNA Polymerase from *Pyrococcus* Sp. Strain KOD1 and Its Application to PCR", Appl. Environ. Microbial, 1997, 63(11):4504-4510.
Taylor et al., "Characterization of Chemisorbed Monolayers by Surface Potential Measurements", Journal of Physics D, 1991, 24(8):1443-1450.
The International SNP Map, "A Map of Human Genome Sequence Variation Containing 1.42 Million Single Nucleotide Polymorphisms", Nature, 2001, 409:928-933.
Timp et al., "Nanopore Sequencing: Electrical Measurements of the Code of Life", IEEE Transactions on Nanotechnology, 2010, 9(3):281-294.
Trapnell et al., "How to Map Billions of Short Reads onto Genomes", Nature Biotechnology, May 2009, 27(5):455-457.
Van Den Berghe et al., "A New Characteristic Karyotypic Anomaly in Lymphoproliferative Disorders", Cancer, 1979, 44:188-195.
Veltman et al., "High-Throughput Analysis of Subtelomeric Chromosome Rearrangements by Use of Array-Based Comparative Genomic Hybridization", American Journal of Human Genetics, May 2002, 70(5):1269-1276.
Venkatraman et al., "A Faster Circular Binary Segmentation Algorithm for the Analysis of Array CGH Data", Bioinformatics, 2007, 23(6):657-663.
Verbeck et al., "A Fundamental Introduction to Ion Mobility Mass Spectrometry Applied to the Analysis of Biomolecules", Journal of Biomolecular Techniques, 2002, 13(2):56-61.
Verma et al., "Rapid and Simple Prenatal DNA Diagnosis of Down's Syndrome", Lancet, Jul. 4, 1998, 352(9121):9-12.
Verma, "The Reverse Transcriptase", Biochim Biophys Acta, Mar. 21, 1977, 473(1):1-38.
Vincent et al., "Helicase-Dependent Isothermal DNA Amplification", EMBO Reports, 2004, 5(8):795-800.
Voelkerding et al., "Next-generation Sequencing: from Basic Research to Diagnostics", Clinical Chemistry, 2009, 55(4):641-658.
Vogelstein et al., "Digital PCR", PNAS, Aug. 3, 1999, 96(16):9236-9241.
Wang et al., "A Method for Calling Gains and Losses in Array CGH Data", Biostatistics, 2005, 6:45-58.
Wang et al., "A Novel Stationary Wavelet Denoising Algorithm for Array-Based DNA Copy Number Data", International Journal of Bioinformatics Research and Applications, 2007, 3(2):206-222.
Wapner et al., "First-Trimester Screening for Trisomies 21 and 18", The New England Journal of Medicine, Oct. 9, 2003, 349(15):1405-1413.
Wavethresh, "Wavelets Statistics and Transforms and a Detailed Description of WaveThresh", <URL:*>http://cran.r-project.org/web/packages/wavethresh/index.html<><URL:*>http://cran.r-project.org/web/packages/wavethresh/wavethresh.pdf<>, 2013, 396 pages.
Wei et al., "Detection and Quantification by Homogenous PCR of Cell-Free Fetal DNA in Maternal Plasma", Clinical Chemistry, 2001, 47(2):336-338.
Willenbrock et al., "A Comparison Study: Applying Segmentation to Array CGH Data for Downstream Analyses", Bioinformatics, Nov. 15, 2005, 21(22):4084-4091.
Wright et al., "The Use of Cell-Free Fetal Nucleic Acids in Maternal Blood for Non-Invasive Diagnosis", Human Reproduction Update, Jan. 1, 2009, 15(1):139-151.
Wu et al., "Genetic and Environmental Influences on Blood Pressure and Body Mass Index in Han Chinese: A Twin Study", Hypertension Research, Nov. 4, 2010, 34:173-179.
Wu et al., "Reverse Transcriptase", Critical Reviews in Biochemistry and Molecular Biology, Jan. 1975, 3(3):289-347.
Yang et al., "A Novel K-Mer Mixture Logistic Regression for Methylation Susceptibility Modeling of CpG Dinucleotides in Human Gene Promoters", BMC Bioinformatics, 2012, 13(Suppl. 3):S15.
Yershov et al., "DNA Analysis and Diagnostics on Oligonucleotide Microchips", PNAS, May 14, 1996, 93(10):4913-4918.
Yoon et al., "Sensitive and Accurate Detection of Copy Number Variants Using Read Depth of Coverage", Genome Research, 2009, 19:1586-1592.

(56) References Cited

OTHER PUBLICATIONS

Yu et al., "Noninvasive Prenatal Molecular Karyotyping from Maternal Plasma", PLoS ONE, 2013, 8(1):e54236:8 pages.
Yu et al., "Size-Based Molecular Diagnostics Using Plasma DNA for Noninvasive Prenatal Testing", Proceedings of the National Academy of Sciences of the United States of America, 2014, 111(23):8583-8588.
Yuk et al., "Genomic Analysis of Fetal Nucleic Acids in Maternal Blood", Annual Review of Genomics and Human Genetics, May 29, 2012, 13(1):285-306.
Zhang et al., "A Single Cell Level Based Method for Copy Number Variation Analysis by Low Coverage Massively Parallel Sequencing", PLoS ONE, 2013, 8(1):e54236:9 pages.
Zhao et al., "Detection of Fetal Subchromosomal Abnormalities by Sequencing Circulating Cell-Free DNA from Maternal Plasma", Clinical Chemistry, 2015, 61(4):608-616.
Zhao et al., "Quantification and Application of the Placental Epigenetic Signature of the RASSF1A Gene in Maternal Plasma", Prenatal Diagnosis, Aug. 2010, 30(8):778-782.
Zhong et al., "Cell-Free Fetal DNA in the Maternal Circulation Does Not Stem from the Transplacental Passage of Fetal Erythroblasts", Molecular Human Reproduction, 2002, 8(9):864-870.
Zhong et al., "Elevation of Both Maternal and Fetal Extracellular Circulating Deoxyribonucleic Acid Concentrations in the Plasma of Pregnant Women with Preeclampsia", American Journal of Obstetrics and Gynecology, 2001, 184(3):414-419.
Zhou et al., "Detection of DNA Copy Number Abnormality by Microarray Expression Analysis", Human Genetics, 2004, 114:464-467.
Zhou et al., "Recent Patents of Nanopore DNA Sequencing Technology: Progress and Challenges", Recent Patents on DNA & Gene Sequences, 2010, 4:192-201.
Zimmermann et al., "Real-Time Quantitative Polymerase Chain Reaction Measurement of Male Fetal DNA in Maternal Plasma", Methods in Molecular Medicine: Single Cell Diagnostics, 2007, 132:43-49.
Office Action dated Sep. 25, 2020 in U.S. Appl. No. 15/329,016, filed Jan. 25, 2017 and published as US 2017-0351811 on Dec. 7, 2017, 13 pages.
Office Action dated Sep. 25, 2020 in U.S. Appl. No. 15/661,804, filed Jul. 27, 2017 and published as US 2018-0032671 on Feb. 1, 2018, 8 pages.
Larrabee et al., "Microarray Analysis of Cell-Free Fetal DNA in Amniotic Fluid: A Prenatal Molecular Karyotype", The American Journal of Human Genetics, 2004, 75:485-491.

Rava et al., "Circulating Fetal Cell-Free DNA Fractions Differ in Autosomal Aneuploidies and Monosomy X", Clinical Chemistry, 2014, 60(1):243-250.
Office Action dated Apr. 16, 2021 in U.S. Appl. No. 15/661,804, filed Jul. 27, 2017 and published as US 2018-0032671 on Feb. 1, 2018, 12 pages.
Office Action dated Jun. 9, 2021 in U.S. Appl. No. 15/329,016, filed Jan. 25, 2017 and published as US 2017-0351811 on Dec. 7, 2017, 19 pages.
Li et al., "A Survey of Sequence Alignment Algorithms for Next-Generation Sequencing", Briefings in Bioinformatics, May 11, 2010, 11(5):473-483.
Sayres et al., "Cell-Free Fetal Nucleic Acid Testing: A Review of the Technology and Its Applications", Obstetrical and Gynecological Survey, 2011, 66(7):431-442.
Office Action dated Aug. 9, 2021 in U.S. Appl. No. 15/661,804, filed Jul. 27, 2017 and published as US 2018-0032671 on Feb. 1, 2018, 8 pages.
Bagos, Pantelis G. "Genetic Model Selection in Genome-Wide Association Studies: Robust Methods and the Use of Meta-Analysis", Statistical Applications in Genetics and Molecular Biology, 2013, 24 pages.
Holdenrieder, et al. "Circulating Nucleosomes Predict the Response to Chemotherapy in Patients with Advanced Non-Small Cell Lung Cancer", Clinical Cancer Research, Sep. 15, 2004, 10:5981-5987.
International Preliminary Report on Patentability dated Aug. 8, 2019 in International Application No. PCT/US2018/015081, 9 pages.
International Preliminary Report on Patentability dated Sep. 26, 2019 in International Application No. PCT/US2018/023151, 9 pages.
Abyzov et al., "CNVnator: An Approach to Discover, Genotype, and Characterize Typical and Atypical CNVs from Family and Population Genome Sequencing", Genome Research, 2011, 21(6):974-984.
Mouliere et al., "Multi-Marker Analysis of Circulating Cell-Free DNA Toward Personalized Medicine for Colorectal Cancer", Molecular Oncology, Mar. 24, 2014, 8:927-941.
Tynan et al., "Optimized Detection of 22q11.2 Deletions Using Whole Genome Sequencing", Available online at: https://www.integratedgenetics.com/sites/default/files/OptimizedDetectionof22q112DeletionsUsingWholeGenomeSequencing.pdf, Jan. 2017, 1 page.
Sebastiani, et al. "Naive Bayesian Classifier and Genetic Risk Score for Genetic Risk Prediction of a Categorical Trait: Not so Different After All!", Frontiers in Genetics, Feb. 29, 2012, 3(26):9 pages.
Grati et al., "Fetoplacental Mosaicism: Potential Implications for False-Positive and False-Negative Noninvasive Prenatal Screening Results", Genetics in Medicine, Aug. 2014, 16(8):620-624.

* cited by examiner

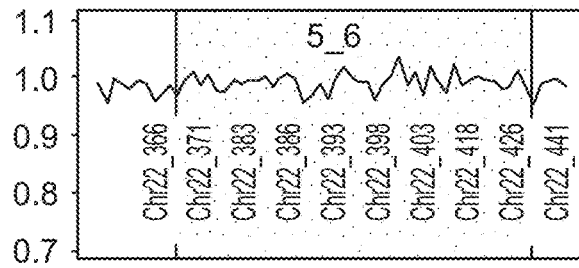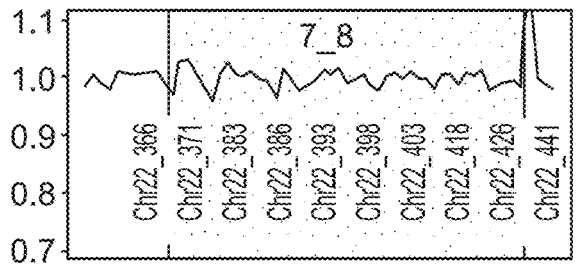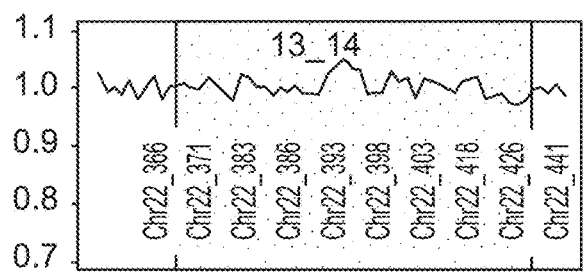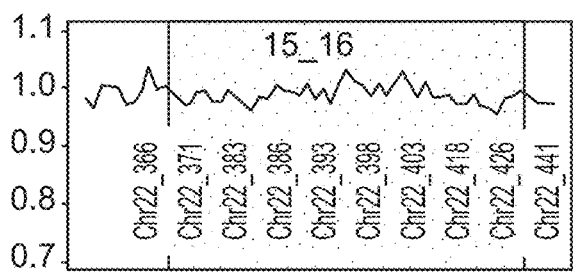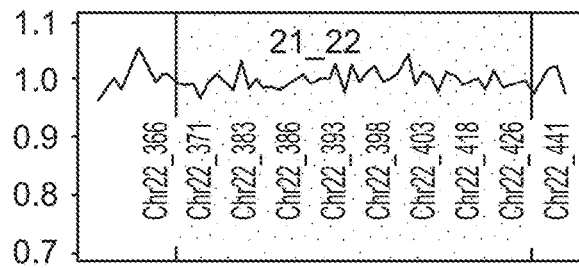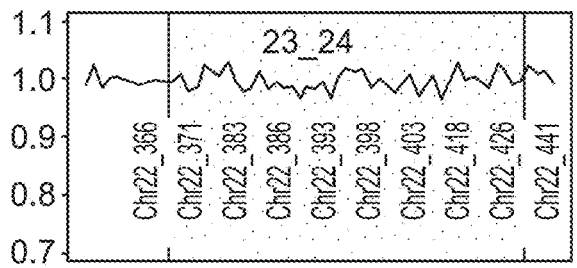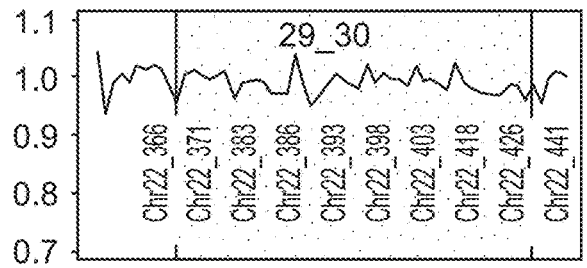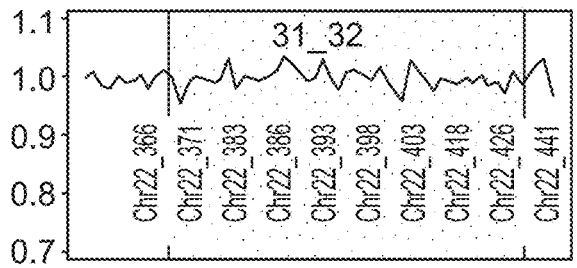
FIG. 13 (Cont.)

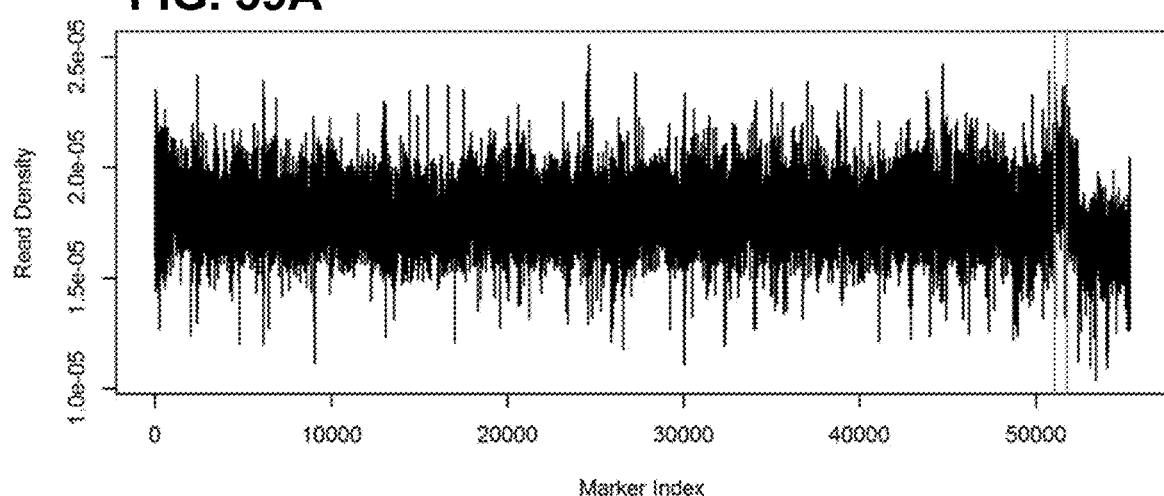
FIG. 39A Raw Read Density
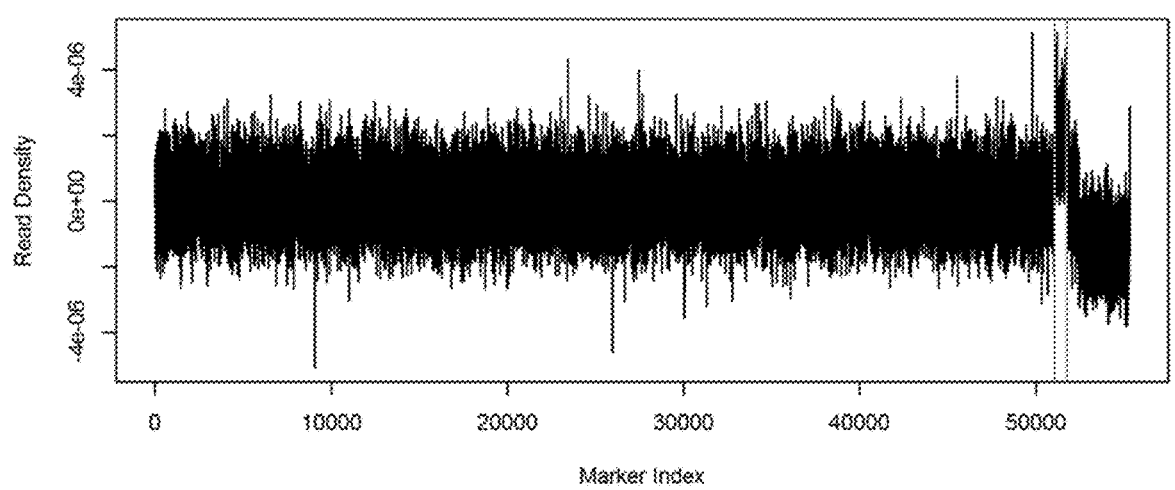
FIG. 39B Median-adjusted Read Density
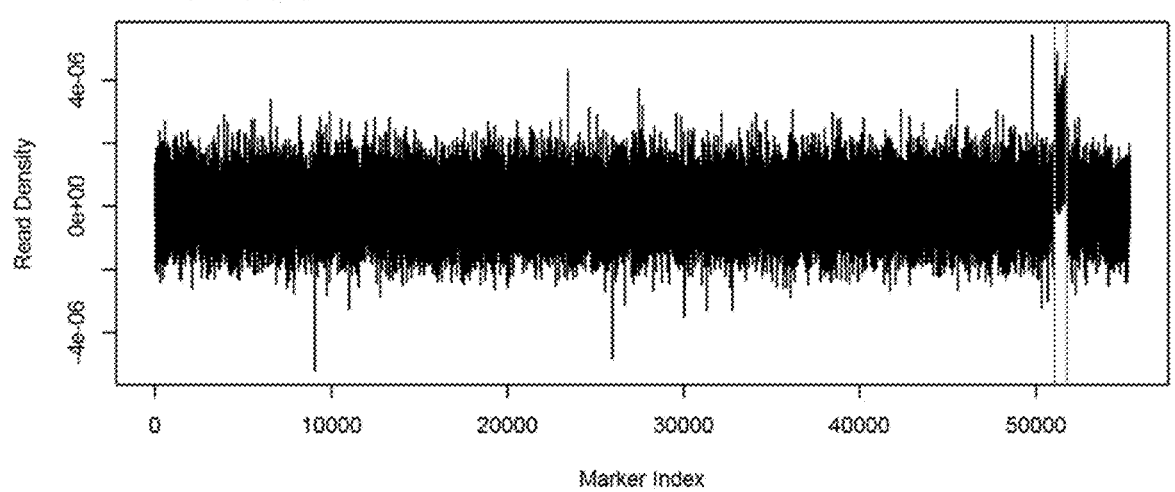
FIG. 39C Median- & PC-adjusted Read Density

METHODS AND PROCESSES FOR NON-INVASIVE ASSESSMENT OF GENETIC VARIATIONS

RELATED PATENT APPLICATIONS

This patent application is a continuation of U.S. patent application Ser. No. 14/892,782, filed on Nov. 20, 2015, entitled METHODS AND PROCESSES FOR NON-INVASIVE ASSESSMENT OF GENETIC VARIATIONS, naming Chen Zhao et al. as inventors, which is a 35 U.S.C. 371 national phase application of International Patent Cooperation Treaty (PCT) Application No. PCT/US2014/039389, filed on May 23, 2014, entitled METHODS AND PROCESSES FOR NON-INVASIVE ASSESSMENT OF GENETIC VARIATIONS, naming Chen Zhao et al. as inventors, which claims the benefit of U.S. provisional patent application No. 61/827,385 filed on May 24, 2013, entitled METHODS AND PROCESSES FOR NON-INVASIVE ASSESSMENT OF GENETIC VARIATIONS, naming Zeljko Dzakula et al. as inventors. This patent application is related to U.S. patent application Ser. No. 13/669,136 filed Nov. 5, 2012, entitled METHODS AND PROCESSES FOR NON-INVASIVE ASSESSMENT OF GENETIC VARIATIONS, naming Cosmin Deciu, Zeljko Dzakula, Mathias Ehrich and Sung Kim as inventors, which is a continuation of International PCT Application No. PCT/US2012/059123 filed Oct. 5, 2012, entitled METHODS AND PROCESSES FOR NON-INVASIVE ASSESSMENT OF GENETIC VARIATIONS, naming Cosmin Deciu, Zeljko Dzakula, Mathias Ehrich and Sung Kim as inventors, which (i) claims the benefit of U.S. Provisional Patent Application No. 61/709,899 filed on Oct. 4, 2012, entitled METHODS AND PROCESSES FOR NON-INVASIVE ASSESSMENT OF GENETIC VARIATIONS, naming Cosmin Deciu, Zeljko Dzakula, Mathias Ehrich and Sung Kim as inventors, (ii) claims the benefit of U.S. Provisional Patent Application No. 61/663,477 filed on Jun. 22, 2012, entitled METHODS AND PROCESSES FOR NON-INVASIVE ASSESSMENT OF GENETIC VARIATIONS, naming Zeljko Dzakula and Mathias Ehrich as inventors, and (iii) claims the benefit of U.S. Provisional Patent Application No. 61/544,251 filed on Oct. 6, 2011, entitled METHODS AND PROCESSES FOR NON-INVASIVE ASSESSMENT OF GENETIC VARIATIONS, naming Zeljko Dzakula and Mathias Ehrich as inventors. The entire content of the foregoing applications is incorporated herein by reference, including all text, tables and drawings.

FIELD

Technology provided herein relates in part to methods, processes and apparatuses for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure. In certain embodiments, identification of one or more genetic variations or variances involves the analysis of cell-free DNA. Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

SUMMARY

Provided herein, in certain aspects, is a method of determining the presence or absence of a chromosome aneuploidy, microduplication or microdeletion in a fetus with reduced false negative and reduced false positive determinations, comprising (a) obtaining counts of nucleic acid sequence reads mapped to portions of a reference genome, which sequence reads are reads of circulating cell-free nucleic acid from a pregnant female, (b) normalizing the counts mapped to each portion, thereby providing calculated genomic section levels, (c) generating a profile for a segment of a genome according to the calculated genomic section levels, (d) segmenting the profile thereby providing two or more decomposition renderings and (e) determining the presence or absence of a chromosome aneuploidy, microduplication or microdeletion in a fetus with reduced false negative and reduced false positive determinations according to the two or more decomposition renderings.

Also provided herein, in certain aspects, is a method for determining the presence or absence of a wavelet event with reduced false negative and reduced false positive determinations, comprising (a) obtaining counts of nucleic acid sequence reads mapped to portions of a reference genome, which sequence reads are reads of circulating cell-free nucleic acid from a pregnant female, (b) normalizing the counts mapped to each of the portions, thereby providing calculated genomic section levels, (c) segmenting a set of portions into multiple subsets of portions, (d) determining a level for each of the subsets according to the calculated genomic section levels, (e) determining a level of significance for each of the levels and (f) determining the presence or absence of a wavelet event with reduced false negative and reduced false positive determinations according to the level of significance determined for each the levels.

Also provided herein, in certain aspects, is a method of determining the presence or absence of a chromosome aneuploidy, microduplication or microdeletion in a fetus with reduced false negative and reduced false positive determinations, comprising (a) obtaining counts of nucleic acid sequence reads mapped to portions of a reference genome, which sequence reads are reads of circulating cell-free nucleic acid from a pregnant female, (b) normalizing the counts mapped to each portion, thereby providing calculated genomic section levels, (c) selecting a segment of the genome thereby providing a set of portions, (d) partitioning the set of portions recursively thereby providing two or more subsets of portions, (e) determining a level for each of the two or more subsets of portions, (f) determining the presence or absence of a chromosome aneuploidy, microduplication or microdeletion in a fetus for a sample with reduced false negative and reduced false positive determinations, according to the levels determined in (e).

Also provided herein is a system comprising one or more processors and memory, which memory comprises instructions executable by the one or more processors and which memory comprises counts of nucleic acid sequence reads mapped to portions of a reference genome, which sequence reads are reads of circulating cell-free nucleic acid from a pregnant female, and which instructions executable by the one or more processors are configured to (a) obtain counts of nucleic acid sequence reads mapped to portions of a reference genome, which sequence reads are reads of circulating cell-free nucleic acid from a pregnant female, (b) normalize the counts mapped to each portion, thereby providing calculated genomic section levels, (c) generate a profile for a segment of a genome according to the calculated genomic section levels, (d) segment the profile thereby providing two or more decomposition renderings and (e) determine the presence or absence of a chromosome aneuploidy, microduplication or microdeletion in a fetus with reduced false negative and reduced false positive determinations according to the two or more decomposition renderings.

Certain aspects of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 39A-C shows an example of a read density profile of a sample for a genome comprising a trisomy of Chromosome 21 (e.g., bracketed with two vertical lines). Relative positions of each genomic portion are shown on the x-axis. Read densities are provided on the y-axis. FIG. 39A shows a raw (e.g., not adjusted) read density profile. FIG. 39B shows the profile of 39A comprising a first adjustment comprising a subtraction of the median profile. FIG. 39C shows the profile of 39B comprising a second adjustment. The second adjustment comprises subtraction of 8x principal component profiles, weighted based on their representation found in this sample. (e.g., a model is built). For example a SampleProfile=A*PC1+B*PC2+C*PC3 . . . and a corrected profile, for example as shown in 39C=SampleProfile−A*PC1+B*PC2+C*PC3 . . . .

FIG. 40 shows a comparison of ChAI scores (y-axis) from test samples to a uniform distribution (i.e., expected distribution of p-values, x-axis). Each point represents log-p value scores of a single test sample. The samples are sorted and assigned an 'expected' value (x-axis) based on the uniform distribution. The lower dashed line represents the diagonal and the upper line represents a Bonferroni threshold. Samples that follow a uniform distribution would be expected to land on the lower diagonal (lower dashed line). The data values lie well off of the diagonals due to correlations in the portions (e.g., bias) indicating more high-scoring (low p-value) samples than expected. Methods described herein (e.g., ChAI, e.g., see Example 7) can correct for this observed bias.

DETAILED DESCRIPTION

Figure 1:
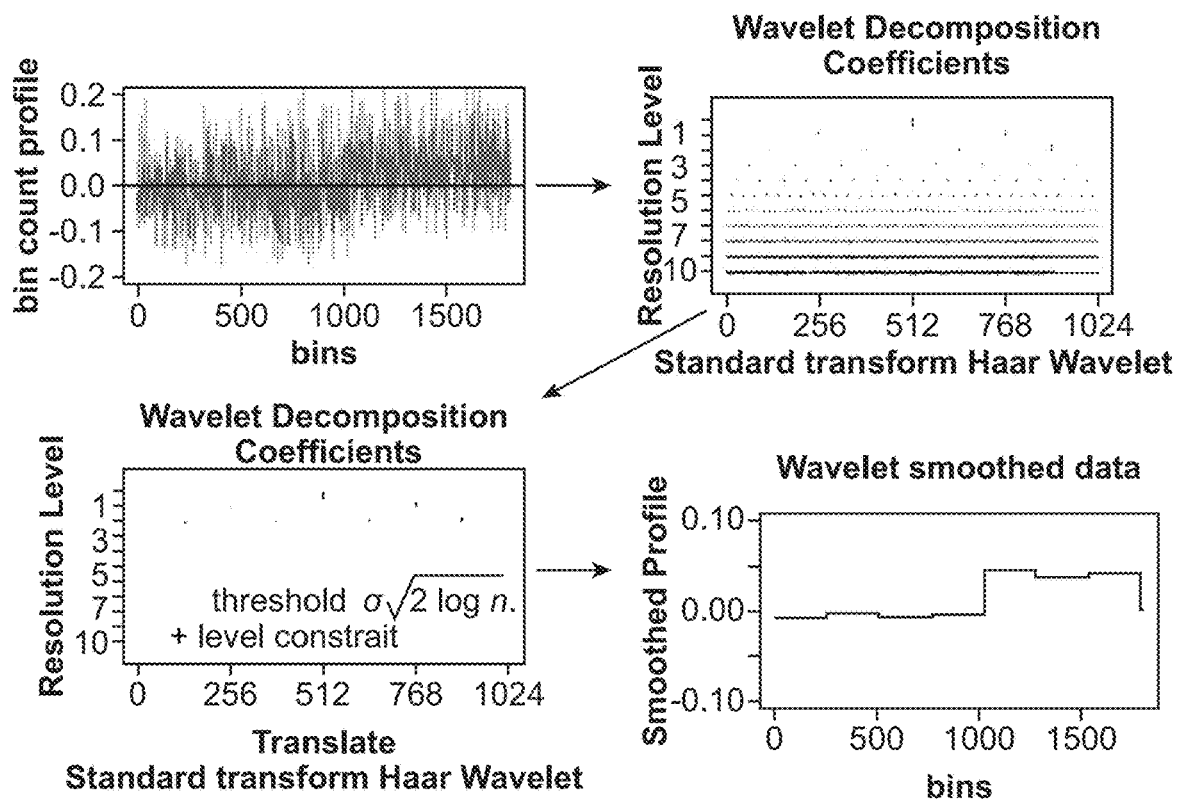
FIG. 1 shows a schematic of a wavelet method. Normalized portion count data (upper right panel) is wavelet transformed producing a wavelet smoothed profile (bottom right). A non-uniform event is clearly visible after wavelet denoising.

Provided herein are methods for determining the presence or absence of a fetal genetic variation (e.g., a chromosome aneuploidy, microduplication or microdeletion) in a fetus where a determination is made, in part and/or in full, according to nucleic acid sequences. In some embodiments nucleic acid sequences are obtained from a sample obtained from a pregnant female (e.g., from the blood of a pregnant female). Also provided herein are improved data manipulation methods as well as systems, apparatuses and modules that, in some embodiments, carry out the methods described herein. In some embodiments, identifying a genetic variation by a method described herein can lead to a diagnosis of, or determine a predisposition to, a particular medical condition. Identifying a genetic variance can result in facilitating a medical decision and/or employing a helpful medical procedure.

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods and apparatuses described herein often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, infant, child, adult).

Nucleic acid may be isolated from any type of suitable biological specimen or sample (e.g., a test sample). A sample or test sample can be any specimen that is isolated or obtained from a subject or part thereof (e.g., a human subject, a pregnant female, a fetus). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo), celocentesis sample, cells (blood cells, placental cells, embryo or fetal cells, fetal nucleated cells or fetal cellular remnants) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a biological sample is a cervical swab from a subject. In some embodiments, a biological sample may be blood and sometimes plasma or serum. The term "blood" as used herein refers to a blood sample or preparation from a pregnant woman or a woman being tested for possible pregnancy. The term encompasses whole blood, blood product or any fraction of blood, such as serum, plasma, buffy coat, or the like as conventionally defined. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain embodiments buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments fetal cells or cancer cells may be included in the sample.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In certain embodiments a fluid or tissue sample is collected from a pregnant female during or just after (e.g., 0 to 72 hours after) giving birth (e.g., vaginal or non-vaginal birth (e.g., surgical delivery)).

Acquisition of Blood Samples and Extraction of DNA

Methods herein often include separating, enriching and analyzing fetal DNA found in maternal blood as a non-invasive means to detect the presence or absence of a maternal and/or fetal genetic variation and/or to monitor the health of a fetus and/or a pregnant female during and sometimes after pregnancy. Thus, the first steps of practicing certain methods herein often include obtaining a blood sample from a pregnant woman and extracting DNA from a sample.

Acquisition of Blood Samples

A blood sample can be obtained from a pregnant woman at a gestational age suitable for testing using a method of the present technology. A suitable gestational age may vary depending on the disorder tested, as discussed below. Collection of blood from a woman often is performed in accordance with the standard protocol hospitals or clinics generally follow. An appropriate amount of peripheral blood, e.g., typically between 5-50 ml, often is collected and may be stored according to standard procedure prior to further preparation. Blood samples may be collected, stored or transported in a manner that minimizes degradation or the quality of nucleic acid present in the sample.

Preparation of Blood Samples

An analysis of fetal DNA found in maternal blood may be performed using, e.g., whole blood, serum, or plasma. Methods for preparing serum or plasma from maternal blood are known. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

In some embodiments, the sample may first be enriched or relatively enriched for fetal nucleic acid by one or more methods. For example, the discrimination of fetal and maternal DNA can be performed using the compositions and processes of the present technology alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons). Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

Nucleic Acid Isolation and Processing

Nucleic acid may be derived from one or more sources (e.g., cells, serum, plasma, buffy coat, lymphatic fluid, skin, soil, and the like) by methods known in the art. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), the like or combinations thereof.

Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a source having substantially no cells and also is referred to as "cell-free" nucleic acid and/or "cell-free circulating" nucleic acid. Extracellular nucleic acid can be present in and obtained from blood (e.g., from the blood of a pregnant female). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less, about 250 base pairs or less, about 200 base pairs or less, about 150 base pairs or less, about 100 base pairs or less, about 50 base pairs or less or about 25 base pairs or less.

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, nucleosomes comprising small fragments of fetal nucleic acid can be purified from a mixture of larger nucleosome complexes comprising larger fragments of maternal nucleic acid.

In some embodiments nucleic acids are fragmented or cleaved prior to, during or after a method described herein. Fragmented or cleaved nucleic acid may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by a suitable method known in the art, and the average, mean or nominal length of nucleic acid fragments can be controlled by selecting an appropriate fragment-generating procedure.

Nucleic acid fragments may contain overlapping nucleotide sequences, and such overlapping sequences can facilitate construction of a nucleotide sequence of the non-fragmented counterpart nucleic acid, or a segment thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

In some embodiments nucleic acid is fragmented or cleaved by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), processes described in U.S. Patent Application Publication No. 20050112590, the like or combinations thereof.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the segment of an amplified product thereof containing the corresponding nucleotide sequence of a nucleic acid template gene molecule. The term "amplified" as used herein refers to subjecting a target nucleic acid in a sample to a process that linearly or exponentially generates amplicon nucleic acids having the same or substantially the same nucleotide sequence as the target nucleic acid, or segment thereof. In certain embodiments the term "amplified" refers to a method that comprises a polymerase chain reaction (PCR). For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from segments or parts of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel). The term "specific cleavage agent" as used herein refers to an agent, sometimes a chemical or an enzyme that can cleave a nucleic acid at one or more specific sites.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a suitable sequence analysis.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of E. Coli RecA protein and/or by alteration of salt concentration, for example, using methods known in the art.

Determining Fetal Nucleic Acid Content

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction". In some embodiments "fetal fraction" refers to the fraction of fetal nucleic acid in circulating cell-free nucleic acid in a sample (e.g., a blood sample, a serum sample, a plasma sample) obtained from a pregnant female. In certain embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. In certain embodiments, the amount of fetal nucleic acid from a maternal sample can be determined relative to the total amount of nucleic acid present, thereby providing the percentage of fetal nucleic acid in the sample. In certain embodiments, the copy number of fetal nucleic acid can be determined in a maternal sample. In certain embodiments, the amount of fetal nucleic acid can be determined in a sequence-specific (or portion-specific) manner and sometimes with sufficient sensitivity to allow for accurate chromosomal dosage analysis (for example, to detect the presence or absence of a fetal aneuploidy, microduplication or microdeletion).

A fetal quantifier assay (FQA) can be performed in conjunction with any of the methods described herein. Such an assay can be performed by any method known in the art and/or described in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching the fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In certain embodiments, the restriction efficiency can be determined and the efficiency rate is used to further determine the amount of fetal DNA.

In certain embodiments, a fetal quantifier assay (FQA) can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. In certain embodiments, the absolute copy number of fetal nucleic acid in a maternal sample can be determined, for example, using mass spectrometry and/or a system that uses a competitive PCR approach for absolute copy number measurements. See for example, Ding and Cantor (2003) Proc. Natl. Acad. Sci. USA 100:3059-3064, and U.S. Patent Application Publication No. 2004/0081993, both of which are hereby incorporated by reference.

In certain embodiments, fetal fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. In certain embodiments, fetal alleles are identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target nucleic acid sequence on a reference genome for each of the two alleles of a polymorphic site.

Fetal fraction can be determined, in some embodiments, using methods that incorporate fragment length information (e.g., fragment length ratio (FLR) analysis, fetal ratio statistic (FRS) analysis as described in International Application Publication No. WO2013/177086, which is incorporated by reference herein). Cell-free fetal nucleic acid fragments generally are shorter than maternally-derived nucleic acid fragments (see e.g., Chan et al. (2004) Clin. Chem. 50:88-92; Lo et al. (2010) Sci. Transl. Med. 2:61ra91). Thus, fetal fraction can be determined, in some embodiments, by counting fragments under a particular length threshold and comparing the counts, for example, to counts from fragments over a particular length threshold and/or to the amount of total nucleic acid in the sample. Methods for counting nucleic acid fragments of a particular length are described in further detail in International Application Publication No. WO2013/177086.

Fetal fraction can be determined, in some embodiments, according to portion-specific fetal fraction estimates. Without being limited to theory, the amount of reads from fetal CCF fragments (e.g., fragments of a particular length, or range of lengths) often map with ranging frequencies to portions (e.g., within the same sample, e.g., within the same sequencing run). Also, without being limited to theory, certain portions, when compared among multiple samples, tend to have a similar representation of reads from fetal CCF fragments (e.g., fragments of a particular length, or range of lengths), and that the representation correlates with portion-specific fetal fractions (e.g., the relative amount, percentage or ratio of CCF fragments originating from a fetus).

In some embodiments portion-specific fetal fraction estimates are determined based in part on portion-specific parameters and their relation to fetal fraction. Portion-specific parameters can be any suitable parameter that is reflective of (e.g., correlates with) the amount or proportion of reads from CCF fragment lengths of a particular size (e.g., size range) in a portion. A portion-specific parameter can be an average, mean or median of portion-specific parameters determined for multiple samples. Any suitable portion-specific parameter can be used. Non-limiting examples of portion-specific parameters include FLR (e.g., FRS), an amount of reads having a length less than a selected fragment length, genomic coverage (i.e., coverage), mappability, counts (e.g., counts of sequence reads mapped to the portion, e.g., normalized counts, PERUN normalized counts, ChAI normalized counts), DNaseI-sensitivity, methylation state, acetylation, histone distribution, guanine-cytosine (GC) content, chromatin structure, the like or combinations thereof. A portion-specific parameter can be any suitable parameter that correlates with FLR and/or FRS in a portion-specific manner. In some embodiments, some or all portion-specific parameters are a direct or indirect representation of an FLR for a portion. In some embodiments a portion-specific parameter is not guanine-cytosine (GC) content.

In some embodiments a portion-specific parameter is any suitable value representing, correlated with or proportional to an amount of reads from CCF fragments where the reads mapped to a portion have a length less than a selected fragment length. In certain embodiments, a portion-specific parameter is a representation of the amount of reads derived from relatively short CCF fragments (e.g., about 200 base pairs or less) that map to a portion. CCF fragments having a length less than a selected fragment length often are relatively short CCF fragments, and sometimes a selected fragment length is about 200 base pairs or less (e.g., CCF fragments that are about 190, 180, 170, 160, 150, 140, 130, 120, 110, 100, 90, or 80 bases in length). The length of a CCF fragment or a read derived from a CCF fragment can be determined (e.g., deduced or inferred) by any suitable method (e.g., a sequencing method, a hybridization approach). In some embodiments the length of a CCF fragment is determined (e.g., deduced or inferred) by a read obtained from a paired-end sequencing method. In certain embodiments the length of a CCF fragment template is determined directly from the length of a read derived from the CCF fragment (e.g., single-end read).

Portion-specific parameters can be weighted or adjusted by one or more weighting factors. In some embodiments weighted or adjusted portion-specific parameters can provide portion-specific fetal fraction estimates for a sample (e.g., a test sample). In some embodiments weighting or adjusting generally converts the counts of a portion (e.g., reads mapped to a portion) or another portion-specific parameter into a portion-specific fetal fraction estimate, and such a conversion sometimes is considered a transformation.

In some embodiments a weighting factor is a coefficient or constant that, in part, describes and/or defines a relation between a fetal fraction (e.g., a fetal fraction determined from multiple samples) and a portion-specific parameter for multiple samples (e.g., a training set). In some embodiments a weighting factor is determined according to a relation for multiple fetal fraction determinations and multiple portion-specific parameters. A relation may be defined by one or more weighting factors and one or more weighting factors may be determined from a relation. In some embodiments a weighting factor (e.g., one or more weighting factors) is determined from a fitted relation for a portion according to (i) a fraction of fetal nucleic acid determined for each of multiple samples, and (ii) a portion-specific parameter for multiple samples.

A weighting factor can be any suitable coefficient, estimated coefficient or constant derived from a suitable relation (e.g., a suitable mathematical relation, an algebraic relation, a fitted relation, a regression, a regression analysis, a regression model). A weighting factor can be determined according to, derived from, or estimated from a suitable relation. In some embodiments weighting factors are estimated coefficients from a fitted relation. Fitting a relation for multiple samples is sometimes referred to as training a model. Any suitable model and/or method of fitting a relationship (e.g., training a model to a training set) can be used. Non-limiting examples of a suitable model that can be used include a regression model, linear regression model, simple regression model, ordinary least squares regression model, multiple regression model, general multiple regression model, polynomial regression model, general linear model, generalized linear model, discrete choice regression model, logistic regression model, multinomial logit model, mixed logit model, probit model, multinomial probit model, ordered logit model, ordered probit model, Poisson model, multivariate response regression model, multilevel model, fixed effects model, random effects model, mixed model, nonlinear regression model, nonparametric model, semiparametric model, robust model, quantile model, isotonic model, principal components model, least angle model, local model, segmented model, and errors-in-variables model. In some embodiments a fitted relation is not a regression model. In some embodiments a fitted relations is chosen from a decision tree model, support-vector machine model and neural network model. The result of training a model (e.g., a regression model, a relation) is often a relation that can be described mathematically where the relation comprises one or more coefficients (e.g., weighting factors). More complex multivariate models may determine one, two, three or more weighting factors. In some embodiments a model is trained according to fetal fraction and two or more portion-specific parameters (e.g., coefficients) obtained from multiple samples (e.g., fitted relationships fitted to multiple samples, e.g., by a matrix).

A weighting factor can be derived from a suitable relation (e.g., a suitable mathematical relation, an algebraic relation, a fitted relation, a regression, a regression analysis, a regression model) by a suitable method. In some embodiments fitted relations are fitted by an estimation, non-limiting examples of which include least squares, ordinary least squares, linear, partial, total, generalized, weighted, non-linear, iteratively reweighted, ridge regression, least absolute deviations, Bayesian, Bayesian multivariate, reduced-rank, LASSO, Weighted Rank Selection Criteria (WRSC), Rank Selection Criteria (RSC), an elastic net estimator (e.g., an elastic net regression) and combinations thereof.

A weighting factor can be determined for or associated with any suitable portion of a genome. A weighting factor can be determined for or associated with any suitable portion of any suitable chromosome. In some embodiments a weighting factor is determined for or associated with some or all portions in a genome. In some embodiments a weighting factor is determined for or associated with portions of some or all chromosomes in a genome. A weighting factor is sometimes determined for or associated with portions of selected chromosomes. A weighting factor can be determined for or associated with portions of one or more autosomes. A weighting factor can be determined for or associated with portions in a plurality of portions that include portions in autosomes or a subset thereof. In some embodiments a weighting factor is determined for or associated with portions of a sex chromosome (e.g. ChrX and/or ChrY). A weighting factor can be determined for or associated with portions of one or more autosomes and one or more sex chromosomes. In certain embodiments a weighting factor is determined for or associated with portions in a plurality of portions in all autosomes and chromosomes X and Y. A weighting factor can be determined for or associated with portions in a plurality of portions that does not include portions in an X and/or Y chromosome. In certain embodiments a weighting factor is determined for or associated with portions of a chromosome where the chromosome comprises an aneuploidy (e.g., a whole chromosome aneuploidy). In certain embodiments a weighting factor is determined for or associated only with portions of a chromosome where the chromosome is not aneuploid (e.g., a euploid chromosome). A weighting factor can be determined for or associated with portions in a plurality of portions that does not include portions in chromosomes 13, 18 and/or 21.

In some embodiments a weighting factor is determined for a portion according to one or more samples (e.g., a training set of samples). Weighting factors are often specific to a portion. In some embodiments one or more weighting factors are independently assigned to a portion. In some embodiments a weighting factor is determined according to a relation for a fetal fraction determination (e.g., a sample specific fetal fraction determination) for multiple samples and a portion-specific parameter determined according to multiple samples. Weighting factors are often determined from multiple samples, for example, from about 20 to about 100,000 or more, from about 100 to about 100,000 or more, from about 500 to about 100,000 or more, from about 1000 to about 100,000 or more, or from about 10,000 to about 100,000 or more samples. Weighting factors can be determined from samples that are euploid (e.g., samples from subjects comprising a euploid fetus, e.g., samples where no aneuploid chromosome is present). In some embodiments weighting factors are obtained from samples comprising an aneuploid chromosome (e.g., samples from subjects comprising a euploid fetus). In some embodiments weighting factors are determined from multiple samples from subjects having a euploid fetus and from subjects having a trisomy fetus. Weighting factors can be derived from multiple samples where the samples are from subjects having a male fetus and/or a female fetus.

A fetal fraction is often determined for one or more samples of a training set from which a weighting factor is derived. A fetal fraction from which a weighting factor is determined is sometimes a sample specific fetal fraction determination. A fetal fraction from which a weighting factor is determined can be determined by any suitable method described herein or known in the art. In some embodiments a determination of fetal nucleic acid content (e.g., fetal fraction) is performed using a suitable fetal quantifier assay (FQA) described herein or known in the art, non-limiting examples of which include fetal fraction determinations according to markers specific to a male fetus, based on allelic ratios of polymorphic sequences, according to one or more markers specific to fetal nucleic acid and not maternal nucleic acid, by use of methylation-based DNA discrimination (e.g., A. Nygren, et al., (2010) Clinical Chemistry 56(10):1627-1635), by a mass spectrometry method and/or a system that uses a competitive PCR approach, by a method described in U.S. Patent Application Publication No. 2010/0105049, which is hereby incorporated by reference, the like or combinations thereof. Often a fetal fraction is determined, in part, according to a level (e.g., one or more genomic section levels, a level of a profile) of a Y chromosome. In some embodiments a fetal fraction is determined according to a suitable assay of a Y chromosome (e.g., by comparing the amount of fetal-specific locus (such as the SRY locus on chromosome Y in male pregnancies) to that of a locus on any autosome that is common to both the mother and the fetus by using quantitative real-time PCR (e.g., Lo Y M, et al. (1998) Am J Hum Genet 62:768-775.)).

Portion-specific parameters (e.g., for a test sample) can be weighted or adjusted by one or more weighting factors (e.g., weighting factors derived from a training set). For example, a weighting factor can be derived for a portion according to a relation of a portion-specific parameter and a fetal fraction determination for a training set of multiple samples. A portion-specific parameter of a test sample can then be adjusted and/or weighted according to the weighting factor derived from the training set. In some embodiments a portion-specific parameter from which a weighting factor is derived, is the same as the portion-specific parameter (e.g., of a test sample) that is adjusted or weighted (e.g., both parameters are an FLR). In certain embodiment, a portion-specific parameter, from which a weighting factor is derived, is different than the portion-specific parameter (e.g., of a test sample) that is adjusted or weighted. For example, a weighting factor may be determined from a relation between coverage (i.e., a portion-specific parameter) and fetal fraction for a training set of samples, and an FLR (i.e., another portion-specific parameter) for a portion of a test sample can be adjusted according to the weighting factor derived from coverage. Without being limited by theory, a portion-specific parameter (e.g., for a test sample) can sometimes be adjusted and/or weighted by a weighting factor derived from a different portion-specific parameter (e.g., of a training set) due to a relation and/or correlation between each portion-specific parameter and a common portion-specific FLR.

A portion-specific fetal fraction estimate can be determined for a sample (e.g., a test sample) by weighting a portion-specific parameter by a weighting factor determined for that portion. Weighting can comprise adjusting, converting and/or transforming a portion-specific parameter according to a weighting factor by applying any suitable mathematical manipulation, non-limiting examples of which include multiplication, division, addition, subtraction, integration, symbolic computation, algebraic computation, algorithm, trigonometric or geometric function, transformation (e.g., a Fourier transform), the like or combinations thereof. Weighting can comprise adjusting, converting and/or transforming a portion-specific parameter according to a weighting factor a suitable mathematical model.

In some embodiments a fetal fraction is determined for a sample according to one or more portion-specific fetal fraction estimates. In some embodiments a fetal fraction is determined (e.g., estimated) for a sample (e.g., a test sample) according to weighting or adjusting a portion-specific parameter for one or more portions. In certain embodiments a fraction of fetal nucleic acid for a test sample is estimated based on adjusted counts or an adjusted subset of counts. In certain embodiments a fraction of fetal nucleic acid for a test sample is estimated based on an adjusted FLR, an adjusted FRS, adjusted coverage, and/or adjusted mappability for a portion. In some embodiments about 1 to about 500,000, about 100 to about 300,000, about 500 to about 200,000, about 1000 to about 200,000, about 1500 to about 200,000, or about 1500 to about 50,000 portion-specific parameters are weighted or adjusted.

A fetal fraction (e.g., for a test sample) can be determined according to multiple portion-specific fetal fraction estimates (e.g., for the same test sample) by any suitable method. In some embodiments a method for increasing the accuracy of the estimation of a fraction of fetal nucleic acid in a test sample from a pregnant female comprises determining one or more portion-specific fetal fraction estimates where the estimate of fetal fraction for the sample is determined according to the one or more portion-specific fetal fraction estimates. In some embodiments estimating or determining a fraction of fetal nucleic acid for a sample (e.g., a test sample) comprises summing one or more portion-specific fetal fraction estimates. Summing can comprise determining an average, mean, median, AUC, or integral value according to multiple portion-specific fetal fraction estimates.

In some embodiments a method for increasing the accuracy of the estimation of a fraction of fetal nucleic acid in a test sample from a pregnant female, comprises obtaining counts of sequence reads mapped to portions of a reference genome, which sequence reads are reads of circulating cell-free nucleic acid from a test sample from a pregnant female, where at least a subset of the counts obtained are derived from a region of the genome that contributes a greater number of counts derived from fetal nucleic acid relative to total counts from the region than counts of fetal nucleic acid relative to total counts of another region of the genome. In some embodiments an estimate of the fraction of fetal nucleic acid is determined according to a subset of the portions, where the subset of the portions is selected according to portions to which are mapped a greater number of counts derived from fetal nucleic acid than counts of fetal nucleic acid of another portion. In some embodiments the subset of the portions is selected according to portions to which are mapped a greater number of counts derived from fetal nucleic acid, relative to non-fetal nucleic acid, than counts of fetal nucleic acid, relative to non-fetal nucleic acid, of another portion. The counts mapped to all or a subset of the portions can be weighted, thereby providing weighted counts. The weighted counts can be utilized for estimating the fraction of fetal nucleic acid, and the counts can be weighted according to portions to which are mapped a greater number of counts derived from fetal nucleic acid than counts of fetal nucleic acid of another portion. In some embodiments the counts are weighted according to portions to which are mapped a greater number of counts derived from fetal nucleic acid, relative to non-fetal nucleic acid, than counts of fetal nucleic acid, relative to non-fetal nucleic acid, of another portion.

A fetal fraction can be determined for a sample (e.g., a test sample) according to multiple portion-specific fetal fraction estimates for the sample where the portions-specific estimates are from portions of any suitable region or segment of a genome. Portion-specific fetal fraction estimates can be determined for one or more portions of a suitable chromosome (e.g., one or more selected chromosomes, one or more autosomes, a sex chromosome (e.g. ChrX and/or ChrY), an aneuploid chromosome, a euploid chromosome, the like or combinations thereof).

In some embodiments, determining fetal fraction comprises (a) obtaining counts of sequence reads mapped to portions of a reference genome, which sequence reads are reads of circulating cell-free nucleic acid from a test sample from a pregnant female; (b) weighting, using a microprocessor, (i) the counts of the sequence reads mapped to each portion, or (ii) other portion-specific parameter, to a portion-specific fraction of fetal nucleic acid according to a weighting factor independently associated with each portion, thereby providing portion-specific fetal fraction estimates according to the weighting factors, where each of the weighting factors have been determined from a fitted relation for each portion between (i) a fraction of fetal nucleic acid for each of multiple samples, and (ii) counts of sequence reads mapped to each portion, or other portion-specific parameter, for the multiple samples; and (c) estimating a fraction of fetal nucleic acid for the test sample based on the portion-specific fetal fraction estimates.

The amount of fetal nucleic acid in extracellular nucleic acid can be quantified and used in conjunction with a method provided herein. Thus, in certain embodiments, methods of the technology described herein comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call).

The determination step can be performed before, during, at any one point in a method described herein, or after certain (e.g., aneuploidy detection, microduplication or microdeletion detection, fetal gender determination) methods described herein. For example, to achieve a fetal gender or aneuploidy, microduplication or microdeletion determination method with a given sensitivity or specificity, a fetal nucleic acid quantification method may be implemented prior to, during or after fetal gender or aneuploidy, microduplication or microdeletion determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for fetal gender or aneuploidy, microduplication or microdeletion determination, or the presence or absence of aneuploidy or genetic variation, for example. In certain embodiments, determinations of, for example, fetal gender or the presence or absence of aneuploidy, microduplication or microdeletion are selected (e.g., selected and communicated to a patient) only for samples having a certain threshold amount of fetal nucleic acid (e.g., about 15% or more fetal nucleic acid; about 4% or more fetal nucleic acid).

In some embodiments, the determination of fetal fraction or determining the amount of fetal nucleic acid is not required or necessary for identifying the presence or absence of a chromosome aneuploidy, microduplication or microdeletion. In some embodiments, identifying the presence or absence of a chromosome aneuploidy, microduplication or microdeletion does not require the sequence differentiation of fetal versus maternal DNA. In certain embodiments this is because the summed contribution of both maternal and fetal sequences in a particular chromosome, chromosome portion or segment thereof is analyzed. In some embodiments, identifying the presence or absence of a chromosome aneuploidy, microduplication or microdeletion does not rely on a priori sequence information that would distinguish fetal DNA from maternal DNA.

Enriching Nucleic Acids

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, fetal nucleic acid. In certain embodiments, a method for determining fetal fraction described above also can be used to enrich for fetal nucleic acid. In certain embodiments, maternal nucleic acid is selectively removed (partially, substantially, almost completely or completely) from the sample. In certain embodiments, enriching for a particular low copy number species nucleic acid (e.g., fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, all of which are incorporated by reference herein.

In some embodiments, nucleic acid is enriched for certain target fragment species and/or reference fragment species. In certain embodiments, nucleic acid is enriched for a specific nucleic acid fragment length or range of fragment lengths using one or more length-based separation methods described below. In certain embodiments, nucleic acid is enriched for fragments from a select genomic region (e.g., chromosome) using one or more sequence-based separation methods described herein and/or known in the art. Certain methods for enriching for a nucleic acid subpopulation (e.g., fetal nucleic acid) in a sample are described in detail below.

Some methods for enriching for a nucleic acid subpopulation (e.g., fetal nucleic acid) that can be used with a method described herein include methods that exploit epigenetic differences between maternal and fetal nucleic acid. For example, fetal nucleic acid can be differentiated and separated from maternal nucleic acid based on methylation differences. Methylation-based fetal nucleic acid enrichment methods are described in U.S. Patent Application Publication No. 2010/0105049, which is incorporated by reference herein. Such methods sometimes involve binding a sample nucleic acid to a methylation-specific binding agent (methyl-CpG binding protein (MBD), methylation specific antibodies, and the like) and separating bound nucleic acid from unbound nucleic acid based on differential methylation status. Such methods also can include the use of methylation-sensitive restriction enzymes (as described above; e.g., HhaI and HpaII), which allow for the enrichment of fetal nucleic acid regions in a maternal sample by selectively digesting nucleic acid from the maternal sample with an enzyme that selectively and completely or substantially digests the maternal nucleic acid to enrich the sample for at least one fetal nucleic acid region.

Another method for enriching for a nucleic acid subpopulation (e.g., fetal nucleic acid) that can be used with a method described herein is a restriction endonuclease enhanced polymorphic sequence approach, such as a method described in U.S. Patent Application Publication No. 2009/0317818, which is incorporated by reference herein. Such methods include cleavage of nucleic acid comprising a non-target allele with a restriction endonuclease that recognizes the nucleic acid comprising the non-target allele but not the target allele; and amplification of uncleaved nucleic acid but not cleaved nucleic acid, where the uncleaved, amplified nucleic acid represents enriched target nucleic acid (e.g., fetal nucleic acid) relative to non-target nucleic acid (e.g., maternal nucleic acid). In certain embodiments, nucleic acid may be selected such that it comprises an allele having a polymorphic site that is susceptible to selective digestion by a cleavage agent, for example.

Some methods for enriching for a nucleic acid subpopulation (e.g., fetal nucleic acid) that can be used with a method described herein include selective enzymatic degradation approaches. Such methods involve protecting target sequences from exonuclease digestion thereby facilitating the elimination in a sample of undesired sequences (e.g., maternal DNA). For example, in one approach, sample nucleic acid is denatured to generate single stranded nucleic acid, single stranded nucleic acid is contacted with at least one target-specific primer pair under suitable annealing conditions, annealed primers are extended by nucleotide polymerization generating double stranded target sequences, and digesting single stranded nucleic acid using a nuclease that digests single stranded (i.e. non-target) nucleic acid. In certain embodiments, the method can be repeated for at least one additional cycle. In certain embodiments, the same target-specific primer pair is used to prime each of the first and second cycles of extension, and In certain embodiments, different target-specific primer pairs are used for the first and second cycles.

Some methods for enriching for a nucleic acid subpopulation (e.g., fetal nucleic acid) that can be used with a method described herein include massively parallel signature sequencing (MPSS) approaches. MPSS typically is a solid phase method that uses adapter (i.e. tag) ligation, followed by adapter decoding, and reading of the nucleic acid sequence in small increments. Tagged PCR products are typically amplified such that each nucleic acid generates a PCR product with a unique tag. Tags are often used to attach the PCR products to microbeads. After several rounds of ligation-based sequence determination, for example, a sequence signature can be identified from each bead. Each signature sequence (MPSS tag) in a MPSS dataset is analyzed, compared with all other signatures, and all identical signatures are counted.

In certain embodiments, certain enrichment methods (e.g., certain MPS and/or MPSS-based enrichment methods) can include amplification (e.g., PCR)-based approaches. In certain embodiments, loci-specific amplification methods can be used (e.g., using loci-specific amplification primers). In certain embodiments, a multiplex SNP allele PCR approach can be used. In certain embodiments, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In certain embodiments, a multiplex SNP allele PCR approach can be used in combination with a three-primer system and indexed sequencing. For example, such an approach can involve the use of multiplex PCR (e.g., MASSARRAY system) with primers having a first capture probe incorporated into certain loci-specific forward PCR primers and adapter sequences incorporated into loci-specific reverse PCR primers, to thereby generate amplicons, followed by a secondary PCR to incorporate reverse capture sequences and molecular index barcodes for sequencing using, for example, the Illumina MPSS system. In certain embodiments, a multiplex SNP allele PCR approach can be used in combination with a four-primer system and indexed sequencing. For example, such an approach can involve the use of multiplex PCR (e.g., MASSARRAY system) with primers having adaptor sequences incorporated into both loci-specific forward and loci-specific reverse PCR primers, followed by a secondary PCR to incorporate both forward and reverse capture sequences and molecular index barcodes for sequencing using, for example, the Illumina MPSS system. In certain embodiments, a microfluidics approach can be used. In certain embodiments, an array-based microfluidics approach can be used. For example, such an approach can involve the use of a microfluidics array (e.g., Fluidigm) for amplification at low plex and incorporation of index and capture probes, followed by sequencing. In certain embodiments, an emulsion microfluidics approach can be used, such as, for example, digital droplet PCR.

In certain embodiments, universal amplification methods can be used (e.g., using universal or non-loci-specific amplification primers). In certain embodiments, universal amplification methods can be used in combination with pull-down approaches. In certain embodiments, a method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In certain embodiments, pull-down approaches can be used in combination with ligation-based methods. In certain embodiments, a method can include biotinylated ultramer pull down with sequence specific adapter ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In certain embodiments, pull-down approaches can be used in combination with extension and ligation-based methods. In certain embodiments, a method can include molecular inversion probe (MIP) extension and ligation. For example, such an approach can involve the use of molecular inversion probes in combination with sequence adapters followed by universal amplification and sequencing. In certain embodiments, complementary DNA can be synthesized and sequenced without amplification.

In certain embodiments, extension and ligation approaches can be performed without a pull-down component. In certain embodiments, a method can include loci-specific forward and reverse primer hybridization, extension and ligation. Such methods can further include universal amplification or complementary DNA synthesis without amplification, followed by sequencing. Such methods can reduce or exclude background sequences during analysis, in certain embodiments.

In certain embodiments, pull-down approaches can be used with an optional amplification component or with no amplification component. In certain embodiments, a method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In certain embodiments, a method can include a biotinylated pull-down assay with extension and ligation of adaptor sequence in combination with circular single stranded ligation. For example, such an approach can involve the use of selector probes to capture regions of interest (i.e. target sequences), extension of the probes, adaptor ligation, single stranded circular ligation, optional amplification, and sequencing. In certain embodiments, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments often are isolated away from the remaining fragments in the nucleic acid sample. In certain embodiments, the separated target fragments and the separated reference fragments also are isolated away from each other (e.g., isolated in separate assay compartments). In certain embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a segment or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome). In certain embodiments, a hybridization-based method (e.g., using oligonucleotide arrays) can be used to enrich for nucleic acid sequences from certain chromosomes (e.g., a potentially aneuploid chromosome, reference chromosome or other chromosome of interest) or segments of interest thereof.

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain embodiments, length-based separation approaches can include fragment circularization, chemical treatment (e.g., formaldehyde, polyethylene glycol (PEG)), mass spectrometry and/or size-specific nucleic acid amplification, for example.

Certain length-based separation methods that can be used with methods described herein employ a selective sequence tagging approach, for example. The term "sequence tagging" refers to incorporating a recognizable and distinct sequence into a nucleic acid or population of nucleic acids. The term "sequence tagging" as used herein has a different meaning than the term "sequence tag" described later herein. In such sequence tagging methods, a fragment size species (e.g., short fragments) nucleic acids are subjected to selective sequence tagging in a sample that includes long and short nucleic acids. Such methods typically involve performing a nucleic acid amplification reaction using a set of nested primers which include inner primers and outer primers. In certain embodiments, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence.

Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Nucleic Acid Library

In some embodiments a nucleic acid library is a plurality of polynucleotide molecules (e.g., a sample of nucleic acids) that are prepared, assemble and/or modified for a specific process, non-limiting examples of which include immobilization on a solid phase (e.g., a solid support, e.g., a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof. Polynucleotides of known sequence can be added at a suitable position, for example on the 5' end, 3' end or within a nucleic acid sequence. Polynucleotides of known sequence can be the same or different sequences. In some embodiments a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments a library of nucleic acid can comprise chromosome-specific tags, capture sequences, labels and/or adaptors. In some embodiments a library of nucleic acids comprise one or more detectable labels. In some embodiments one or more detectable labels may be incorporated into a nucleic acid library at a 5' end, at a 3' end, and/or at any nucleotide position within a nucleic acid in the library. In some embodiments a library of nucleic acids comprises hybridized oligonucleotides. In certain embodiments hybridized oligonucleotides are labeled probes. In some embodiments a library of nucleic acids comprises hybridized oligonucleotide probes prior to immobilization on a solid phase.

In some embodiments a polynucleotide of known sequence comprises a universal sequence. A universal sequence is a specific nucleotide acid sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using ccfDNA).

In certain embodiments, a ligation-based library preparation method is used (e.g., ILLUMINA TRUSEQ, Illumina, San Diego Calif.). Ligation-based library preparation methods often make use of an adaptor (e.g., a methylated adaptor) design which can incorporate an index sequence at the initial ligation step and often can be used to prepare samples for single-read sequencing, paired-end sequencing and multiplexed sequencing. For example, sometimes nucleic acids (e.g., fragmented nucleic acids or ccfDNA) are end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides. In some embodiments nucleic acid library preparation comprises ligating an adapter oligonucleotide. Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing).

An identifier can be a suitable detectable label incorporated into or attached to a nucleic acid (e.g., a polynucleotide) that allows detection and/or identification of nucleic acids that comprise the identifier. In some embodiments an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method or apparatus, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In some embodiments, a transposon-based library preparation method is used (e.g., EPICENTRE NEXTERA, Epicentre, Madison Wis.). Transposon-based methods typically use in vitro transposition to simultaneously fragment and tag DNA in a single-tube reaction (often allowing incorporation of platform-specific tags and optional barcodes), and prepare sequencer-ready libraries.

In some embodiments a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., US patent publication US20130012399), the like or combinations thereof.

Sequencing

In some embodiments, nucleic acids (e.g., nucleic acid fragments, sample nucleic acid, cell-free nucleic acid) are sequenced. In certain embodiments, a full or substantially full sequence is obtained and sometimes a partial sequence is obtained.

In some embodiments some or all nucleic acids in a sample are enriched and/or amplified (e.g., non-specifically, e.g., by a PCR based method) prior to or during sequencing. In certain embodiments specific nucleic acid portions or subsets in a sample are enriched and/or amplified prior to or during sequencing. In some embodiments, a portion or subset of a pre-selected pool of nucleic acids is sequenced randomly. In some embodiments, nucleic acids in a sample are not enriched and/or amplified prior to or during sequencing.

As used herein, "reads" (i.e., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length about 1000 bp or more.

In some embodiments the nominal, average, mean or absolute length of single-end reads sometimes is about 15 contiguous nucleotides to about 50 or more contiguous nucleotides, about 15 contiguous nucleotides to about 40 or more contiguous nucleotides, and sometimes about 15 contiguous nucleotides or about 36 or more contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28 or about 29 bases or more in length.

In certain embodiments, the nominal, average, mean or absolute length of the paired-end reads sometimes is about 10 contiguous nucleotides to about 25 contiguous nucleotides or more (e.g., about 10, 11, 12, 13, 14, 15, 16, 17, 18, 19, 20, 21, 22, 23, 24 or 25 nucleotides in length or more), about 15 contiguous nucleotides to about 20 contiguous nucleotides or more, and sometimes is about 17 contiguous nucleotides or about 18 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, microduplication or microdeletion, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, a representative fraction of a genome is sequenced and is sometimes referred to as "coverage" or "fold coverage". For example, a 1-fold coverage indicates that roughly 100% of the nucleotide sequences of the genome are represented by reads. In some embodiments "fold coverage" is a relative term referring to a prior sequencing run as a reference. For example, a second sequencing run may have 2-fold less coverage than a first sequencing run. In some embodiments a genome is sequenced with redundancy, where a given region of the genome can be covered by two or more reads or overlapping reads (e.g., a "fold coverage" greater than 1, e.g., a 2-fold coverage).

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals, and the pool is sequenced. In the latter embodiments, a nucleic acid sample from each biological sample often is identified by one or more unique identifiers.

In some embodiments a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane are dependent on the number of unique identifiers utilized during library preparation and/or probe design. single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments sequencing technologies that include the use of nucleic acid imaging technologies (e.g. transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments MPS sequencing methods utilize a targeted approach, where specific chromosomes, genes or regions of interest are sequences. In certain embodiments a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

Sequencing by synthesis, in some embodiments, comprises iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof. Other sequencing methods that may be used to conduct methods herein include digital PCR and sequencing by hybridization.

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number.

In certain embodiments, sequencing by hybridization can be used. The method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in a method described herein. Nanopore sequencing is a single-molecule sequencing technology whereby a single nucleic acid molecule (e.g. DNA) is sequenced directly as it passes through a nanopore.

A suitable MPS method, system or technology platform for conducting methods described herein can be used to obtain nucleic acid sequencing reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, US patent publication no. US20130012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligonucleotide to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

Mapping Reads

Sequence reads can be mapped and the number of reads mapping to a specified nucleic acid region (e.g., a chromosome, portion or segment thereof) are referred to as counts. Any suitable mapping method (e.g., process, algorithm, program, software, module, the like or combination thereof) can be used. Certain aspects of mapping processes are described hereafter.

Mapping nucleotide sequence reads (i.e., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped", "a mapped sequence read" or "a mapped read". In certain embodiments, a mapped sequence read is referred to as a "hit" or "count". In some embodiments, mapped sequence reads are grouped together according to various parameters and assigned to particular portions, which are discussed in further detail below.

As used herein, the terms "aligned", "alignment", or "aligning" refer to two or more nucleic acid sequences that can be identified as a match (e.g., 100% identity) or partial match. Alignments can be done manually or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In certain embodiments a nucleic acid sequence is aligned with the reverse complement of another nucleic acid sequence.

Various computational methods can be used to map each sequence read to a portion. Non-limiting examples of computer algorithms that can be used to align sequences include, without limitation, BLAST, BLITZ, FASTA, BOWTIE 1, BOWTIE 2, ELAND, MAQ, PROBEMATCH, SOAP or SEQMAP, or variations thereof or combinations thereof. In some embodiments, sequence reads can be aligned with sequences in a reference genome. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to sort the identified sequences into appropriate portions (described hereafter), for example.

In some embodiments mapped sequence reads and/or information associated with a mapped sequence read are stored on and/or accessed from a non-transitory computer-readable storage medium in a suitable computer-readable format. A "computer-readable format" is sometimes referred to generally herein as a format. In some embodiments mapped sequence reads are stored and/or accessed in a suitable binary format, a text format, the like or a combination thereof. A binary format is sometimes a BAM format. A text format is sometimes a sequence alignment/map (SAM) format. Non-limiting examples of binary and/or text formats include BAM, SAM, SRF, FASTQ, Gzip, the like, or combinations thereof. In some embodiments mapped sequence reads are stored in and/or are converted to a format that requires less storage space (e.g., less bytes) than a traditional format (e.g., a SAM format or a BAM format). In some embodiments mapped sequence reads in a first format are compressed into a second format requiring less storage space than the first format. The term "compressed" as used herein refers to a process of data compression, source coding, and/or bit-rate reduction where a computer readable data file is reduced in size. In some embodiments mapped sequence reads are compressed from a SAM format in a binary format. Some data sometimes is lost after a file is compressed. Sometimes no data is lost in a compression process. In some file compression embodiments, some data is replaced with an index and/or a reference to another data file comprising information regarding a mapped sequence read. In some embodiments a mapped sequence read is stored in a binary format comprising or consisting of a read count, a chromosome identifier (e.g., that identifies a chromosome to which a read is mapped) and a chromosome position identifier (e.g., that identifies a position on a chromosome to which a read is mapped). In some embodiments a binary format comprises a 20 byte array, a 16 byte array, an 8 byte array, a 4 byte array or a 2 byte array. In some embodiments mapped read information is stored in an array in a 10 byte format, 9 byte format, 8 byte format, 7 byte format, 6 byte format, 5 byte format, 4 byte format, 3 byte format or 2 byte format. Sometimes mapped read data is stored in a 4 byte array comprising a 5 byte format. In some embodiments a binary format comprises a 5-byte format comprising a 1-byte chromosome ordinal and a 4-byte chromosome position. In some embodiments mapped reads are stored in a compressed binary format that is about 100 times, about 90 times, about 80 times, about 70 times, about 60 times, about 55 times, about 50 times, about 45 times, about 40 times or about 30 times smaller than a sequence alignment/map (SAM) format. In some embodiments mapped reads are stored in a compress binary format that is about 2 times smaller to about 50 times smaller than (e.g., about 30, 25, 20, 19, 18, 17, 16, 15, 14, 13, 12, 11, 10, 9, 8, 7, 6, or about 5 times smaller than) a GZip format.

Figure 42A:
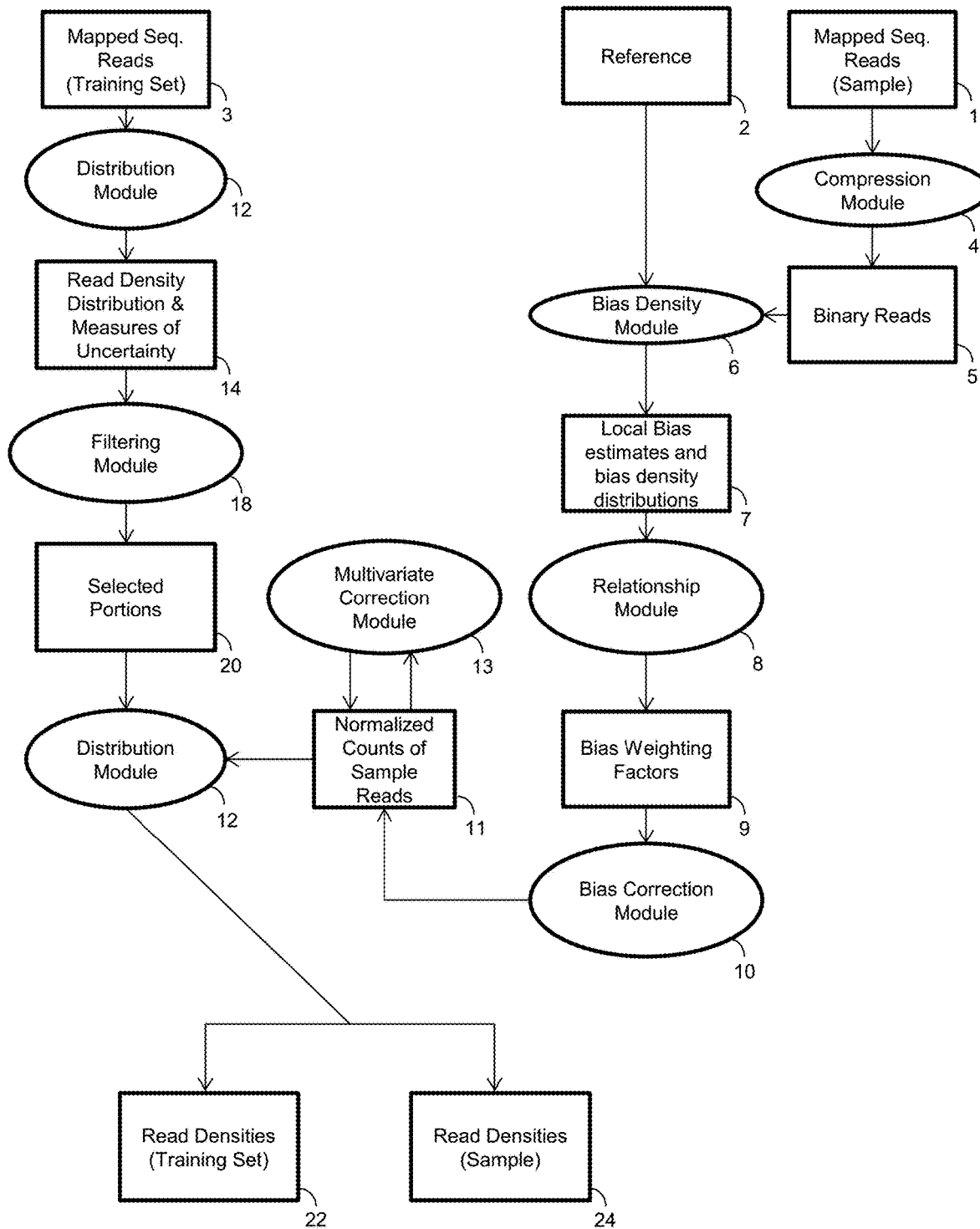
FIG. 42A-42B shows an embodiment of a system.

In some embodiments a system comprises a compression module (e.g., 4, FIG. 42A). In some embodiments mapped sequence read information stored on a non-transitory computer-readable storage medium in a computer-readable format is compressed by a compression module. A compression module sometimes converts mapped sequence reads to and from a suitable format. A compression module can accept mapped sequence reads in a first format (e.g., 1, FIG. 42A), convert them into a compressed format (e.g., a binary format, 5) and transfer the compressed reads to another module (e.g., a bias density module 6) in some embodiments. A compression module often provides sequence reads in a binary format 5 (e.g., a BReads format). Non-limiting examples of a compression module include GZIP, BGZF, and BAM, the like or modifications thereof).

The following provides an example of converting an integer into a 4-byte array using java:

```
public static final byte[ ]
convertToByteArray(int value)
{
return new byte [ ] {
(byte)(value >>> 24),
(byte)(value >>> 16),
(byte)(value >>> 8),
(byte)value};
}
```

In some embodiments, a read may uniquely or non-uniquely map to portions in a reference genome. A read is considered as "uniquely mapped" if it aligns with a single sequence in the reference genome. A read is considered as "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at World Wide Web URL ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. When a reference from the pregnant female is prepared ("maternal reference sequence") based on an external reference, reads from DNA of the pregnant female that contains substantially no fetal DNA often are mapped to the external reference sequence and assembled. In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

In certain embodiments, mappability is assessed for a genomic region (e.g., portion, genomic portion, portion). Mappability is the ability to unambiguously align a nucleotide sequence read to a portion of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

Portions

In some embodiments, mapped sequence reads (i.e. sequence tags) are grouped together according to various parameters and assigned to particular portions (e.g., portions of a reference genome). Often, individual mapped sequence reads can be used to identify a portion (e.g., the presence, absence or amount of a portion) present in a sample. In some embodiments, the amount of a portion is indicative of the amount of a larger sequence (e.g. a chromosome) in the sample. The term "portion" can also be referred to herein as a "genomic section", "bin", "region", "partition", "portion of a reference genome", "portion of a chromosome" or "genomic portion." In some embodiments a portion is an entire chromosome, a segment of a chromosome, a segment of a reference genome, a segment spanning multiple chromosome, multiple chromosome segments, and/or combinations thereof. In some embodiments, a portion is predefined based on specific parameters. In some embodiments, a portion is arbitrarily defined based on partitioning of a genome (e.g., partitioned by size, GC content, contiguous regions, contiguous regions of an arbitrarily defined size, and the like).

In some embodiments, a portion is delineated based on one or more parameters which include, for example, length or a particular feature or features of the sequence. Portions can be selected, filtered and/or removed from consideration using any suitable criteria know in the art or described herein. In some embodiments, a portion is based on a particular length of genomic sequence. In some embodiments, a method can include analysis of multiple mapped sequence reads to a plurality of portions. Portions can be approximately the same length or portions can be different lengths. In some embodiments, portions are of about equal length. In some embodiments portions of different lengths are adjusted or weighted. In some embodiments, a portion is about 10 kilobases (kb) to about 100 kb, about 20 kb to about 80 kb, about 30 kb to about 70 kb, about 40 kb to about 60 kb, and sometimes about 50 kb. In some embodiments, a portion is about 10 kb to about 20 kb. A portion is not limited to contiguous runs of sequence. Thus, portions can be made up of contiguous and/or non-contiguous sequences. A portion is not limited to a single chromosome. In some embodiments, a portion includes all or part of one chromosome or all or part of two or more chromosomes. In some embodiments, portions may span one, two, or more entire chromosomes. In addition, portions may span jointed or disjointed regions of multiple chromosomes.

In some embodiments, portions can be particular chromosome segments in a chromosome of interest, such as, for example, a chromosome where a genetic variation is assessed (e.g. an aneuploidy of chromosomes 13, 18 and/or 21 or a sex chromosome). A portion can also be a pathogenic genome (e.g. bacterial, fungal or viral) or fragment thereof. Portions can be genes, gene fragments, regulatory sequences, introns, exons, and the like.

In some embodiments, a genome (e.g. human genome) is partitioned into portions based on information content of particular regions. In some embodiments, partitioning a genome may eliminate similar regions (e.g., identical or homologous regions or sequences) across the genome and only keep unique regions. Regions removed during partitioning may be within a single chromosome or may span multiple chromosomes. In some embodiments a partitioned genome is trimmed down and optimized for faster alignment, often allowing for focus on uniquely identifiable sequences.

In some embodiments, partitioning may down weight similar regions. A process for down weighting a portion is discussed in further detail below.

In some embodiments, partitioning of a genome into regions transcending chromosomes may be based on information gain produced in the context of classification. For example, information content may be quantified using a p-value profile measuring the significance of particular genomic locations for distinguishing between groups of confirmed normal and abnormal subjects (e.g. euploid and trisomy subjects, respectively). In some embodiments, partitioning of a genome into regions transcending chromosomes may be based on any other criterion, such as, for example, speed/convenience while aligning tags, GC content (e.g., high or low GC content), uniformity of GC content, other measures of sequence content (e.g. fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual portions of a reference genome, and/or a targeted search for particular features.

A "segment" of a chromosome generally is part of a chromosome, and typically is a different part of a chromosome than a portion. A segment of a chromosome sometimes is in a different region of a chromosome than a portion, sometimes does not share a polynucleotide with a portion, and sometimes includes a polynucleotide that is in a portion. A segment of a chromosome often contains a larger number of nucleotides than a portion (e.g., a segment sometimes includes a portion), and sometimes a segment of a chromosome contains a smaller number of nucleotides than a portion (e.g., a segment sometimes is within a portion).

Counts

Sequence reads that are mapped or partitioned based on a selected feature or variable can be quantified to determine the number of reads that are mapped to one or more portions (e.g., portion of a reference genome), in some embodiments. In certain embodiments the quantity of sequence reads that are mapped to a portion are termed counts (e.g., a count). Often a count is associated with a portion. In certain embodiments counts for two or more portions (e.g., a set of portions) are mathematically manipulated (e.g., averaged, added, normalized, the like or a combination thereof). In some embodiments a count is determined from some or all of the sequence reads mapped to (i.e., associated with) a portion. In certain embodiments, a count is determined from a pre-defined subset of mapped sequence reads. Pre-defined subsets of mapped sequence reads can be defined or selected utilizing any suitable feature or variable. In some embodiments, pre-defined subsets of mapped sequence reads can include from 1 to n sequence reads, where n represents a number equal to the sum of all sequence reads generated from a test subject or reference subject sample.

In certain embodiments a count is derived from sequence reads that are processed or manipulated by a suitable method, operation or mathematical process known in the art. A count (e.g., counts) can be determined by a suitable method, operation or mathematical process. In certain embodiments a count is derived from sequence reads associated with a portion where some or all of the sequence reads are weighted, removed, filtered, normalized, adjusted, averaged, derived as a mean, added, or subtracted or processed by a combination thereof. In some embodiments, a count is derived from raw sequence reads and or filtered sequence reads. In certain embodiments a count value is determined by a mathematical process. In certain embodiments a count value is an average, mean or sum of sequence reads mapped to a portion. Often a count is a mean number of counts. In some embodiments, a count is associated with an uncertainty value.

In some embodiments, counts can be manipulated or transformed (e.g., normalized, combined, added, filtered, selected, averaged, derived as a mean, the like, or a combination thereof). In some embodiments, counts can be transformed to produce normalized counts. Counts can be processed (e.g., normalized) by a method known in the art and/or as described herein (e.g., portion-wise normalization, normalization by GC content, linear and nonlinear least squares regression, GC LOESS, LOWESS, PERUN, ChAl, RM, GCRM, cQn and/or combinations thereof).

Counts (e.g., raw, filtered and/or normalized counts) can be processed and normalized to one or more levels. Levels and profiles are described in greater detail hereafter. In certain embodiments counts can be processed and/or normalized to a reference level. Reference levels are addressed later herein. Counts processed according to a level (e.g., processed counts) can be associated with an uncertainty value (e.g., a calculated variance, an error, standard deviation, Z-score, p-value, mean absolute deviation, etc.). In some embodiments an uncertainty value defines a range above and below a level. A value for deviation can be used in place of an uncertainty value, and non-limiting examples of measures of deviation include standard deviation, average absolute deviation, median absolute deviation, standard score (e.g., Z-score, Z-score, normal score, standardized variable) and the like.

Counts are often obtained from a nucleic acid sample from a pregnant female bearing a fetus. Counts of nucleic acid sequence reads mapped to one or more portions often are counts representative of both the fetus and the mother of the fetus (e.g., a pregnant female subject). In certain embodiments some of the counts mapped to a portion are from a fetal genome and some of the counts mapped to the same portion are from a maternal genome.

Data Processing and Normalization

Mapped sequence reads that have been counted are referred to herein as raw data, since the data represents unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing". Processing can render data more amenable to further analysis, and can generate an outcome in some embodiments. In some embodiments one or more or all processing methods (e.g., normalization methods, portion filtering, mapping, validation, the like or combinations thereof) are performed by a processor, a micro-processor, a computer, in conjunction with memory and/or by a microprocessor controlled apparatus.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being over represented when prepared using PCR-based methods. Methods described herein can reduce or eliminate the contribution of noisy data, and therefore reduce the effect of noisy data on the provided outcome.

The terms "uninformative data", "uninformative portions of a reference genome", and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation (e.g. a copy number variation, an aneuploidy, a microduplication, a microdeletion, a chromosomal aberration, and the like). In certain embodiments a threshold is exceeded by results obtained by methods described herein and a subject is diagnosed with a genetic variation (e.g. trisomy 21). A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula in Example 4.

Any suitable procedure can be utilized for processing data sets described herein. Non-limiting examples of procedures suitable for use for processing data sets include filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments, one or more processing steps can comprise one or more filtering steps. The term "filtering" as used herein refers to removing portions or portions of a reference genome from consideration. Portions of a reference genome can be selected for removal based on any suitable criteria, including but not limited to redundant data (e.g., redundant or overlapping mapped reads), non-informative data (e.g., portions of a reference genome with zero median counts), portions of a reference genome with over represented or under represented sequences, noisy data, the like, or combinations of the foregoing. A filtering process often involves removing one or more portions of a reference genome from consideration and subtracting the counts in the one or more portions of a reference genome selected for removal from the counted or summed counts for the portions of a reference genome, chromosome or chromosomes, or genome under consideration. In some embodiments, portions of a reference genome can be removed successively (e.g., one at a time to allow evaluation of the effect of removal of each individual portion), and in certain embodiments all portions of a reference genome marked for removal can be removed at the same time. In some embodiments, portions of a reference genome characterized by a variance above or below a certain level are removed, which sometimes is referred to herein as filtering "noisy" portions of a reference genome. In certain embodiments, a filtering process comprises obtaining data points from a data set that deviate from the mean profile level of a portion, a chromosome, or segment of a chromosome by a predetermined multiple of the profile variance, and in certain embodiments, a filtering process comprises removing data points from a data set that do not deviate from the mean profile level of a portion, a chromosome or segment of a chromosome by a predetermined multiple of the profile variance. In some embodiments, a filtering process is utilized to reduce the number of candidate portions of a reference genome analyzed for the presence or absence of a genetic variation. Reducing the number of candidate portions of a reference genome analyzed for the presence or absence of a genetic variation (e.g., micro-deletion, micro-duplication) often reduces the complexity and/or dimensionality of a data set, and sometimes increases the speed of searching for and/or identifying genetic variations and/or genetic aberrations by two or more orders of magnitude.

In some embodiments one or more processing steps can comprise one or more normalization steps. Normalization can be performed by a suitable method described herein or known in the art. In certain embodiments normalization comprises adjusting values measured on different scales to a notionally common scale. In certain embodiments normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Non-limiting examples of normalization methods include portion-wise normalization, normalization by GC content, linear and nonlinear least squares regression, LOESS, GC LOESS, LOWESS (locally weighted scatterplot smoothing), PERUN, ChAI, repeat masking (RM), GC-normalization and repeat masking (GCRM), cQn and/or combinations thereof. In some embodiments, the determination of a presence or absence of a genetic variation (e.g., an aneuploidy, a microduplication, a microdeletion) utilizes a normalization method (e.g., portion-wise normalization, normalization by GC content, linear and nonlinear least squares regression, LOESS, GC LOESS, LOWESS (locally weighted scatterplot smoothing), PERUN, ChAI, repeat masking (RM), GC-normalization and repeat masking (GCRM), cQn, a normalization method known in the art and/or a combination thereof).

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference portions to the total number of counts mapped to the chromosome or the entire genome on which the selected portion or sections are mapped; normalizing raw count data for one or more selected portions to a median reference count for one or more portions or the chromosome on which a selected portion or segments is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing portions, or portions of a reference genome, with respect to a normalizing value sometimes is referred to as "portion-wise normalization".

In certain embodiments, a processing step comprising normalization includes normalizing to a static window, and in some embodiments, a processing step comprising normalization includes normalizing to a moving or sliding window. The term "window" as used herein refers to one or more portions chosen for analysis, and sometimes used as a reference for comparison (e.g., used for normalization and/or other mathematical or statistical manipulation). The term "normalizing to a static window" as used herein refers to a normalization process using one or more portions selected for comparison between a test subject and reference subject data set. In some embodiments the selected portions are utilized to generate a profile. A static window generally includes a predetermined set of portions that do not change during manipulations and/or analysis. The terms "normalizing to a moving window" and "normalizing to a sliding window" as used herein refer to normalizations performed to portions localized to the genomic region (e.g., immediate genetic surrounding, adjacent portion or sections, and the like) of a selected test portion, where one or more selected test portions are normalized to portions immediately surrounding the selected test portion. In certain embodiments, the selected portions are utilized to generate a profile. A sliding or moving window normalization often includes repeatedly moving or sliding to an adjacent test portion, and normalizing the newly selected test portion to portions immediately surrounding or adjacent to the newly selected test portion, where adjacent windows have one or more portions in common. In certain embodiments, a plurality of selected test portions and/or chromosomes can be analyzed by a sliding window process.

In some embodiments, normalizing to a sliding or moving window can generate one or more values, where each value represents normalization to a different set of reference portions selected from different regions of a genome (e.g., chromosome). In certain embodiments, the one or more values generated are cumulative sums (e.g., a numerical estimate of the integral of the normalized count profile over the selected portion, domain (e.g., part of chromosome), or chromosome). The values generated by the sliding or moving window process can be used to generate a profile and facilitate arriving at an outcome. In some embodiments, cumulative sums of one or more portions can be displayed as a function of genomic position. Moving or sliding window analysis sometimes is used to analyze a genome for the presence or absence of micro-deletions and/or microinsertions. In certain embodiments, displaying cumulative sums of one or more portions is used to identify the presence or absence of regions of genetic variation (e.g., micro-deletions, micro-duplications). In some embodiments, moving or sliding window analysis is used to identify genomic regions containing micro-deletions and in certain embodiments, moving or sliding window analysis is used to identify genomic regions containing micro-duplications.

Described in greater detail hereafter are certain examples of normalization processes that can be utilized, such as LOESS, PERUN, ChAI and principal component normalization methods, for example.

In some embodiments, a processing step comprises a weighting. The terms "weighted", "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more portions or portions of a reference genome, based on the quality or usefulness of the data in the selected portion or portions of a reference genome). A weighting function can be used to increase the influence of data with a relatively small measurement variance, and/or to decrease the influence of data with a relatively large measurement variance, in some embodiments. For example, portions of a reference genome with under represented or low quality sequence data can be "down weighted" to minimize the influence on a data set, whereas selected portions of a reference genome can be "up weighted" to increase the influence on a data set. A non-limiting example of a weighting function is $[1/(\text{standard deviation})^2]$. A weighting step sometimes is performed in a manner substantially similar to a normalizing step. In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak levels, determination of peak edge locations, calculation of peak area ratios, analysis of median chromosomal level, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median levels, mean levels, count distribution within a genomic region, relative representation of nucleic acid species, the like or combinations thereof.

In some embodiments, a processing step can comprise the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median levels, mean levels, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

After data sets have been counted, optionally filtered and normalized, the processed data sets can be further manipulated by one or more filtering and/or normalizing procedures, in some embodiments. A data set that has been further manipulated by one or more filtering and/or normalizing procedures can be used to generate a profile, in certain embodiments. The one or more filtering and/or normalizing procedures sometimes can reduce data set complexity and/or dimensionality, in some embodiments. An outcome can be provided based on a data set of reduced complexity and/or dimensionality.

In some embodiments portions may be filtered according to a measure of error (e.g., standard deviation, standard error, calculated variance, p-value, mean absolute error (MAE), average absolute deviation and/or mean absolute deviation (MAD). In certain embodiments a measure of error refers to count variability. In some embodiments portions are filtered according to count variability. In certain embodiments count variability is a measure of error determined for counts mapped to a portion (i.e., portion) of a reference genome for multiple samples (e.g., multiple sample obtained from multiple subjects, e.g., 50 or more, 100 or more, 500 or more 1000 or more, 5000 or more or 10,000 or more subjects). In some embodiments portions with a count variability above a pre-determined upper range are filtered (e.g., excluded from consideration). In some embodiments a pre-determined upper range is a MAD value equal to or greater than about 50, about 52, about 54, about 56, about 58, about 60, about 62, about 64, about 66, about 68, about 70, about 72, about 74 or equal to or greater than about 76. In some embodiments portions with a count variability below a pre-determined lower range are filtered (e.g., excluded from consideration). In some embodiments a pre-determined lower range is a MAD value equal to or less than about 40, about 35, about 30, about 25, about 20, about 15, about 10, about 5, about 1, or equal to or less than about 0. In some embodiments portions with a count variability outside a pre-determined range are filtered (e.g., excluded from consideration). In some embodiments a pre-determined range is a MAD value greater than zero and less than about 76, less than about 74, less than about 73, less than about 72, less than about 71, less than about 70, less than about 69, less than about 68, less than about 67, less than about 66, less than about 65, less than about 64, less than about 62, less than about 60, less than about 58, less than about 56, less than about 54, less than about 52 or less than about 50. In some embodiments a pre-determined range is a MAD value greater than zero and less than about 67.7. In some embodiments portions with a count variability within a pre-determined range are selected (e.g., used for determining the presence or absence of a genetic variation).

In some embodiments the count variability of portions represent a distribution (e.g., a normal distribution). In some embodiments portions are selected within a quantile of the distribution. In some embodiments portions within a quantile equal to or less than about 99.9%, 99.8%, 99.7%, 99.6%, 99.5%, 99.4%, 99.3%, 99.2%, 99.1%, 99.0%, 98.9%, 98.8%, 98.7%, 98.6%, 98.5%, 98.4%, 98.3%, 98.2%, 98.1%, 98.0%, 97%, 96%, 95%, 94%, 93%, 92%, 91%, 90%, 85%, 80%, or equal to or less than a quantile of about 75% for the distribution are selected. In some embodiments portions within a 99% quantile of the distribution of count variability are selected. In some embodiments portions with a MAD>0 and a MAD<67.725 a within the 99% quantile and are selected, resulting in the identification of a set of stable portions of a reference genome.

Non-limiting examples of portion filtering with respect to PERUN, for example, is provided herein and in international patent application no. PCT/US12/59123 (WO2013/052913) the entire content of which is incorporated herein by reference, including all text, tables, equations and drawings. Portions may be filtered based on, or based on part on, a measure of error. A measure of error comprising absolute values of deviation, such as an R-factor, can be used for portion removal or weighting in certain embodiments. An R-factor, in some embodiments, is defined as the sum of the absolute deviations of the predicted count values from the actual measurements divided by the predicted count values from the actual measurements (e.g., Equation B herein). While a measure of error comprising absolute values of deviation may be used, a suitable measure of error may be alternatively employed. In certain embodiments, a measure of error not comprising absolute values of deviation, such as a dispersion based on squares, may be utilized. In some embodiments, portions are filtered or weighted according to a measure of mappability (e.g., a mappability score). A portion sometimes is filtered or weighted according to a relatively low number of sequence reads mapped to the portion (e.g., 0, 1, 2, 3, 4, 5 reads mapped to the portion). Portions can be filtered or weighted according to the type of analysis being performed. For example, for chromosome 13, 18 and/or 21 aneuploidy analysis, sex chromosomes may be filtered, and only autosomes, or a subset of autosomes, may be analyzed.

In particular embodiments, the following filtering process may be employed. The same set of portions (e.g., portions of a reference genome) within a given chromosome (e.g., chromosome 21) are selected and the number of reads in affected and unaffected samples are compared. The gap relates trisomy 21 and euploid samples and it involves a set of portions covering most of chromosome 21. The set of portions is the same between euploid and T21 samples. The distinction between a set of portions and a single section is not crucial, as a portion can be defined. The same genomic region is compared in different patients. This process can be utilized for a trisomy analysis, such as for T13 or T18 in addition to, or instead of, T21.

After data sets have been counted, optionally filtered and normalized, the processed data sets can be manipulated by weighting, in some embodiments. One or more portions can be selected for weighting to reduce the influence of data (e.g., noisy data, uninformative data) contained in the selected portions, in certain embodiments, and in some embodiments, one or more portions can be selected for weighting to enhance or augment the influence of data (e.g., data with small measured variance) contained in the selected portions. In some embodiments, a data set is weighted utilizing a single weighting function that decreases the influence of data with large variances and increases the influence of data with small variances. A weighting function sometimes is used to reduce the influence of data with large variances and augment the influence of data with small variances (e.g., $[1/(\text{standard deviation})^2]$). In some embodiments, a profile plot of processed data further manipulated by weighting is generated to facilitate classification and/or providing an outcome. An outcome can be provided based on a profile plot of weighted data Filtering or weighting of portions can be performed at one or more suitable points in an analysis. For example, portions may be filtered or weighted before or after sequence reads are mapped to portions of a reference genome. Portions may be filtered or weighted before or after an experimental bias for individual genome portions is determined in some embodiments. In certain embodiments, portions may be filtered or weighted before or after genomic section levels are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected portions, chromosomes, or portions of chromosomes. In some embodiments, processed data sets can be further manipulated by calculating P-values. One embodiment of an equation for calculating a Z-score and a p-value is presented in Equation 1 (Example 2). In certain embodiments, mathematical and/or statistical manipulations include one or more assumptions pertaining to ploidy and/or fetal fraction. In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fetal fraction.

In certain embodiments, multiple manipulations are performed on processed data sets to generate an N-dimensional space and/or N-dimensional point, after data sets have been counted, optionally filtered and normalized. An outcome can be provided based on a profile plot of data sets analyzed in N-dimensions.

In some embodiments, data sets are processed utilizing one or more peak level analysis, peak width analysis, peak edge location analysis, peak lateral tolerances, the like, derivations thereof, or combinations of the foregoing, as part of or after data sets have processed and/or manipulated. In some embodiments, a profile plot of data processed utilizing one or more peak level analysis, peak width analysis, peak edge location analysis, peak lateral tolerances, the like, derivations thereof, or combinations of the foregoing is generated to facilitate classification and/or providing an outcome. An outcome can be provided based on a profile plot of data that has been processed utilizing one or more peak level analysis, peak width analysis, peak edge location analysis, peak lateral tolerances, the like, derivations thereof, or combinations of the foregoing.

In some embodiments, the use of one or more reference samples that are substantially free of a genetic variation in question can be used to generate a reference median count profile, which may result in a predetermined value representative of the absence of the genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for the selected portion or sections is expected to vary significantly from the predetermined value for non-affected genomic locations. In certain embodiments, the use of one or more reference samples known to carry the genetic variation in question can be used to generate a reference median count profile, which may result in a predetermined value representative of the presence of the genetic variation, and often deviates from a predetermined value in areas corresponding to the genomic location in which a test subject does not carry the genetic variation. In test subjects not at risk for, or suffering from a medical condition associated with a genetic variation, the numerical value for the selected portion or sections is expected to vary significantly from the predetermined value for affected genomic locations.

In some embodiments, analysis and processing of data can include the use of one or more assumptions. A suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

In those instances where the quality and/or depth of mapped sequence reads does not permit an outcome prediction of the presence or absence of a genetic variation at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

LOESS Normalization

LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relationship between fragment count (e.g., sequence reads, counts) and GC composition for portions of a reference genome. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

PERUN Normalization

A normalization methodology for reducing error associated with nucleic acid indicators is referred to herein as Parameterized Error Removal and Unbiased Normalization (PERUN) described herein and in international patent application no. PCT/US12/59123 (WO2013/052913) the entire content of which is incorporated herein by reference, including all text, tables, equations and drawings. PERUN methodology can be applied to a variety of nucleic acid indicators (e.g., nucleic acid sequence reads) for the purpose of reducing effects of error that confound predictions based on such indicators.

For example, PERUN methodology can be applied to nucleic acid sequence reads from a sample and reduce the effects of error that can impair genomic section level determinations. Such an application is useful for using nucleic acid sequence reads to determine the presence or absence of a genetic variation in a subject manifested as a varying level of a nucleotide sequence (e.g., a portion, a genomic section level). Non-limiting examples of variations in portions are chromosome aneuploidies (e.g., trisomy 21, trisomy 18, trisomy 13) and presence or absence of a sex chromosome (e.g., XX in females versus XY in males). A trisomy of an autosome (e.g., a chromosome other than a sex chromosome) can be referred to as an affected autosome. Other non-limiting examples of variations in genomic section levels include microdeletions, microinsertions, duplications and mosaicism.

In certain applications, PERU N methodology can reduce experimental bias by normalizing nucleic acid reads mapped to particular portions of a reference genome, the latter of which are referred to as portions and sometimes as portions of a reference genome. In such applications, PERUN methodology generally normalizes counts of nucleic acid reads at particular portions of a reference genome across a number of samples in three dimensions. A detailed description of PERUN and applications thereof is provided in the Examples section herein, in international patent application no. PCT/US12/59123 (WO2013/052913) and U.S. patent application publication no. US20130085681, the entire content of which is incorporated herein by reference, including all text, tables, equations and drawings.

In certain embodiments, PERUN methodology includes calculating a genomic section level for portions of a reference genome from (a) sequence read counts mapped to a portion of a reference genome for a test sample, (b) experimental bias (e.g., GC bias) for the test sample, and (c) one or more fit parameters (e.g., estimates of fit) for a fitted relationship between (i) experimental bias for a portion of a reference genome to which sequence reads are mapped and (ii) counts of sequence reads mapped to the portion. Experimental bias for each of the portions of a reference genome can be determined across multiple samples according to a fitted relationship for each sample between (i) the counts of sequence reads mapped to each of the portions of a reference genome, and (ii) a mapping feature for each of the portions of a reference genome. This fitted relationship for each sample can be assembled for multiple samples in three dimensions. The assembly can be ordered according to the experimental bias in certain embodiments, although PERUN methodology may be practiced without ordering the assembly according to the experimental bias. The fitted relationship for each sample and the fitted relationship for each portion of the reference genome can be fitted independently to a linear function or non-linear function by a suitable fitting process known in the art.

In some embodiments, a relationship is a geometric and/or graphical relationship. In some embodiments a relationship is a mathematical relationship. In some embodiments, a relationship is plotted. In some embodiments a relationship is a linear relationship. In certain embodiments a relationship is a non-linear relationship. In certain embodiments a relationship is a regression (e.g., a regression line). A regression can be a linear regression or a non-linear regression. A relationship can be expressed by a mathematical equation. Often a relationship is defined, in part, by one or more constants. A relationship can be generated by a method known in the art. A relationship in two dimensions can be generated for one or more samples, in certain embodiments, and a variable probative of error, or possibly probative of error, can be selected for one or more of the dimensions. A relationship can be generated, for example, using graphing software known in the art that plots a graph using values of two or more variables provided by a user. A relationship can be fitted using a method known in the art (e.g., graphing software). Certain relationships can be fitted by linear regression, and the linear regression can generate a slope value and intercept value. Certain relationships sometimes are not linear and can be fitted by a non-linear function, such as a parabolic, hyperbolic or exponential function (e.g., a quadratic function), for example.

In PERUN methodology, one or more of the fitted relationships may be linear. For an analysis of cell-free circulating nucleic acid from pregnant females, where the experimental bias is GC bias and the mapping feature is GC content, a fitted relationship for a sample between the (i) the counts of sequence reads mapped to each portion, and (ii) GC content for each of the portions of a reference genome, can be linear. For the latter fitted relationship, the slope pertains to GC bias, and a GC bias coefficient can be determined for each sample when the fitted relationships are assembled across multiple samples. In such embodiments, the fitted relationship for multiple samples and a portion between (i) GC bias coefficient for the portion, and (ii) counts of sequence reads mapped to portion, also can be linear. An intercept and slope can be obtained from the latter fitted relationship. In such applications, the slope addresses sample-specific bias based on GC-content and the intercept addresses a portion-specific attenuation pattern common to all samples. PERUN methodology can significantly reduce such sample-specific bias and portion-specific attenuation when calculating genomic section levels for providing an outcome (e.g., presence or absence of genetic variation; determination of fetal sex).

In some embodiments PERUN normalization makes use of fitting to a linear function and is described by Equation A, Equation B or a derivation thereof.

Equation A:

$$M = LI + GS \quad (A)$$

Equation B:

$$L = (M - GS)/I \quad (B)$$

In some embodiments L is a PERUN normalized level or profile. In some embodiments L is the desired output from the PERUN normalization procedure. In certain embodiments L is portion specific. In some embodiments L is determined according to multiple portions of a reference genome and represents a PERUN normalized level of a genome, chromosome, portions or segment thereof. The level L is often used for further analyses (e.g., to determine Z-values, maternal deletions/duplications, fetal microdeletions/microduplications, fetal gender, sex aneuploidies, and so on). The method of normalizing according to Equation B is named Parameterized Error Removal and Unbiased Normalization (PERUN).

In some embodiments G is a GC bias coefficient measured using a linear model, LOESS, or any equivalent approach. In some embodiments G is a slope. In some embodiments the GC bias coefficient G is evaluated as the slope of the regression for counts M (e.g., raw counts) for portion i and the GC content of portion i determined from a reference genome. In some embodiments G represents secondary information, extracted from M and determined according to a relationship. In some embodiments G represents a relationship for a set of portion-specific counts and a set of portion-specific GC content values for a sample (e.g., a test sample). In some embodiments portion-specific GC content is derived from a reference genome. In some embodiments portion-specific GC content is derived from observed or measured GC content (e.g., measured from the sample). A GC bias coefficient often is determined for each sample in a group of samples and generally is determined for a test sample. A GC bias coefficient often is sample specific. In some embodiments a GC bias coefficient is a constant. In certain embodiments a GC bias coefficient, once derived for a sample, does not change.

In some embodiments I is an intercept and S is a slope derived from a linear relationship. In some embodiments the relationship from which I and S are derived is different than the relationship from which G is derived. In some embodiments the relationship from which I and S are derived is fixed for a given experimental setup. In some embodiments I and S are derived from a linear relationship according to counts (e.g., raw counts) and a GC bias coefficient according to multiple samples. In some embodiments I and S are derived independently of the test sample. In some embodiments I and S are derived from multiple samples. I and S often are portion specific. In some embodiments, I and S are determined with the assumption that L=1 for all portions of a reference genome in euploid samples. In some embodiments a linear relationship is determined for euploid samples and/and S values specific for a selected portion (assuming L=1) are determined. In certain embodiments the same procedure is applied to all portions of a reference genome in a human genome and a set of intercepts/and slopes S is determined for every portion.

In some embodiments a cross-validation approach is applied. Cross-validation, sometimes is referred to as rotation estimation. In some embodiments a cross-validation approach is applied to assess how accurately a predictive model (e.g., such as PERUN) will perform in practice using a test sample. In some embodiments one round of cross-validation comprises partitioning a sample of data into complementary subsets, performing a cross validation analysis on one subset (e.g., sometimes referred to as a training set), and validating the analysis using another subset (e.g., sometimes called a validation set or test set). In certain embodiments, multiple rounds of cross-validation are performed using different partitions and/or different subsets). Non-limiting examples of cross-validation approaches include leave-one-out, sliding edges, K-fold, 2-fold, repeat random sub-sampling, the like or combinations thereof. In some embodiments a cross-validation randomly selects a work set containing 90% of a set of samples comprising known euploid fetuses and uses that subset to train a model. In certain embodiments, the random selection is repeated 100 times, yielding a set of 100 slopes and 100 intercepts for every portion.

In some embodiments the value of M is a measured value derived from a test sample. In some embodiments M is measured raw counts for a portion. In some embodiments, where the values/and S are available for a portion, measurement M is determined from a test sample and is used to determine the PERUN normalized level L for a genome, chromosome, segment or portion thereof according to Equation B Thus, application of PERUN methodology to sequence reads across multiple samples in parallel can significantly reduce error caused by (i) sample-specific experimental bias (e.g., GC bias) and (ii) portion-specific attenuation common to samples. Other methods in which each of these two sources of error are addressed separately or serially often are not able to reduce these as effectively as PERUN methodology. Without being limited by theory, it is expected that PERUN methodology reduces error more effectively in part because its generally additive processes do not magnify spread as much as generally multiplicative processes utilized in other normalization approaches (e.g., GC-LOESS).

Additional normalization and statistical techniques may be utilized in combination with PERUN methodology. An additional process can be applied before, after and/or during employment of PERUN methodology. Non-limiting examples of processes that can be used in combination with PERUN methodology are described hereafter.

In some embodiments, a secondary normalization or adjustment of a genomic section level for GC content can be utilized in conjunction with PERUN methodology. A suitable GC content adjustment or normalization procedure can be utilized (e.g., GC-LOESS, GCRM). In certain embodiments, a particular sample can be identified for application of an additional GC normalization process. For example, application of PERUN methodology can determine GC bias for each sample, and a sample associated with a GC bias above a certain threshold can be selected for an additional GC normalization process. In such embodiments, a predetermined threshold level can be used to select such samples for additional GC normalization.

In certain embodiments, a portion filtering or weighting process can be utilized in conjunction with PERUN methodology. A suitable portion filtering or weighting process can be utilized, non-limiting examples are described herein, in international patent application no. PCT/US12/59123 (WO2013/052913) and U.S. patent application publication no. US20130085681, the entire content of which is incorporated herein by reference, including all text, tables, equations and drawings. In some embodiments, a normalization technique that reduces error associated with maternal insertions, duplications and/or deletions (e.g., maternal and/or fetal copy number variations), is utilized in conjunction with PERUN methodology.

Genomic section levels calculated by PERUN methodology can be utilized directly for providing an outcome. In some embodiments, genomic section levels can be utilized directly to provide an outcome for samples in which fetal fraction is about 2% to about 6% or greater (e.g., fetal fraction of about 4% or greater). Genomic section levels calculated by PERUN methodology sometimes are further processed for the provision of an outcome. In some embodiments, calculated genomic section levels are standardized. In certain embodiments, the sum, mean or median of calculated genomic section levels for a test portion (e.g., chromosome 21) can be divided by the sum, mean or median of calculated genomic section levels for portions other than the test portion (e.g., autosomes other than chromosome 21), to generate an experimental genomic section level. An experimental genomic section level or a raw genomic section level can be used as part of a standardization analysis, such as calculation of a Z-score or Z-score. A Z-score can be generated for a sample by subtracting an expected genomic section level from an experimental genomic section level or raw genomic section level and the resulting value may be divided by a standard deviation for the samples. Resulting Z-scores can be distributed for different samples and analyzed, or can be related to other variables, such as fetal fraction and others, and analyzed, to provide an outcome, in certain embodiments.

As noted herein, PERUN methodology is not limited to normalization according to GC bias and GC content per se, and can be used to reduce error associated with other sources of error. A non-limiting example of a source of non-GC content bias is mappability. When normalization parameters other than GC bias and content are addressed, one or more of the fitted relationships may be non-linear (e.g., hyperbolic, exponential). Where experimental bias is determined from a non-linear relationship, for example, an experimental bias curvature estimation may be analyzed in some embodiments.

PERUN methodology can be applied to a variety of nucleic acid indicators. Non-limiting examples of nucleic acid indicators are nucleic acid sequence reads and nucleic acid levels at a particular location on a microarray. Non-limiting examples of sequence reads include those obtained from cell-free circulating DNA, cell-free circulating RNA, cellular DNA and cellular RNA. PERUN methodology can be applied to sequence reads mapped to suitable reference sequences, such as genomic reference DNA, cellular reference RNA (e.g., transcriptome), and portions thereof (e.g., part(s) of a genomic complement of DNA or RNA transcriptome, part(s) of a chromosome).

Thus, in certain embodiments, cellular nucleic acid (e.g., DNA or RNA) can serve as a nucleic acid indicator. Cellular nucleic acid reads mapped to reference genome portions can be normalized using PERU N methodology. Cellular nucleic acid bound to a particular protein sometimes are referred to chromatin immunoprecipitation (ChIP) processes. ChIP-enriched nucleic acid is a nucleic acid in association with cellular protein, such as DNA or RNA for example. Reads of ChIP-enriched nucleic acid can be obtained using technology known in the art. Reads of ChIP-enriched nucleic acid can be mapped to one or more portions of a reference genome, and results can be normalized using PERUN methodology for providing an outcome.

In certain embodiments, cellular RNA can serve as nucleic acid indicators. Cellular RNA reads can be mapped to reference RNA portions and normalized using PERUN methodology for providing an outcome. Known sequences for cellular RNA, referred to as a transcriptome, or a segment thereof, can be used as a reference to which RNA reads from a sample can be mapped. Reads of sample RNA can be obtained using technology known in the art. Results of RNA reads mapped to a reference can be normalized using PERUN methodology for providing an outcome.

In some embodiments, microarray nucleic acid levels can serve as nucleic acid indicators. Nucleic acid levels across samples for a particular address, or hybridizing nucleic acid, on an array can be analyzed using PERUN methodology, thereby normalizing nucleic acid indicators provided by microarray analysis. In this manner, a particular address or hybridizing nucleic acid on a microarray is analogous to a portion for mapped nucleic acid sequence reads, and PERUN methodology can be used to normalize microarray data to provide an improved outcome.

ChAI Normalization

Another normalization methodology that can be used to reduce error associated with nucleic acid indicators is referred to herein as ChAI and often makes use of a principal component analysis. In certain embodiments, a principal component analysis includes (a) filtering, according to a read density distribution, portions of a reference genome, thereby providing a read density profile for a test sample comprising read densities of filtered portions, where the read densities comprise sequence reads of circulating cell-free nucleic acid from a test sample from a pregnant female, and the read density distribution is determined for read densities of portions for multiple samples, (b) adjusting the read density profile for the test sample according to one or more principal components, which principal components are obtained from a set of known euploid samples by a principal component analysis, thereby providing a test sample profile comprising adjusted read densities, and (c) comparing the test sample profile to a reference profile, thereby providing a comparison. In some embodiments, a principal component analysis includes (d) determining the presence or absence of a genetic variation for the test sample according to the comparison.

Filtering Portions

Figure 37A:
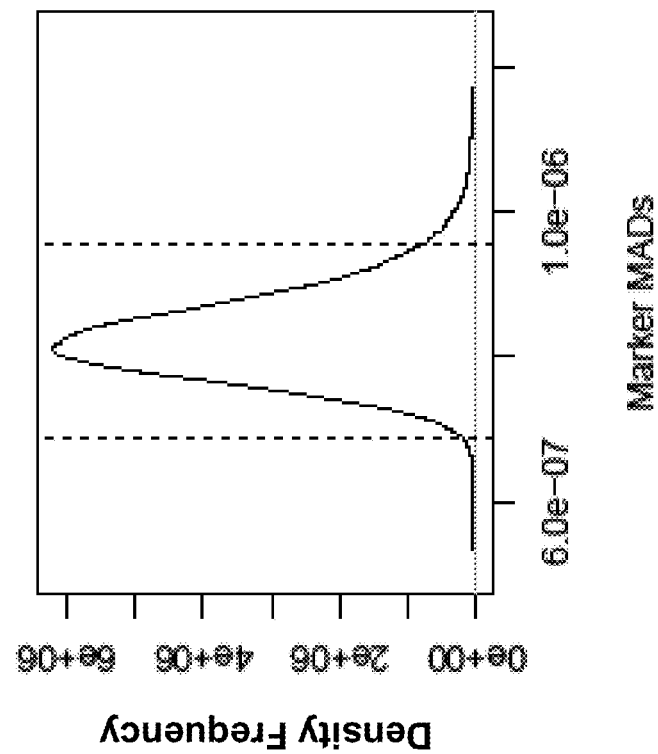
FIG. 37A shows a distribution of median GC densities (x-axis) for all portions of a genome.
Figure 37B:
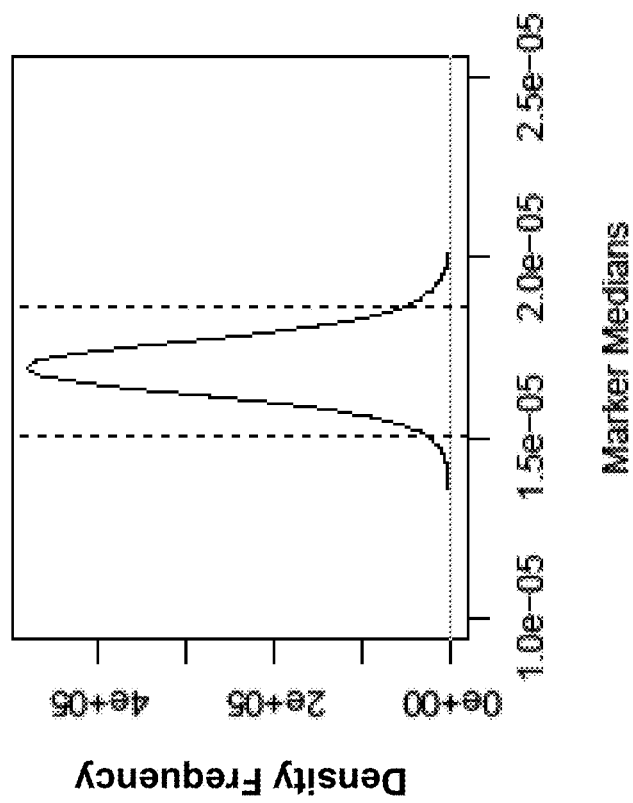
FIG. 37B shows median absolute deviation (MAD) values (x-axis) determined according to the GC density distributions for multiple samples. GC density frequencies are shown on the y-axis. Portions were filtered according to median GC density distributions for multiple reference samples (e.g., a training set) and MAD values determined according to GC density distributions of multiple samples. Portions comprising GC densities outside of an established threshold (e.g., four times the inter-quartile range of MAD) were removed from consideration according to the filtering process.

In certain embodiments one or more portions (e.g., portions of a genome) are removed from consideration by a filtering process. In certain embodiments one or more portions are filtered (e.g., subjected to a filtering process) thereby providing filtered portions. In some embodiments a filtering process removes certain portions and retains portions (e.g., a subset of portions). Following a filtering process, retained portions are often referred to herein as filtered portions. In some embodiments portions of a reference genome are filtered. In some embodiments portions of a reference genome that are removed by a filtering process are not included in a determination of the presence or absence of a genetic variation (e.g., a chromosome aneuploidy, microduplication, microdeletion). In some embodiments portions associated with read densities (e.g., where a read density is for a portion) are removed by a filtering process and read densities associated with removed portions are not included in a determination of the presence or absence of a genetic variation (e.g., a chromosome aneuploidy, microduplication, microdeletion). In some embodiments a read density profile comprises and/or consist of read densities of filtered portions. Portions can be selected, filtered, and/or removed from consideration using any suitable criteria and/or method known in the art or described herein. Non-limiting examples of criteria used for filtering portions include redundant data (e.g., redundant or overlapping mapped reads), non-informative data (e.g., portions of a reference genome with zero mapped counts), portions of a reference genome with over represented or under represented sequences, GC content, noisy data, mappability, counts, count variability, read density, variability of read density, a measure of uncertainty, a repeatability measure, the like, or combinations of the foregoing. Portions are sometimes filtered according to a distribution of counts and/or a distribution of read densities. In some embodiments portions are filtered according to a distribution of counts and/or read densities where the counts and/or read densities are obtained from one or more reference samples 22. One or more reference samples is sometimes referred to herein as a training set 3. In some embodiments portions are filtered according to a distribution of counts and/or read densities where the counts and/or read densities are obtained from one or more test samples 24. In some embodiments portions are filtered according to a measure of uncertainty for a read density distribution 14. In certain embodiments, portions that demonstrate a large deviation in read densities are removed by a filtering process. For example, a distribution of read densities (e.g., a distribution of average mean, or median read densities e.g., FIG. 37A) can be determined, where each read density in the distribution maps to the same portion. A measure of uncertainty (e.g., a MAD) can be determined by comparing a distribution of read densities for multiple samples where each portion of a genome is associated with measure of uncertainty. According to the foregoing example, portions can be filtered according to a measure of uncertainty (e.g., a standard deviation (SD), a MAD) associated with each portion and a predetermined threshold. FIG. 37B shows a distribution of MAD values for portions, determined according to read density distributions for multiple samples. A predetermined threshold is indicated by the dashed vertical lines enclosing a range of acceptable MAD values. In the example of FIG. 37B, portions comprising MAD values within the acceptable range are retained and portions comprising MAD values outside of the acceptable range are removed from consideration by a filtering process. In some embodiments, according to the foregoing example, portions comprising read densities values (e.g., median, average or mean read densities) outside a predetermined measure of uncertainty are often removed from consideration by a filtering process. In some embodiments portions comprising read densities values (e.g., median, average or mean read densities) outside an inter-quartile range of a distribution are removed from consideration by a filtering process. In some embodiments portions comprising read densities values outside more than 2 times, 3 times, 4 times or 5 times an inter-quartile range of a distribution are removed from consideration by a filtering process. In some embodiments portions comprising read densities values outside more than 2 sigma, 3 sigma, 4 sigma, 5 sigma, 6 sigma, 7 sigma or 8 sigma (e.g., where sigma is a range defined by a standard deviation) are removed from consideration by a filtering process.

In some embodiments a system comprises a filtering module (18, FIG. 42A). A filtering module often accepts, retrieves and/or stores portions (e.g., portions of pre-determined sizes and/or overlap, portion locations within a reference genome) and read densities associated with portions, often from another suitable module (e.g., a distribution module 12, FIG. 42A). In some embodiments selected portions (e.g., 20 (FIG. 42A), e.g., filtered portions) are provided by a filtering module. In some embodiments, a filtering module is required to provide filtered portions and/or to remove portions from consideration. In certain embodiments a filtering module removes read densities from consideration where read densities are associated with removed portions. A filtering module often provides selected portions (e.g., filtered portions) to another suitable module (e.g., a distribution module 12, FIG. 42A). A non-limiting example of a filtering module is provided in Example 7.

Bias Estimates

Sequencing technologies can be vulnerable to multiple sources of bias. Sometimes sequencing bias is a local bias (e.g., a local genome bias). Local bias often is manifested at the level of a sequence read. A local genome bias can be any suitable local bias. Non-limiting examples of a local bias include sequence bias (e.g., GC bias, AT bias, and the like), bias correlated with DNase I sensitivity, entropy, repetitive sequence bias, chromatin structure bias, polymerase error-rate bias, palindrome bias, inverted repeat bias, PCR related bias, the like or combinations thereof. In some embodiments the source of a local bias is not determined or known.

In some embodiments a local genome bias estimate is determined. A local genome bias estimate is sometimes referred to herein as a local genome bias estimation. A local genome bias estimate can be determined for a reference genome, a segment or a portion thereof. In some embodiments a local genome bias estimate is determined for one or more sequence reads (e.g., some or all sequence reads of a sample). A local genome bias estimate is often determined for a sequence read according to a local genome bias estimation for a corresponding location and/or position of a reference (e.g., a reference genome). In some embodiments a local genome bias estimate comprises a quantitative measure of bias of a sequence (e.g., a sequence read, a sequence of a reference genome). A local genome bias estimation can be determined by a suitable method or mathematical process. In some embodiments a local genome bias estimate is determined by a suitable distribution and/or a suitable distribution function (e.g., a PDF). In some embodiments a local genome bias estimate comprises a quantitative representation of a PDF. In some embodiments a local genome bias estimate (e.g., a probability density estimation (PDE), a kernel density estimation) is determined by a probability density function (e.g., a PDF, e.g., a kernel density function) of a local bias content. In some embodiments a density estimation comprises a kernel density estimation. A local genome bias estimate is sometimes expressed as an average, mean, or median of a distribution. Sometimes a local genome bias estimate is expressed as a sum or an integral (e.g., an area under a curve (AUC) of a suitable distribution.

A PDF (e.g., a kernel density function, e.g., an Epanechnikov kernel density function) often comprises a bandwidth variable (e.g., a bandwidth). A bandwidth variable often defines the size and/or length of a window from which a probability density estimate (PDE) is derived when using a PDF. A window from which a PDE is derived often comprises a defined length of polynucleotides. In some embodiments a window from which a PDE is derived is a portion. A portion (e.g., a portion size, a portion length) is often determined according to a bandwidth variable. A bandwidth variable determines the length or size of the window used to determine a local genome bias estimate. a length of a polynucleotide segment (e.g., a contiguous segment of nucleotide bases) from which a local genome bias estimate is determined. A PDE (e.g., read density, local genome bias estimate (e.g., a GC density)) can be determined using any suitable bandwidth, non-limiting examples of which include a bandwidth of about 5 bases to about 100,000 bases, about 5 bases to about 50,000 bases, about 5 bases to about 25,000 bases, about 5 bases to about 10,000 bases, about 5 bases to about 5,000 bases, about 5 bases to about 2,500 bases, about 5 bases to about 1000 bases, about 5 bases to about 500 bases, about 5 bases to about 250 bases, about 20 bases to about 250 bases, or the like. In some embodiments a local genome bias estimate (e.g., a GC density) is determined using a bandwidth of about 400 bases or less, about 350 bases or less, about 300 bases or less, about 250 bases or less, about 225 bases or less, about 200 bases or less, about 175 bases or less, about 150 bases or less, about 125 bases or less, about 100 bases or less, about 75 bases or less, about 50 bases or less or about 25 bases or less. In certain embodiments a local genome bias estimate (e.g., a GC density) is determined using a bandwidth determined according to an average, mean, median, or maximum read length of sequence reads obtained for a given subject and/or sample. Sometimes a local genome bias estimate (e.g., a GC density) is determined using a bandwidth about equal to an average, mean, median, or maximum read length of sequence reads obtained for a given subject and/or sample. In some embodiments a local genome bias estimate (e.g., a GC density) is determined using a bandwidth of about 250, 240, 230, 220, 210, 200, 190, 180, 160, 150, 140, 130, 120, 110, 100, 90, 80, 70, 60, 50, 40, 30, 20 or about 10 bases.

A local genome bias estimate can be determined at a single base resolution, although local genome bias estimates (e.g., local GC content) can be determined at a lower resolution. In some embodiments a local genome bias estimate is determined for a local bias content. A local genome bias estimate (e.g., as determined using a PDF) often is determined using a window. In some embodiments, a local genome bias estimate comprises use of a window comprising a pre-selected number of bases. Sometimes a window comprises a segment of contiguous bases. Sometimes a window comprises one or more portions of non-contiguous bases. Sometimes a window comprises one or more portions (e.g., portions of a genome). A window size or length is often determined by a bandwidth and according to a PDF. In some embodiments a window is about 10 or more, 8 or more, 7 or more, 6 or more, 5 or more, 4 or more, 3 or more, or about 2 or more times the length of a bandwidth. A window is sometimes twice the length of a selected bandwidth when a PDF (e.g., a kernel density function) is used to determine a density estimate. A window may comprise any suitable number of bases. In some embodiments a window comprises about 5 bases to about 100,000 bases, about 5 bases to about 50,000 bases, about 5 bases to about 25,000 bases, about 5 bases to about 10,000 bases, about 5 bases to about 5,000 bases, about 5 bases to about 2,500 bases, about 5 bases to about 1000 bases, about 5 bases to about 500 bases, about 5 bases to about 250 bases, or about 20 bases to about 250 bases. In some embodiments a genome, or segments thereof, is partitioned into a plurality of windows. Windows encompassing regions of a genome may or may not overlap. In some embodiments windows are positioned at equal distances from each other. In some embodiments windows are positioned at different distances from each other. In certain embodiment a genome, or segment thereof, is partitioned into a plurality of sliding windows, where a window is slid incrementally across a genome, or segment thereof, where each window at each increment comprises a local genome bias estimate (e.g., a local GC density). A window can be slid across a genome at any suitable increment, according to any numerical pattern or according to any athematic defined sequence. In some embodiments, for a local genome bias estimate determination, a window is slid across a genome, or a segment thereof, at an increment of about 10,000 bp or more about 5,000 bp or more, about 2,500 bp or more, about 1,000 bp or more, about 750 bp or more, about 500 bp or more, about 400 bases or more, about 250 bp or more, about 100 bp or more, about 50 bp or more, or about 25 bp or more. In some embodiments, for a local genome bias estimate determination, a window is slid across a genome, or a segment thereof, at an increment of about 25, 24, 23, 22, 21, 20, 19, 18, 17, 16, 15, 14, 13, 12, 11, 10, 9, 8, 7, 6, 5, 4, 3, 2, or about 1 bp. For example, for a local genome bias estimate determination, a window may comprise about 400 bp (e.g., a bandwidth of 200 bp) and may be slid across a genome in increments of 1 bp. In some embodiments, a local genome bias estimate is determined for each base in a genome, or segment thereof, using a kernel density function and a bandwidth of about 200 bp.

In some embodiments a local genome bias estimate is a local GC content and/or a representation of local GC content. The term "local" as used herein (e.g., as used to describe a local bias, local bias estimate, local bias content, local genome bias, local GC content, and the like) refers to a polynucleotide segment of 10,000 bp or less. In some embodiments the term "local" refers to a polynucleotide segment of 5000 bp or less, 4000 bp or less, 3000 bp or less, 2000 bp or less, 1000 bp or less, 500 bp or less, 250 bp or less, 200 bp or less, 175 bp or less, 150 bp or less, 100 bp or less, 75 bp or less, or 50 bp or less. A local GC content is often a representation (e.g., a mathematical, a quantitative representation) of GC content for a local segment of a genome, sequence read, sequence read assembly (e.g., a contig, a profile, and the like). For example, a local GC content can be a local GC bias estimate or a GC density.

One or more GC densities are often determined for polynucleotides of a reference or sample (e.g., a test sample). In some embodiments a GC density is a representation (e.g., a mathematical, a quantitative representation) of local GC content (e.g., for a polynucleotide segment of 5000 bp or less). In some embodiments a GC density is a local genome bias estimate. A GC density can be determined using a suitable process described herein and/or known in the art. A GC density can be determined using a suitable PDF (e.g., a kernel density function (e.g., an Epanechnikov kernel density function, e.g., see FIG. 33)). In some embodiments a GC density is a PDE (e.g., a kernel density estimation). In certain embodiments, a GC density is defined by the presence or absence of one or more guanine (G) and/or cytosine (C) nucleotides. Inversely, in some embodiments, a GC density can be defined by the presence or absence of one or more a adenine (A) and/or thymidine (T) nucleotides. GC densities for local GC content, in some embodiments, are normalized according to GC densities determined for an entire genome, or segment thereof (e.g., autosomes, set of chromosomes, single chromosome, a gene e.g., see FIG. 34). One or more GC densities can be determined for polynucleotides of a sample (e.g., a test sample) or a reference sample. A GC density often is determined for a reference genome. In some embodiments a GC density is determined for a sequence read according to a reference genome. A GC density of a read is often determined according to a GC density determined for a corresponding location and/or position of a reference genome to which a read is mapped. In some embodiments a GC density determined for a location on a reference genome is assigned and/or provided for a read, where the read, or a segment thereof, maps to the same location on the reference genome. Any suitable method can be used to determine a location of a mapped read on a reference genome for the purpose of generating a GC density for a read. In some embodiments a median position of a mapped read determines a location on a reference genome from which a GC density for the read is determined. For example, where the median position of a read maps to Chromosome 12 at base number x of a reference genome, the GC density of the read is often provided as the GC density determined by a kernel density estimation for a position located on Chromosome 12 at or near base number x of the reference genome. In some embodiments a GC density is determined for some or all base positions of a read according to a reference genome. Sometimes a GC density of a read comprises an average, sum, median or integral of two or more GC densities determined for a plurality of base positions on a reference genome.

In some embodiments a local genome bias estimation (e.g., a GC density) is quantitated and/or is provided a value. A local genome bias estimation (e.g., a GC density) is sometimes expressed as an average, mean, and/or median. A local genome bias estimation (e.g., a GC density) is sometimes expressed as a maximum peak height of a PDE. Sometimes a local genome bias estimation (e.g., a GC density) is expressed as a sum or an integral (e.g., an area under a curve (AUC)) of a suitable PDE. In some embodiments a GC density comprises a kernel weight. In certain embodiments a GC density of a read comprises a value about equal to an average, mean, sum, median, maximum peak height or integral of a kernel weight.

Bias Frequencies

Bias frequencies are sometimes determined according to one or more local genome bias estimates (e.g., GC densities). A bias frequency is sometimes a count or sum of the number of occurrences of a local genome bias estimate for a sample, reference (e.g., a reference genome, a reference sequence) or part thereof. A bias frequency is sometimes a count or sum of the number of occurrences of a local genome bias estimate (e.g., each local genome bias estimate) for a sample, reference, or part thereof. In some embodiments a bias frequency is a GC density frequency. A GC density frequency is often determined according to one or more GC densities. For example, a GC density frequency may represent the number of times a GC density of value x is represented over an entire genome, or a segment thereof. A bias frequency is often a distribution of local genome bias estimates, where the number of occurrences of each local genome bias estimate is represented as a bias frequency (e.g., see FIG. 35). Bias frequencies are sometimes mathematically manipulated and/or normalized. Bias frequencies can be mathematically manipulated and/or normalized by a suitable method. In some embodiments, bias frequencies are normalized according to a representation (e.g., a fraction, a percentage) of each local genome bias estimate for a sample, reference or part thereof (e.g., autosomes, a subset of chromosomes, a single chromosome, or reads thereof). Bias frequencies can be determined for some or all local genome bias estimates of a sample or reference. In some embodiments bias frequencies can be determined for local genome bias estimates for some or all sequence reads of a test sample.

In some embodiments a system comprises a bias density module 6. A bias density module can accept, retrieve and/or store mapped sequence reads 5 and reference sequences 2 in any suitable format and generate local genome bias estimates, local genome bias distributions, bias frequencies, GC densities, GC density distributions and/or GC density frequencies (collectively represented by box 7). In some embodiments a bias density module transfers data and/or information (e.g., 7) to another suitable module (e.g., a relationship module 8).

Relationships

In some embodiments one or more relationships are generated between local genome bias estimates and bias frequencies. The term "relationship" as use herein refers to a mathematical and/or a graphical relationship between two or more variables or values. A relationship can be generated by a suitable mathematical and/or graphical process. Non-limiting examples of a relationship include a mathematical and/or graphical representation of a function, a correlation, a distribution, a linear or non-linear equation, a line, a regression, a fitted regression, the like or a combination thereof. Sometimes a relationship comprises a fitted relationship. In some embodiments a fitted relationship comprises a fitted regression. Sometimes a relationship comprises two or more variables or values that are weighted. In some embodiments a relationship comprise a fitted regression where one or more variables or values of the relationship a weighted. Sometimes a regression is fitted in a weighted fashion. Sometimes a regression is fitted without weighting. In certain embodiments, generating a relationship comprises plotting or graphing.

In some embodiments a suitable relationship is determined between local genome bias estimates and bias frequencies. In some embodiments generating a relationship between (i) local genome bias estimates and (ii) bias frequencies for a sample provides a sample bias relationship. In some embodiments generating a relationship between (i) local genome bias estimates and (ii) bias frequencies for a reference provides a reference bias relationship. In certain embodiments, a relationship is generated between GC densities and GC density frequencies. In some embodiments generating a relationship between (i) GC densities and (ii) GC density frequencies for a sample provides a sample GC density relationship. In some embodiments generating a relationship between (i) GC densities and (ii) GC density frequencies for a reference provides a reference GC density relationship. In some embodiments, where local genome bias estimates are GC densities, a sample bias relationship is a sample GC density relationship and a reference bias relationship is a reference GC density relationship. GC densities of a reference GC density relationship and/or a sample GC density relationship are often representations (e.g., mathematical or quantitative representation) of local GC content. In some embodiments a relationship between local genome bias estimates and bias frequencies comprises a distribution. In some embodiments a relationship between local genome bias estimates and bias frequencies comprises a fitted relationship (e.g., a fitted regression). In some embodiments a relationship between local genome bias estimates and bias frequencies comprises a fitted linear or non-linear regression (e.g., a polynomial regression). In certain embodiments a relationship between local genome bias estimates and bias frequencies comprises a weighted relationship where local genome bias estimates and/or bias frequencies are weighted by a suitable process. In some embodiments a weighted fitted relationship (e.g., a weighted fitting) can be obtained by a process comprising a quantile regression, parameterized distributions or an empirical distribution with interpolation. In certain embodiments a relationship between local genome bias estimates and bias frequencies for a test sample, a reference or part thereof, comprises a polynomial regression where local genome bias estimates are weighted. In some embodiments a weighed fitted model comprises weighting values of a distribution. Values of a distribution can be weighted by a suitable process. In some embodiments, values located near tails of a distribution are provided less weight than values closer to the median of the distribution. For example, for a distribution between local genome bias estimates (e.g., GC densities) and bias frequencies (e.g., GC density frequencies), a weight is determined according to the bias frequency for a given local genome bias estimate, where local genome bias estimates comprising bias frequencies closer to the mean of a distribution are provided greater weight than local genome bias estimates comprising bias frequencies further from the mean.

In some embodiments a system comprises a relationship module 8. A relationship module can generate relationships as well as functions, coefficients, constants and variables that define a relationship. A relationship module can accept, store and/or retrieve data and/or information (e.g., 7) from a suitable module (e.g., a bias density module 6) and generate a relationship. A relationship module often generates and compares distributions of local genome bias estimates. A relationship module can compare data sets and sometimes generate regressions and/or fitted relationships. In some embodiments a relationship module compares one or more distributions (e.g., distributions of local genome bias estimates of samples and/or references) and provides weighting factors and/or weighting assignments 9 for counts of sequence reads to another suitable module (e.g., a bias correction module). Sometimes a relationship module provides normalized counts of sequence reads directly to a distribution module 21 where the counts are normalized according to a relationship and/or a comparison.

Generating a Comparison and Use Thereof

In some embodiments a process for reducing local bias in sequence reads comprises normalizing counts of sequence reads. Counts of sequence reads are often normalized according to a comparison of a test sample to a reference. For example, sometimes counts of sequence reads are normalized by comparing local genome bias estimates of sequence reads of a test sample to local genome bias estimates of a reference (e.g., a reference genome, or part thereof). In some embodiments counts of sequence reads are normalized by comparing bias frequencies of local genome bias estimates of a test sample to bias frequencies of local genome bias estimates of a reference. In some embodiments counts of sequence reads are normalized by comparing a sample bias relationship and a reference bias relationship, thereby generating a comparison.

Counts of sequence reads are often normalized according to a comparison of two or more relationships. In certain embodiments two or more relationships are compared thereby providing a comparison that is used for reducing local bias in sequence reads (e.g., normalizing counts). Two or more relationships can be compared by a suitable method. In some embodiments a comparison comprises adding, subtracting, multiplying and/or dividing a first relationship from a second relationship. In certain embodiments comparing two or more relationships comprises a use of a suitable linear regression and/or a non-linear regression. In certain embodiments comparing two or more relationships comprises a suitable polynomial regression (e.g., a 3rd order polynomial regression). In some embodiments a comparison comprises adding, subtracting, multiplying and/or dividing a first regression from a second regression. In some embodiments two or more relationships are compared by a process comprising an inferential framework of multiple regressions. In some embodiments two or more relationships are compared by a process comprising a suitable multivariate analysis. In some embodiments two or more relationships are compared by a process comprising a basis function (e.g., a blending function, e.g., polynomial bases, Fourier bases, or the like), splines, a radial basis function and/or wavelets.

Figure 36:
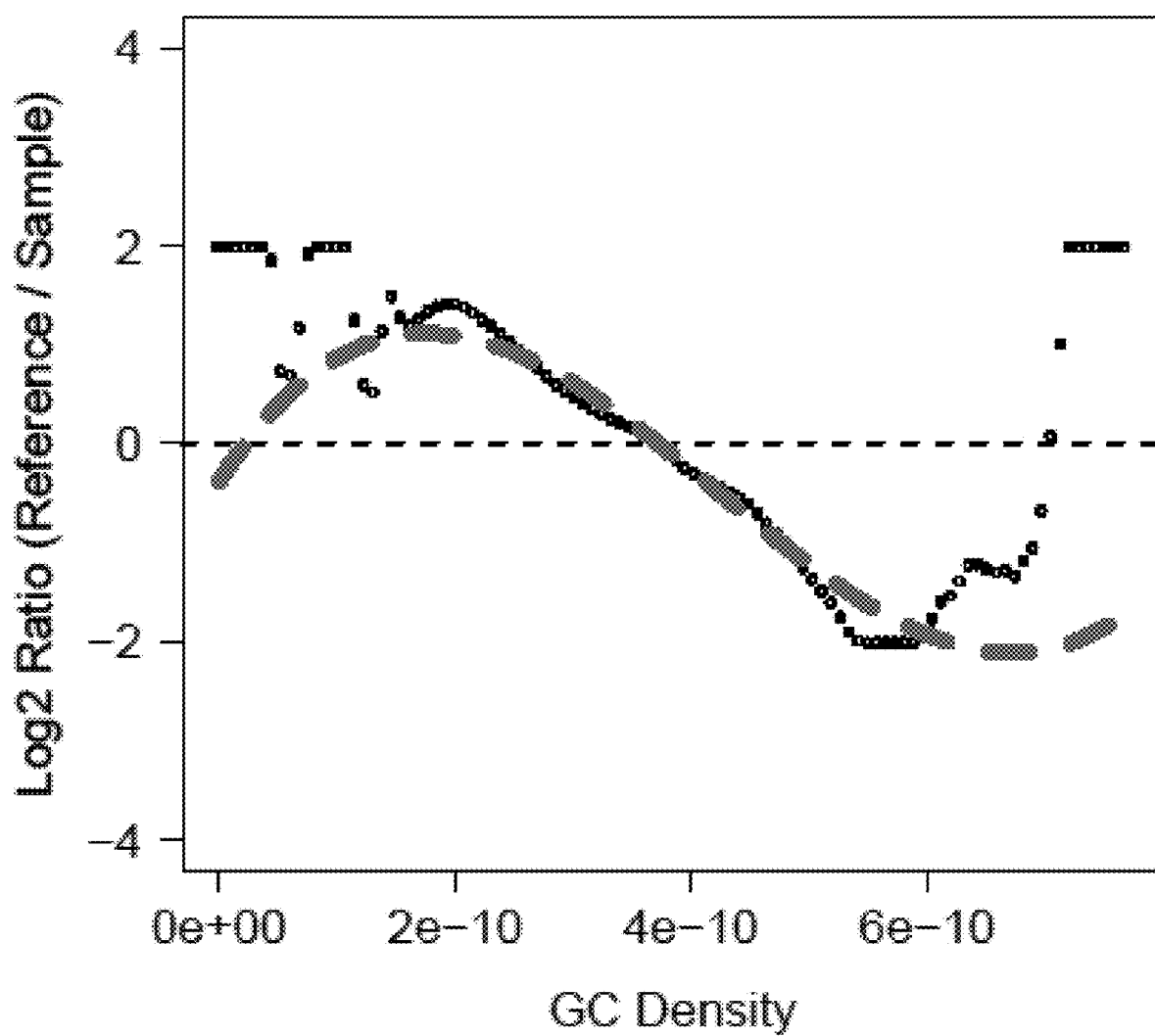
FIG. 36 shows a comparison of a distribution of GC density estimates for a reference genome and GC density estimates of sequence reads for a sample using a weighted $3^{rd}$ order polynomial fitted relationship. GC density estimates (x-axis) were normalized across an entire genome. GC density frequencies are represented on the y-axis as a log 2 ratio of density frequencies of the reference divided by those of the sample

In certain embodiments a distribution of local genome bias estimates comprising bias frequencies for a test sample and a reference is compared by a process comprising a polynomial regression where local genome bias estimates are weighted. In some embodiments a polynomial regression is generated between (i) ratios, each of which ratios comprises bias frequencies of local genome bias estimates of a reference and bias frequencies of local genome bias estimates of a sample and (ii) local genome bias estimates. In some embodiments a polynomial regression is generated between (i) a ratio of bias frequencies of local genome bias estimates of a reference to bias frequencies of local genome bias estimates of a sample and (ii) local genome bias estimates. In some embodiments a comparison of a distribution of local genome bias estimates for reads of a test sample and a reference comprises determining a log ratio (e.g., a log 2 ratio) of bias frequencies of local genome bias estimates for the reference and the sample. In some embodiments a comparison of a distribution of local genome bias estimates comprises dividing a log ratio (e.g., a log 2 ratio)

of bias frequencies of local genome bias estimates for the reference by a log ratio (e.g., a log 2 ratio) of bias frequencies of local genome bias estimates for the sample (e.g., see Example 7 and FIG. 36).

Normalizing counts according to a comparison typically adjusts some counts and not others. Normalizing counts sometimes adjusts all counts and sometimes does not adjust any counts of sequence reads. A count for a sequence read sometimes is normalized by a process that comprises determining a weighting factor and sometimes the process does not include directly generating and utilizing a weighting factor. Normalizing counts according to a comparison sometimes comprises determining a weighting factor for each count of a sequence read. A weighting factor is often specific to a sequence read and is applied to a count of a specific sequence read. A weighting factor is often determined according to a comparison of two or more bias relationships (e.g., a sample bias relationship compared to a reference bias relationship). A normalized count is often determined by adjusting a count value according to a weighting factor. Adjusting a count according to a weighting factor sometimes includes adding, subtracting, multiplying and/or dividing a count for a sequence read by a weighting factor. A weighting factor and/or a normalized count is sometimes determined from a regression (e.g., a regression line). A normalized count is sometimes obtained directly from a regression line (e.g., a fitted regression line) resulting from a comparison between bias frequencies of local genome bias estimates of a reference (e.g., a reference genome) and a test sample. In some embodiments each count of a read of a sample is provided a normalized count value according to a comparison of (i) bias frequencies of a local genome bias estimates of reads compared to (ii) bias frequencies of a local genome bias estimates of a reference. In certain embodiments, counts of sequence reads obtained for a sample are normalized and bias in the sequence reads is reduced.

Sometimes a system comprises a bias correction module 10. In some embodiments, functions of a bias correction module are performed by a relationship modeling module 8. A bias correction module can accept, retrieve, and/or store mapped sequence reads and weighting factors (e.g., 9) from a suitable module (e.g., a relationship module 8, a compression module 4). In some embodiments a bias correction module provides a count to mapped reads. In some embodiments a bias correction module applies weighting assignments and/or bias correction factors to counts of sequence reads thereby providing normalized and/or adjusted counts. A bias correction module often provides normalized counts to a another suitable module (e.g., a distribution module 21).

In certain embodiments normalizing counts comprises factoring one or more features in addition to GC density, and normalizing counts of the sequence reads. In certain embodiments normalizing counts comprises factoring one or more different local genome bias estimates, and normalizing counts of the sequence reads. In certain embodiments counts of sequence reads are weighted according to a weighting determined according to one or more features (e.g., one or more biases). In some embodiments counts are normalized according to one or more combined weights. Sometimes factoring one or more features and/or normalizing counts according to one or more combined weights is by a process comprising use of a multivariate model. Any suitable multivariate model can be used to normalize counts. Non-limiting examples of a multivariate model include a multivariate linear regression, multivariate quantile regression, a multivariate interpolation of empirical data, a non-linear multivariate model, the like, or a combination thereof.

In some embodiments a system comprises a multivariate correction module 13. A multivariate correction module can perform functions of a bias density module 6, relationship module 8 and/or a bias correction module 10 multiple times thereby adjusting counts for multiple biases. In some embodiments a multivariate correction module comprises one or more bias density modules 6, relationship modules 8 and/or bias correction modules 10. Sometimes a multivariate correction module provides normalized counts 11 to another suitable module (e.g., a distribution module 21).

Weighted Portions

In some embodiments portions are weighted. In some embodiments one or more portions are weighted thereby providing weighted portions. Weighting portions sometimes removes portion dependencies. Portions can be weighted by a suitable process. In some embodiments one or more portions are weighted by an eigen function (e.g., an eigenfunction). In some embodiments an eigen function comprises replacing portions with orthogonal eigen-portions. In some embodiments a system comprises a portion weighting module 42. In some embodiments a weighting module accepts, retrieves and/or stores read densities, read density profiles, and/or adjusted read density profiles. In some embodiments weighted portions are provided by a portion weighting module. In some embodiments, a weighting module is required to weight portions. A weighting module can weight portions by one or more weighting methods known in the art or described herein. A weighting module often provides weighted portions to another suitable module (e.g., a scoring module 46, a PCA statistics module 33, a profile generation module 26 and the like).

Principal Component Analysis

Figure 38A:
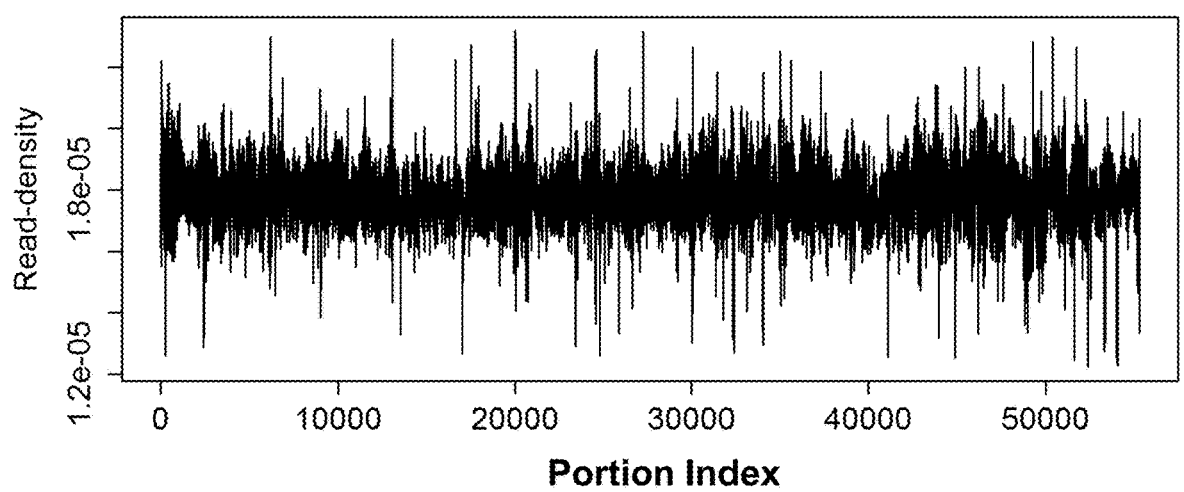
FIG. 38A shows a read density profile of a sample for a genome comprising median read densities (y-axis, e.g., read density/portion) and relative positions of each genomic portion (x-axis, portion index) within a genome.
Figure 38B:
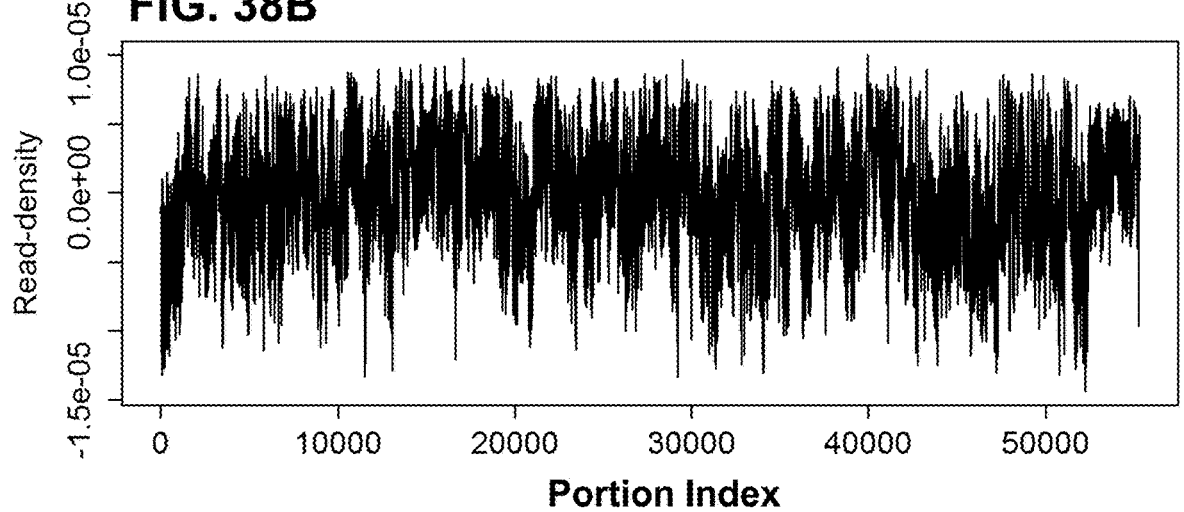
FIG. 38B shows a first principal component (PC1) and FIG. 38C shows a second principal component (PC2) obtained from a principal component analysis of read density profiles obtained from a training set of 500 euploids.
Figure 38C:
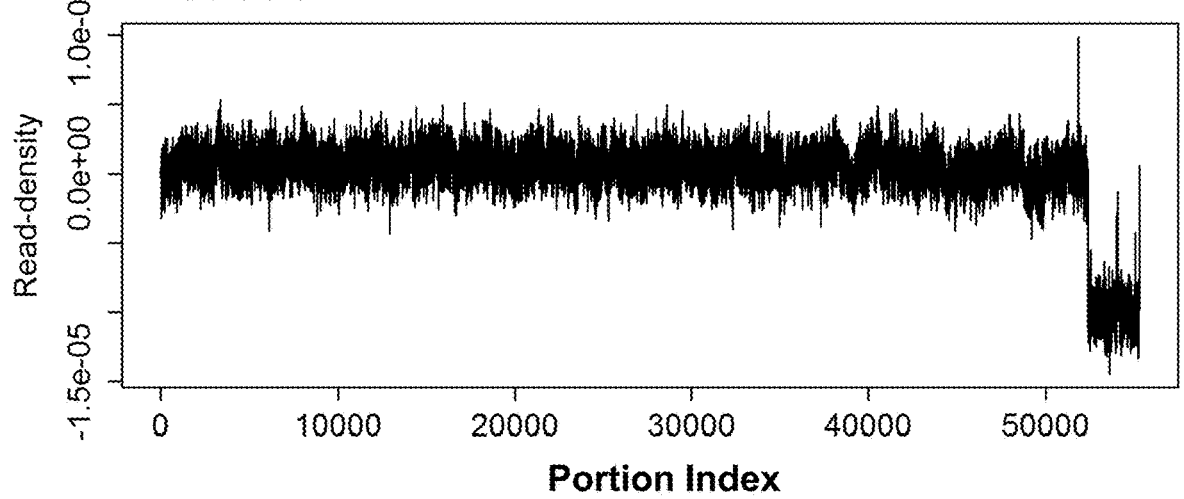

In some embodiments a read density profile (e.g., a read density profile of a test sample (e.g., FIG. 39A) is adjusted according to a principal component analysis (PCA). A read density profile of one or more reference samples and/or a read density profile of a test subject can be adjusted according to a PCA. Removing bias from a read density profile by a PCA related process is sometimes referred to herein as adjusting a profile. A PCA can be performed by a suitable PCA method, or a variation thereof. Non-limiting examples of a PCA method include a canonical correlation analysis (CCA), a Karhunen-Loève transform (KLT), a Hotelling transform, a proper orthogonal decomposition (POD), a singular value decomposition (SVD) of X, an eigenvalue decomposition (EVD) of XTX, a factor analysis, an Eckart-Young theorem, a Schmidt-Mirsky theorem, empirical orthogonal functions (EOF), an empirical eigenfunction decomposition, an empirical component analysis, quasiharmonic modes, a spectral decomposition, an empirical modal analysis, the like, variations or combinations thereof. A PCA often identifies one or more biases in a read density profile. A bias identified by a PCA is sometimes referred to herein as a principal component. In some embodiments one or more biases can be removed by adjusting a read density profile according to one or more principal component using a suitable method. A read density profile can be adjusted by adding, subtracting, multiplying and/or dividing one or more principal components from a read density profile. In some embodiments one or more biases can be removed from a read density profile by subtracting one or more principal components from a read density profile. Although bias in a read density profile is often identified and/or quantitated by a PCA of a profile, principal components are often subtracted from a profile at the level of read densities. A PCA often identifies one or more principal components. In some embodiments a PCA identifies a $1^{st}$, $2^{nd}$, $3^{rd}$, $4^{th}$, $5^{th}$, $6^{th}$, $7^{th}$, 8th, 9th, and a 10th or more principal components. In certain embodiments 1, 2, 3, 4, 5, 6, 7, 8, 9, 10 or more principal components are used to adjust a profile. Often, principal components are used to adjust a profile in the order of there appearance in a PCA. For example, where three principal components are subtracted from a read density profile, a 1st, 2nd and 3rd principal component are used. Sometimes a bias identified by a principal component comprises a feature of a profile that is not used to adjust a profile. For example, a PCA may identify a genetic variation (e.g., an aneuploidy, microduplication, microdeletion, deletion, translocation, insertion) and/or a gender difference (e.g., as seen in FIG. 38C) as a principal component. Thus, in some embodiments, one or more principal components are not used to adjust a profile. For example, sometimes a 1st 2nd and 4th principal component are used to adjust a profile where a 3rd principal component is not used to adjust a profile. A principal component can be obtained from a PCA using any suitable sample or reference. In some embodiments principal components are obtained from a test sample (e.g., a test subject). In some embodiments principal components are obtained from one or more references (e.g., reference samples, reference sequences, a reference set). As shown, for example, in FIGS. 38A-C a PCA is performed on a median read density profile obtained from a training set (FIG. 38A) comprising multiple samples resulting in the identification of a 1st principal component (FIG. 38B) and a second principal component (FIG. 38C). In some embodiments principal components are obtained from a set of subjects known to be devoid of a genetic variation in question. In some embodiments principal components are obtained from a set of known euploids. Principal component are often identified according to a PCA performed using one or more read density profiles of a reference (e.g., a training set). One or more principal components obtained from a reference are often subtracted from a read density profile of a test subject (e.g., FIG. 39B) thereby providing an adjusted profile (e.g., FIG. 39C).

In some embodiments a system comprises a PCA statistics module 33. A PCA statistics module can accepts and/or retrieve read density profiles from another suitable module (e.g., a profile generation module 26). A PCA is often performed by a PCA statistics module. A PCA statistics module often accepts, retrieves and/or stores read density profiles and processes read density profiles from a reference set 32, training set 30 and/or from one or more test subjects 28. A PCA statistics module can generate and/or provide principal components and/or adjust read density profiles according to one or more principal components. Adjusted read density profiles (e.g., 40, 38) are often provided by a PCA statistics module. A PCA statistics module can provide and/or transfer adjusted read density profiles (e.g., 38, 40) to another suitable module (e.g., a portion weighting module 42, a scoring module 46). In some embodiments a PCA statistics module can provide a gender call 36. A gender call is sometimes a determination of fetal gender determined according to a PCA and/or according to one or more principal components. In some embodiments a PCA statistics module comprises some, all or a modification of the R code shown below. An R code for computing principal components generally starts with cleaning the data (e.g., subtracting median, filtering portions, and trimming extreme values):

```
#Clean the data outliers for PCA
dclean <- (dat - m)[mask,]
for (j in 1:ncol(dclean))
{
q <- quantile(dclean[,j],c(.25,.75))
qmin <- q[1] - 4*(q[2]-q[1])
qmax <- q[2] + 4*(q[2]-q[1])
dclean[dclean[, j] < qmin,j] <- qmin
dclean[dclean[, j] > qmax,j] <- qmax
}
Then the principal components are computed:
#Compute principal components
pc <- prcomp(dclean)$x
Finally, each sample's PCA-adjusted profile can be computed with:
#Compute residuals
mm <- model.matrix(~pc[,1:numpc])
for (j in 1:ncol(dclean))
dclean[,j] <- dclean[,j] - predict(lm(dclean[,j]~mm))
```

Comparing Profiles

In some embodiments, determining an outcome comprises a comparison. In certain embodiments, a read density profile, or a portion thereof, is utilized to provide an outcome. In some embodiments determining an outcome (e.g., a determination of the presence or absence of a genetic variation) comprises a comparison of two or more read density profiles. Comparing read density profiles often comprises comparing read density profiles generated for a selected segment of a genome. For example, a test profile is often compared to a reference profile where the test and reference profiles were determined for a segment of a genome (e.g., a reference genome) that is substantially the same segment. Comparing read density profiles sometimes comprises comparing two or more subsets of portions of a read density profile. A subset of portions of a read density profile may represent a segment of a genome (e.g., a chromosome, or segment thereof). A read density profile can comprise any amount of subsets of portions. Sometimes a read density profile comprises two or more, three or more, four or more, or five or more subsets. In certain embodiments a read density profile comprises two subsets of portions where each portion represents segments of a reference genome that are adjacent. In some embodiments a test profile can be compared to a reference profile where the test profile and reference profile both comprise a first subset of portions and a second subset of portions where the first and second subsets represent different segments of a genome. Some subsets of portions of a read density profile may comprise genetic variations and other subsets of portions are sometimes substantially free of genetic variations. Sometimes all subsets of portions of a profile (e.g., a test profile) are substantially free of a genetic variation. Sometimes all subsets of portions of a profile (e.g., a test profile) comprise a genetic variation. In some embodiments a test profile can comprise a first subset of portions that comprise a genetic variation and a second subset of portions that are substantially free of a genetic variation.

In some embodiments methods described herein comprise preforming a comparison (e.g., comparing a test profile to a reference profile). Two or more data sets, two or more relationships and/or two or more profiles can be compared by a suitable method. Non-limiting examples of statistical methods suitable for comparing data sets, relationships and/or profiles include Behrens-Fisher approach, bootstrapping, Fisher's method for combining independent tests of significance, Neyman-Pearson testing, confirmatory data analysis, exploratory data analysis, exact test, F-test, Z-test, T-test, calculating and/or comparing a measure of uncertainty, a null hypothesis, counternulls and the like, a chi-square test, omnibus test, calculating and/or comparing level of significance (e.g., statistical significance), a meta analysis, a multivariate analysis, a regression, simple linear regression, robust linear regression, the like or combinations of the foregoing. In certain embodiments comparing two or more data sets, relationships and/or profiles comprises determining and/or comparing a measure of uncertainty. A "measure of uncertainty" as used herein refers to a measure of significance (e.g., statistical significance), a measure of error, a measure of variance, a measure of confidence, the like or a combination thereof. A measure of uncertainty can be a value (e.g., a threshold) or a range of values (e.g., an interval, a confidence interval, a Bayesian confidence interval, a threshold range). Non-limiting examples of a measure of uncertainty include p-values, a suitable measure of deviation (e.g., standard deviation, sigma, absolute deviation, mean absolute deviation, the like), a suitable measure of error (e.g., standard error, mean squared error, root mean squared error, the like), a suitable measure of variance, a suitable standard score (e.g., standard deviations, cumulative percentages, percentile equivalents, Z-scores, T-scores, R-scores, standard nine (stanine), percent in stanine, the like), the like or combinations thereof. In some embodiments determining the level of significance comprises determining a measure of uncertainty (e.g., a p-value). In certain embodiments, two or more data sets, relationships and/or profiles can be analyzed and/or compared by utilizing multiple (e.g., 2 or more) statistical methods (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or any suitable mathematical and/or statistical manipulations (e.g., referred to herein as manipulations).

In certain embodiments comparing two or more read density profiles comprises determining and/or comparing a measure of uncertainty for two or more read density profiles. Read density profiles and/or associated measures of uncertainty are sometimes compared to facilitate interpretation of mathematical and/or statistical manipulations of a data set and/or to provide an outcome. A read density profile generated for a test subject sometimes is compared to a read density profile generated for one or more references (e.g., reference samples, reference subjects, and the like). In some embodiments an outcome is provided by comparing a read density profile from a test subject to a read density profile from a reference for a chromosome, portions or segments thereof, where a reference read density profile is obtained from a set of reference subjects known not to possess a genetic variation (e.g., a reference). In some embodiments an outcome is provided by comparing a read density profile from a test subject to a read density profile from a reference for a chromosome, portions or segments thereof, where a reference read density profile is obtained from a set of reference subjects known to possess a specific genetic variation (e.g., a chromosome aneuploidy, a trisomy, a microduplication, a microdeletion).

In certain embodiments, a read density profile of a test subject is compared to a predetermined value representative of the absence of a genetic variation, and sometimes deviates from a predetermined value at one or more genomic locations (e.g., portions) corresponding to a genomic location in which a genetic variation is located. For example, in test subjects (e.g., subjects at risk for, or suffering from a medical condition associated with a genetic variation), read density profiles are expected to differ significantly from read density profiles of a reference (e.g., a reference sequence, reference subject, reference set) for selected portions when a test subject comprises a genetic variation in question. Read density profiles of a test subject are often substantially the same as read density profiles of a reference (e.g., a reference sequence, reference subject, reference set) for selected portions when a test subject does not comprise a genetic variation in question. Read density profiles are often compared to a predetermined threshold and/or threshold range (e.g., see FIG. 40). The term "threshold" as used herein refers to any number that is calculated using a qualifying data set and serves as a limit of diagnosis of a genetic variation (e.g., a copy number variation, an aneuploidy, a chromosomal aberration, a microduplication, a microdeletion, and the like). In certain embodiments a threshold is exceeded by results obtained by methods described herein and a subject is diagnosed with a genetic variation (e.g., a trisomy). In some embodiments a threshold value or range of values often is calculated by mathematically and/or statistically manipulating sequence read data (e.g., from a reference and/or subject). A predetermined threshold or threshold range of values indicative of the presence or absence of a genetic variation can vary while still providing an outcome useful for determining the presence or absence of a genetic variation. In certain embodiments, a read density profile comprising normalized read densities and/or normalized counts is generated to facilitate classification and/or providing an outcome. An outcome can be provided based on a plot of a read density profile comprising normalized counts (e.g., using a plot of such a read density profile).

In some embodiments a system comprises a scoring module 46. A scoring module can accept, retrieve and/or store read density profiles (e.g., adjusted, normalized read density profiles) from another suitable module (e.g., a profile generation module 26, a PCA statistics module 33, a portion weighting module 42, and the like). A scoring module can accept, retrieve, store and/or compare two or more read density profiles (e.g., test profiles, reference profiles, training sets, test subjects). A scoring module can often provide a score (e.g., a plot, profile statistics, a comparison (e.g., a difference between two or more profiles), a Z-score, a measure of uncertainty, a call zone, a sample call 50 (e.g., a determination of the presence or absence of a genetic variation), and/or an outcome). A scoring module can provide a score to an end user and/or to another suitable module (e.g., a display, printer, the like). In some embodiments a scoring module comprises some, all or a modification of the R code shown below which comprises an R function for computing Chi-square statistics for a specific test (e.g., High-chr21 counts).

The three parameters are:

x=sample read data (portion x sample)

m=median values for portions y=test vector (Ex. False for all portions except True for chr21)

```
getChisqP <- function(x,m,y)
{
ahigh <- apply(x[!y,],2,function(x) sum((x>m[!y])))
alow <- sum((!y))-ahigh
bhigh <- apply(x[y,],2,function(x) sum((x>m[y])))
blow <- sum(y)-bhigh
```

```
p <- sapply(1:length(ahigh), function(i) {
p <- chisq.test(matrix(c(ahigh[i],alow[i],bhigh[i],blow[i]),2))$p.value/2
if (ahigh[i]/alow[i]> bhigh[i]/blow[i]) p <- max(p,1-p)
else p <- min(p,1-p); p})
return(p)
```

Hybrid Regression Normalization

In some embodiments a hybrid normalization method is used. In some embodiments a hybrid normalization method reduces bias (e.g., GC bias). A hybrid normalization, in some embodiments, comprises (i) an analysis of a relationship of two variables (e.g., counts and GC content) and (ii) selection and application of a normalization method according to the analysis. A hybrid normalization, in certain embodiments, comprises (i) a regression (e.g., a regression analysis) and (ii) selection and application of a normalization method according to the regression. In some embodiments counts obtained for a first sample (e.g., a first set of samples) are normalized by a different method than counts obtained from another sample (e.g., a second set of samples). In some embodiments counts obtained for a first sample (e.g., a first set of samples) are normalized by a first normalization method and counts obtained from a second sample (e.g., a second set of samples) are normalized by a second normalization method. For example, in certain embodiments a first normalization method comprises use of a linear regression and a second normalization method comprises use of a non-linear regression (e.g., a LOESS, GC-LOESS, LOWESS regression, LOESS smoothing).

In some embodiments a hybrid normalization method is used to normalize sequence reads mapped to portions of a genome or chromosome (e.g., counts, mapped counts, mapped reads). In certain embodiments raw counts are normalized and in some embodiments adjusted, weighted, filtered or previously normalized counts are normalized by a hybrid normalization method. In certain embodiments, genomic section levels or Z-scores are normalized. In some embodiments counts mapped to selected portions of a genome or chromosome are normalized by a hybrid normalization approach. Counts can refer to a suitable measure of sequence reads mapped to portions of a genome, non-limiting examples of which include raw counts (e.g., unprocessed counts), normalized counts (e.g., normalized by PERUN, ChAI or a suitable method), portion levels (e.g., average levels, mean levels, median levels, or the like), Z-scores, the like, or combinations thereof. The counts can be raw counts or processed counts from one or more samples (e.g., a test sample, a sample from a pregnant female). In some embodiments counts are obtained from one or more samples obtained from one or more subjects.

In some embodiments a normalization method (e.g., the type of normalization method) is selected according to a regression (e.g., a regression analysis) and/or a correlation coefficient. A regression analysis refers to a statistical technique for estimating a relationship among variables (e.g., counts and GC content). In some embodiments a regression is generated according to counts and a measure of GC content for each portion of multiple portions of a reference genome. A suitable measure of GC content can be used, non-limiting examples of which include a measure of guanine, cytosine, adenine, thymine, purine (GC), or pyrimidine (AT or ATU) content, melting temperature ($T_m$) (e.g., denaturation temperature, annealing temperature, hybridization temperature), a measure of free energy, the like or combinations thereof. A measure of guanine (G), cytosine (C), adenine (A), thymine (T), purine (GC), or pyrimidine (AT or ATU) content can be expressed as a ratio or a percentage. In some embodiments any suitable ratio or percentage is used, non-limiting examples of which include GC/AT, GC/total nucleotide, GC/A, GC/T, AT/total nucleotide, AT/GC, AT/G, AT/C, G/A, C/A, G/T, G/A, G/AT, C/T, the like or combinations thereof. In some embodiments a measure of GC content is a ratio or percentage of GC to total nucleotide content. In some embodiments a measure of GC content is a ratio or percentage of GC to total nucleotide content for sequence reads mapped to a portion of reference genome. In certain embodiments the GC content is determined according to and/or from sequence reads mapped to each portion of a reference genome and the sequence reads are obtained from a sample (e.g., a sample obtained from a pregnant female). In some embodiments a measure of GC content is not determined according to and/or from sequence reads. In certain embodiments, a measure of GC content is determined for one or more samples obtained from one or more subjects.

In some embodiments generating a regression comprises generating a regression analysis or a correlation analysis. A suitable regression can be used, non-limiting examples of which include a regression analysis, (e.g., a linear regression analysis), a goodness of fit analysis, a Pearson's correlation analysis, a rank correlation, a fraction of variance unexplained, Nash-Sutcliffe model efficiency analysis, regression model validation, proportional reduction in loss, root mean square deviation, the like or a combination thereof. In some embodiments a regression line is generated. In certain embodiments generating a regression comprises generating a linear regression. In certain embodiments generating a regression comprises generating a non-linear regression (e.g., an LOESS regression, an LOWESS regression).

In some embodiments a regression determines the presence or absence of a correlation (e.g., a linear correlation), for example between counts and a measure of GC content. In some embodiments a regression (e.g., a linear regression) is generated and a correlation coefficient is determined. In some embodiments a suitable correlation coefficient is determined, non-limiting examples of which include a coefficient of determination, an $R^2$ value, a Pearson's correlation coefficient, or the like.

In some embodiments goodness of fit is determined for a regression (e.g., a regression analysis, a linear regression). Goodness of fit sometimes is determined by visual or mathematical analysis. An assessment sometimes includes determining whether the goodness of fit is greater for a non-linear regression or for a linear regression. In some embodiments a correlation coefficient is a measure of a goodness of fit. In some embodiments an assessment of a goodness of fit for a regression is determined according to a correlation coefficient and/or a correlation coefficient cutoff value. In some embodiments an assessment of a goodness of fit comprises comparing a correlation coefficient to a correlation coefficient cutoff value. In some embodiments an assessment of a goodness of fit for a regression is indicative of a linear regression. For example, in certain embodiments, a goodness of fit is greater for a linear regression than for a non-linear regression and the assessment of the goodness of fit is indicative of a linear regression. In some embodiments an assessment is indicative of a linear regression and a linear regression is used to normalized the counts. In some embodiments an assessment of a goodness of fit for a regression is indicative of a non-linear regression. For example, in certain embodiments, a goodness of fit is greater for a non-linear regression than for a linear regression and the assessment of the goodness of fit is indicative of a non-linear regression. In some embodiments an assessment is indicative of a non-linear regression and a non-linear regression is used to normalized the counts.

In some embodiments an assessment of a goodness of fit is indicative of a linear regression when a correlation coefficient is equal to or greater than a correlation coefficient cutoff. In some embodiments an assessment of a goodness of fit is indicative of a non-linear regression when a correlation coefficient is less than a correlation coefficient cutoff. In some embodiments a correlation coefficient cutoff is pre-determined. In some embodiments a correlation coefficient cut-off is about 0.5 or greater, about 0.55 or greater, about 0.6 or greater, about 0.65 or greater, about 0.7 or greater, about 0.75 or greater, about 0.8 or greater or about 0.85 or greater.

For example, in certain embodiments, a normalization method comprising a linear regression is used when a correlation coefficient is equal to or greater than about 0.6. In certain embodiments, counts of a sample (e.g., counts per portion of a reference genome, counts per portion) are normalized according to a linear regression when a correlation coefficient is equal to or greater than a correlation coefficient cut-off of 0.6, otherwise the counts are normalized according to a non-linear regression (e.g., when the coefficient is less than a correlation coefficient cut-off of 0.6). In some embodiments a normalization process comprises generating a linear regression or non-linear regression for the (i) the counts and (ii) the GC content, for each portion of multiple portions of a reference genome. In certain embodiments, a normalization method comprising a non-linear regression (e.g., a LOWESS, a LOESS) is used when a correlation coefficient is less than a correlation coefficient cut-off of 0.6. In some embodiments a normalization method comprising a non-linear regression (e.g., a LOWESS) is used when a correlation coefficient (e.g., a correlation coefficient) is less than a correlation coefficient cut-off of about 0.7, less than about 0.65, less than about 0.6, less than about 0.55 or less than about 0.5. For example, in some embodiments a normalization method comprising a non-linear regression (e.g., a LOWESS, a LOESS) is used when a correlation coefficient is less than a correlation coefficient cut-off of about 0.6.

In some embodiments a specific type of regression is selected (e.g., a linear or non-linear regression) and, after the regression is generated, counts are normalized by subtracting the regression from the counts. In some embodiments subtracting a regression from the counts provides normalized counts with reduced bias (e.g., GC bias). In some embodiments a linear regression is subtracted from the counts. In some embodiments a non-linear regression (e.g., a LOESS, GC-LOESS, LOWESS regression) is subtracted from the counts. Any suitable method can be used to subtract a regression line from the counts. For example, if counts x are derived from portion i (e.g., a portion i) comprising a GC content of 0.5 and a regression line determines counts y at a GC content of 0.5, then x-y=normalized counts for portion i. In some embodiments counts are normalized prior to and/or after subtracting a regression. In some embodiments, counts normalized by a hybrid normalization approach are used to generate genomic section levels, Z-cores, levels and/or profiles of a genome or a segment thereof. In certain embodiments, counts normalized by a hybrid normalization approach are analyzed by methods described herein to determine the presence or absence of a genetic variation (e.g., in a fetus).

In some embodiments a hybrid normalization method comprises filtering or weighting one or more portions before or after normalization. A suitable method of filtering portions, including methods of filtering portions (e.g., portions of a reference genome) described herein can be used. In some embodiments, portions (e.g., portions of a reference genome) are filtered prior to applying a hybrid normalization method. In some embodiments, only counts of sequencing reads mapped to selected portions (e.g., portions selected according to count variability) are normalized by a hybrid normalization. In some embodiments counts of sequencing reads mapped to filtered portions of a reference genome (e.g., portions filtered according to count variability) are removed prior to utilizing a hybrid normalization method. In some embodiments a hybrid normalization method comprises selecting or filtering portions (e.g., portions of a reference genome) according to a suitable method (e.g., a method described herein). In some embodiments a hybrid normalization method comprises selecting or filtering portions (e.g., portions of a reference genome) according to an uncertainty value for counts mapped to each of the portions for multiple test samples. In some embodiments a hybrid normalization method comprises selecting or filtering portions (e.g., portions of a reference genome) according to count variability. In some embodiments a hybrid normalization method comprises selecting or filtering portions (e.g., portions of a reference genome) according to GC content, repetitive elements, repetitive sequences, introns, exons, the like or a combination thereof.

For example, in some embodiments multiple samples from multiple pregnant female subjects are analyzed and a subset of portions (e.g., portions of a reference genome) are selected according to count variability. In certain embodiments a linear regression is used to determine a correlation coefficient for (i) counts and (ii) GC content, for each of the selected portions for a sample obtained from a pregnant female subject. In some embodiments a correlation coefficient is determined that is greater than a pre-determined correlation cutoff value (e.g., of about 0.6), an assessment of the goodness of fit is indicative of a linear regression and the counts are normalized by subtracting the linear regression from the counts. In certain embodiments a correlation coefficient is determined that is less than a pre-determined correlation cutoff value (e.g., of about 0.6), an assessment of the goodness of fit is indicative of a non-linear regression, an LOESS regression is generated and the counts are normalized by subtracting the LOESS regression from the counts.

Profiles

In some embodiments, a processing step can comprise generating one or more profiles (e.g., profile plot) from various aspects of a data set or derivation thereof (e.g., product of one or more mathematical and/or statistical data processing steps known in the art and/or described herein). The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a part or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a portion. In certain embodiments, a data point in a profile includes results of data manipulation for groups of portions. In some embodiments, groups of portions may be adjacent to one another, and in certain embodiments, groups of portions may be from different parts of a chromosome or genome.

Data points in a profile derived from a data set can be representative of any suitable data categorization. Non-limiting examples of categories into which data can be grouped to generate profile data points include: portions based on size, portions based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile (e.g., a genomic profile, a chromosome profile, a profile of a segment of a chromosome) often is a collection of normalized or non-normalized counts for two or more portions. A profile often includes at least one level (e.g., a genomic section level), and often comprises two or more levels (e.g., a profile often has multiple levels). A level generally is for a set of portions having about the same counts or normalized counts. Levels are described in greater detail herein. In certain embodiments, a profile comprises one or more portions, which portions can be weighted, removed, filtered, normalized, adjusted, averaged, derived as a mean, added, subtracted, processed or transformed by any combination thereof. A profile often comprises normalized counts mapped to portions defining two or more levels, where the counts are further normalized according to one of the levels by a suitable method. Often counts of a profile (e.g., a profile level) are associated with an uncertainty value.

A profile comprising one or more levels is sometimes padded (e.g., hole padding). Padding (e.g., hole padding) refers to a process of identifying and adjusting levels in a profile that are due to maternal microdeletions or maternal duplications (e.g., copy number variations). In some embodiments levels are padded that are due to fetal microduplications or fetal microdeletions. Microduplications or microdeletions in a profile can, in some embodiments, artificially raise or lower the overall level of a profile (e.g., a profile of a chromosome) leading to false positive or false negative determinations of a chromosome aneuploidy (e.g., a trisomy). In some embodiments levels in a profile that are due to microduplications and/or deletions are identified and adjusted (e.g., padded and/or removed) by a process sometimes referred to as padding or hole padding. In certain embodiments a profile comprises one or more first levels that are significantly different than a second level within the profile, each of the one or more first levels comprise a maternal copy number variation, fetal copy number variation, or a maternal copy number variation and a fetal copy number variation and one or more of the first levels are adjusted.

A profile comprising one or more levels can include a first level and a second level. In some embodiments a first level is different (e.g., significantly different) than a second level. In some embodiments a first level comprises a first set of portions, a second level comprises a second set of portions and the first set of portions is not a subset of the second set of portions. In certain embodiments, a first set of portions is different than a second set of portions from which a first and second level are determined. In some embodiments a profile can have multiple first levels that are different (e.g., significantly different, e.g., have a significantly different value) than a second level within the profile. In some embodiments a profile comprises one or more first levels that are significantly different than a second level within the profile and one or more of the first levels are adjusted. In some embodiments a profile comprises one or more first levels that are significantly different than a second level within the profile, each of the one or more first levels comprise a maternal copy number variation, fetal copy number variation, or a maternal copy number variation and a fetal copy number variation and one or more of the first levels are adjusted. In some embodiments a first level within a profile is removed from the profile or adjusted (e.g., padded). A profile can comprise multiple levels that include one or more first levels significantly different than one or more second levels and often the majority of levels in a profile are second levels, which second levels are about equal to one another. In some embodiments greater than 50%, greater than 60%, greater than 70%, greater than 80%, greater than 90% or greater than 95% of the levels in a profile are second levels.

A profile sometimes is displayed as a plot. For example, one or more levels representing counts (e.g., normalized counts) of portions can be plotted and visualized. Non-limiting examples of profile plots that can be generated include raw count (e.g., raw count profile or raw profile), normalized count, portion-weighted, z-score, p-value, area ratio versus fitted ploidy, median level versus ratio between fitted and measured fetal fraction, principle components, the like, or combinations thereof. Profile plots allow visualization of the manipulated data, in some embodiments. In certain embodiments, a profile plot can be utilized to provide an outcome (e.g., area ratio versus fitted ploidy, median level versus ratio between fitted and measured fetal fraction, principle components). The terms "raw count profile plot" or "raw profile plot" as used herein refer to a plot of counts in each portion in a region normalized to total counts in a region (e.g., genome, portion, chromosome, chromosome portions of a reference genome or a segment of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions (e.g., maternal contribution of nucleic acid (e.g., maternal fraction), fetal contribution of nucleic acid (e.g., fetal fraction), ploidy of reference sample, the like or combinations thereof). In certain embodiments, a test profile often centers around a predetermined value representative of the absence of a genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for a selected portion is expected to vary significantly from the predetermined value for non-affected genomic locations. Depending on starting assumptions (e.g., fixed ploidy or optimized ploidy, fixed fetal fraction or optimized fetal fraction or combinations thereof) the predetermined threshold or cutoff value or threshold range of values indicative of the presence or absence of a genetic variation can vary while still providing an outcome useful for determining the presence or absence of a genetic variation. In some embodiments, a profile is indicative of and/or representative of a phenotype.

By way of a non-limiting example, normalized sample and/or reference count profiles can be obtained from raw sequence read data by (a) calculating reference median counts for selected chromosomes, portions or segments thereof from a set of references known not to carry a genetic variation, (b) removal of uninformative portions from the reference sample raw counts (e.g., filtering); (c) normalizing the reference counts for all remaining portions of a reference genome to the total residual number of counts (e.g., sum of remaining counts after removal of uninformative portions of a reference genome) for the reference sample selected chromosome or selected genomic location, thereby generating a normalized reference subject profile; (d) removing the corresponding portions from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered portions in (b), can be included between (c) and (d).

A data set profile can be generated by one or more manipulations of counted mapped sequence read data. Some embodiments include the following. Sequence reads are mapped and the number of sequence tags mapping to each genomic portion are determined (e.g., counted). A raw count profile is generated from the mapped sequence reads that are counted. An outcome is provided by comparing a raw count profile from a test subject to a reference median count profile for chromosomes, portions or segments thereof from a set of reference subjects known not to possess a genetic variation, in certain embodiments.

In some embodiments, sequence read data is optionally filtered to remove noisy data or uninformative portions. After filtering, the remaining counts typically are summed to generate a filtered data set. A filtered count profile is generated from a filtered data set, in certain embodiments.

After sequence read data have been counted and optionally filtered, data sets can be normalized to generate levels or profiles. A data set can be normalized by normalizing one or more selected portions to a suitable normalizing reference value. In some embodiments, a normalizing reference value is representative of the total counts for the chromosome or chromosomes from which portions are selected. In certain embodiments, a normalizing reference value is representative of one or more corresponding portions, portions of chromosomes or chromosomes from a reference data set prepared from a set of reference subjects known not to possess a genetic variation. In some embodiments, a normalizing reference value is representative of one or more corresponding portions, portions of chromosomes or chromosomes from a test subject data set prepared from a test subject being analyzed for the presence or absence of a genetic variation. In certain embodiments, the normalizing process is performed utilizing a static window approach, and in some embodiments the normalizing process is performed utilizing a moving or sliding window approach. In certain embodiments, a profile comprising normalized counts is generated to facilitate classification and/or providing an outcome. An outcome can be provided based on a plot of a profile comprising normalized counts (e.g., using a plot of such a profile).

Levels

In some embodiments, a value (e.g., a number, a quantitative value) is ascribed to a level. A level can be determined by a suitable method, operation or mathematical process (e.g., a processed level). A level often is, or is derived from, counts (e.g., normalized counts) for a set of portions. In some embodiments a level of a portion is substantially equal to the total number of counts mapped to a portion (e.g., counts, normalized counts). Often a level is determined from counts that are processed, transformed or manipulated by a suitable method, operation or mathematical process known in the art. In some embodiments a level is derived from counts that are processed and non-limiting examples of processed counts include weighted, removed, filtered, normalized, adjusted, averaged, derived as a mean (e.g., mean level), added, subtracted, transformed counts or combination thereof. In some embodiments a level comprises counts that are normalized (e.g., normalized counts of portions). A level can be for counts normalized by a suitable process, non-limiting examples of which include portion-wise normalization, normalization by GC content, linear and nonlinear least squares regression, GC LOESS, LOWESS, PERUN, ChAl, RM, GCRM, cQn, the like and/or combinations thereof. A level can comprise normalized counts or relative amounts of counts. In some embodiments a level is for counts or normalized counts of two or more portions that are averaged and the level is referred to as an average level. In some embodiments a level is for a set of portions having a mean count or mean of normalized counts which is referred to as a mean level. In some embodiments a level is derived for portions that comprise raw and/or filtered counts. In some embodiments, a level is based on counts that are raw. In some embodiments a level is associated with an uncertainty value (e.g., a standard deviation, a MAD). In some embodiments a level is represented by a Z-score or p-value. A level for one or more portions is synonymous with a "genomic section level" herein.

Normalized or non-normalized counts for two or more levels (e.g., two or more levels in a profile) can sometimes be mathematically manipulated (e.g., added, multiplied, averaged, normalized, the like or combination thereof) according to levels. For example, normalized or non-normalized counts for two or more levels can be normalized according to one, some or all of the levels in a profile. In some embodiments normalized or non-normalized counts of all levels in a profile are normalized according to one level in the profile. In some embodiments normalized or non-normalized counts of a first level in a profile are normalized according to normalized or non-normalized counts of a second level in the profile.

Non-limiting examples of a level (e.g., a first level, a second level) are a level for a set of portions comprising processed counts, a level for a set of portions comprising a mean, median or average of counts, a level for a set of portions comprising normalized counts, the like or any combination thereof. In some embodiments, a first level and a second level in a profile are derived from counts of portions mapped to the same chromosome. In some embodiments, a first level and a second level in a profile are derived from counts of portions mapped to different chromosomes.

In some embodiments a level is determined from normalized or non-normalized counts mapped to one or more portions. In some embodiments, a level is determined from normalized or non-normalized counts mapped to two or more portions, where the normalized counts for each portion often are about the same. There can be variation in counts (e.g., normalized counts) in a set of portions for a level. In a set of portions for a level there can be one or more portions having counts that are significantly different than in other portions of the set (e.g., peaks and/or dips). Any suitable number of normalized or non-normalized counts associated with any suitable number of portions can define a level.

In some embodiments one or more levels can be determined from normalized or non-normalized counts of all or some of the portions of a genome. Often a level can be determined from all or some of the normalized or non-normalized counts of a chromosome, or segment thereof. In some embodiments, two or more counts derived from two or more portions (e.g., a set of portions) determine a level. In some embodiments two or more counts (e.g., counts from two or more portions) determine a level. In some embodiments, counts from 2 to about 100,000 portions determine a level. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 portions determine a level. In some embodiments counts from about 10 to about 50 portions determine a level. In some embodiments counts from about 20 to about 40 or more portions determine a level. In some embodiments, a level comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more portions. In some embodiments, a level corresponds to a set of portions (e.g., a set of portions of a reference genome, a set of portions of a chromosome or a set of portions of a segment of a chromosome).

In some embodiments, a level is determined for normalized or non-normalized counts of portions that are contiguous. In some embodiments portions (e.g., a set of portions) that are contiguous represent neighboring segments of a genome or neighboring segments of a chromosome or gene. For example, two or more contiguous portions, when aligned by merging the portions end to end, can represent a sequence assembly of a DNA sequence longer than each portion. For example two or more contiguous portions can represent of an intact genome, chromosome, gene, intron, exon or segment thereof. In some embodiments a level is determined from a collection (e.g., a set) of contiguous portions and/or non-contiguous portions.

Different Levels

In some embodiments, a profile of normalized counts comprises a level (e.g., a first level) significantly different than another level (e.g., a second level) within the profile. A first level may be higher or lower than a second level. In some embodiments, a first level is for a set of portions comprising one or more reads comprising a copy number variation (e.g., a maternal copy number variation, fetal copy number variation, or a maternal copy number variation and a fetal copy number variation) and the second level is for a set of portions comprising reads having substantially no copy number variation. In some embodiments, significantly different refers to an observable difference. In some embodiments significantly different refers to statistically different or a statistically significant difference. A statistically significant difference is sometimes a statistical assessment of an observed difference. A statistically significant difference can be assessed by a suitable method in the art. Any suitable threshold or range can be used to determine that two levels are significantly different. In certain embodiments two levels (e.g., mean levels) that differ by about 0.01 percent or more (e.g., 0.01 percent of one or either of the level values) are significantly different. In some embodiments two levels (e.g., mean levels) that differ by about 0.1 percent or more are significantly different. In certain embodiments, two levels (e.g., mean levels) that differ by about 0.5 percent or more are significantly different. In some embodiments two levels (e.g., mean levels) that differ by about 0.5, 0.75, 1, 1.5, 2, 2.5, 3, 3.5, 4, 4.5, 5, 5.5, 6, 6.5, 7, 7.5, 8, 8.5, 9, 9.5 or more than about 10% are significantly different. In some embodiments two levels (e.g., mean levels) are significantly different and there is no overlap in either level and/or no overlap in a range defined by an uncertainty value calculated for one or both levels. In certain embodiments the uncertainty value is a standard deviation expressed as sigma. In some embodiments two levels (e.g., mean levels) are significantly different and they differ by about 1 or more times the uncertainty value (e.g., 1 sigma). In some embodiments two levels (e.g., mean levels) are significantly different and they differ by about 2 or more times the uncertainty value (e.g., 2 sigma), about 3 or more, about 4 or more, about 5 or more, about 6 or more, about 7 or more, about 8 or more, about 9 or more, or about 10 or more times the uncertainty value. In some embodiments two levels (e.g., mean levels) are significantly different when they differ by about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 times the uncertainty value or more. In some embodiments, the confidence level increases as the difference between two levels increases. In certain embodiments, the confidence level decreases as the difference between two levels decreases and/or as the uncertainty value increases. For example, sometimes the confidence level increases with the ratio of the difference between levels and the standard deviation (e.g., MADs).

One or more prediction algorithms may be used to determine significance or give meaning to the detection data collected under variable conditions that may be weighed independently of or dependently on each other. The term "variable" as used herein refers to a factor, quantity, or function of an algorithm that has a value or set of values.

In some embodiments, a first set of portions often includes portions that are different than (e.g., non-overlapping with) a second set of portions. For example, sometimes a first level of normalized counts is significantly different than a second level of normalized counts in a profile, and the first level is for a first set of portions, the second level is for a second set of portions and the portions do not overlap in the first set and second set of portions. In certain embodiments, a first set of portions is not a subset of a second set of portions from which a first level and second level are determined, respectively. In some embodiments a first set of portions is different and/or distinct from a second set of portions from which a first level and second level are determined, respectively.

In some embodiments a first set of portions is a subset of a second set of portions in a profile. For example, sometimes a second level of normalized counts for a second set of portions in a profile comprises normalized counts of a first set of portions for a first level in the profile and the first set of portions is a subset of the second set of portions in the profile. In some embodiments an average, mean or median level is derived from a second level where the second level comprises a first level. In some embodiments, a second level comprises a second set of portions representing an entire chromosome and a first level comprises a first set of portions where the first set is a subset of the second set of portions and the first level represents a maternal copy number variation, fetal copy number variation, or a maternal copy number variation and a fetal copy number variation that is present in the chromosome.

In some embodiments, a value of a second level is closer to the mean, average or median value of a count profile for a chromosome, or segment thereof, than the first level. In some embodiments, a second level is a mean level of a chromosome, a portion of a chromosome or a segment thereof. In some embodiments, a first level is significantly different from a predominant level (e.g., a second level) representing a chromosome, or segment thereof. A profile may include multiple first levels that significantly differ from a second level, and each first level independently can be higher or lower than the second level. In some embodiments, a first level and a second level are derived from the same chromosome and the first level is higher or lower than the second level, and the second level is the predominant level of the chromosome. In some embodiments, a first level and a second level are derived from the same chromosome, a first level is indicative of a copy number variation (e.g., a maternal and/or fetal copy number variation, deletion, insertion, duplication) and a second level is a mean level or predominant level of portions for a chromosome, or segment thereof.

In certain embodiments, a read in a second set of portions for a second level substantially does not include a genetic variation (e.g., a copy number variation, a maternal and/or fetal copy number variation). Often, a second set of portions for a second level includes some variability (e.g., variability in level, variability in counts for portions). In some embodiments, one or more portions in a set of portions for a level associated with substantially no copy number variation include one or more reads having a copy number variation present in a maternal and/or fetal genome. For example, sometimes a set of portions include a copy number variation that is present in a small segment of a chromosome (e.g., less than 10 portions) and the set of portions is for a level associated with substantially no copy number variation. Thus a set of portions that include substantially no copy number variation still can include a copy number variation that is present in less than about 10, 9, 8, 7, 6, 5, 4, 3, 2 or 1 portions of a level.

In some embodiments a first level is for a first set of portions and a second level is for a second set of portions and the first set of portions and second set of portions are contiguous (e.g., adjacent with respect to the nucleic acid sequence of a chromosome or segment thereof). In some embodiments the first set of portions and second set of portions are not contiguous.

Relatively short sequence reads from a mixture of fetal and maternal nucleic acid can be utilized to provide counts which can be transformed into a level and/or a profile. Counts, levels and profiles can be depicted in electronic or tangible form and can be visualized. Counts mapped to portions (e.g., represented as levels and/or profiles) can provide a visual representation of a fetal and/or a maternal genome, chromosome, or a portion or a segment of a chromosome that is present in a fetus and/or pregnant female.

Reference Level and Normalized Reference Value

In some embodiments a profile comprises a reference level (e.g., a level used as a reference). Often a profile of normalized counts provides a reference level from which expected levels and expected ranges are determined (see discussion below on expected levels and ranges). A reference level often is for normalized counts of portions comprising mapped reads from both a mother and a fetus. A reference level is often the sum of normalized counts of mapped reads from a fetus and a mother (e.g., a pregnant female). In some embodiments a reference level is for portions comprising mapped reads from a euploid mother and/or a euploid fetus. In some embodiments a reference level is for portions comprising mapped reads having a fetal and/or maternal genetic variation (e.g., an aneuploidy (e.g., a trisomy), a copy number variation, a microduplication, a microdeletion, an insertion). In some embodiments a reference level is for portions that include substantially no maternal and/or fetal genetic variations (e.g., an aneuploidy (e.g., a trisomy), a copy number variation, a microduplication, a microdeletion, an insertion). In some embodiments a second level is used as a reference level. In certain embodiments a profile comprises a first level of normalized counts and a second level of normalized counts, the first level is significantly different from the second level and the second level is the reference level. In certain embodiments a profile comprises a first level of normalized counts for a first set of portions, a second level of normalized counts for a second set of portions, the first set of portions includes mapped reads having a maternal and/or fetal copy number variation, the second set of portions comprises mapped reads having substantially no maternal copy number variation and/or fetal copy number variation, and the second level is a reference level.

In some embodiments counts mapped to portions for one or more levels of a profile are normalized according to counts of a reference level. In some embodiments, normalizing counts of a level according to counts of a reference level comprise dividing counts of a level by counts of a reference level or a multiple or fraction thereof. Counts normalized according to counts of a reference level often have been normalized according to another process (e.g., PERUN, ChAI) and counts of a reference level also often have been normalized (e.g., by PERUN, ChAI). In some embodiments the counts of a level are normalized according to counts of a reference level and the counts of the reference level are scalable to a suitable value either prior to or after normalizing. The process of scaling the counts of a reference level can comprise any suitable constant (i.e., number) and any suitable mathematical manipulation may be applied to the counts of a reference level.

A normalized reference value (NRV) is often determined according to the normalized counts of a reference level. Determining an NRV can comprise any suitable normalization process (e.g., mathematical manipulation) applied to the counts of a reference level where the same normalization process is used to normalize the counts of other levels within the same profile. Determining an NRV often comprises dividing a reference level by itself. Determining an NRV often comprises dividing a reference level by a multiple of itself. Determining an NRV often comprises dividing a reference level by the sum or difference of the reference level and a constant (e.g., any number).

An NRV is sometimes referred to as a null value. An NRV can be any suitable value. In some embodiments, an NRV is any value other than zero. In some embodiments an NRV is a whole number. In some embodiments an NRV is a positive integer. In some embodiments, an NRV is 1, 10, 100 or 1000. Often, an NRV is equal to 1. In some embodiments an NRV is equal to zero. The counts of a reference level can be normalized to any suitable NRV. In some embodiments, the counts of a reference level are normalized to an NRV of zero. Often the counts of a reference level are normalized to an NRV of 1.

Expected Levels

An expected level is sometimes a pre-defined level (e.g., a theoretical level, predicted level). An "expected level" is sometimes referred to herein as a "predetermined level value". In some embodiments, an expected level is a predicted value for a level of normalized counts for a set of portions that include a copy number variation. In certain embodiments, an expected level is determined for a set of portions that include substantially no copy number variation. An expected level can be determined for a chromosome ploidy (e.g., 0, 1, 2 (i.e., diploid), 3 or 4 chromosomes) or a microploidy (homozygous or heterozygous deletion, duplication, insertion or absence thereof). Often an expected level is determined for a maternal microploidy (e.g., a maternal and/or fetal copy number variation).

An expected level for a genetic variation or a copy number variation can be determined by any suitable manner. Often an expected level is determined by a suitable mathematical manipulation of a level (e.g., counts mapped to a set of portions for a level). In some embodiments an expected level is determined by utilizing a constant sometimes referred to as an expected level constant. An expected level for a copy number variation is sometimes calculated by multiplying a reference level, normalized counts of a reference level or an NRV by an expected level constant, adding an expected level constant, subtracting an expected level constant, dividing by an expected level constant, or by a combination thereof. Often an expected level (e.g., an expected level of a maternal and/or fetal copy number variation) determined for the same subject, sample or test group is determined according to the same reference level or NRV.

Often an expected level is determined by multiplying a reference level, normalized counts of a reference level or an NRV by an expected level constant where the reference level, normalized counts of a reference level or NRV is not equal to zero. In some embodiments an expected level is determined by adding an expected level constant to reference level, normalized counts of a reference level or an NRV that is equal to zero. In some embodiments, an expected level, normalized counts of a reference level, NRV and expected level constant are scalable. The process of scaling can comprise any suitable constant (i.e., number) and any suitable mathematical manipulation where the same scaling process is applied to all values under consideration.

Expected Level Constant

An expected level constant can be determined by a suitable method. In some embodiments an expected level constant is arbitrarily determined. Often an expected level constant is determined empirically. In some embodiments an expected level constant is determined according to a mathematical manipulation. In some embodiments an expected level constant is determined according to a reference (e.g., a reference genome, a reference sample, reference test data).

In some embodiments, an expected level constant is predetermined for a level representative of the presence or absence of a genetic variation or copy number variation (e.g., a duplication, insertion or deletion). In some embodiments, an expected level constant is predetermined for a level representative of the presence or absence of a maternal copy number variation, fetal copy number variation, or a maternal copy number variation and a fetal copy number variation. An expected level constant for a copy number variation can be any suitable constant or set of constants.

In some embodiments, the expected level constant for a homozygous duplication (e.g., a homozygous duplication) can be from about 1.6 to about 2.4, from about 1.7 to about 2.3, from about 1.8 to about 2.2, or from about 1.9 to about 2.1. In some embodiments the expected level constant for a homozygous duplication is about 1.6, 1.7, 1.8, 1.9, 2.0, 2.1, 2.2, 2.3 or about 2.4. Often the expected level constant for a homozygous duplication is about 1.90, 1.92, 1.94, 1.96, 1.98, 2.0, 2.02, 2.04, 2.06, 2.08 or about 2.10. Often the expected level constant for a homozygous duplication is about 2.

In some embodiments, the expected level constant for a heterozygous duplication (e.g., a homozygous duplication) is from about 1.2 to about 1.8, from about 1.3 to about 1.7, or from about 1.4 to about 1.6. In some embodiments the expected level constant for a heterozygous duplication is about 1.2, 1.3, 1.4, 1.5, 1.6, 1.7 or about 1.8. Often the expected level constant for a heterozygous duplication is about 1.40, 1.42, 1.44, 1.46, 1.48, 1.5, 1.52, 1.54, 1.56, 1.58 or about 1.60. In some embodiments, the expected level constant for a heterozygous duplication is about 1.5.

In some embodiments, the expected level constant for the absence of a copy number variation (e.g., the absence of a maternal copy number variation and/or fetal copy number variation) is from about 1.3 to about 0.7, from about 1.2 to about 0.8, or from about 1.1 to about 0.9. In some embodiments the expected level constant for the absence of a copy number variation is about 1.3, 1.2, 1.1, 1.0, 0.9, 0.8 or about 0.7. Often the expected level constant for the absence of a copy number variation is about 1.09, 1.08, 1.06, 1.04, 1.02, 1.0, 0.98, 0.96, 0.94, or about 0.92. In some embodiments, the expected level constant for the absence of a copy number variation is about 1.

In some embodiments, the expected level constant for a heterozygous deletion (e.g., a maternal, fetal, or a maternal and a fetal heterozygous deletion) is from about 0.2 to about 0.8, from about 0.3 to about 0.7, or from about 0.4 to about 0.6. In some embodiments the expected level constant for a heterozygous deletion is about 0.2, 0.3, 0.4, 0.5, 0.6, 0.7 or about 0.8. Often the expected level constant for a heterozygous deletion is about 0.40, 0.42, 0.44, 0.46, 0.48, 0.5, 0.52, 0.54, 0.56, 0.58 or about 0.60. In some embodiments, the expected level constant for a heterozygous deletion is about 0.5.

In some embodiments, the expected level constant for a homozygous deletion (e.g., a homozygous deletion) can be from about −0.4 to about 0.4, from about −0.3 to about 0.3, from about −0.2 to about 0.2, or from about −0.1 to about 0.1. In some embodiments the expected level constant for a homozygous deletion is about −0.4, −0.3, −0.2, −0.1, 0.0, 0.1, 0.2, 0.3 or about 0.4. Often the expected level constant for a homozygous deletion is about −0.1, −0.08, −0.06, −0.04, −0.02, 0.0, 0.02, 0.04, 0.06, 0.08 or about 0.10. Often the expected level constant for a homozygous deletion is about 0.

Expected Level Range

In some embodiments the presence or absence of a genetic variation or copy number variation (e.g., a maternal copy number variation, fetal copy number variation, or a maternal copy number variation and a fetal copy number variation) is determined by a level that falls within or outside of an expected level range. An expected level range is often determined according to an expected level. In some embodiments an expected level range is determined for a level comprising substantially no genetic variation or substantially no copy number variation. A suitable method can be used to determine an expected level range.

In some embodiments, an expected level range is defined according to a suitable uncertainty value calculated for a level. Non-limiting examples of an uncertainty value are a standard deviation, standard error, calculated variance, p-value, and mean absolute deviation (MAD). In some embodiments, an expected level range for a genetic variation or a copy number variation is determined, in part, by calculating the uncertainty value for a level (e.g., a first level, a second level, a first level and a second level). In some embodiments an expected level range is defined according to an uncertainty value calculated for a profile (e.g., a profile of normalized counts for a chromosome or segment thereof). In some embodiments, an uncertainty value is calculated for a level comprising substantially no genetic variation or substantially no copy number variation. In some embodiments, an uncertainty value is calculated for a first level, a second level or a first level and a second level. In some embodiments an uncertainty value is determined for a first level, a second level or a second level comprising a first level.

An expected level range is sometimes calculated, in part, by multiplying, adding, subtracting, or dividing an uncertainty value by a constant (e.g., a predetermined constant) n. A suitable mathematical procedure or combination of procedures can be used. The constant n (e.g., predetermined constant n) is sometimes referred to as a confidence interval. A selected confidence interval is determined according to the constant n that is selected. The constant n (e.g., the predetermined constant n, the confidence interval) can be determined by a suitable manner. The constant n can be a number or fraction of a number greater than zero. The constant n can be a whole number. Often the constant n is a number less than 10. In some embodiments the constant n is a number less than about 10, less than about 9, less than about 8, less than about 7, less than about 6, less than about 5, less than about 4, less than about 3, or less than about 2. In some embodiments the constant n is about 10, 9.5, 9, 8.5, 8, 7.5, 7, 6.5, 6, 5.5, 5, 4.5, 4, 3.5, 3, 2.5, 2 or 1. The constant n can be determined empirically from data derived from subjects (a pregnant female and/or a fetus) with a known genetic disposition.

Often an uncertainty value and constant n defines a range (e.g., an uncertainty cutoff). For example, sometimes an uncertainty value is a standard deviation (e.g., +/−5) and is multiplied by a constant n (e.g., a confidence interval) thereby defining a range or uncertainty cutoff (e.g., 5n to −5n).

In some embodiments, an expected level range for a genetic variation (e.g., a maternal copy number variation, fetal copy number variation, or a maternal copy number variation and fetal copy number variation) is the sum of an expected level plus a constant n times the uncertainty (e.g., n x sigma (e.g., 6 sigma)). In some embodiments the expected level range for a genetic variation or copy number variation designated by k can be defined by the formula:

$$\text{(Expected Level Range)}_k = \text{(Expected Level)}_k + n\sigma \qquad \text{Formula R:}$$

where $\sigma$ is an uncertainty value, n is a constant (e.g., a predetermined constant) and the expected level range and expected level are for the genetic variation k (e.g., k=a heterozygous deletion, e.g., k=the absence of a genetic variation). For example, for an expected level equal to 1 (e.g., the absence of a copy number variation), an uncertainty value (i.e. a) equal to +/−0.05, and n=3, the expected level range is defined as 1.15 to 0.85. In some embodiments, the expected level range for a heterozygous duplication is determined as 1.65 to 1.35 when the expected level for a heterozygous duplication is 1.5, n=3, and the uncertainty value $\sigma$ is +/−0.05. In some embodiments the expected level range for a heterozygous deletion is determined as 0.65 to 0.35 when the expected level for a heterozygous duplication is 0.5, n=3, and the uncertainty value $\sigma$ is +/−0.05. In some embodiments the expected level range for a homozygous duplication is determined as 2.15 to 1.85 when the expected level for a heterozygous duplication is 2.0, n=3 and the uncertainty value $\sigma$ is +/−0.05. In some embodiments the expected level range for a homozygous deletion is determined as 0.15 to −0.15 when the expected level for a heterozygous duplication is 0.0, n=3 and the uncertainty value $\sigma$ is +/−0.05.

In some embodiments an expected level range for a homozygous copy number variation (e.g., a maternal, fetal or maternal and fetal homozygous copy number variation) is determined, in part, according to an expected level range for a corresponding heterozygous copy number variation. For example, sometimes an expected level range for a homozygous duplication comprises all values greater than an upper limit of an expected level range for a heterozygous duplication. In some embodiments an expected level range for a homozygous duplication comprises all values greater than or equal to an upper limit of an expected level range for a heterozygous duplication. In some embodiments an expected level range for a homozygous duplication comprises all values greater than an upper limit of an expected level range for a heterozygous duplication and less than the upper limit defined by the formula R where a is an uncertainty value and is a positive value, n is a constant and k is a homozygous duplication. In some embodiments an expected level range for a homozygous duplication comprises all values greater than or equal to an upper limit of an expected level range for a heterozygous duplication and less than or equal to the upper limit defined by the formula R where a is an uncertainty value, a is a positive value, n is a constant and k is a homozygous duplication.

In some embodiments, an expected level range for a homozygous deletion comprises all values less than a lower limit of an expected level range for a heterozygous deletion. In some embodiments an expected level range for a homozygous deletion comprises all values less than or equal to a lower limit of an expected level range for a heterozygous deletion. In some embodiments an expected level range for a homozygous deletion comprises all values less than a lower limit of an expected level range for a heterozygous deletion and greater than the lower limit defined by the formula R where a is an uncertainty value, a is a negative value, n is a constant and k is a homozygous deletion. In some embodiments an expected level range for a homozygous deletion comprises all values less than or equal to a lower limit of an expected level range for a heterozygous deletion and greater than or equal to the lower limit defined by the formula R where σ is an uncertainty value, a is a negative value, n is a constant and k is a homozygous deletion.

An uncertainty value can be utilized to determine a threshold value. In some embodiments, a range (e.g., a threshold range) is obtained by calculating the uncertainty value determined from a raw, filtered and/or normalized counts. A range can be determined by multiplying the uncertainty value for a level (e.g. normalized counts of a level) by a predetermined constant (e.g., 1, 2, 3, 4, 5, 6, etc.) representing the multiple of uncertainty (e.g., number of standard deviations) chosen as a cutoff threshold (e.g., multiply by 3 for 3 standard deviations), whereby a range is generated, in some embodiments. A range can be determined by adding and/or subtracting a value (e.g., a predetermined value, an uncertainty value, an uncertainty value multiplied by a predetermined constant) to and/or from a level whereby a range is generated, in some embodiments. For example, for a level equal to 1, a standard deviation of +/−0.2, where a predetermined constant is 3, the range can be calculated as (1+3(0.2)) to (1+3(−0.2)), or 1.6 to 0.4. A range sometimes can define an expected range or expected level range for a copy number variation. In certain embodiments, some or all of the portions exceeding a threshold value, falling outside a range or falling inside a range of values, are removed as part of, prior to, or after a normalization process. In some embodiments, some or all of the portions exceeding a calculated threshold value, falling outside a range or falling inside a range are weighted or adjusted as part of, or prior to the normalization or classification process. Examples of weighting are described herein. The terms "redundant data", and "redundant mapped reads" as used herein refer to sample derived sequence reads that are identified as having already been assigned to a genomic location (e.g., base position) and/or counted for a portion.

In some embodiments an uncertainty value is determined according to the formula below:

$$Z = \frac{L_A - L_o}{\sqrt{\frac{\sigma_A^2}{N_A} + \frac{\sigma_o^2}{N_o}}}$$

Where Z represents the standardized deviation between two levels, L is the mean (or median) level and sigma is the standard deviation (or MAD). The subscript O denotes a segment of a profile (e.g., a second level, a chromosome, an NRV, a "euploid level", a level absent a copy number variation), and A denotes another segment of a profile (e.g., a first level, a level representing a copy number variation, a level representing an aneuploidy (e.g., a trisomy). The variable $N_o$ represents the total number of portions in the segment of the profile denoted by the subscript O. $N_A$ represents the total number of portions in the segment of the profile denoted by subscript A.

Categorizing a Copy Number Variation

A level (e.g., a first level) that significantly differs from another level (e.g., a second level) can often be categorized as a copy number variation (e.g., a maternal and/or fetal copy number variation, a fetal copy number variation, a deletion, duplication, insertion) according to an expected level range.

In some embodiments, the presence of a copy number variation is categorized when a first level is significantly different from a second level and the first level falls within the expected level range for a copy number variation. For example, a copy number variation (e.g., a maternal and/or fetal copy number variation, a fetal copy number variation) can be categorized when a first level is significantly different from a second level and the first level falls within the expected level range for a copy number variation. In some embodiments a heterozygous duplication (e.g., a maternal or fetal, or maternal and fetal, heterozygous duplication) or heterozygous deletion (e.g., a maternal or fetal, or maternal and fetal, heterozygous deletion) is categorized when a first level is significantly different from a second level and the first level falls within the expected level range for a heterozygous duplication or heterozygous deletion, respectively. In some embodiments a homozygous duplication or homozygous deletion is categorized when a first level is significantly different from a second level and the first level falls within the expected level range for a homozygous duplication or homozygous deletion, respectively.

Level Adjustments

In some embodiments, one or more levels are adjusted. A process for adjusting a level often is referred to as padding. In some embodiments, multiple levels in a profile (e.g., a profile of a genome, a chromosome profile, a profile of a portion or segment of a chromosome) are adjusted. In some embodiments, about 1 to about 10,000 or more levels in a profile are adjusted. In some embodiments about 1 to about a 1000, 1 to about 900, 1 to about 800, 1 to about 700, 1 to about 600, 1 to about 500, 1 to about 400, 1 to about 300, 1 to about 200, 1 to about 100, 1 to about 50, 1 to about 25, 1 to about 20, 1 to about 15, 1 to about 10, or 1 to about 5 levels in a profile are adjusted. In some embodiments one level is adjusted. In some embodiments, a level (e.g., a first level of a normalized count profile) that significantly differs from a second level is adjusted. In some embodiments a level categorized as a copy number variation is adjusted. In some embodiments a level (e.g., a first level of a normalized count profile) that significantly differs from a second level is categorized as a copy number variation (e.g., a copy number variation, e.g., a maternal copy number variation) and is adjusted. In some embodiments, a level (e.g., a first level) is within an expected level range for a maternal copy number variation, fetal copy number variation, or a maternal copy number variation and a fetal copy number variation and the level is adjusted. In some embodiments, one or more levels (e.g., levels in a profile) are not adjusted. In some embodiments, a level (e.g., a first level) is outside an expected level range for a copy number variation and the level is not adjusted. Often, a level within an expected level range for the absence of a copy number variation is not adjusted. Any suitable number of adjustments can be made to one or more levels in a profile. In some embodiments, one or more levels are adjusted. In some embodiments 2 or more, 3 or more, 5 or more, 6 or more, 7 or more, 8 or more, 9 or more and sometimes 10 or more levels are adjusted.

In some embodiments, a value of a first level is adjusted according to a value of a second level. In some embodiments a first level, identified as representative of a copy number variation, is adjusted to the value of a second level, where the second level is often associated with no copy number variation. In certain embodiments, a value of a first level, identified as representative of a copy number variation, is adjusted so the value of the first level is about equal to a value of a second level.

An adjustment can comprise a suitable mathematical operation. In some embodiments an adjustment comprises one or more mathematical operations. In some embodiments a level is adjusted by normalizing, filtering, averaging, multiplying, dividing, adding or subtracting or combination thereof. In some embodiments a level is adjusted by a predetermined value or a constant. In some embodiments a level is adjusted by modifying the value of the level to the value of another level. For example, a first level may be adjusted by modifying its value to the value of a second level. A value in such cases may be a processed value (e.g., mean, normalized value and the like).

In some embodiments a level is categorized as a copy number variation (e.g., a maternal copy number variation) and is adjusted according to a predetermined value referred to herein as a predetermined adjustment value (PAV). Often a PAV is determined for a specific copy number variation. Often a PAV determined for a specific copy number variation (e.g., homozygous duplication, homozygous deletion, heterozygous duplication, heterozygous deletion) is used to adjust a level categorized as a specific copy number variation (e.g., homozygous duplication, homozygous deletion, heterozygous duplication, heterozygous deletion). In certain embodiments, a level is categorized as a copy number variation and is then adjusted according to a PAV specific to the type of copy number variation categorized. In some embodiments a level (e.g., a first level) is categorized as a maternal copy number variation, fetal copy number variation, or a maternal copy number variation and a fetal copy number variation and is adjusted by adding or subtracting a PAV from the level. Often a level (e.g., a first level) is categorized as a maternal copy number variation and is adjusted by adding a PAV to the level. For example, a level categorized as a duplication (e.g., a maternal, fetal or maternal and fetal homozygous duplication) can be adjusted by adding a PAV determined for a specific duplication (e.g., a homozygous duplication) thereby providing an adjusted level. Often a PAV determined for a copy number duplication is a negative value. In some embodiments providing an adjustment to a level representative of a duplication by utilizing a PAV determined for a duplication results in a reduction in the value of the level. In some embodiments, a level (e.g., a first level) that significantly differs from a second level is categorized as a copy number deletion (e.g., a homozygous deletion, heterozygous deletion, homozygous duplication, homozygous duplication) and the first level is adjusted by adding a PAV determined for a copy number deletion. Often a PAV determined for a copy number deletion is a positive value. In some embodiments providing an adjustment to a level representative of a deletion by utilizing a PAV determined for a deletion results in an increase in the value of the level.

A PAV can be any suitable value. Often a PAV is determined according to and is specific for a copy number variation (e.g., a categorized copy number variation). In certain embodiments a PAV is determined according to an expected level for a copy number variation (e.g., a categorized copy number variation) and/or a PAV factor. A PAV sometimes is determined by multiplying an expected level by a PAV factor. For example, a PAV for a copy number variation can be determined by multiplying an expected level determined for a copy number variation (e.g., a heterozygous deletion) by a PAV factor determined for the same copy number variation (e.g., a heterozygous deletion). For example, PAV can be determined by the formula below:

$$PAV_k = (\text{Expected Level})_k \times (\text{PAV factor})_k$$

for the copy number variation k (e.g., k=a heterozygous deletion)

A PAV factor can be any suitable value. In some embodiments a PAV factor for a homozygous duplication is between about −0.6 and about −0.4. In some embodiments a PAV factor for a homozygous duplication is about −0.60, −0.59, −0.58, −0.57, −0.56, −0.55, −0.54, −0.53, −0.52, −0.51, −0.50, −0.49, −0.48, −0.47, −0.46, −0.45, −0.44, −0.43, −0.42, −0.41 and −0.40. Often a PAV factor for a homozygous duplication is about −0.5.

For example, for an NRV of about 1 and an expected level of a homozygous duplication equal to about 2, the PAV for the homozygous duplication is determined as about −1 according to the formula above. In this case, a first level categorized as a homozygous duplication is adjusted by adding about −1 to the value of the first level, for example.

In some embodiments a PAV factor for a heterozygous duplication is between about −0.4 and about −0.2. In some embodiments a PAV factor for a heterozygous duplication is about −0.40, −0.39, −0.38, −0.37, −0.36, −0.35, −0.34, −0.33, −0.32, −0.31, −0.30, −0.29, −0.28, −0.27, −0.26, −0.25, −0.24, −0.23, −0.22, −0.21 and −0.20. Often a PAV factor for a heterozygous duplication is about −0.33.

For example, for an NRV of about 1 and an expected level of a heterozygous duplication equal to about 1.5, the PAV for the homozygous duplication is determined as about −0.495 according to the formula above. In this case, a first level categorized as a heterozygous duplication is adjusted by adding about −0.495 to the value of the first level, for example.

In some embodiments a PAV factor for a heterozygous deletion is between about 0.4 and about 0.2. In some embodiments a PAV factor for a heterozygous deletion is about 0.40, 0.39, 0.38, 0.37, 0.36, 0.35, 0.34, 0.33, 0.32, 0.31, 0.30, 0.29, 0.28, 0.27, 0.26, 0.25, 0.24, 0.23, 0.22, 0.21 and 0.20. Often a PAV factor for a heterozygous deletion is about 0.33.

For example, for an NRV of about 1 and an expected level of a heterozygous deletion equal to about 0.5, the PAV for the heterozygous deletion is determined as about 0.495 according to the formula above. In this case, a first level categorized as a heterozygous deletion is adjusted by adding about 0.495 to the value of the first level, for example.

In some embodiments a PAV factor for a homozygous deletion is between about 0.6 and about 0.4. In some embodiments a PAV factor for a homozygous deletion is about 0.60, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41 and 0.40. Often a PAV factor for a homozygous deletion is about 0.5.

For example, for an NRV of about 1 and an expected level of a homozygous deletion equal to about 0, the PAV for the homozygous deletion is determined as about 1 according to the formula above. In this case, a first level categorized as a homozygous deletion is adjusted by adding about 1 to the value of the first level, for example.

In certain embodiments, a PAV is about equal to or equal to an expected level for a copy number variation (e.g., the expected level of a copy number variation).

In some embodiments, counts of a level are normalized prior to making an adjustment. In certain embodiments, counts of some or all levels in a profile are normalized prior to making an adjustment. For example, counts of a level can be normalized according to counts of a reference level or an NRV. In certain embodiments, counts of a level (e.g., a second level) are normalized according to counts of a reference level or an NRV and the counts of all other levels (e.g., a first level) in a profile are normalized relative to the counts of the same reference level or NRV prior to making an adjustment.

In some embodiments, a level of a profile results from one or more adjustments. In certain embodiments, a level of a profile is determined after one or more levels in the profile are adjusted. In some embodiments, a level of a profile is re-calculated after one or more adjustments are made.

In some embodiments, a copy number variation (e.g., a maternal copy number variation, fetal copy number variation, or a maternal copy number variation and a fetal copy number variation) is determined (e.g., determined directly or indirectly) from an adjustment. For example, a level in a profile that was adjusted (e.g., an adjusted first level) can be identified as a maternal copy number variation. In some embodiments, the magnitude of the adjustment indicates the type of copy number variation (e.g., heterozygous deletion, homozygous duplication, and the like). In certain embodiments, an adjusted level in a profile can be identified as representative of a copy number variation according to the value of a PAV for the copy number variation. For example, for a given profile, PAV is about −1 for a homozygous duplication, about −0.5 for a heterozygous duplication, about 0.5 for a heterozygous deletion and about 1 for a homozygous deletion. In the preceding example, a level adjusted by about −1 can be identified as a homozygous duplication, for example. In some embodiments, one or more copy number variations can be determined from a profile or a level comprising one or more adjustments.

In certain embodiments, adjusted levels within a profile are compared. In some embodiments anomalies and errors are identified by comparing adjusted levels. For example, often one or more adjusted levels in a profile are compared and a particular level may be identified as an anomaly or error. In some embodiments an anomaly or error is identified within one or more portions making up a level. An anomaly or error may be identified within the same level (e.g., in a profile) or in one or more levels that represent portions that are adjacent, contiguous, adjoining or abutting. In some embodiments one or more adjusted levels are levels of portions that are adjacent, contiguous, adjoining or abutting where the one or more adjusted levels are compared and an anomaly or error is identified. An anomaly or error can be a peak or dip in a profile or level where a cause of the peak or dip is known or unknown. In certain embodiments adjusted levels are compared and an anomaly or error is identified where the anomaly or error is due to a stochastic, systematic, random or user error. In some embodiments adjusted levels are compared and an anomaly or error is removed from a profile. In certain embodiments, adjusted levels are compared and an anomaly or error is adjusted.

Fetal Fraction Determination Based on Level

In some embodiments, a fetal fraction is determined according to a level categorized as representative of a maternal and/or fetal copy number variation. For example determining fetal fraction often comprises assessing an expected level for a maternal and/or fetal copy number variation utilized for the determination of fetal fraction. In some embodiments a fetal fraction is determined for a level (e.g., a first level) categorized as representative of a copy number variation according to an expected level range determined for the same type of copy number variation. Often a fetal fraction is determined according to an observed level that falls within an expected level range and is thereby categorized as a maternal and/or fetal copy number variation. In some embodiments a fetal fraction is determined when an observed level (e.g., a first level) categorized as a maternal and/or fetal copy number variation is different than the expected level determined for the same maternal and/or fetal copy number variation.

In some embodiments a level (e.g., a first level, an observed level), is significantly different than a second level, the first level is categorized as a maternal and/or fetal copy number variation, and a fetal fraction is determined according to the first level. In some embodiments a first level is an observed and/or experimentally obtained level that is significantly different than a second level in a profile and a fetal fraction is determined according to the first level. In some embodiments the first level is an average, mean or summed level and a fetal fraction is determined according to the first level. In certain embodiments a first level and a second level are observed and/or experimentally obtained levels and a fetal fraction is determined according to the first level. In some instances a first level comprises normalized counts for a first set of portions and a second level comprises normalized counts for a second set of portions and a fetal fraction is determined according to the first level. In some embodiments a first set of portions of a first level includes a copy number variation (e.g., the first level is representative of a copy number variation) and a fetal fraction is determined according to the first level. In some embodiments the first set of portions of a first level includes a homozygous or heterozygous maternal copy number variation and a fetal fraction is determined according to the first level. In some embodiments a profile comprises a first level for a first set of portions and a second level for a second set of portions, the second set of portions includes substantially no copy number variation (e.g., a maternal copy number variation, fetal copy number variation, or a maternal copy number variation and a fetal copy number variation) and a fetal fraction is determined according to the first level.

In some embodiments a level (e.g., a first level, an observed level), is significantly different than a second level, the first level is categorized as for a maternal and/or fetal copy number variation, and a fetal fraction is determined according to the first level and/or an expected level of the copy number variation. In some embodiments a first level is categorized as for a copy number variation according to an expected level for a copy number variation and a fetal fraction is determined according to a difference between the first level and the expected level. In certain embodiments a level (e.g., a first level, an observed level) is categorized as a maternal and/or fetal copy number variation, and a fetal fraction is determined as twice the difference between the first level and expected level of the copy number variation. In some embodiments a level (e.g., a first level, an observed level) is categorized as a maternal and/or fetal copy number variation, the first level is subtracted from the expected level thereby providing a difference, and a fetal fraction is determined as twice the difference. In some embodiments a level (e.g., a first level, an observed level) is categorized as a maternal and/or fetal copy number variation, an expected level is subtracted from a first level thereby providing a difference, and the fetal fraction is determined as twice the difference.

Often a fetal fraction is provided as a percent. For example, a fetal fraction can be divided by 100 thereby providing a percent value. For example, for a first level representative of a maternal homozygous duplication and having a level of 155 and an expected level for a maternal homozygous duplication having a level of 150, a fetal fraction can be determined as 10% (e.g., (fetal fraction=2× (155−150)).

In some embodiments a fetal fraction is determined from two or more levels within a profile that are categorized as copy number variations. For example, sometimes two or more levels (e.g., two or more first levels) in a profile are identified as significantly different than a reference level (e.g., a second level, a level that includes substantially no copy number variation), the two or more levels are categorized as representative of a maternal and/or fetal copy number variation and a fetal fraction is determined from each of the two or more levels. In some embodiments a fetal fraction is determined from about 3 or more, about 4 or more, about 5 or more, about 6 or more, about 7 or more, about 8 or more, or about 9 or more fetal fraction determinations within a profile. In some embodiments a fetal fraction is determined from about 10 or more, about 20 or more, about 30 or more, about 40 or more, about 50 or more, about 60 or more, about 70 or more, about 80 or more, or about 90 or more fetal fraction determinations within a profile. In some embodiments a fetal fraction is determined from about 100 or more, about 200 or more, about 300 or more, about 400 or more, about 500 or more, about 600 or more, about 700 or more, about 800 or more, about 900 or more, or about 1000 or more fetal fraction determinations within a profile. In some embodiments a fetal fraction is determined from about 10 to about 1000, about 20 to about 900, about 30 to about 700, about 40 to about 600, about 50 to about 500, about 50 to about 400, about 50 to about 300, about 50 to about 200, or about 50 to about 100 fetal fraction determinations within a profile.

In some embodiments a fetal fraction is determined as the average or mean of multiple fetal fraction determinations within a profile. In certain embodiments, a fetal fraction determined from multiple fetal fraction determinations is a mean (e.g., an average, a mean, a standard average, a median, or the like) of multiple fetal fraction determinations. Often a fetal fraction determined from multiple fetal fraction determinations is a mean value determined by a suitable method known in the art or described herein. In some embodiments a mean value of a fetal fraction determination is a weighted mean. In some embodiments a mean value of a fetal fraction determination is an unweighted mean. A mean, median or average fetal fraction determination (i.e., a mean, median or average fetal fraction determination value) generated from multiple fetal fraction determinations is sometimes associated with an uncertainty value (e.g., a variance, standard deviation, MAD, or the like). Before determining a mean, median or average fetal fraction value from multiple determinations, one or more deviant determinations are removed in some embodiments (described in greater detail herein).

Some fetal fraction determinations within a profile sometimes are not included in the overall determination of a fetal fraction (e.g., mean or average fetal fraction determination). In some embodiments a fetal fraction determination is derived from a first level (e.g., a first level that is significantly different than a second level) in a profile and the first level is not indicative of a genetic variation. For example, some first levels (e.g., spikes or dips) in a profile are generated from anomalies or unknown causes. Such values often generate fetal fraction determinations that differ significantly from other fetal fraction determinations obtained from true copy number variations. In some embodiments fetal fraction determinations that differ significantly from other fetal fraction determinations in a profile are identified and removed from a fetal fraction determination. For example, some fetal fraction determinations obtained from anomalous spikes and dips are identified by comparing them to other fetal fraction determinations within a profile and are excluded from the overall determination of fetal fraction.

In some embodiments, an independent fetal fraction determination that differs significantly from a mean, median or average fetal fraction determination is an identified, recognized and/or observable difference. In certain embodiments, the term "differs significantly" can mean statistically different and/or a statistically significant difference. An "independent" fetal fraction determination can be a fetal fraction determined (e.g., in some embodiments a single determination) from a specific level categorized as a copy number variation. Any suitable threshold or range can be used to determine that a fetal fraction determination differs significantly from a mean, median or average fetal fraction determination. In certain embodiments a fetal fraction determination differs significantly from a mean, median or average fetal fraction determination and the determination can be expressed as a percent deviation from the average or mean value. In certain embodiments a fetal fraction determination that differs significantly from a mean, median or average fetal fraction determination differs by about 10 percent or more. In some embodiments a fetal fraction determination that differs significantly from a mean, median or average fetal fraction determination differs by about 15 percent or more. In some embodiments a fetal fraction determination that differs significantly from a mean, median or average fetal fraction determination differs by about 15% to about 100% or more.

In certain embodiments a fetal fraction determination differs significantly from a mean, median or average fetal fraction determination according to a multiple of an uncertainty value associated with the mean or average fetal fraction determination. Often an uncertainty value and constant n (e.g., a confidence interval) defines a range (e.g., an uncertainty cutoff). For example, sometimes an uncertainty value is a standard deviation for fetal fraction determinations (e.g., +/−5) and is multiplied by a constant n (e.g., a confidence interval) thereby defining a range or uncertainty cutoff (e.g., 5n to −5n, sometimes referred to as 5 sigma). In some embodiments an independent fetal fraction determination falls outside a range defined by the uncertainty cutoff and is considered significantly different from a mean, median or average fetal fraction determination. For example, for a mean value of 10 and an uncertainty cutoff of 3, an independent fetal fraction greater than 13 or less than 7 is significantly different. In some embodiments a fetal fraction determination that differs significantly from a mean, median or average fetal fraction determination differs by more than n times the uncertainty value (e.g., n x sigma) where n is about equal to or greater than 1, 2, 3, 4, 5, 6, 7, 8, 9 or 10. In some embodiments a fetal fraction determination that differs significantly from a mean, median or average fetal fraction determination differs by more than n times the uncertainty value (e.g., n x sigma) where n is about equal to or greater than 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0.

In some embodiments, a level is representative of a fetal and/or maternal microploidy. In some embodiments a level (e.g., a first level, an observed level), is significantly different than a second level, the first level is categorized as a maternal and/or fetal copy number variation, and the first level and/or second level is representative of a fetal microploidy and/or a maternal microploidy. In certain embodiments a first level is representative of a fetal microploidy, In some embodiments a first level is representative of a maternal microploidy. Often a first level is representative of a fetal microploidy and a maternal microploidy. In some embodiments a level (e.g., a first level, an observed level), is significantly different than a second level, the first level is categorized as a maternal and/or fetal copy number variation, the first level is representative of a fetal and/or maternal microploidy and a fetal fraction is determined according to the fetal and/or maternal microploidy. In some instances a first level is categorized as a maternal and/or fetal copy number variation, the first level is representative of a fetal microploidy and a fetal fraction is determined according to the fetal microploidy. In some embodiments a first level is categorized as a maternal and/or fetal copy number variation, the first level is representative of a maternal microploidy and a fetal fraction is determined according to the maternal microploidy. In some embodiments a first level is categorized as a maternal and/or fetal copy number variation, the first level is representative of a maternal and a fetal microploidy and a fetal fraction is determined according to the maternal and fetal microploidy.

In some embodiments, a determination of a fetal fraction comprises determining a fetal and/or maternal microploidy. In some embodiments a level (e.g., a first level, an observed level), is significantly different than a second level, the first level is categorized as a maternal and/or fetal copy number variation, a fetal and/or maternal microploidy is determined according to the first level and/or second level and a fetal fraction is determined. In some embodiments a first level is categorized as a maternal and/or fetal copy number variation, a fetal microploidy is determined according to the first level and/or second level and a fetal fraction is determined according to the fetal microploidy. In certain embodiments a first level is categorized as a maternal and/or fetal copy number variation, a maternal microploidy is determined according to the first level and/or second level and a fetal fraction is determined according to the maternal microploidy. In some embodiments a first level is categorized as a maternal and/or fetal copy number variation, a maternal and fetal microploidy is determined according to the first level and/or second level and a fetal fraction is determined according to the maternal and fetal microploidy.

A fetal fraction often is determined when the microploidy of the mother is different from (e.g., not the same as) the microploidy of the fetus for a given level or for a level categorized as a copy number variation. In some embodiments a fetal fraction is determined when the mother is homozygous for a duplication (e.g., a microploidy of 2) and the fetus is heterozygous for the same duplication (e.g., a microploidy of 1.5). In some embodiments a fetal fraction is determined when the mother is heterozygous for a duplication (e.g., a microploidy of 1.5) and the fetus is homozygous for the same duplication (e.g., a microploidy of 2) or the duplication is absent in the fetus (e.g., a microploidy of 1). In some embodiments a fetal fraction is determined when the mother is homozygous for a deletion (e.g., a microploidy of 0) and the fetus is heterozygous for the same deletion (e.g., a microploidy of 0.5). In some embodiments a fetal fraction is determined when the mother is heterozygous for a deletion (e.g., a microploidy of 0.5) and the fetus is homozygous for the same deletion (e.g., a microploidy of 0) or the deletion is absent in the fetus (e.g., a microploidy of 1).

In certain embodiments, a fetal fraction cannot be determined when the microploidy of the mother is the same (e.g., identified as the same) as the microploidy of the fetus for a given level identified as a copy number variation. For example, for a given level where both the mother and fetus carry the same number of copies of a copy number variation, a fetal fraction is not determined, in some embodiments. For example, a fetal fraction cannot be determined for a level categorized as a copy number variation when both the mother and fetus are homozygous for the same deletion or homozygous for the same duplication. In certain embodiments, a fetal fraction cannot be determined for a level categorized as a copy number variation when both the mother and fetus are heterozygous for the same deletion or heterozygous for the same duplication. In embodiments where multiple fetal fraction determinations are made for a sample, determinations that significantly deviate from a mean, median or average value can result from a copy number variation for which maternal ploidy is equal to fetal ploidy, and such determinations can be removed from consideration.

In some embodiments the microploidy of a maternal copy number variation and fetal copy number variation is unknown. In some embodiments, in cases when there is no determination of fetal and/or maternal microploidy for a copy number variation, a fetal fraction is generated and compared to a mean, median or average fetal fraction determination. A fetal fraction determination for a copy number variation that differs significantly from a mean, median or average fetal fraction determination is sometimes because the microploidy of the mother and fetus are the same for the copy number variation. A fetal fraction determination that differs significantly from a mean, median or average fetal fraction determination is often excluded from an overall fetal fraction determination regardless of the source or cause of the difference. In some embodiments, the microploidy of the mother and/or fetus is determined and/or verified by a method known in the art (e.g., by targeted sequencing methods).

Fetal Ploidy

A fetal ploidy determination, in some embodiments, is used, in part, to make a determination of the presence or absence of a genetic variation (e.g., a chromosome aneuploidy, a trisomy). A fetal ploidy can be determined, in part, from a measure of fetal fraction determined by a suitable method of fetal fraction determination, including methods described herein. In some embodiments fetal ploidy is determined according to a fetal fraction determination and equation (8), (20), (21) or a variation or derivation thereof (Example 2). In some embodiments, fetal ploidy is determined by a method described below. In some embodiments each method described below requires a calculated reference count $F_i$ (sometimes represented as $f_i$) determined for a portion (i.e. a portion, i) of a genome for multiple samples where the ploidy of the fetus for portion i of the genome is euploid. In some embodiments an uncertainty value (e.g., a standard deviation, a) is determined for the reference count $f_i$. In some embodiments a reference count $f_i$, an uncertainty value, a test sample count and/or a measured fetal fraction (F) are used to determine fetal ploidy according to a method described below. In some embodiments a reference count (e.g., an average, mean or median reference count) is normalized by a method described herein (e.g., portion-wise normalization, normalization by GC content, linear and nonlinear least squares regression, LOESS, GC LOESS, LOWESS, PERUN, ChAI, RM, GCRM and/or combinations thereof). In some embodiments a reference count of a segment of a genome that is euploid is equal to 1 when the reference count is normalized by PERUN. In some embodiments both the reference count (e.g., for a fetus known to be euploid) and the counts of a test sample for a portion or segment of a genome are normalized by PERUN and the reference count is equal to 1. Likewise, in some embodiments, a reference count of a portion or segment of a genome that is euploid is equal to 1 when the counts are normalized by (i.e., divided by) a median of the reference count. For example, in some embodiments both the reference count (e.g., for a fetus that is euploid) and the counts of a test sample for a portion or segment of a genome are normalized by a median reference count, the normalized reference count is equal to 1 and the test sample count is normalized (e.g., divided by) the median reference count. In some embodiments both the reference count (e.g., for a fetus that is euploid) and the counts of a test sample for a portion or segment of a genome are normalized by GCRM, GC, RM or a suitable method. In some embodiments a reference count is an average, mean or median reference count. A reference count is often a normalized count for a portion (e.g., a normalized genomic section level). In some embodiments a reference count and the counts for a test sample are raw counts. A reference count, in some embodiments, is determined from an average, mean or median count profile. In some embodiments, a reference count is a calculated genomic section level. In some embodiments a reference count of a reference sample and a count of a test sample (e.g., a patient sample, e.g., y) are normalized by the same method or process.

In some embodiments a measurement of fetal fraction (F) is determined. This fetal fraction value is then used to determine fetal ploidy according to equation (8), a derivation or a variation thereof. In some embodiments, a negative value is returned if the fetus is euploid and a positive value is returned if the fetus is not euploid. In some embodiments a negative value indicates the fetus is euploid for the segment of the genome considered. In certain embodiments, a value that is not negative indicates the fetus comprises an aneuploidy (e.g., a duplication). In certain embodiments, a value that is not negative indicates the fetus comprises a trisomy. In certain embodiments, any positive value indicates the fetus comprises an aneuploidy (e.g., a trisomy, a duplication).

In some embodiments a sum of square residuals is determined. For example, an equation representing the sum of square residuals derived from equation (8) is illustrated in equation (18). In some embodiments a sum of square residuals is determined from equation (8) for a ploidy value X set to a value of 1 (see equation (9)) and for a ploidy value set to a value of 3/2 (see equation (13)). In some embodiments the sum of square residuals (equations (9) and (13)) are determined for a segment of a genome or chromosome (e.g., for all portions of a reference genome i in a segment of the genome). For example, the sum of square residuals (e.g., equations (9) and (13)) can be determined for chromosome 21, 13, 18 or a portion thereof. In some embodiments, to determine a ploidy status of a fetus, the result of equation (13) is subtracted from equation (9) to arrive at a value, phi (e.g., see equation (14)). In certain embodiments, the sign (i.e. positive or negative) of the value phi determines the presence or absence of a fetal aneuploidy. In certain embodiments, a phi value (e.g., from equation (14)) that is negative indicates the absence of an aneuploidy (e.g., the fetus is euploid for portions of a reference genome i) and a phi value that is not negative indicates the presence of an aneuploidy (e.g., a trisomy).

In some embodiments the reference count $f_i$, the uncertainty value for the reference count a and/or the measured fetal fraction (F) are used in equations (9) and (13) to determine the sum of square residuals for the sum of all portions of a reference genome i. In some embodiments the reference count $f_i$, the uncertainty value for the reference count a and/or the measured fetal fraction (F) are used in equations (9) and (13) to determine fetal ploidy. In some embodiments the counts (e.g., normalized counts, e.g., calculated genomic section level), represented by $y_i$ for portion i, for a test sample are used to determine the ploidy status of a fetus for portion i. For example, in certain embodiments, the ploidy status for a segment of a genome is determined according to a reference count $f_i$, an uncertainty value (e.g., from the reference count), a feta fraction (F) determined for a test sample and the counts $y_i$ determined for the test sample where the ploidy status is determined according to equation (14) or a derivation or variation thereof. In some embodiments the counts $y_i$ and/or reference counts are normalized by a method described herein (e.g., portion-wise normalization, normalization by GC content, linear and nonlinear least squares regression, LOESS, GC LOESS, LOWESS, PERUN, ChAI, RM, GCRM and combinations thereof). In some embodiments a fetal ploidy status (e.g., euploid, aneuploid, trisomy) for a portion or segment of a genome or chromosome is determined by the non-limiting example described above and in the Examples section.

In some embodiments a fetal fraction is determined from a test sample, counts y are determined for a test sample and both are used to determine a ploidy for a fetus from a test sample. In certain embodiments of the method described here, the value of fetal ploidy represented by X is not fixed or assumed. In certain embodiments of the method described here, fetal fraction F is fixed. In some embodiments, a ploidy (e.g., a ploidy value) is determined for a portion or segment of a genome according to equation (20) or (21) (Example 2). In some embodiments of this method, a ploidy value is determined, where the value is close to 1, 3/2, or 5/4. In some embodiments a ploidy value of about 1 indicates a euploid fetus, a value of about 3/2 indicates a fetal trisomy and, in the case of twins, a value of about 5/4 indicates that one fetus comprises a trisomy and the other is euploid for the portion or segment of the genome considered. Additional information regarding determining the presence or absence of a fetal aneuploidy from a fetal ploidy determination is discussed in another section below.

In some embodiments, fetal fraction is determined, fixed at its determined value and fetal ploidy is determined from a regression. Any suitable regression can be utilized, non-limiting examples of which include a linear regression, a non-linear regression (e.g., a polynomial regression), and the like. In some embodiments, a linear regression is used according to equation (8), (20), (21) and/or a derivation or variation thereof. In some embodiments, the linear regression used is according to a sum of square residuals derived from equation (8), (20), (21) and/or a derivation or variation thereof. In some embodiments, fetal ploidy is determined according to equation (8), (20), (21) and/or a derivation or variation thereof and a regression is not used. In some embodiments, fetal ploidy is determined according to a sum of square residuals derived from equation (8), (20), (21) and/or a derivation or variation thereof for multiple portions of a reference genome i and a regression is not used. A derivation of an equation is any variation of the equation obtained from a mathematical proof of an equation.

In some embodiments a reference count $f_i$ (described previously herein), an uncertainty value $\sigma$ and/or a measured fetal fraction (F) are used in equations (20) and (21) to determine a fetal ploidy. In some embodiments a reference count $f_i$, an uncertainty value $\sigma$ and/or a measured fetal fraction (F) are used in equations (20) or (21) to determine a fetal ploidy X for portion i or for a sum of multiple portions of a reference genome i (e.g., for the sum of all portions of a reference genome i for a chromosome or segment thereof). In some embodiments the counts (e.g., normalized counts, calculated genomic section level), represented by y for portion i, for a test sample are used to determine the ploidy of a fetus for a segment of a genome represented by multiple portions of a reference genome i. For example, in certain embodiments, the ploidy X for a segment of a genome is determined according to a reference count $f_i$, an uncertainty value, a feta fraction (F) determined for a test sample and the counts $y_i$ determined for the test sample where the ploidy is determined according to equation (20), (21) or a derivation or variation thereof. In some embodiments the counts $y_i$ and/or reference counts are normalized by a method described herein (e.g., portion-wise normalization, normalization by GC content, linear and nonlinear least squares regression, LOESS, GC LOESS, LOWESS, PERUN, ChAI, RM, GCRM and combinations thereof). In some embodiments the counts $y_i$ and/or reference counts are normalized and/or processed by the same method (e.g., portion-wise normalization, normalization by GC content, linear and nonlinear least squares regression, LOESS, GC LOESS, LOWESS, PERUN, ChAI, RM, GCRM, a method described herein or combinations thereof). In some embodiments counts $y_i$ and $f_i$ are counts mapped to the same portion or segment of a genome or chromosome.

The uncertainty value $\sigma$ can be a suitable measure of error, non-limiting examples of which include standard deviation, standard error, calculated variance, p-value, and/or mean absolute deviation (MAD). The uncertainty value $\sigma$ can be determined for any suitable measurement, non-limiting examples of which include Z-scores, Z-values, t-values, p-values, cross-validation error, genomic section level, calculated genomic section levels, levels, counts, the like, or combinations thereof. In some embodiments a is set to a value of 1. In some embodiments a is not set to a value of 1. In some embodiments the value of a is estimated and sometimes it is measured and/or calculated.

In some embodiments $M_i$ is the ploidy of the mother (i.e., maternal ploidy) for a portion of the genome i. In some embodiments $M_i$ is determined for the same patient (e.g., same test sample) from which $y_i$ is determined. In some embodiments the maternal ploidy $M_i$ is known or determined according to a method described herein. In some embodiments maternal ploidy is determined before or after padding (e.g., after making level adjustments). In certain embodiments $M_i$ is estimated or determined from visualizing a profile. In some embodiments the maternal ploidy $M_i$ is not known. In some embodiments the maternal ploidy $M_i$ is assumed. For example, in some embodiments it is assumed or known that the mother has no deletions and/or duplications in the segment of the genome being evaluated. In some embodiments it is assumed or known that maternal ploidy is 1. In some embodiments maternal ploidy is set to a value of 1 after padding (e.g., after making levels adjustments). In some embodiments maternal ploidy is ignored and is set to a value of 1. In some embodiments equation (21) is derived from equation (20) with the assumption that the mother has no deletions and/or duplications in the segment of the genome being evaluated.

In some embodiments a method for determining fetal ploidy is according to nucleic acid sequence reads for a test sample obtained from a pregnant female. In some embodiments the sequence reads are reads of circulating cell-free nucleic acid from a sample (e.g., a test sample). In some embodiments, a method for determining fetal ploidy comprises obtaining counts of sequence reads mapped to portions of a reference genome. In some embodiments the sequence reads are mapped to a subset of portions of the reference genome. In some embodiments determining fetal ploidy comprises determining a fetal fraction. In some embodiments determining fetal ploidy comprises calculating or determining genomic section levels. In certain embodiments determining fetal ploidy comprises determining a fetal fraction and calculating or determining genomic section levels. In some embodiments the fetal fraction and the calculated genomic section levels are determined from the same test sample (e.g., same part of the test sample). In some embodiments the fetal fraction and the calculated genomic section levels are determined from the same reads obtained from the same test sample (e.g., same part of the test sample). In some embodiments the fetal fraction and the calculated genomic section levels are determined from the same reads obtained from the same sequencing run and/or from the same flow cell. In some embodiments the fetal fraction and the calculated genomic section levels are determined from the same equipment and/or machine (e.g., sequencing apparatus, flow cell, or the like).

In some embodiments a method for determining fetal ploidy is determined according to a fetal fraction determination and normalized counts (e.g., calculated genomic section levels) where the fetal fraction determination and the normalized counts (e.g., calculated genomic section levels) are determined from different parts of a test sample (e.g., different aliquots, or e.g., different test samples taken at about the same time from the same subject or patient). For example, sometimes a fetal fraction is determined from a first part of a test sample and normalized counts and/or genomic section levels are determined from a second part of the test sample. In some embodiments the fetal fraction and the calculated genomic section levels are determined from different test samples (e.g., different parts of a test sample) taken from the same subject (e.g., patient). In some embodiments the fetal fraction and the calculated genomic section levels are determined from reads obtained at different times. In some embodiments the fetal fraction determination and the normalized counts (e.g., calculated genomic section levels) are determined from different equipment and/or from different machines (e.g., sequencing apparatus, flow cell, or the like).

Decision Analysis Features

In some embodiments a determination of an outcome (e.g., making a call) or a determination of the presence or absence of a chromosome aneuploidy, microduplication or microdeletion is made according to a decision analysis. For example, a decision analysis sometimes comprises applying one or more methods that produce one or more results, an evaluation of the results, and a series of decisions based on the results, evaluations and/or the possible consequences of the decisions and terminating at some juncture of the process where a final decision is made. In some embodiments a decision analysis is a decision tree. A decision analysis, in some embodiments, comprises coordinated use of one or more processes (e.g., process steps, e.g., algorithms). A decision analysis can be performed by person, a system, apparatus, software (e.g., a module), a computer, a processor (e.g., a microprocessor), the like or a combination thereof. In some embodiments a decision analysis comprises a method of determining the presence or absence of a chromosome aneuploidy, microduplication or microdeletion in a fetus with reduced false negative and reduced false positive determinations, compared to an instance in which no decision analysis is utilized (e.g., a determination is made directly from normalized counts). In some embodiments a decision analysis comprises determining the presence or absence of a condition associated with one or more microduplications or microdeletions. For example, in some embodiments a decision analysis comprises determining the presence or absence of one or more genetic variations associated with DiGeorge syndrome for a test sample from a subject. In some embodiments a decision analysis comprises determining the presence or absence of DiGeorge syndrome for a test sample from a subject.

In some embodiments a decision analysis comprises generating a profile for a genome or a segment of a genome (e.g., a chromosome or part thereof). A profile can be generated by any suitable method, known or described herein, and often includes obtaining counts of sequence reads mapped to portions of a reference genome, normalizing counts, normalizing levels, padding, the like or combinations thereof. Obtaining counts of sequence reads mapped to a reference genome can include obtaining a sample (e.g., from a pregnant female subject), sequencing nucleic acids from a sample (e.g., circulating cell-free nucleic acids), obtaining sequence reads, mapping sequence reads to portions of a reference genome, the like and combinations thereof. In some embodiments generating a profile comprises normalizing counts mapped to portions of a reference genome, thereby providing calculated genomic section levels.

In some embodiments a decision analysis comprises segmenting. In some embodiments segmenting modifies and/or transforms a profile thereby providing one or more decomposition renderings of a profile. A profile subjected to a segmenting process often is a profile of normalized counts mapped to portions (e.g., bins) in a reference genome or portion thereof (e.g., autosomes and sex chromosomes). As addressed herein, raw counts mapped to the portions can be normalized by one or more suitable normalization processes (e.g. PERUN, LOESS, GC-LOESS, principal component normalization (ChAI) or combination thereof) to generate a profile that is segmented as part of a decision analysis. A decomposition rendering of a profile is often a transformation of a profile. A decomposition rendering of a profile is sometimes a transformation of a profile into a representation of a genome, chromosome or segment thereof.

In certain embodiments a segmenting process utilized for the segmenting locates and identifies one or more levels within a profile that are different (e.g., substantially or significantly different) than one or more other levels within a profile. A level identified in a profile according to a segmenting process that is different than another level in the profile, and has edges that are different than another level in the profile, is referred to herein as a wavelet, and more generally as a level for a discrete segment. A segmenting process can generate, from a profile of normalized counts or levels, a decomposition rendering in which one or more discrete segments or wavelets can be identified. A discrete segment generally covers fewer portions (e.g., bins) than what is segmented (e.g., chromosome, chromosomes, autosomes).

In some embodiments segmenting locates and identifies edges of discrete segments and wavelets within a profile. In certain embodiments one or both edges of one or more discrete segments and wavelets are identified. For example, a segmentation process can identify the location (e.g., genomic coordinates, e.g., portion location) of the right and/or the left edges of a discrete segment or wavelet in a profile. A discrete segment or wavelet often comprises two edges. For example, a discrete segment or wavelet can include a left edge and a right edge. In some embodiments, depending upon the representation or view, a left edge can be a 5'-edge and a right edge can be a 3'-edge of a nucleic acid segment in a profile. In some embodiments a left edge can be a 3'-edge and a right edge can be a 5'-edge of a nucleic acid segment in a profile. Often the edges of a profile are known prior to segmentation and therefore, in some embodiments, the edges of a profile determine which edge of a level is a 5'-edge and which edge is 3'-edge. In some embodiments one or both edges of a profile and/or discrete segment (e.g., wavelet) is an edge of a chromosome.

Figure 3:
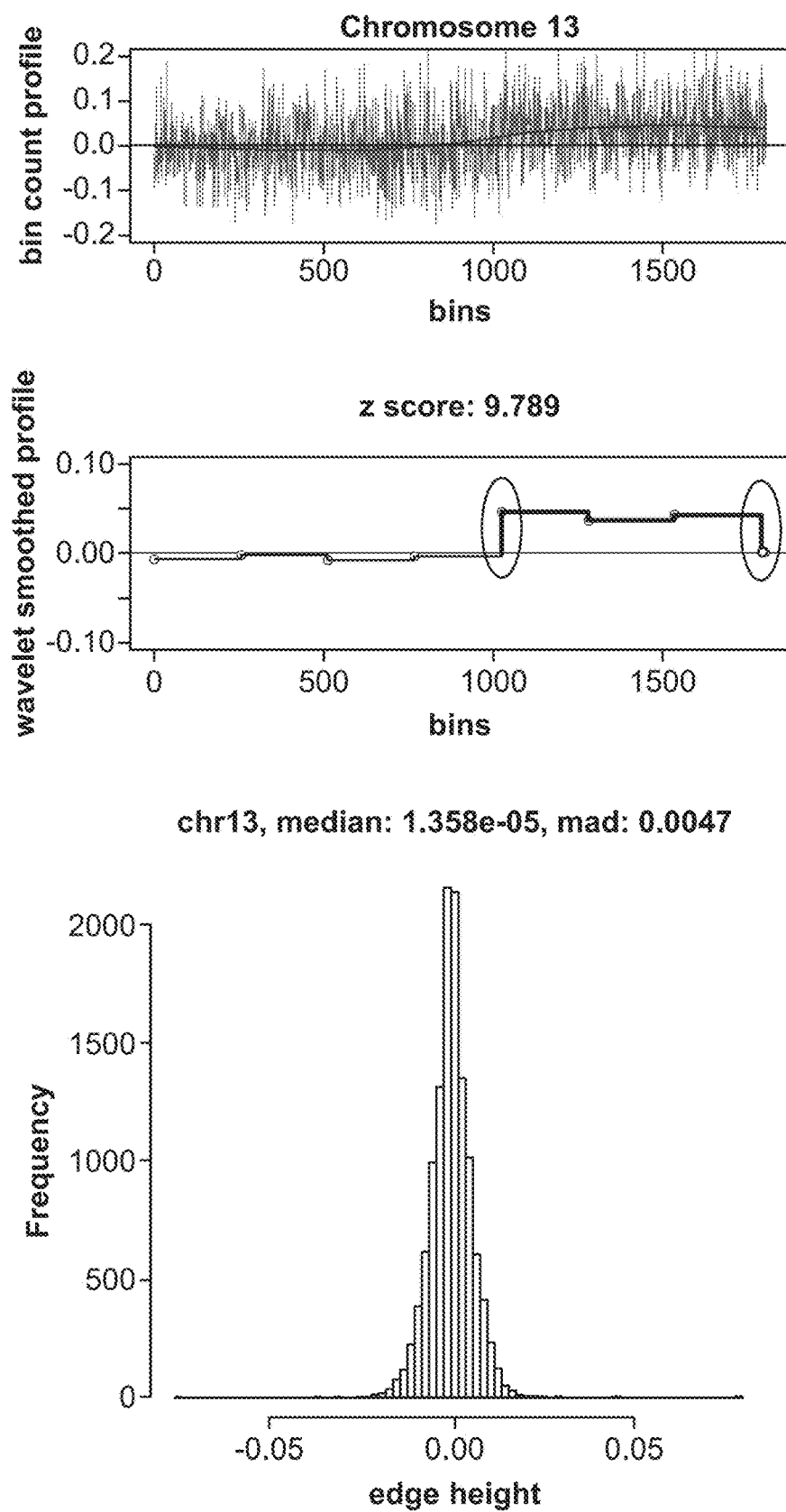
FIG. 3 shows a profile comprising a non-uniform profile (Top) and a wavelet transformed profile (Middle) for a sample for Chromosome 13. The bottom panel shows a null edge height distribution obtained from multiple euploid reference samples for Chromosome 13. In the middle panel, two large differences (circled) correspond to the boundary of the non-uniform event.

In some embodiments the edges of a discrete segment or wavelet are determined according to a decomposition rendering generated for a reference sample (e.g., a reference profile). In some embodiments a null edge height distribution is determined according to a decomposition rendering of a reference profile (e.g., a profile of a chromosome or segment thereof) (e.g., see FIG. 3). In certain embodiments, the edges of a discrete segment or wavelet in a profile are identified when the level of the discrete segment or wavelet is outside a null edge height distribution. In some embodiments the edges of a discrete segment or wavelet in a profile are identified according a Z-score calculated according to a decomposition rendering for a reference profile.

Sometimes segmenting generates two or more discrete segments or wavelets (e.g., two or more fragmented levels, two or more fragmented segments) in a profile. In some embodiments a decomposition rendering derived from a segmenting process is over-segmented or fragmented and comprises multiple discrete segments or wavelets. Sometimes discrete segments or wavelets generated by segmenting are substantially different and sometimes discrete segments or wavelets generated by segmenting are substantially similar. Substantially similar discrete segments or wavelets (e.g., substantially similar levels) often refers to two or more adjacent discrete segments or wavelets in a segmented profile each having a genomic section level (e.g., a level) that differs by less than a predetermined level of uncertainty. In some embodiments substantially similar discrete segments or wavelets are adjacent to each other and are not separated by an intervening segment or wavelet. In some embodiments substantially similar discrete segments or wavelets are separated by one or more smaller segments or wavelets. In some embodiments substantially similar discrete segments or wavelets are separated by about 1 to about 20, about 1 to about 15, about 1 to about 10 or about 1 to about 5 portions (e.g., bins) where one or more of the intervening portions have a level significantly different that the level of each of the substantially similar discrete segments or wavelets. In some embodiments the level of substantially similar discrete segments or wavelets differs by less than about 3 times, less than about 2 times, less than about 1 times or less than about 0.5 times a level of uncertainty. Substantially similar discrete segments or wavelets, in some embodiments, comprise a median genomic section level that differs by less than 3 MAD (e.g., less than 3 sigma), less than 2 MAD, less than 1 MAD or less than about 0.5 MAD, where a MAD is calculated from a median genomic section level of each of the segments or wavelets. Substantially different discrete segments or wavelets, in some embodiments are not adjacent or are separated by 10 or more, 15 or more or 20 or more portions. Substantially different discrete segments or wavelets generally have substantially different levels. In certain embodiments substantially different discrete segments or wavelets comprises levels that differ by more than about 2.5 times, more than about 3 times, more than about 4 times, more than about 5 times, more than about 6 times a level of uncertainty. Substantially different discrete segments or wavelets, in some embodiments, comprise a median genomic section level that differs by more than 2.5 MAD (e.g., more than 2.5 sigma), more than 3 MAD, more than 4 MAD, more than about 5 MAD or more than about 6 MAD, where a MAD is calculated from a median genomic section level of each of the discrete segments or wavelets.

In some embodiments a segmentation process comprises determining (e.g., calculating) a level (e.g., a quantitative value, e.g., a mean or median level), a level of uncertainty (e.g., an uncertainty value), Z-score, Z-value, p-value, the like or combinations thereof for one or more discrete segments or wavelets (e.g., levels) in a profile or segment thereof. In some embodiments a level (e.g., a quantitative value, e.g., a mean or median level), a level of uncertainty (e.g., an uncertainty value), Z-score, Z-value, p-value, the like or combinations thereof are determined (e.g., calculated) for a discrete segment or wavelet.

In some embodiments segmenting is accomplished by a process that comprises one process or multiple sub-processes, non-limiting examples of which include a decomposition generating process (e.g., a wavelet decomposition generating process), thresholding, leveling, smoothing, the like or combination thereof. Thresholding, leveling, smoothing and the like can be performed in conjunction with a decomposition generating process, and are described hereafter with reference to a wavelet decomposition rendering process.

Wavelet Segmentation Processes

In some embodiments segmenting is performed according to a wavelet decomposition generating process. In some embodiments segmenting is performed according to two or more wavelet decomposition generating processes. In some embodiments a wavelet decomposition generating process identifies one or more wavelets in a profile and provides a decomposition rendering of a profile.

Segmenting can be performed, in full or in part, by any suitable wavelet decomposition generating process described herein or known in the art. Non-limiting examples of a wavelet decomposition generating process include a Haar wavelet segmentation (Haar, Alfred (1910) "Zur Theorie der orthogonalen Funktionensysteme", Mathematische Annalen 69 (3): 331-371; Nason, G. P. (2008) "Wavelet methods in Statistics", R. Springer, New York.) (e.g., WaveThresh), Wavethresh, a suitable recursive binary segmentation process, circular binary segmentation (CBS) (Olshen, AB, Venkatraman, E S, Lucito, R, Wgler, M (2004) "Circular binary segmentation for the analysis of array-based DNA copy number data", Biostatistics, 5, 4:557-72; Venkatraman, E S, Olshen, AB (2007) "A faster circular binary segmentation algorithm for the analysis of array CGH data", Bioinformatics, 23, 6:657-63), Maximal Overlap Discrete Wavelet Transform (MODWT) (L. Hsu, S. Self, D. Grove, T. Randolph, K. Wang, J. Delrow, L. Loo, and P. Porter, "Denoising array-based comparative genomic hybridization data using wavelets", Biostatistics (Oxford, England), vol. 6, no. 2, pp. 211-226, 2005), stationary wavelet (SWT) (Y. Wang and S. Wang, "A novel stationary wavelet denoising algorithm for array-based DNA copy number data", International Journal of Bioinformatics Research and Applications, vol. 3, no. 2, pp. 206-222, 2007), dual-tree complex wavelet transform (DTCWT) (Nha, N., H. Heng, S. Oraintara and W. Yuhang (2007) "Denoising of Array-Based DNA Copy Number Data Using The Dual-tree Complex Wavelet Transform." 137-144), maximum entropy segmentation, convolution with edge detection kernel, Jensen Shannon Divergence, Kullback-Leibler divergence, Binary Recursive Segmentation, a Fourier transform, the like or combinations thereof.

A wavelet decomposition generating process can be represented or performed by a suitable software, module and/or code written in a suitable language (e.g., a computer programming language known in the art) and/or operating system, non-limiting examples of which include UNIX, Linux, oracle, windows, Ubuntu, ActionScript, C, C++, C #, Haskell, Java, JavaScript, Objective-C, Perl, Python, Ruby, Smalltalk, SQL, Visual Basic, COBOL, Fortran, UML, HTML (e.g., with PHP), PGP, G, R, S, the like or combinations thereof. In some embodiments a suitable wavelet decomposition generating process is represented in S or R code or by a package (e.g., an R package). R, R source code, R programs, R packages and R documentation for wavelet decomposition generating processes are available for download from a CRAN or CRAN mirror site (e.g., The Comprehensive R Archive Network (CRAN); World Wide Web URL cran.us.r-project.org). CRAN is a network of ftp and web servers around the world that store identical, up-to-date, versions of code and documentation for R. For example, WaveThresh (WaveThresh: Wavelets statistics and transforms; World Wide Web URL cran.r-project.org/web/packages/wavethresh/index.html) and a detailed description of WaveThresh (Package 'wavethresh'; World Wide Web URL crans-project.org/web/packages/wavethresh/wavethresh.pdf) can be available for download. In some embodiments R code for a wavelet decomposition generating process (e.g., maximum entropy segmentation) is described in Example 4. An example of R code for a CBS method can be downloaded (e.g., DNAcopy; World Wide Web URL bioconductor.org/packages/2.12/bioc/html/DNAcopy.html or Package 'DNAcopy'; World Wide Web URL bioconductor.org/packages/release/bioc/manuals/DNAcopy/man/DNAcopy.pdf).

In some embodiments a wavelet decomposition generating process (e.g., a Haar wavelet segmentation, e.g., WaveThresh) comprises thresholding. In some embodiments thresholding distinguishes signals from noise. In certain embodiments thresholding determines which wavelet coefficients (e.g., nodes) are indicative of signals and should be retained and which wavelet coefficients are indicative of a reflection of noise and should be removed. In some embodiments thresholding comprises one or more variable parameters where a user sets the value of the parameter. In some embodiments thresholding parameters (e.g., a thresholding parameter, a policy parameter) can describe or define the amount of segmentation utilized in a wavelet decomposition generating process. Any suitable parameter values can be used. In some embodiments a thresholding parameter is used. In some embodiments a thresholding parameter value is a soft thresholding. In certain embodiments a soft thresholding is utilized to remove small and non-significant coefficients. In certain embodiments a hard thresholding is utilized. In certain embodiments a thresholding comprises a policy parameter. Any suitable policy value can be used. In some embodiments a policy used is "universal" and in some embodiments a policy used is "sure".

In some embodiments a wavelet decomposition generating process (e.g., a Haar wavelet segmentation, e.g., WaveThresh) comprises leveling. In some embodiments, after thresholding, some high level coefficients remain. These coefficients represent steep changes or large spikes in the original signal and, in certain embodiments, are removed by leveling. In some embodiments leveling includes assignment of a value to a parameter known as a decomposition level c. In certain embodiments an optimal decomposition level is determined according to one or more determined values, such as the length of the chromosome (e.g., length of profile), the desired wavelet length to detect, fetal fraction, sequence coverage (e.g., plex level) and the noise level of a normalized profile. For a given length of a segment of a genome, chromosome or profile ($N_{chr}$), the wavelet decomposition level c is sometimes related to the minimum wavelet length $N_{micro}$ according to the equation $N_{micro}=N_{chr}/2^{c+1}$. In some embodiments, to detect a microdeletion of size $N_{micro}$ or greater, the desired decomposition level c is determined according to the following equation: $c=\log 2 (N_{chr}/N_{micro})-1$. For example, if $N_{chr}=4096$ portions of a reference genome and $N_{micro}=128$ portions of a reference genome, then the decomposition level c is 4, and a c±1 level can be used in certain instances (i.e., about 3 to about 5). In some embodiments, a decomposition level c is about 1, 2, 3, 4, 5, 6, 7, 8, 9 or 10. In some embodiments the minimum desired wavelet length to detect, $N_{micro}$ is about 1 Mb, 2 Mb, 3 Mb, 4 Mb, 5 Mb, 6 Mb, 7 Mb, 8 Mb, 10 Mb, 15 Mb, or greater than about 20 Mb. In some embodiments $N_{micro}$ is predetermined. In some embodiments the amount of sequence coverage (e.g., plex level) and fetal fraction are inversely proportional to $N_{micro}$. For example, the minimum desired wavelet length to detect decreases (i.e. resolution increases) as the amount of fetal fraction in a sample increases. In some embodiments the minimum desired wavelet length to detect decreases (i.e. resolution increases) as the coverage increases (i.e., plex-level decreases). For example, for a sample comprising about 10% fetal fraction, a 4-plex yields an $N_{micro}$ of about 1 Mb or greater and a 12-plex yields an $N_{micro}$ of about 3 Mb or greater. In some embodiments thresholding is performed prior to leveling and sometimes thresholding is performed after leveling.

Maximum Entropy Segmentation Process

In some embodiments a suitable decomposition generating process includes a maximum entropy segmentation process. In some embodiments a maximum entropy segmentation comprises determining a decomposition rendering. In some embodiments a maximum entropy segmentation comprises determining the presence or absence of a sub-chromosomal abnormalities (e.g., a microduplication, a microdeletion).

In certain embodiments maximum entropy segmentation comprises recursively partitioning a segment of a genome (e.g., a set of portions, a profile). In certain embodiments a maximum entropy segmentation process partitions a segment of a genome according to levels (e.g., genomic section levels). In certain embodiments maximum entropy segmentation comprises determining a level for segmented parts of a profile. In some embodiments maximum entropy segmentation divides a segment of a genome into two segments (e.g., two sets of portions) and calculates a level for the two segments. In some embodiments the level for the two segments is calculated before or after a division (e.g., a segmentation) is made. In some embodiments a partition site (e.g., the location of segmentation, the location of division) is selected to maximize the difference between the level of the two resulting segments. In some embodiments maximum entropy segmentation determines a difference in level between two hypothetical segments that would result from a hypothetical segmentation event for every possible partition site in a profile (e.g., segment), selects the site where the maximum difference in level is predicted and then divides (e.g., partitions) the profile into two segments. In some embodiments two adjacent segments that were recently divided are determined as significantly different or not significantly different by a suitable statistical method, non-limiting examples of which include a t-test, a t-based criterion, or the like. In some embodiments maximum entropy segmentation comprises partitioning a first and a second subset of portions when the level of the first subset of portions is significantly different than the level of the second subset of portions. In some embodiments the first and the second subset of portions are adjacent to each other.

In some embodiments two adjacent segments that were recently divided are determined as significantly different and each of the segments is partitioned again according to maximum entropy segmentation (e.g., according to a partition site resulting in a maximum difference in level). In some embodiments maximum entropy segmentation comprises partitioning a set of portions (e.g., a profile) recursively thereby providing two or more subsets of portions where each of the resulting subsets comprise levels that are significantly different than the level of an adjacent subset of portions.

In some embodiments maximum entropy segmentation comprises identifying one or more discrete segments. In some embodiments maximum entropy segmentation comprises identifying a first level significantly different that a second level. A discrete segment often has a first level significantly different than a second level of a segment in the profile (e.g., a reference level). In certain embodiments, a discrete segment is determined according to a reference level (e.g., a null level, a null profile). In some embodiments a reference level is a level of an entire profile or a part thereof. In some embodiments a reference level is a reference profile or a portion of a reference profile (e.g., or segment) that is known as being euploid or known as being devoid of a copy number variation (e.g., a microduplication or microdeletion). In some embodiments a discrete segment has a first level (e.g., wavelet) significantly different that a second level (e.g., a reference level) and the second level is a reference level. In some embodiments maximum entropy segmentation comprises determining the presence or absence of a chromosome aneuploidy, microduplication or microdeletion in a fetus for a sample with reduced false negative and reduced false positive determinations according to an identified discrete segment and/or according to a first level significantly different that a second level.

In some embodiments maximum entropy segmentation comprises rejoining two subsets of portions that were segmented (e.g., divided). In some embodiments two segments that were divided are not significantly different and the two segments are rejoined. In some embodiments the level of each of two subsets of portions that were segmented are not significantly different (e.g., according to a predefined threshold, e.g., a Z-score and/or a level of uncertainty, e.g., a MAD) and the subsets are rejoined. In some embodiments rejoined segments are not partitioned again.

In some embodiments a decision analysis comprises two or more segmenting processes that result in two or more decomposition renderings. In certain embodiments a decision analysis comprises employing two or more different segmenting processes (e.g., decomposition generating processes) that independently generate decomposition renderings. In some embodiments a decision analysis comprises a first segmenting process and a second segmenting process and the first and second segmenting process are performed in parallel. In certain embodiments a first and a second segmenting process is performed in series. In certain embodiments a decision analysis comprises two or more different segmenting processes that independently generate decomposition renderings that are substantially the same or different depending on the sample analyzed and the types of segmenting processes employed. In some embodiments a first segmenting process comprises a wavelet segmenting process (e.g., Haar Wavelet process) and a second segmenting process comprises a circular binary segmentation process.

Polishing

In some embodiments a decomposition rendering is polished thereby providing a polished decomposition rendering. In some embodiments a decomposition rendering is polished two or more times. In some embodiments a decomposition rendering is polished before and/or after one or more steps of a segmenting process. In some embodiments a decision analysis comprises two or more segmenting processes and each segmenting process comprises one or more polishing processes. A decomposition rendering can refer to a polished decomposition rendering or a decomposition rendering that is not polished.

Thus, in some embodiments a segmenting process comprises polishing. In some embodiments a polishing process identifies two or more substantially similar discrete segments or wavelets (e.g., in a decomposition rendering) and merges them into a single discrete segment or wavelet (e.g., FIG. 4). In some embodiments a polishing process identifies two or more adjacent segments or wavelets that are substantially similar and merges them into a single level, segment or wavelet. Thus, In some embodiments a polishing process comprises a merging process. In certain embodiments adjacent fragmented discrete segments or wavelets are merged according to their genomic section levels. In some embodiments merging two or more adjacent discrete segments or wavelets comprises calculating a median level for the two or more adjacent discrete segments or wavelets that are eventually merged. In some embodiments two or more adjacent discrete segments or wavelets that a substantially similar are merged and thereby polished resulting in a single segment, wavelet or level. In certain embodiments, two or more adjacent discrete segments or wavelets are merged by a process described by Willenbrock and Fridly (Willenbrock H, Fridlyand J. A comparison study: applying segmentation to array CGH data for downstream analyses. Bioinformatics (2005) November 15; 21(22):4084-91). In some embodiments two or more adjacent discrete segments or wavelets are merged by a process known as GLAD and described in Hupe, P. et al. (2004) "Analysis of array CGH data: from signal ratio to gain and loss of DNA regions", Bioinformatics, 20, 3413-3422.

Identifying a Candidate Segment or Wavelet Event

In some embodiments a decision analysis comprises identifying a candidate segment, or wavelet event, in a decomposition rendering. A candidate segment is determined as being the most significant discrete segment in a decomposition rendering, and a wavelet event is determined as being the most significant wavelet identified in a wavelet decomposition rendering. A "candidate segment" also is the most significant discrete segment within a decomposition rendering resulting from segmenting using any type of segmentation process and decomposition rendering. A candidate segment is synonymous with a "wavelet event" when a wavelet segmentation process is utilized. A candidate segment generally is the most significant discrete segment in a decomposition rendering, and sometimes is the most significant in terms of the number of portions (e.g., bins) covered by the segment and/or in terms of the absolute value of the level of normalized counts for the segment. A candidate segment sometimes is larger and sometimes substantially larger than other discrete segments in a decomposition rendering. In some embodiments only one candidate segment is identified in a decomposition rendering. In some embodiments one or more discrete segments are identified in a decomposition rendering and one of the one or more discrete segments is identified as a candidate segment. In some embodiments a candidate segment is a first discrete segment having a level substantially larger than the level of a second discrete segment where the first discrete level is the largest level in a decomposition rendering. A candidate segment can be identified by a suitable method. In some embodiments a candidate segment is identified by an area under the curve (AUC) analysis. In some embodiments a decision analysis comprises an AUC analysis. In certain embodiments where a first discrete segment has a level and/or covers a number of portions substantially larger than for another discrete segment in a decomposition rendering, the first segment comprises a larger AUC. Where a level is analyzed for AUC, an absolute value of a level often is utilized (e.g., a level corresponding to normalized counts can have a negative value for a deletion and a positive value for a duplication). In certain embodiments an AUC is determined as an absolute value of a calculated AUC (e.g., a resulting positive value). In certain embodiments a candidate segment, once identified (e.g., by an AUC analysis or by a suitable method) and optionally after it is validated, is selected for a z-score calculation, or the like, to determine if the candidate segment represents a genetic variation (e.g., an aneuploidy, microdeletion or microduplication).

Log Odds Ratio Analysis

An odds ratio, or log odds ratio (LOR), sometimes is calculated for use in a comparison, and/or for use in a decision (e.g., a decision of the presence or absence of a genetic variation) for a sample. A LOR sometimes is calculated as the log of the quotient of (A) and (B), where (A) is a first multiplication product of (1) a conditional probability of having a genetic variation and (2) a prior probability of having the genetic variation, and (B) is a second multiplication product of (1) a conditional probability of not having the genetic variation and (2) a prior probability of not having the genetic variation. The genetic variation sometimes is a chromosome aneuploidy (e.g., one, three, four copies of a whole chromosome), microdeletion or microinsertion.

A LOR calculation sometimes comprises applying a fetal fraction determined for a test sample, and sometimes comprises applying a count representation for a chromosome or candidate segment identified for the test sample. In some embodiments, the conditional probability of having the chromosome aneuploidy is determined according to a fetal fraction and a count representation. Thus in some embodiments certain methods include determining a chromosome count representation and/or a candidate segment count representation according to counts of nucleic acid sequence reads mapped to portions of a reference genome, where the sequence reads often are reads of circulating cell-free nucleic acid for a test sample from a pregnant female bearing a fetus. A candidate segment sometimes is a validated candidate segment (described herein).

A chromosome count representation sometimes is counts mapped to portions (e.g., bins) in the chromosome divided by counts in portions of the genome or a subset thereof larger than the chromosome (e.g., all autosomes). A chromosome count representation sometimes is quantified, and any suitable quantification can be utilized (e.g., z-score). For embodiments in which a z-score quantifies a chromosome count representation, the z-score sometimes is subtraction product (A) divided by value (B). The subtraction product (A) sometimes is (i) a test sample chromosome count representation less (ii) a median of a euploid chromosome count representation. Value (B) sometimes is a MAD of the euploid chromosome count representation. The test sample chromosome count representation sometimes is a ratio of (a) counts in portions in the chromosome, to (b) counts in portions in the autosomes, for the test sample. The median of the euploid chromosome count representation sometimes is the median of a ratio of (a) counts in portions in the chromosome, to (b) counts in portions in autosomes, for euploids. The counts sometimes are normalized counts, whereby counts mapped to genomic portions can be normalized by one or more suitable normalization processes. Non-limiting examples of normalization processes that can be utilized are known in the art and described herein (e.g., LOESS, GC-LOESS, PERUN, ChAI, principal component normalization processes).

A candidate segment count representation sometimes is counts mapped to portions (e.g., bins) in, or covered by, the candidate segment divided by counts in portions of the genome or a subset thereof larger than the candidate segment (e.g., all autosomes). A candidate segment count representation sometimes is quantified, and any suitable quantification can be utilized (e.g., z-score). For embodiments in which a z-score quantifies a candidate segment count representation, the z-score sometimes is subtraction product (A) divided by value (B). The subtraction product (A) sometimes is (i) a test sample candidate segment count representation less (ii) a median of a euploid candidate segment count representation. Value (B) sometimes is a MAD of the euploid candidate segment count representation. The test sample candidate segment count representation sometimes is a ratio of (a) counts in portions in the candidate segment, to (b) counts in portions in the autosomes, for the test sample. The median of the euploid candidate segment count representation sometimes is the median of a ratio of (a) counts in portions in the candidate segment, to (b) counts in portions in autosomes, for euploids. The counts sometimes are normalized counts, whereby counts mapped to genomic portions can be normalized by one or more suitable normalization processes. Non-limiting examples of normalization processes that can be utilized are known in the art and described herein (e.g., LOESS, GC-LOESS, PERUN, ChAI, principal component normalization processes).

Methods involving a LOR calculation sometimes include determining fetal fraction for the test sample. Fetal fraction can be determined using any suitable method known in the art, non-limiting examples of which are described herein (e.g., Y chromosome locus (e.g., SRY locus) quantification, FRS quantification).

In certain LOR calculation embodiments, the conditional probability of having the genetic variation is assessed according to fetal fraction determined for the test sample, a z-score for the chromosome count representation, or candidate segment count representation, for the test sample, and a fetal fraction-specific distribution of z-scores for the chromosome count representation, or candidate segment count representation. In some embodiments the conditional probability of having the genetic variation is determined by the relationship in equation 23 shown in Example 6 hereafter, where f is fetal fraction, X is the summed portions for the chromosome or candidate segment, $X \sim f(\mu X, \sigma X)$, where $\mu X$ and $\sigma X$ are the mean and standard deviation of X, respectively, and $f(\bullet)$ is a distribution function. The conditional probability of having the genetic variation sometimes is the intersection between the z-score for the test sample chromosome count representation, or candidate segment count representation, and a fetal fraction-specific distribution of z-scores for the chromosome count representation, or the candidate segment count representation (e.g., see FIG. 32 for T21 example). Example 6 describes, with reference to FIG. 32, distribution shifts with reference to the euploid distribution in situations where presence or absence of a microduplication event or microdeletion event is determined.

The conditional probability of not having the chromosome aneuploidy sometimes is determined according to the chromosome count representation, or candidate segment count representation, and count representations for euploids. The conditional probability of not having the genetic variation sometimes is the intersection between the z-score of the chromosome count representation and a distribution of z-scores for the chromosome count representation in euploids (e.g., see FIG. 32 for T21 example).

The prior probability of having the genetic variation and the prior probability of not having the genetic variation often are determined using statistical data known in the art for one or more patient populations, for example. The probability of T21 occurrence, and the probability of no occurrence of T21, for example, can be readily determined for a population in a particular geographic region. The prior probabilities often are determined from multiple samples that do not include the test subject.

Comparisons and Decision Analysis

In some embodiments a decision analysis comprises a comparison. In some embodiments a comparison comprises comparing at least two decomposition renderings. In some embodiments a comparison comprises comparing at least two candidate segments. In certain embodiments each of the at least two candidate segments is from a different decomposition rendering. For example, a first candidate segment can be from a first decomposition rendering and a second candidate segment can be from a second decomposition rendering. In some embodiments a comparison comprises determining if two decomposition renderings are substantially the same or different. In some embodiments a comparison comprises determining if two candidate segments are substantially the same or different.

In some embodiments two decomposition renderings are substantially the same when each rendering comprises a candidate segment and the candidate segments from each decomposition rendering are determined as substantially the same. Two candidate segments can be determined as substantially the same or different by a suitable comparison method, non-limiting examples of which include by visual inspection, by comparing levels or Z-scores of the two candidate segments, by comparing the edges of the two candidate segments, by overlaying either the two candidate segments or their corresponding decomposition renderings, the like or combinations thereof. In some embodiments the edges of two candidate segments are substantially the same and the two candidate segments are substantially the same. In certain embodiments, an edge of a candidate segment is substantially the same as an edge of another candidate segment and the two edges are separated by less than 10, less than 9, less than 8, less than 7, less than 6, less than 5, less than 4, less than 3, less than 2, or by less than 1 portion (e.g., bin). In some embodiments two edges are substantially the same and are at the same location (e.g., same portion). In some embodiments two candidate segments that are substantially the same comprise levels, Z-scores, or the like that are substantially the same (e.g., within a level of uncertainty, e.g., about 3, 2, 1 or less times a level of uncertainty). In some embodiments two candidate segments comprise substantially different edges and/or substantially different levels and are determined, according to a comparison, not substantially the same (e.g., different).

Figure 11A:
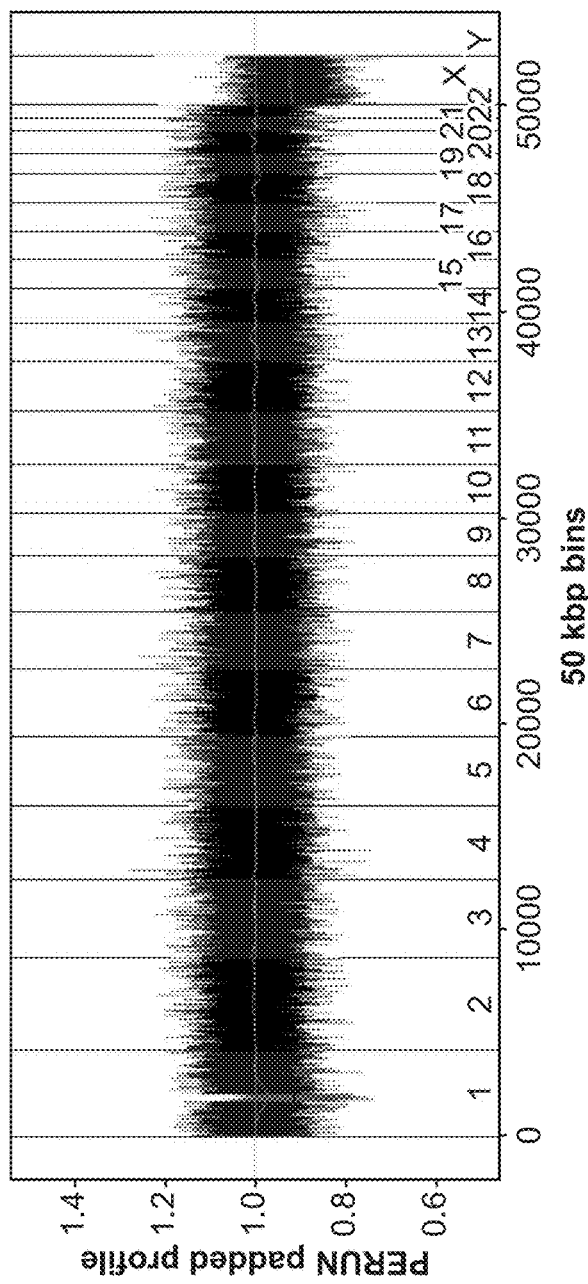
FIG. 11A shows a composite wavelet event representing the detection of a microdeletion in a profile of Chromosome 1.

In certain embodiments a comparison comprises generating one or more composite candidate segments and making a determination of presence or absence of an aneuploidy, microdeletion or microduplication based on (e.g., based in part on or solely on) on a comparison comprising comparison of the one or more composite candidate segments. A composite candidate segment can be generated by any suitable method. In some embodiments a composite candidate segment is generated by averaging two or more candidate segments (e.g., the levels, AUC and/or edges). In some embodiments a composite candidate segment is generated by overlaying two or more candidate segments. In some embodiments two or more candidate segments are substantially the same and a composite candidate segment is generated (e.g., FIG. 11).

A comparison sometimes includes quantifying candidate segments (e.g., a wavelet event) derived from two more decomposition renderings, as described hereafter, and utilizing the comparison to determine presence or absence of a genetic variation in the sample (e.g., a chromosome aneuploidy, microduplication or microdeletion).

Figure 11B:
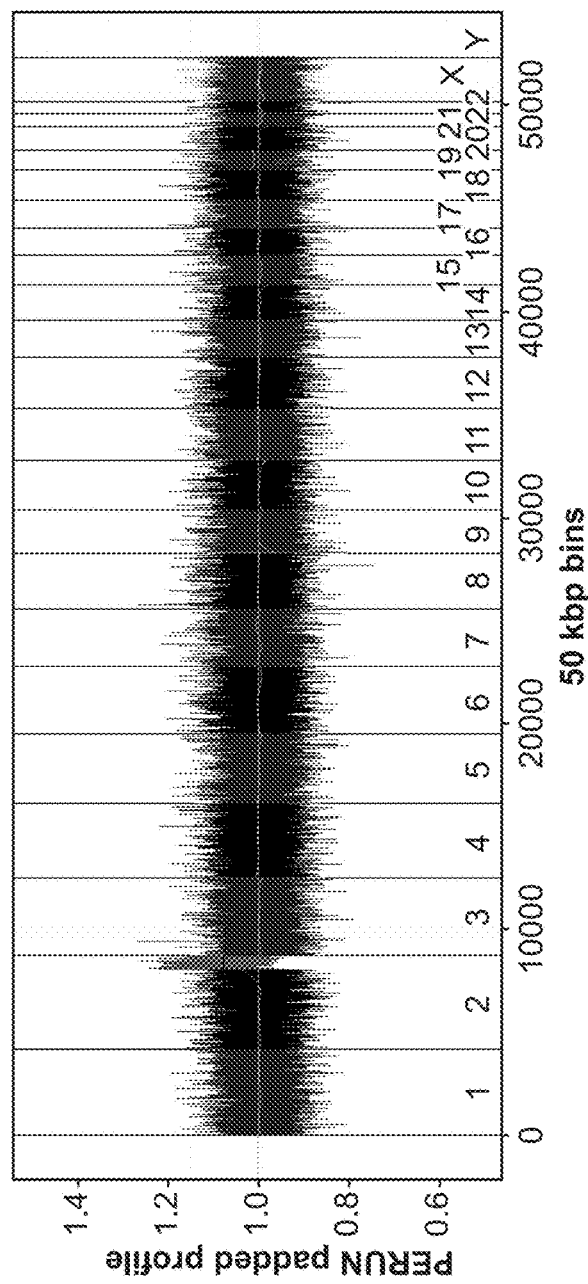
FIG. 11B shows a composite wavelet event representing the detection of a microduplication in a profile of Chromosome 2.

In certain embodiments a comparison comprises determining the presence or absence of a composite candidate segment (e.g., composite wavelet event) from candidate segments (e.g., wavelet events) identified in two or more decomposition renderings. In some embodiments two or more candidate segments (e.g., wavelet events, e.g., derived from two or more decomposition renderings) overlap or are substantially the same and the presence of a composite candidate segment (e.g., composite wavelet event) is determined (FIG. 11). The presence or absence of a composite wavelet event can be determined by any suitable method. In some embodiments the presence or absence of a composite candidate segment (e.g., composite wavelet event) is determined by averaging two or more candidate segment (e.g., composite wavelet events, e.g., the levels, AUC and/or edges). In some embodiments the presence or absence of a composite candidate segment (e.g., composite wavelet event) is determined by overlaying two or more candidate segments (e.g., wavelet events). In certain embodiments the presence of a composite candidate segment (e.g., composite wavelet event) is determined when two or more candidate segments (e.g., wavelet events) overlap or are substantially the same.

In some embodiments two or more candidate segments (e.g., composite wavelet events, e.g., derived from two or more decomposition renderings) do not overlap or are different (e.g., substantially different) and the absence of a composite candidate segment (e.g., absence of a composite wavelet event) is determined. In some embodiments the absence of a composite candidate segment (e.g., composite wavelet event) indicates the absence of a chromosome aneuploidy, microduplication or microdeletion.

Figure 7:
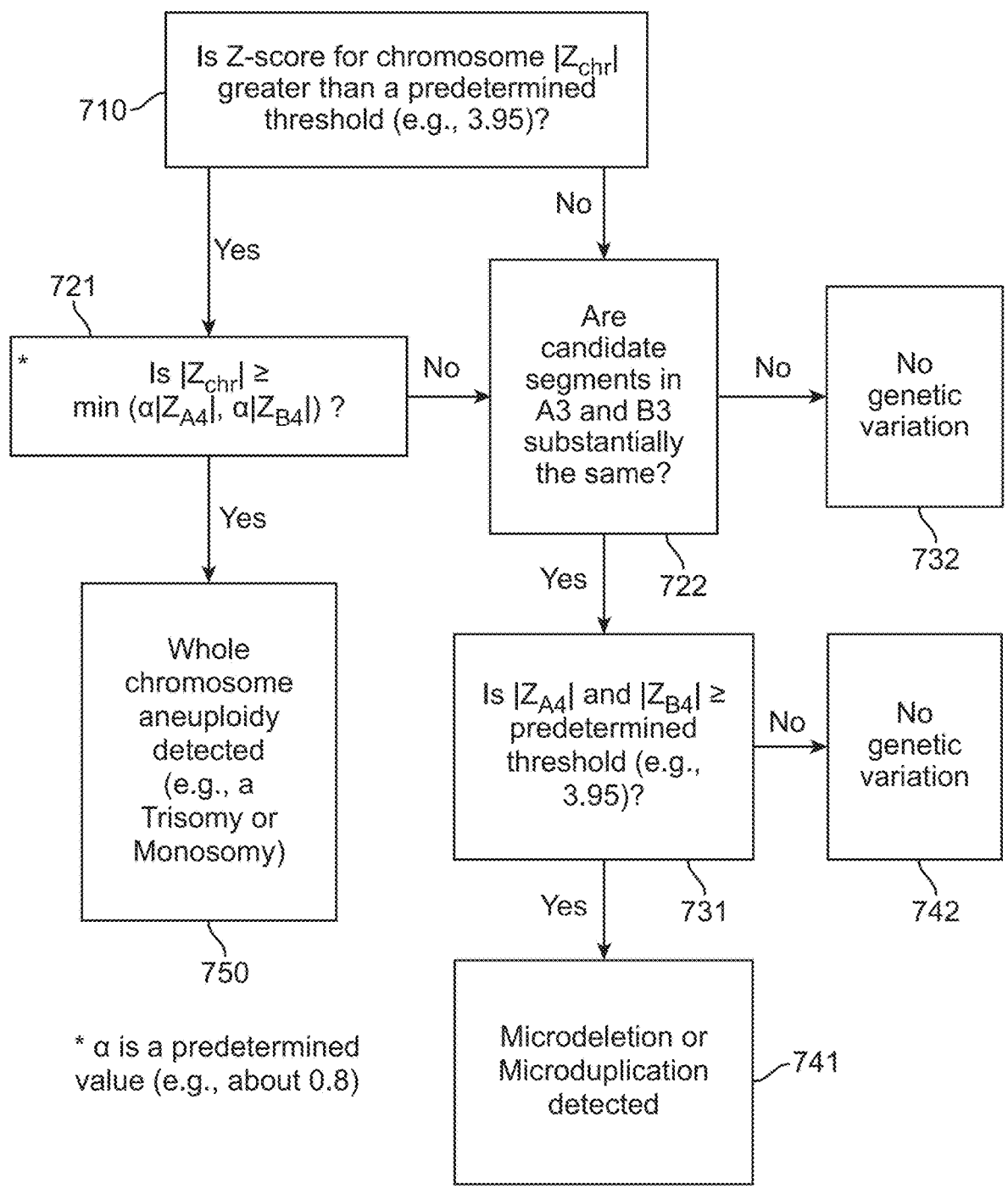
FIG. 7 shows a non-limiting example of a comparison expanded from 650.
Figure 8:
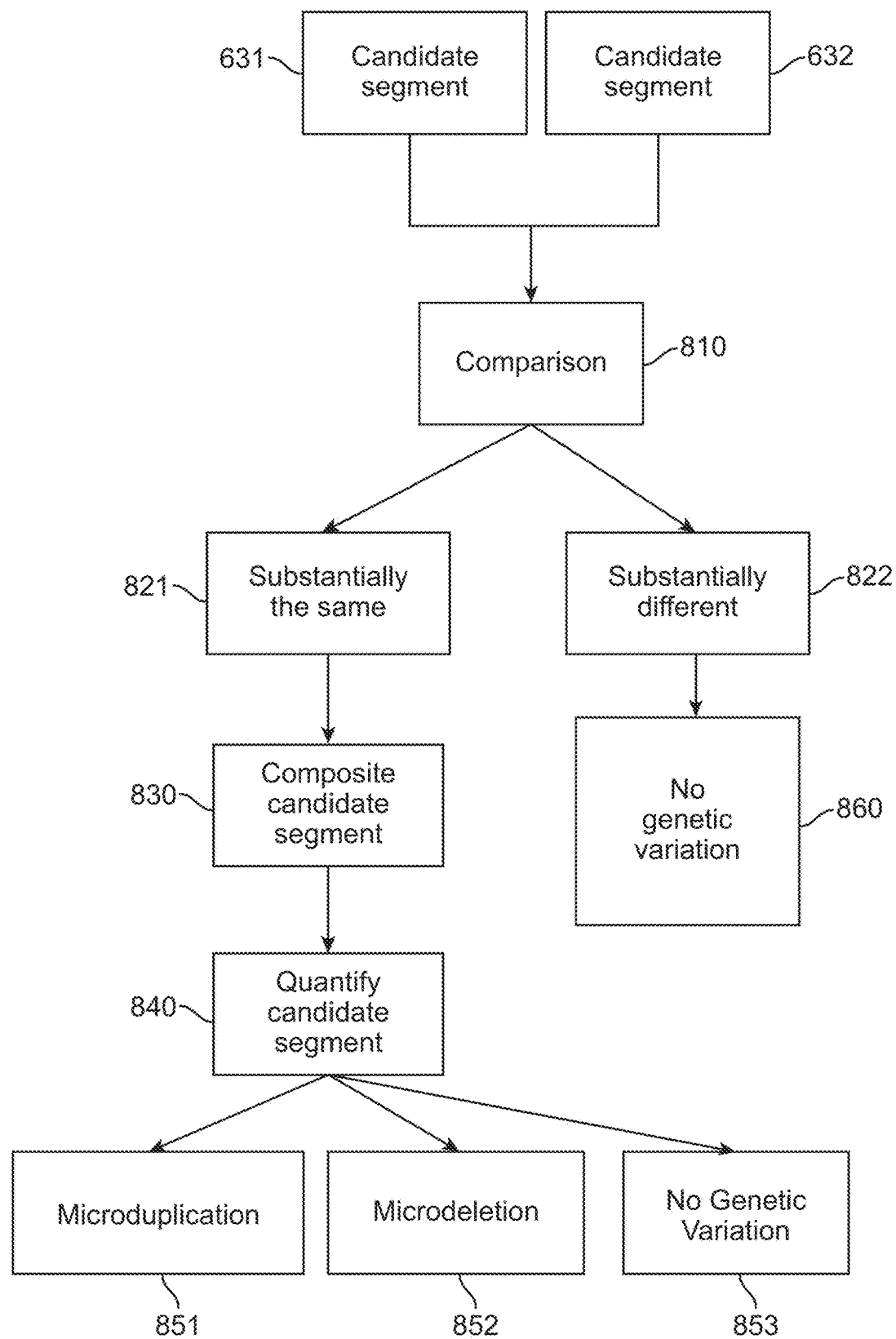
FIG. 8 shows a non-limiting example of a comparison of two wavelet events represented by 631 and 632.

In some embodiments a decision analysis comprises determining an outcome (e.g., determining the presence or absence of a genetic variation e.g., in a fetus). In some embodiments a decision analysis comprises a method of determining the presence or absence of a chromosome aneuploidy, microduplication or microdeletion. In some embodiments a decision analysis comprises a method of determining the presence or absence of a genetic variation (e.g., in a fetus) with reduced false negative and reduced false positive determinations as compared to determining the presence or absence of the genetic variation not using a decision analysis described herein (e.g., without segmenting, identifying presence or absence of one or more candidate segments and/or quantifying one or more candidate segments). In some embodiments a decision analysis comprises a series of methods or method steps. Non-limiting examples of a decision analysis are shown in FIGS. 6-8 and are described herein. In certain embodiments, a decision analysis comprises obtaining counts 600 and generating and/or obtaining a profile 601. In some embodiments a decision analysis comprises segmenting a profile and generating a decomposition rendering. In some embodiments of a decomposition rendering or a segment thereof (e.g., a segment representing a chromosome, a level, a discrete segment or wavelet, a candidate segment or wavelet event, a composite segment or composite wavelet), is quantitated by a suitable method. Non-limiting example of suitable quantitation methods are known in the art and are described, in part, herein and include, for example methods of determining a Z-score, p-value, t-value, level or level, AUC, ploidy, level of uncertainty, the like or combinations thereof.

In some embodiments a decision analysis comprises segmenting a profile by two or more segmenting methods. In some embodiments a decision analysis comprises 50 or more segmenting methods. In certain embodiments a decision analysis comprises 50 or less, 40 or less, 30 or less, 20 or less, 10 or less, or about 5 or less segmenting methods. In certain embodiments a decision analysis comprises about 10, 9, 8, 7, 6, 5, 4, 3, or 2 segmenting methods. In some embodiments each method of segmenting (e.g., FIG. 6A, 611 and 612, e.g., where two methods are utilized) provides a decomposition rendering of a profile 601. In some embodiments decomposition renderings provided by two or more methods of segmenting are the same, substantially the same or different.

Figure 6A:
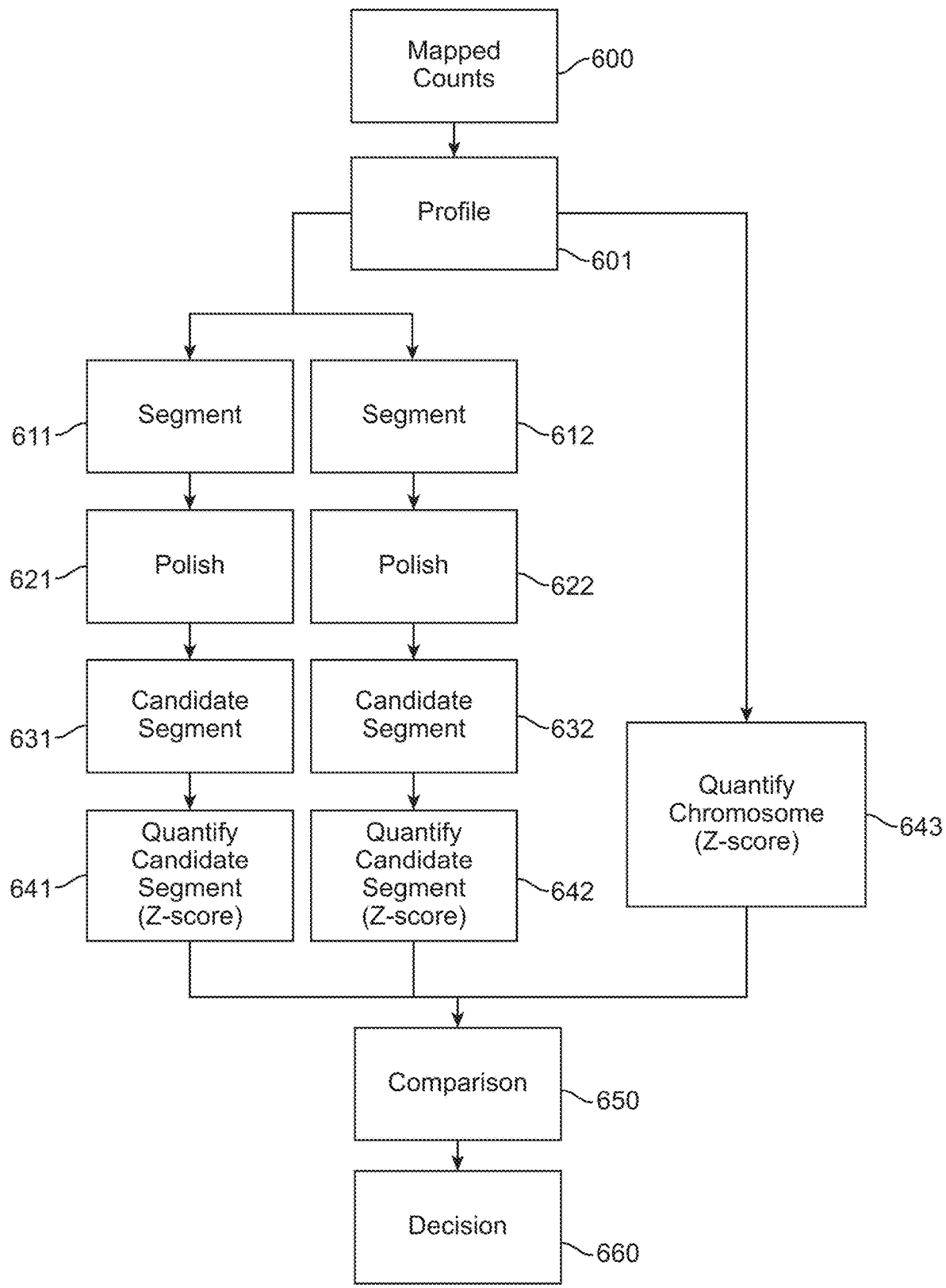
FIG. 6A and FIG. 6B show non-limiting examples of a decision analysis. Some elements (e.g., boxes) of the flow chart shown are optional. In some embodiments additional elements are added (e.g., a validation).
Figure 6B:
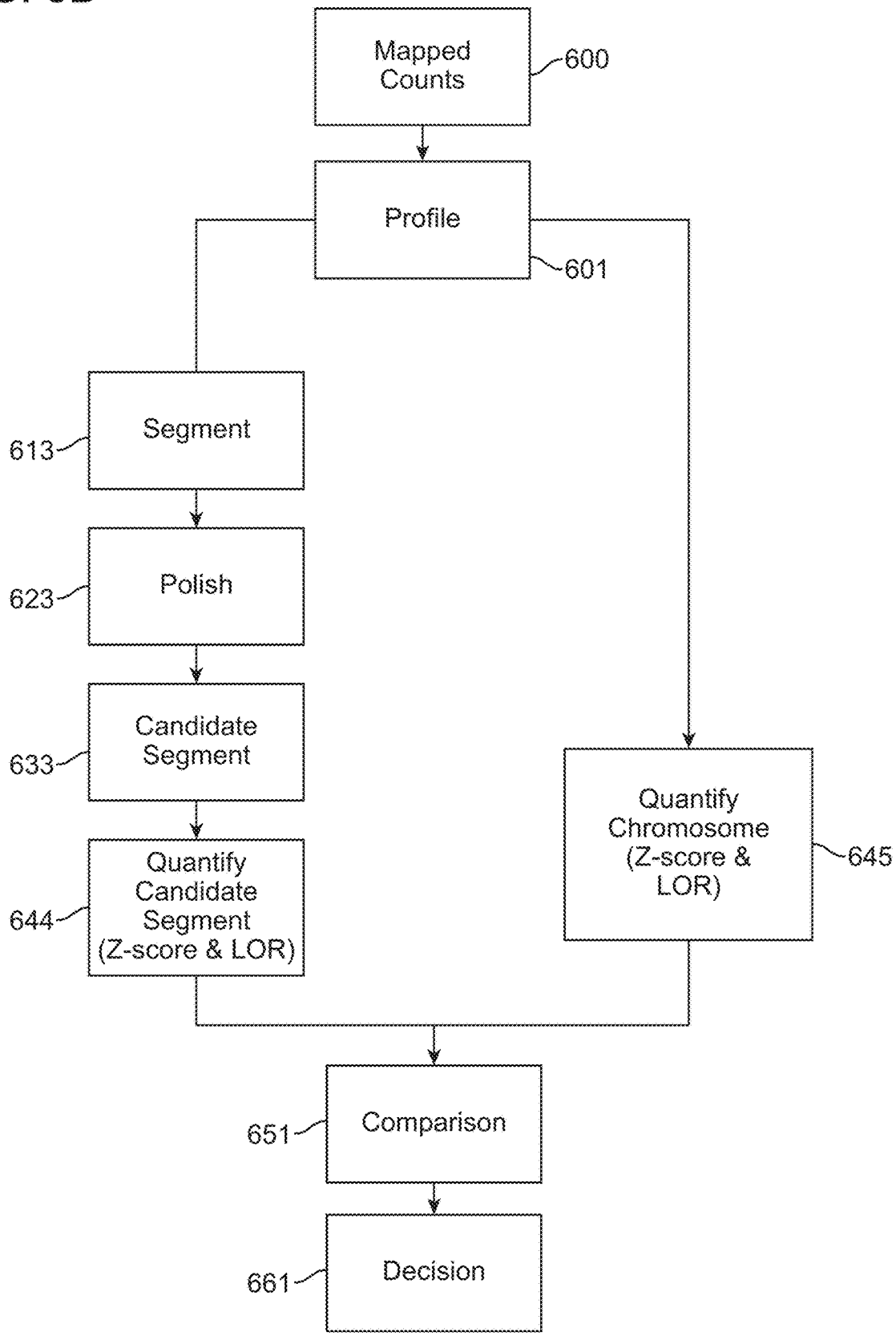

In some embodiments a polishing (e.g., FIG. 6A, 621 and 622; FIG. 6B, 623)) follows segmenting 613. In some embodiments one or more decomposition renderings derived from one or more segmenting process applications are polished sometimes by the same polishing method. In some embodiments one or more decomposition renderings derived from one or more segmenting steps are polished by a different polishing method. In some embodiments a decomposition rendering is polished by one, two, three or more polishing methods. In some embodiments each decomposition rendering is polished by one method and the method is the same for each decomposition rendering.

In some embodiments the presence or absence of a candidate segment candidate segment (e.g., wavelet event) is identified following a segmenting, and optionally after polishing (e.g., FIG. 6A, 631 and 632; FIG. 6B, 623). In some embodiments a polishing process is omitted and a candidate segment (e.g., wavelet event) is identified directly from a decomposition rendering derived from segmenting. In some embodiments a candidate segment (e.g., wavelet event) is identified in and/or from a polished decomposition rendering. In some embodiments a candidate segment (e.g., wavelet event) is not identified in one or more decomposition renderings and the absence of a genetic variation 732, 742 is determined. In some embodiments, where a candidate segment (e.g., wavelet event) is not identified in one of the one or more decomposition renderings (e.g., polished decomposition renderings), a decision analysis is terminated.

In some embodiments a candidate segment (e.g., wavelet event), once identified, is quantitated (e.g., FIG. 6A, 641 and 642; FIG. 6B, 644 (e.g., z-score or LOR quantification)). A candidate segment (e.g., wavelet event) can be quantitated by a suitable method, non-limiting examples of which include calculating a Z-score, calculating a p-value, determining a t-value, determining a level or level, determining a ploidy, calculated a level of uncertainty, the like or combinations thereof.

In some embodiments a decision analysis comprises a comparison (e.g., 650, 651, 810 in FIGS. 6A, 6B and 8). In some embodiments a comparison follows a quantitation (e.g., FIG. 6A, 641, 642 and 643; FIG. 6B, 651). In some embodiments a comparison follows a wavelet or candidate segment identification (e.g., FIG. 6A, 631 and 632; FIG. 6B, 633). Sometimes a comparison follows a chromosome quantification (e.g., FIG. 6A, 643; FIG. 6B, 645 (e.g., a z-score or LOR quantification)). In some embodiments, making a decision follows a comparison (e.g., FIG. 6A, 660; FIG. 6B, 661).

A candidate segment, including a validated candidate segment (collectively referred to as a "candidate segment"), is quantified in certain embodiments. A candidate segment sometimes is quantified as a candidate segment count representation, and a candidate segment count representation sometimes is quantified by a z-score, as described herein. A chromosome count representation sometimes is generated and quantified for a chromosome in which the candidate segment is located. A chromosome count representation is described herein, and can be quantified by a z-score, which also is described herein. Counts for a candidate segment count representation and/or a chromosome count representation sometimes are normalized counts as described herein.

In certain embodiments, a z-score quantification of a first candidate segment count representation is generated, a z-score quantification of a second candidate segment count representation is generated, where the first candidate segment and the second candidate segment are identified from two different types of segmentations. Some embodiments comprise determining the minimum of (i) the z-score quantification of the first candidate segment count representation multiplied by a factor of less than 1 (e.g., about 0.6 to about 0.8) and (ii) the z-score quantification of the second candidate segment count representation multiplied by the factor.

In some embodiments, a quantification of a candidate segment count representation is compared to a quantification of a chromosome count representation for a chromosome in which the candidate segment is located. Certain embodiments comprise determining whether the z-score quantification of the chromosome representation is less than, greater than or equal to the minimum referenced in the previous paragraph. Some embodiments comprise determining whether the z-score quantification of the chromosome count representation is less than, greater than or equal to a threshold z-score value (e.g., a value of about 3.95 (e.g., about 3.5 to about 4.5)).

Certain embodiments comprise determining the presence of a chromosome aneuploidy if, for the test sample, (i) the z-score quantification of the chromosome count representation is greater than or equal to a threshold z-score value (e.g., a value of about 3.95 (e.g., about 3.5 to about 4.5)), and (ii) the z-score quantification of the chromosome count representation is greater than or equal to the minimum referenced in the previous paragraph. Some embodiments comprise determining the absence of a chromosome aneuploidy if, for the test sample, (i) the z-score quantification of the chromosome count representation is less than a threshold z-score value (e.g., a value of about 3.95 (e.g., about 3.5 to about 4.5)), and/or (ii) the z-score quantification of the chromosome count representation is less than the minimum. The chromosome aneuploidy sometimes is a trisomy or monosomy, and sometimes is occurrence of one, three or four chromosomes.

Some embodiments comprise determining whether the z-score quantification of the first candidate segment count representation is less than, greater than or equal to a threshold z-score value (e.g., a value of about 3.95 (e.g., about 3.5 to about 4.5)) and determining whether the z-score quantification of the second candidate segment count representation is less than, greater than or equal to a threshold z-score value (e.g., a value of about 3.95 (e.g., about 3.5 to about 4.5)). Certain embodiments comprise determining whether the first candidate segment and the second candidate segment are substantially the same or overlap.

Some embodiments comprise determining the presence of a microdeletion or microinsertion if, for the test sample, (i) the z-score quantification of the first candidate segment count representation is greater than or equal to a threshold z-score value (e.g., a value of about 3.95 (e.g., about 3.5 to about 4.5)) and the z-score quantification of the second candidate segment count representation is greater than or equal to a threshold z-score value (e.g., a value of about 3.95 (e.g., about 3.5 to about 4.5)), and (ii) the first candidate segment and the second candidate segment are substantially the same or overlap. Certain embodiments comprise determining the absence of a microdeletion or microinsertion if, for the test sample, (i) the z-score quantification of the first candidate segment count representation is less than a threshold z-score value (e.g., a value of about 3.95 (e.g., about 3.5 to about 4.5)) and/or the z-score quantification of the second candidate segment count representation is less than a threshold z-score value (e.g., a value of about 3.95 (e.g., about 3.5 to about 4.5)), and/or (ii) the first candidate segment and the second candidate segment are not substantially the same or do not overlap.

In some embodiments a comparison compares two or more values (e.g., values derived from a quantitation, e.g., a quantitation of a profile and/or a quantitation of a candidate segment (e.g., wavelet event)). In some embodiments a comparison compares a quantitation of a candidate segment (e.g., wavelet event) or profile to a predetermined value or threshold. A non-limiting example of a comparison is shown in FIG. 7. In some embodiments a comparison comprises comparing Z-scores. In certain embodiments a comparison comprises comparing the absolute value of a Z-score for an overall chromosomal representation for an entire chromosome (profile of a chromosome) (i.e., $|Z_{chr}|$). The value $|Z_{chr}|$ sometimes is compared to a predetermined value, threshold or comparison feature (e.g., threshold 3.95 in FIG. 7, 710). In some embodiments the threshold, predetermined value or comparison feature used for comparison of a Z-score is about 2.8, 2.9, 3.0, 3.1, 3.2, 3.3, 3.4, 3.5, 3.6, 3.75, 3.8, 3.85, 3.9, 3.95, 4.0, 4.05, 4.1, 4.15, 4.2, 4.3, 4.4, or about 4.5. The value $|Z_{chr}|$ sometimes is compared to the absolute value of the Z-score for a candidate segment from a decomposition rendering and its portion count representation (e.g., $|Z_{wave}|$ and $|Z_{cbs}|$ in Example 3 and $|Z_{A4}|$ and $|Z_{B4}|$ in FIG. 7).

In some embodiments the result of a comparison is a decision for another comparison or decision of an outcome. In some embodiments the result of a first comparison (e.g., FIG. 7, 710) is a decision that determines the next comparison in a series of comparisons. For example, a first comparison (e.g., FIG. 7, 710) may determine that $|Z_{chr}|$ is greater than or equal to a predetermined value and a second comparison (e.g., FIG. 7, 721) compares $|Z_{chr}|$ to $|Z_{A4}|$ and/or $|Z_{B4}|$. Alternatively, a first comparison (e.g., FIG. 7, 710) may determine that $|Z_{chr}|$ is less than a predetermined value and a second comparison (e.g., FIG. 7, 722) determines if candidate segments (e.g., wavelet events) identified previously in the decision analysis (e.g., FIG. 6A, 631 and 632) are substantially the same or different.

In some embodiments the result of a first comparison (e.g., FIG. 7, 710) is a decision that determines a second comparison in a series, and a decision derived from the second comparison determines a third comparison and so forth. In some embodiments a first comparison may determine that $|Z_{chr}|$ is greater than or equal to a predetermined value and a second comparison (e.g., FIG. 7, 721) may determine that $|Z_{chr}|$ is greater than $|Z_{A4}|$ and/or $|Z_{B4}|$ or a fraction thereof (e.g., $|Z_{A4}|$ and/or $|Z_{B4}|$ multiplied by a predetermined value a) and the presence of a whole chromosome aneuploidy is determined 750. A trisomy and monosomy can be discerned by a suitable method.

In some embodiments, a first comparison may determine that $|Z_{chr}|$ is greater than or equal to a predetermined value and a second comparison (e.g., FIG. 7, 721) may determine that $|Z_{chr}|$ is less than $|Z_{A4}|$ and/or $|Z_{B4}|$ or a fraction thereof (e.g., $|Z_{A4}|$ and/or $|Z_{B4}|$ multiplied by a predetermined value a) and a third comparison is performed. In certain embodiments a first comparison may determine that $|Z_{chr}|$ is less than a predetermined value, a second comparison determines the candidate segments (e.g., wavelet events) identified are overlapping or substantially the same (composite candidate segment), a third comparison 731 determines that $|Z_{A4}|$ and $|Z_{B4}|$ are greater than or equal to a predetermined value (e.g., 3.95) and the presence of a microduplication and/or microdeletion is determined 741. A microduplication and microdeletion can be discerned by a suitable method. For example a microduplication may have a positive Z-score and a microdeletion may have a negative Z-score.

In some embodiments a comparison may determine that two or more candidate segments (e.g., wavelet events) are not overlapping or substantially the same (e.g., they are substantially different, e.g., FIG. 8, 822) and that no genetic variation 860 exist in the profile. In some embodiments a comparison may determine that two or more candidate segments (e.g., wavelet events, e.g., all candidate segments (e.g., wavelet events) identified in one or more decomposition renderings) are overlapping or substantially the same (e.g., FIG. 8, 821) and the presence or absence of a microduplication or microdeletion is determined 851, 852, 853. In some embodiments the presence or absence of a microduplication or microdeletion is determined according to the quantitation 840 of a composite candidate segment 830 (e.g., composite wavelet event).

In some embodiments a decision analysis comprises a two or more of segmenting, polishing and identification of a candidate segment (e.g., wavelet event). In some embodiments a decision analysis may comprise a quantitation of two or more candidate segments (e.g., wavelet events). In some embodiments a decision analysis may comprise quantitation of a profile of a chromosome. In some embodiments a decision analysis comprises one or more comparisons. In some embodiments a decision analysis comprises a determination of the presence or absence of a genetic variation.

In some embodiments a decision analysis comprises and/or consists of segmenting, polishing, identification of a candidate segment (e.g., wavelet event), one or more comparisons and determination of the presence or absence of a genetic variation. In some embodiments a decision analysis comprises and/or consists of segmenting, polishing, identification of a candidate segment (e.g., wavelet event), quantitation, one or more comparisons and determination of the presence or absence of a genetic variation. In some embodiments a decision analysis comprises and/or consists of segmenting, polishing, identification of a candidate segment (e.g., wavelet event), a determination of the presence or absence of a composite candidate segment (e.g., composite wavelet event), quantitation of a composite candidate segment (e.g., composite wavelet event), one or more comparisons and determination of the presence or absence of a genetic variation. In some embodiments a decision analysis comprises and/or consist of segmenting, polishing, identification of a candidate segment (e.g., wavelet event), quantitation of a candidate segment (e.g., wavelet event), quantitation of a profile of a chromosome, a comparison and a determination of the presence or absence of a genetic variation. In some embodiments a decision analysis comprises a validation.

In some embodiments, a comparison or decision analysis includes comparison to an odds ratio or log odds ratio (LOR). In certain embodiments, a comparison or decision includes determining whether a calculated LOR is greater than or less than zero.

In some embodiments, a comparison or decision includes generating a z-score quantification of a chromosome count representation and determining whether the chromosome count representation is less than, greater than or equal to a value (e.g., a z-score value of about 3.95 (e.g., about 3.5 to about 4.5)). In certain embodiments, a decision includes deciding (determining) the presence of a chromosome aneuploidy if, for the test sample, (i) the z-score quantification of the chromosome count representation is greater than or equal to the value (e.g., of about 3.95), and (ii) the LOR is greater than zero. In some embodiments, a decision includes deciding (determining) the absence of a chromosome aneuploidy if, for the test sample, (i) the z-score quantification of the chromosome count representation is less than the value (e.g., of about 3.95), and/or (ii) the LOR is less than zero. The chromosome aneuploidy sometimes is a trisomy or monosomy, or one, three or four copies of a chromosome.

In some embodiments, a comparison or decision includes generating a z-score quantification of a candidate segment count representation and determining whether the candidate segment count representation is less than, greater than or equal to a value (e.g., a z-score value of about 3.95 (e.g., about 3.5 to about 4.5)). In certain embodiments, a decision includes deciding (determining) the presence of a microdeletion or microinsertion event if, for the test sample, (i) the z-score quantification of the candidate segment count representation is greater than or equal to the value (e.g., of about 3.95), and (ii) the LOR is greater than zero. In some embodiments, a decision includes deciding (determining) the absence of a microdeletion or microinsertion event if, for the test sample, (i) the z-score quantification of the candidate segment count representation is less than the value (e.g., of about 3.95), and/or (ii) the LOR is less than zero. A microdeletion event sometimes is an event associated with DiGeorge Syndrome.

Outcome

Methods described herein can provide a determination of the presence or absence of a genetic variation (e.g., fetal aneuploidy) for a sample, thereby providing an outcome (e.g., thereby providing an outcome determinative of the presence or absence of a genetic variation (e.g., fetal aneuploidy)). A genetic variation often includes a gain, a loss and/or alteration (e.g., duplication, deletion, fusion, insertion, mutation, reorganization, substitution or aberrant methylation) of genetic information (e.g., chromosomes, segments of chromosomes, polymorphic regions, translocated regions, altered nucleotide sequence, the like or combinations of the foregoing) that results in a detectable change in the genome or genetic information of a test subject with respect to a reference. Presence or absence of a genetic variation can be determined by transforming, analyzing and/or manipulating sequence reads that have been mapped to portions (e.g., counts, counts of genomic portions of a reference genome). Determining an outcome, in some embodiments, comprises analyzing nucleic acid from a pregnant female. In certain embodiments, an outcome is determined according to counts (e.g., normalized counts) obtained from a pregnant female where the counts are from nucleic acid obtained from the pregnant female.

Methods described herein sometimes determine presence or absence of a fetal aneuploidy (e.g., full chromosome aneuploidy, partial chromosome aneuploidy or segmental chromosomal aberration (e.g., mosaicism, deletion and/or insertion)) for a test sample from a pregnant female bearing a fetus. In certain embodiments methods described herein detect euploidy or lack of euploidy (non-euploidy) for a sample from a pregnant female bearing a fetus. Methods described herein sometimes detect trisomy for one or more chromosomes (e.g., chromosome 13, chromosome 18, chromosome 21 or combination thereof) or segment thereof.

In some embodiments, presence or absence of a genetic variation (e.g., a fetal aneuploidy) is determined by a method described herein, by a method known in the art or by a combination thereof. Presence or absence of a genetic variation generally is determined from counts of sequence reads mapped to portions of a reference genome. Counts of sequence reads utilized to determine presence or absence of a genetic variation sometimes are raw counts and/or filtered counts, and often are normalized counts. A suitable normalization process or processes can be used to generate normalized counts, non-limiting examples of which include portion-wise normalization, normalization by GC content, linear and nonlinear least squares regression, LOESS, GC LOESS, LOWESS, PERUN, ChAI, RM, GCRM and combinations thereof. Normalized counts sometimes are expressed as one or more levels or levels in a profile for a particular set or sets of portions. Normalized counts sometimes are adjusted or padded prior to determining presence or absence of a genetic variation.

In some embodiments an outcome is determined according to one or more levels. In some embodiments, a determination of the presence or absence of a genetic variation (e.g., a chromosome aneuploidy) is determined according to one or more adjusted levels. In some embodiments a determination of the presence or absence of a genetic variation (e.g., a chromosome aneuploidy) is determined according to a profile comprising 1 to about 10,000 adjusted levels. Often a determination of the presence or absence of a genetic variation (e.g., a chromosome aneuploidy) is determined according to a profile comprising about 1 to about a 1000, 1 to about 900, 1 to about 800, 1 to about 700, 1 to about 600, 1 to about 500, 1 to about 400, 1 to about 300, 1 to about 200, 1 to about 100, 1 to about 50, 1 to about 25, 1 to about 20, 1 to about 15, 1 to about 10, or 1 to about 5 adjustments. In some embodiments a determination of the presence or absence of a genetic variation (e.g., a chromosome aneuploidy) is determined according to a profile comprising about 1 adjustment (e.g., one adjusted level). In some embodiments an outcome is determined according to one or more profiles (e.g., a profile of a chromosome or segment thereof) comprising one or more, 2 or more, 3 or more, 5 or more, 6 or more, 7 or more, 8 or more, 9 or more or sometimes 10 or more adjustments. In some embodiments, a determination of the presence or absence of a genetic variation (e.g., a chromosome aneuploidy) is determined according to a profile where some levels in a profile are not adjusted. In some embodiments, a determination of the presence or absence of a genetic variation (e.g., a chromosome aneuploidy) is determined according to a profile where adjustments are not made.

In some embodiments, an adjustment of a level (e.g., a first level) in a profile reduces a false determination or false outcome. In some embodiments, an adjustment of a level (e.g., a first level) in a profile reduces the frequency and/or probability (e.g., statistical probability, likelihood) of a false determination or false outcome. A false determination or outcome can be a determination or outcome that is not accurate. A false determination or outcome can be a determination or outcome that is not reflective of the actual or true genetic make-up or the actual or true genetic disposition (e.g., the presence or absence of a genetic variation) of a subject (e.g., a pregnant female, a fetus and/or a combination thereof). In some embodiments a false determination or outcome is a false negative determination. In some embodiments a negative determination or negative outcome is the absence of a genetic variation (e.g., aneuploidy, copy number variation). In some embodiments a false determination or false outcome is a false positive determination or false positive outcome. In some embodiments a positive determination or positive outcome is the presence of a genetic variation (e.g., aneuploidy, copy number variation). In some embodiments, a determination or outcome is utilized in a diagnosis. In some embodiments, a determination or outcome is for a fetus.

Presence or absence of a genetic variation (e.g., fetal aneuploidy) sometimes is determined without comparing counts for a set of portions to a reference. Counts measured for a test sample and are in a test region (e.g., a set of portions of interest) are referred to as "test counts" herein. Test counts sometimes are processed counts, averaged or summed counts, a representation, normalized counts, or one or more levels or levels as described herein. In certain embodiments test counts are averaged or summed (e.g., an average, mean, median, mode or sum is calculated) for a set of portions, and the averaged or summed counts are compared to a threshold or range. Test counts sometimes are expressed as a representation, which can be expressed as a ratio or percentage of counts for a first set of portions to counts for a second set of portions. In certain embodiments the first set of portions is for one or more test chromosomes (e.g., chromosome 13, chromosome 18, chromosome 21, or combination thereof) and sometimes the second set of portions is for the genome or a part of the genome (e.g., autosomes or autosomes and sex chromosomes). In certain embodiments a representation is compared to a threshold or range. In certain embodiments test counts are expressed as one or more levels or levels for normalized counts over a set of portions, and the one or more levels or levels are compared to a threshold or range. Test counts (e.g., averaged or summed counts, representation, normalized counts, one or more levels or levels) above or below a particular threshold, in a particular range or outside a particular range sometimes are determinative of the presence of a genetic variation or lack of euploidy (e.g., not euploidy). Test counts (e.g., averaged or summed counts, representation, normalized counts, one or more levels or levels) below or above a particular threshold, in a particular range or outside a particular range sometimes are determinative of the absence of a genetic variation or euploidy.

Presence or absence of a genetic variation (e.g., fetal aneuploidy) sometimes is determined by comparing counts, non-limiting examples of which include test counts, reference counts, raw counts, filtered counts, averaged or summed counts, representations (e.g., chromosome representations), normalized counts, one or more levels or levels (e.g., for a set of portions, e.g., genomic section levels, profiles), Z-scores, the like or combinations thereof. In some embodiments test counts are compared to a reference (e.g., reference counts). A reference (e.g., a reference count) can be a suitable determination of counts, non-limiting examples of which include raw counts, filtered counts, averaged or summed counts, representations (e.g., chromosome representations), normalized counts, one or more levels or levels (e.g., for a set of portions, e.g., genomic section levels, profiles), Z-scores, the like or combinations thereof. Reference counts often are counts for a euploid test region or from a segment of a genome or chromosome that is euploid. In some embodiments reference counts and test counts are obtained from the same sample and/or the same subject. In some embodiments reference counts are from different samples and/or from different subjects. In some embodiments reference counts are determined from and/or compared to a corresponding segment of the genome from which the test counts are derived and/or determined. A corresponding segment refers to a segment, portion or set of portions that map to the same location of a reference genome. In some embodiments reference counts are determined from and/or compared to a different segment of the genome from which the test counts are derived and/or determined.

In certain embodiments, test counts sometimes are for a first set of portions and a reference includes counts for a second set of portions different than the first set of portions. Reference counts sometimes are for a nucleic acid sample from the same pregnant female from which the test sample is obtained. In certain embodiments reference counts are for a nucleic acid sample from one or more pregnant females different than the female from which the test sample was obtained. In some embodiments, a first set of portions is in chromosome 13, chromosome 18, chromosome 21, a segment thereof or combination of the foregoing, and the second set of portions is in another chromosome or chromosomes or segment thereof. In a non-limiting example, where a first set of portions is in chromosome 21 or segment thereof, a second set of portions often is in another chromosome (e.g., chromosome 1, chromosome 13, chromosome 14, chromosome 18, chromosome 19, segment thereof or combination of the foregoing). A reference often is located in a chromosome or segment thereof that is typically euploid. For example, chromosome 1 and chromosome 19 often are euploid in fetuses owing to a high rate of early fetal mortality associated with chromosome 1 and chromosome 19 aneuploidies. A measure of deviation between the test counts and the reference counts can be generated.

In certain embodiments a reference comprises counts for the same set of portions as for the test counts, where the counts for the reference are from one or more reference samples (e.g., often multiple reference samples from multiple reference subjects). A reference sample often is from one or more pregnant females different than a female from which a test sample is obtained. A measure of deviation (e.g., a measure of uncertainty, an uncertainty value) between the test counts and the reference counts can be generated. In some embodiments a measure of deviation is determined from the test counts. In some embodiments a measure of deviation is determined from the reference counts. In some embodiments a measure of deviation is determined from an entire profile or a subset of portions within a profile.

A suitable measure of deviation can be selected, non-limiting examples of which include standard deviation, average absolute deviation, median absolute deviation, maximum absolute deviation, standard score (e.g., z-value, z-score, normal score, standardized variable) and the like. In some embodiments, reference samples are euploid for a test region and deviation between the test counts and the reference counts is assessed. In some embodiments a determination of the presence or absence of a genetic variation is according to the number of deviations (e.g., measures of deviations, MAD) between test counts and reference counts for a segment or portion of a genome or chromosome. In some embodiments the presence of a genetic variation is determined when the number of deviations between test counts and reference counts is greater than about 1, greater than about 1.5, greater than about 2, greater than about 2.5, greater than about 2.6, greater than about 2.7, greater than about 2.8, greater than about 2.9, greater than about 3, greater than about 3.1, greater than about 3.2, greater than about 3.3, greater than about 3.4, greater than about 3.5, greater than about 4, greater than about 5, or greater than about 6. For example, sometimes a test count differs from a reference count by more than 3 measures of deviation (e.g., 3 sigma, 3 MAD) and the presence of a genetic variation is determined. In some embodiments a test count obtained from a pregnant female is larger than a reference count by more than 3 measures of deviation (e.g., 3 sigma, 3 MAD) and the presence of a fetal chromosome aneuploidy (e.g., a fetal trisomy) is determined. A deviation of greater than three between test counts and reference counts often is indicative of a non-euploid test region (e.g., presence of a genetic variation). Test counts significantly above reference counts, which reference counts are indicative of euploidy, sometimes are determinative of a trisomy. In some embodiments a test count obtained from a pregnant female is less than a reference count by more than 3 measures of deviation (e.g., 3 sigma, 3 MAD) and the presence of a fetal chromosome aneuploidy (e.g., a fetal monosomy) is determined. Test counts significantly below reference counts, which reference counts are indicative of euploidy, sometimes are determinative of a monosomy.

In some embodiments the absence of a genetic variation is determined when the number of deviations between test counts and reference counts is less than about 3.5, less than about 3.4, less than about 3.3, less than about 3.2, less than about 3.1, less than about 3.0, less than about 2.9, less than about 2.8, less than about 2.7, less than about 2.6, less than about 2.5, less than about 2.0, less than about 1.5, or less than about 1.0. For example, sometimes a test count differs from a reference count by less than 3 measures of deviation (e.g., 3 sigma, 3 MAD) and the absence of a genetic variation is determined. In some embodiments a test count obtained from a pregnant female differs from a reference count by less than 3 measures of deviation (e.g., 3 sigma, 3 MAD) and the absence of a fetal chromosome aneuploidy (e.g., a fetal euploid) is determined. In some embodiments (e.g., deviation of less than three between test counts and reference counts (e.g., 3-sigma for standard deviation) often is indicative of a euploid test region (e.g., absence of a genetic variation). A measure of deviation between test counts for a test sample and reference counts for one or more reference subjects can be plotted and visualized (e.g., z-score plot).

Any other suitable reference can be factored with test counts for determining presence or absence of a genetic variation (or determination of euploid or non-euploid) for a test region of a test sample. For example, a fetal fraction determination can be factored with test counts to determine the presence or absence of a genetic variation. A suitable process for quantifying fetal fraction can be utilized, non-limiting examples of which include a mass spectrometric process, sequencing process or combination thereof.

In some embodiments the presence or absence of a fetal chromosomal aneuploidy (e.g., a trisomy) is determined, in part, from a fetal ploidy determination. In some embodiments a fetal ploidy is determined by a suitable method described herein. In some certain embodiments a fetal ploidy determination of about 1.20 or greater, 1.25 or greater, 1.30 or greater, about 1.35 or greater, about 1.4 or greater, or about 1.45 or greater indicates the presence of a fetal chromosome aneuploidy (e.g., the presence of a fetal trisomy). In some embodiments a fetal ploidy determination of about 1.20 to about 2.0, about 1.20 to about 1.9, about 1.20 to about 1.85, about 1.20 to about 1.8, about 1.25 to about 2.0, about 1.25 to about 1.9, about 1.25 to about 1.85, about 1.25 to about 1.8, about 1.3 to about 2.0, about 1.3 to about 1.9, about 1.3 to about 1.85, about 1.3 to about 1.8, about 1.35 to about 2.0, about 1.35 to about 1.9, about 1.35 to about 1.8, about 1.4 to about 2.0, about 1.4 to about 1.85 or about 1.4 to about 1.8 indicates the presence of a fetal chromosome aneuploidy (e.g., the presence of a fetal trisomy). In some embodiments the fetal aneuploidy is a trisomy. In some embodiments the fetal aneuploidy is a trisomy of chromosome 13, 18 and/or 21.

In some embodiments a fetal ploidy of less than about 1.35, less than about 1.30, less than about 1.25, less than about 1.20 or less than about 1.15 indicates the absence of a fetal aneuploidy (e.g., the absence of a fetal trisomy, e.g., euploid). In some embodiments a fetal ploidy determination of about 0.7 to about 1.35, about 0.7 to about 1.30, about 0.7 to about 1.25, about 0.7 to about 1.20, about 0.7 to about 1.15, about 0.75 to about 1.35, about 0.75 to about 1.30, about 0.75 to about 1.25, about 0.75 to about 1.20, about 0.75 to about 1.15, about 0.8 to about 1.35, about 0.8 to about 1.30, about 0.8 to about 1.25, about 0.8 to about 1.20, or about 0.8 to about 1.15 indicates the absence of a fetal chromosome aneuploidy (e.g., the absence of a fetal trisomy, e.g., euploid).

In some embodiments a fetal ploidy of less than about 0.8, less than about 0.75, less than about 0.70 or less than about 0.6 indicates the presence of a fetal aneuploidy (e.g., the presence of a chromosome deletion). In some embodiments a fetal ploidy determination of about 0 to about 0.8, about 0 to about 0.75, about 0 to about 0.70, about 0 to about 0.65, about 0 to about 0.60, about 0.1 to about 0.8, about 0.1 to about 0.75, about 0.1 to about 0.70, about 0.1 to about 0.65, about 0.1 to about 0.60, about 0.2 to about 0.8, about 0.2 to about 0.75, about 0.2 to about 0.70, about 0.2 to about 0.65, about 0.2 to about 0.60, about 0.25 to about 0.8, about 0.25 to about 0.75, about 0.25 to about 0.70, about 0.25 to about 0.65, about 0.25 to about 0.60, about 0.3 to about 0.8, about 0.3 to about 0.75, about 0.3 to about 0.70, about 0.3 to about 0.65, about 0.3 to about 0.60 indicates the presence of a fetal chromosome aneuploidy (e.g., the presence of a chromosome deletion). In some embodiments the fetal aneuploidy determined is a whole chromosome deletion.

In some embodiments a determination of the presence or absence of a fetal aneuploidy (e.g., according to one or more of the ranges of a ploidy determination above) is determined according to a call zone. In certain embodiments a call is made (e.g., a call determining the presence or absence of a genetic variation, e.g., an outcome) when a value (e.g. a ploidy value, a fetal fraction value, a level of uncertainty) or collection of values falls within a pre-defined range (e.g., a zone, a call zone). In some embodiments a call zone is defined according to a collection of values that are obtained from the same patient sample. In certain embodiments a call zone is defined according to a collection of values that are derived from the same chromosome or segment thereof. In some embodiments a call zone based on a ploidy determination is defined according a level of confidence (e.g., high level of confidence, e.g., low level of uncertainty) and/or a fetal fraction. In some embodiments a call zone is defined according to a ploidy determination and a fetal fraction of about 2.0% or greater, about 2.5% or greater, about 3% or greater, about 3.25% or greater, about 3.5% or greater, about 3.75% or greater, or about 4.0% or greater. For example, in some embodiments a call is made that a fetus comprises a trisomy 21 based on a ploidy determination of greater than 1.25 with a fetal fraction determination of 2% or greater or 4% or greater for a sample obtained from a pregnant female bearing a fetus. In certain embodiments, for example, a call is made that a fetus is euploid based on a ploidy determination of less than 1.25 with a fetal fraction determination of 2% or greater or 4% or greater for a sample obtained from a pregnant female bearing a fetus. In some embodiments a call zone is defined by a confidence level of about 99% or greater, about 99.1% or greater, about 99.2% or greater, about 99.3% or greater, about 99.4% or greater, about 99.5% or greater, about 99.6% or greater, about 99.7% or greater, about 99.8% or greater or about 99.9% or greater. In some embodiments a call is made without using a call zone. In some embodiments a call is made using a call zone and additional data or information. In some embodiments a call is made based on a ploidy value without the use of a call zone. In some embodiments a call is made without calculating a ploidy value. In some embodiments a call is made based on visual inspection of a profile (e.g., visual inspection of genomic section levels). A call can be made by any suitable method based in full, or in part, upon determinations, values and/or data obtained by methods described herein, non-limiting examples of which include a fetal ploidy determination, a fetal fraction determination, maternal ploidy, uncertainty and/or confidence determinations, portion levels, levels, profiles, z-scores, expected chromosome representations, measured chromosome representations, counts (e.g., normalized counts, raw counts), fetal or maternal copy number variations (e.g., categorized copy number variations), significantly different levels, adjusted levels (e.g., padding), the like or combinations thereof.

In some embodiments a no-call zone is where a call is not made. In some embodiments a no-call zone is defined by a value or collection of values that indicate low accuracy, high risk, high error, low level of confidence, high level of uncertainty, the like or a combination thereof. In some embodiments a no-call zone is defined, in part, by a fetal fraction of about 5% or less, about 4% or less, about 3% or less, about 2.5% or less, about 2.0% or less, about 1.5% or less or about 1.0% or less.

A genetic variation sometimes is associated with medical condition. An outcome determinative of a genetic variation is sometimes an outcome determinative of the presence or absence of a condition (e.g., a medical condition), disease, syndrome or abnormality, or includes, detection of a condition, disease, syndrome or abnormality (e.g., non-limiting examples listed in Table 1). In certain embodiments a diagnosis comprises assessment of an outcome. An outcome determinative of the presence or absence of a condition (e.g., a medical condition), disease, syndrome or abnormality by methods described herein can sometimes be independently verified by further testing (e.g., by karyotyping and/or amniocentesis). Analysis and processing of data can provide one or more outcomes. The term "outcome" as used herein can refer to a result of data processing that facilitates determining the presence or absence of a genetic variation (e.g., an aneuploidy, a copy number variation). In certain embodiments the term "outcome" as used herein refers to a conclusion that predicts and/or determines the presence or absence of a genetic variation (e.g., an aneuploidy, a copy number variation). In certain embodiments the term "outcome" as used herein refers to a conclusion that predicts and/or determines a risk or probability of the presence or absence of a genetic variation (e.g., an aneuploidy, a copy number variation) in a subject (e.g., a fetus). A diagnosis sometimes comprises use of an outcome. For example, a health practitioner may analyze an outcome and provide a diagnosis bases on, or based in part on, the outcome. In some embodiments, determination, detection or diagnosis of a condition, syndrome or abnormality (e.g., listed in Table 1) comprises use of an outcome determinative of the presence or absence of a genetic variation. In some embodiments, an outcome based on counted mapped sequence reads or transformations thereof is determinative of the presence or absence of a genetic variation. In certain embodiments, an outcome generated utilizing one or more methods (e.g., data processing methods) described herein is determinative of the presence or absence of one or more conditions, syndromes or abnormalities listed in Table 1. In certain embodiments a diagnosis comprises a determination of a presence or absence of a condition, syndrome or abnormality. Often a diagnosis comprises a determination of a genetic variation as the nature and/or cause of a condition, syndrome or abnormality. In certain embodiments an outcome is not a diagnosis. An outcome often comprises one or more numerical values generated using a processing method described herein in the context of one or more considerations of probability. A consideration of risk or probability can include, but is not limited to: an uncertainty value, a measure of variability, confidence level, sensitivity, specificity, standard deviation, coefficient of variation (CV) and/or confidence level, Z-scores, Chi values, Phi values, ploidy values, fitted fetal fraction, area ratios, median level, the like or combinations thereof. A consideration of probability can facilitate determining whether a subject is at risk of having, or has, a genetic variation, and an outcome determinative of a presence or absence of a genetic disorder often includes such a consideration.

An outcome sometimes is a phenotype. An outcome sometimes is a phenotype with an associated level of confidence (e.g., an uncertainty value, e.g., a fetus is positive for trisomy 21 with a confidence level of 99%, a test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation or portion from a data set, with respect to a reference genome can lead to an identification of the presence or absence of a genetic variation, which genetic variation sometimes is associated with a medical condition (e.g., cancer, preeclampsia, trisomy, monosomy, and the like). In some embodiments, an outcome comprises a level, a profile and/or a plot (e.g., a profile plot).

In those embodiments in which an outcome comprises a profile, a suitable profile or combination of profiles can be used for an outcome. Non-limiting examples of profiles that can be used for an outcome include z-score profiles, p-value profiles, chi value profiles, phi value profiles, the like, and combinations thereof An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in a suitable form, which form comprises without limitation, a probability (e.g., odds ratio, p-value), likelihood, value in or out of a cluster, value over or under a threshold value, value within a range (e.g., a threshold range), value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. In certain embodiments a predetermined threshold or cutoff value is an expected level or an expected level range. An outcome also can describe an assumption used in data processing. In certain embodiments, an outcome comprises a value that falls within or outside a predetermined range of values (e.g., a threshold range) and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein. Specific examples of generating outcomes and associated confidence levels are described in the Examples section and in international patent application no. PCT/US12/59123 (WO2013/052913) the entire content of which is incorporated herein by reference, including all text, tables, equations and drawings.

The term "sensitivity" as used herein refers to the number of true positives divided by the number of true positives plus the number of false negatives, where sensitivity (sens) may be within the range of $0 \leq sens \leq 1$. The term "specificity" as used herein refers to the number of true negatives divided by the number of true negatives plus the number of false positives, where sensitivity (spec) may be within the range of $0 \leq spec \leq 1$. In some embodiments a method that has sensitivity and specificity equal to one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

In some embodiments, presence or absence of a genetic variation (e.g., chromosome aneuploidy) is determined for a fetus. In such embodiments, presence or absence of a fetal genetic variation (e.g., fetal chromosome aneuploidy) is determined.

In certain embodiments, presence or absence of a genetic variation (e.g., chromosome aneuploidy) is determined for a sample. In such embodiments, presence or absence of a genetic variation in sample nucleic acid (e.g., chromosome aneuploidy) is determined. In some embodiments, a variation detected or not detected resides in sample nucleic acid from one source but not in sample nucleic acid from another source. Non-limiting examples of sources include placental nucleic acid, fetal nucleic acid, maternal nucleic acid, cancer cell nucleic acid, non-cancer cell nucleic acid, the like and combinations thereof. In non-limiting examples, a particular genetic variation detected or not detected (i) resides in placental nucleic acid but not in fetal nucleic acid and not in maternal nucleic acid; (ii) resides in fetal nucleic acid but not maternal nucleic acid; or (iii) resides in maternal nucleic acid but not fetal nucleic acid.

After one or more outcomes have been generated, an outcome often is used to provide a determination of the presence or absence of a genetic variation and/or associated medical condition. An outcome typically is provided to a health care professional (e.g., laboratory technician or manager; physician or assistant). Often an outcome is provided by an outcome module. In certain embodiments an outcome is provided by a plotting module. In certain embodiments an outcome is provided on a peripheral or component of an apparatus. For example, sometimes an outcome is provided by a printer or display. In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in a suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing. Various examples of outcome representations are shown in the drawings and are described in the Examples.

Generating an outcome can be viewed as a transformation of nucleic acid sequence read data, or the like, into a representation of a subject's cellular nucleic acid, in certain embodiments. For example, analyzing sequence reads of nucleic acid from a subject and generating a chromosome profile and/or outcome can be viewed as a transformation of relatively small sequence read fragments to a representation of relatively large chromosome structure. In some embodiments, an outcome results from a transformation of sequence reads from a subject (e.g., a pregnant female), into a representation of an existing structure (e.g., a genome, a chromosome or segment thereof) present in the subject (e.g., a maternal and/or fetal nucleic acid). In some embodiments, an outcome comprises a transformation of sequence reads from a first subject (e.g., a pregnant female), into a composite representation of structures (e.g., a genome, a chromosome or segment thereof), and a second transformation of the composite representation that yields a representation of a structure present in a first subject (e.g., a pregnant female) and/or a second subject (e.g., a fetus).

In certain embodiments an outcome can be generated according to analyzing one or more candidate segments. In some embodiments the presence of absence of a genetic variation is determined according to a discrete segment, candidate segment or composite candidate segment (e.g., the presence or absence of a discrete segment, candidate segment or composite candidate segment). In some embodiments two candidate segments derived from two decomposition renderings of the same profile are substantially the same (e.g., according to a comparison) and the presence of a chromosome aneuploidy, microduplication or microdeletion is determined. In some embodiments the presence of a composite candidate segment indicates the presence of a chromosome aneuploidy, microduplication or microdeletion. In some embodiments the presence of a whole chromosome aneuploidy is determined according to the presence of a discrete segment, candidate segment or composite candidate segment in a profile and the profile is a segment of a genome (e.g., a segment larger than a chromosome, e.g., a segment representing two or more chromosomes, a segment representing an entire genome). In some embodiments the presence of a whole chromosome aneuploidy is determined according to the presence of a discrete segment, candidate segment or composite candidate segment in a profile and the discrete segment edges are substantially the same as the edges of a chromosome. In certain embodiments the presence of a microduplication or microdeletion is determined when at least one edge of a discrete segment, candidate segment or composite candidate segment in a profile is different than an edge of a chromosome and/or the discrete segment is within a chromosome. In some embodiments the presence of a microduplication is determined and a level or AUC for a discrete segment, candidate segment or composite candidate segment is substantially larger than a reference level (e.g., a euploid region). In some embodiments the presence of a microdeletion is determined and a level or AUC for a discrete segment, candidate segment or composite candidate segment is substantially less than a reference level (e.g., a euploid region). In some embodiments candidate segments identified in two or more different decomposition renderings are not substantially the same (e.g., are different) and the absence of a chromosome aneuploidy, microduplication and/or microdeletion is determined. In some embodiments the absence of a discrete segment, candidate segment or composite candidate segment in a profile or decomposition rendering of a profile indicates the absence of a chromosome aneuploidy, microduplication or microdeletion.

Validation

In some embodiments a method described herein comprises a validation. In some embodiments a decision analysis (e.g., a decision tree), a determination of the presence or absence of a genetic variation (e.g., a copy number variation, a microduplication, a microdeletion, an aneuploidy), making a call and/or a determination of an outcome comprises a validation. Any suitable validation process can be utilized to validate a method, call or outcome described herein.

In some embodiments a validation comprises validating or invalidating a candidate segment identified in a decomposition rendering. A validated candidate segment confirms the presence of a candidate segment. An invalidated candidate segment changes a call indicating the presence of a candidate segment to the absence of a candidate segment. For example, in some embodiments, following the identification of a candidate segment by a segmenting process, a validation can be performed where the candidate segment is validated or invalidated. A candidate segment that is invalidated indicates the absence of a chromosome aneuploidy, microduplication or microdeletion in a profile. In some embodiments a validation comprises a determination of the presence or absence of a candidate segment with reduced false negative and/or reduced false positive determinations. A candidate segment can be validated by a suitable method, non-limiting examples of which include a "sliding edges" process, a "leave one out" process", the like or a combination thereof.

In some embodiments a validation comprises generating a level of significance for a candidate segment or a composite candidate segment. In some embodiments the level of significance is a Z-score, z-value, p-value or the like. In some embodiments a validation comprises generating a level of uncertainty. In some embodiments a level of uncertainty is associated with a level of significance. For example, sometimes an average, mean or median level of significance is determined and a level of uncertainty is determined for the average, mean or median level of significance.

In some embodiments a candidate segment is validated or invalidated according to a level of significance and/or an uncertainty value. A validated or invalidated discrete segment can be a validated or invalidated composite candidate segment. In some embodiments the presence or absence of a validated candidate segment is determined according to a level of significance and/or a level of uncertainty for a candidate segment. In some embodiments the absence of a validated candidate segment indicates the absence of a chromosome aneuploidy, microduplication or microdeletion. In some embodiments the presence of a validated candidate segment confirms the presence of a candidate segment. In some embodiments the presence of two or more validated candidate segments leads to the determination or generation of a composite candidate segment. In some embodiments the presence of one or more validated candidate segments, in part, determines the presence of a chromosome aneuploidy, microduplication or microdeletion with an increased level of confidence. In some embodiments the presence of candidate segment indicates, in part, the presence of a DiGeorge syndrome. In some embodiments the absence of a validated candidate segment indicates the absence of a chromosome aneuploidy, microduplication or microdeletion.

Sliding Edges Validation

In some embodiments a validation comprises a "sliding edges" process. A suitable "sliding edges" process can be used directly or can be adapted for validating a segment in a decomposition rendering. In some embodiments a "sliding edges" process comprises segmenting a candidate segment (e.g., a candidate segment represented by a set of portions), or a segment suspected of comprising or being a candidate segment, into multiple subsets of portions. In some embodiments the candidate segment is a set of portions for a whole chromosome or a segment of a chromosome. In some embodiments the candidate segment is a set of portions comprising a region associated with a known genetic variation or a known genetic disorder. In some embodiments the candidate segment comprises a DiGeorge region.

In certain embodiments a "sliding edges" process comprises segmenting an identified candidate segment (a set of portions) into multiple subsets of portions where each of the subsets of portions represents a candidate segment with similar, but different edges. In some embodiments the originally identified candidate segment is included in the analysis. For example, the originally identified candidate segment is included as one of the multiple subsets of portions. The subsets of portions can be determined by varying one or both edges of the originally identified discrete segment by any suitable method. In some embodiments the left edge can be changed thereby generating discrete segments with different left edges. In some embodiments the right edge can be changed thereby generating discrete segments with different right edges. In some embodiments both the right and left edges can be changed. In some embodiments the edges are changed by moving the edge by one or more adjacent portions of a reference genome to the left or to the right of the original edges.

In an embodiment of a sliding edges approach described in Example 5, the original discrete segment is changed by moving both edges by 15 portions of a reference genome, thereby creating a 15 by 15 grid of discrete segments (e.g., 225 different subsets of portions). For example, while keeping the right edge stable, the left edge can be moved right by 7 portions of a reference genome and then left by 7 portions of a reference genome thereby generating 15 possible left edges. While keeping each of the 15 left edges stable, the right edge can be move to the right by 7 portions of a reference genome and to the left by seven portions of a reference genome, thereby generating 15 possible right edges. The resulting subsets comprise 225 different discrete segments (e.g., subsets of portions of a reference genome).

In some embodiments either one or both edges are changed by 5 to 30 portions of a reference genome. In some embodiments an edge is moved by 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 portions of a reference genome in either direction. In some embodiments, regardless of the portion size, an edge is changed to generate an edge range of about 100,000 to about 2,000,000 base pairs, 250,000 to about 1,500,000 base pairs, or about 500,000 to about 1,000,000 base pairs for either or both edges. In some embodiments, regardless of the portion size, an edge is changed to generate an edge range of about 500,000, 600,000, 700,000, 750,000, 800,000, 900,000, or about 1,000,000 bases pairs for either or both edges.

In some embodiments an identified discrete segment comprises a first end and a second end and the segmenting comprises (i) removing one or more portions from the first end of the set of portions by recursive removal thereby providing a subset of portions with each recursive removal, (ii) terminating the recursive removal in (i) after n repeats thereby providing n+1 subsets of portions, where the set of portions is a subset, and where each subset comprises a different number of portions, a first subset end and a second subset end, (iii) removing one or more portions from the second subset end of each of the n+1 subsets of portions provided in (ii) by recursive removal; and (iv) terminating the recursive removal in (iii) after n repeats, thereby providing multiple subsets of portions. In some embodiments the multiple subsets equals (n+1)2 subsets. In some embodiments n is equal to an integer between 5 and 30. In some embodiments n is equal to 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

In certain embodiments of a sliding edges approach, a level of significance (e.g., a Z-score, a p-value) is determined for each of the subsets of portions of a reference genome and an average, mean or median level of significance is determined according to the level of significance determined for all of the subsets.

In some embodiments the level of significance is a Z-score or a p-value. In some embodiments a Z-score is calculated according to the following formula:

$$Z_i = (E_i - \text{Med}.E_{(n)})/\text{MAD}$$

where $E_i$ is a quantitative determination of the level of the discrete segment i, $\text{Med}.E_{(n)}$ is the median level for all discrete segments generated by a sliding edges process and MAD is the median absolute deviation for $\text{Med}.E_{(n)}$, and $Z_i$ is the resulting Z-score for discrete segment i. In some embodiments MAD can be replaced by any suitable measure of uncertainty. In some embodiments $E_i$ is any suitable measure of a level, non-limiting examples of which include a median level, average level, mean level, sum of the counts for the portions, or the like.

In some embodiments a median, mean or average Z-score is determined for all discrete segments generated by a sliding edges process and a level of uncertainty (e.g., MAD) is generated from the median, mean or average Z-score. In some embodiments a discrete segment (e.g., the original discrete segment identified) is validated or invalidated according to the median, mean or average Z-score determined for all discrete segments generated by a sliding edges process and a level of uncertainty for the median, mean or average Z-score. In some embodiments a pre-determined range (e.g., a threshold range) for level of significance (e.g., a Z-score) is predetermined. In some embodiments the predetermined range for a Z-score for the absence of a candidate segment is from about 3.5 to about −3.5, about 3.25 to about −3.25, about 3.0 to about −3.0, about 2.75 to about −2.75 or about 2.5 to about −2.5. In some embodiments a median, mean or average Z-score with an value outside the predetermined range confirms the presence of a validated discrete segment according to the "sliding edges" method. In some embodiments a median, mean or average Z-score with a value inside the predetermined range invalidates a candidate segment according to the "sliding edges" method and/or determines the absence of a candidate segment (e.g., the absence of a validated candidate segment). In some embodiments a median, mean or average Z-score with an absolute value greater than about 2, 2.25, 2.5, 2.75, 3.0, 3.25 or 3.5 confirms the presence of and/or validates a discrete segment according to the "sliding edges" method. In some embodiments a median, mean or average Z-score with an absolute value less than about 2, 2.25, 2.5, 2.75, 3.0, 3.25 or 3.5 determines the absence of and/or invalidates a candidate segment according to the "sliding edges" method. In some embodiments an uncertainty value associated with a median Z-score determines, in part, if a discrete segment is validated or invalidated. In some embodiments a candidate segment is validated if the median, mean or average Z-score is outside a threshold range and the uncertainty value (e.g., MAD) overlaps with the threshold range by less than 0% (e.g., does not overlap), 5%, 10%, 20%, 25%, 30%, 35% or 40% of the uncertainty value. In some embodiments a candidate segment is invalidated if the median, mean or average Z-score is outside a threshold range and the uncertainty value (e.g., MAD) overlaps with the threshold range by more than about 25%, 30%, 40%, 50%, 60% or more than about 70% of the uncertainty value.

Figure 13:
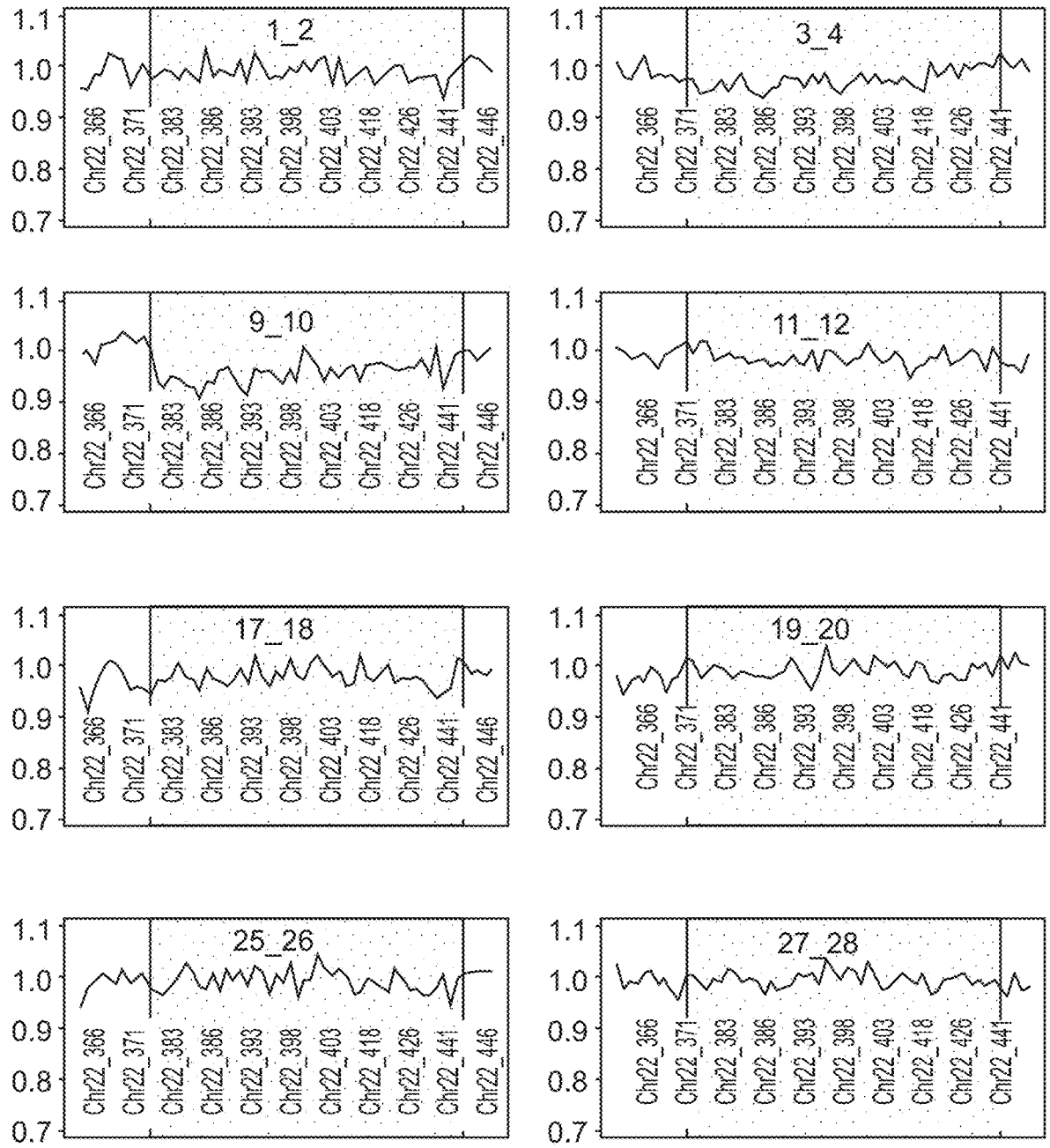
FIG. 13 shows an enlarged view of the DiGeorge region for 16 samples labeled with pairs of numbers indicating the locations of the samples on a plate. The sample pairs 3_4 (second from bottom) and 9_10 (fifth from bottom) belong to fetal DiGeorge pregnancies. All other samples have been karyotyped as euploids. The highlighted box (grey region) outlines the overlap between DiGeorge region and the PERUN portion selection (portions of a reference genome chr22_368-chr22_451).
Figure 14:
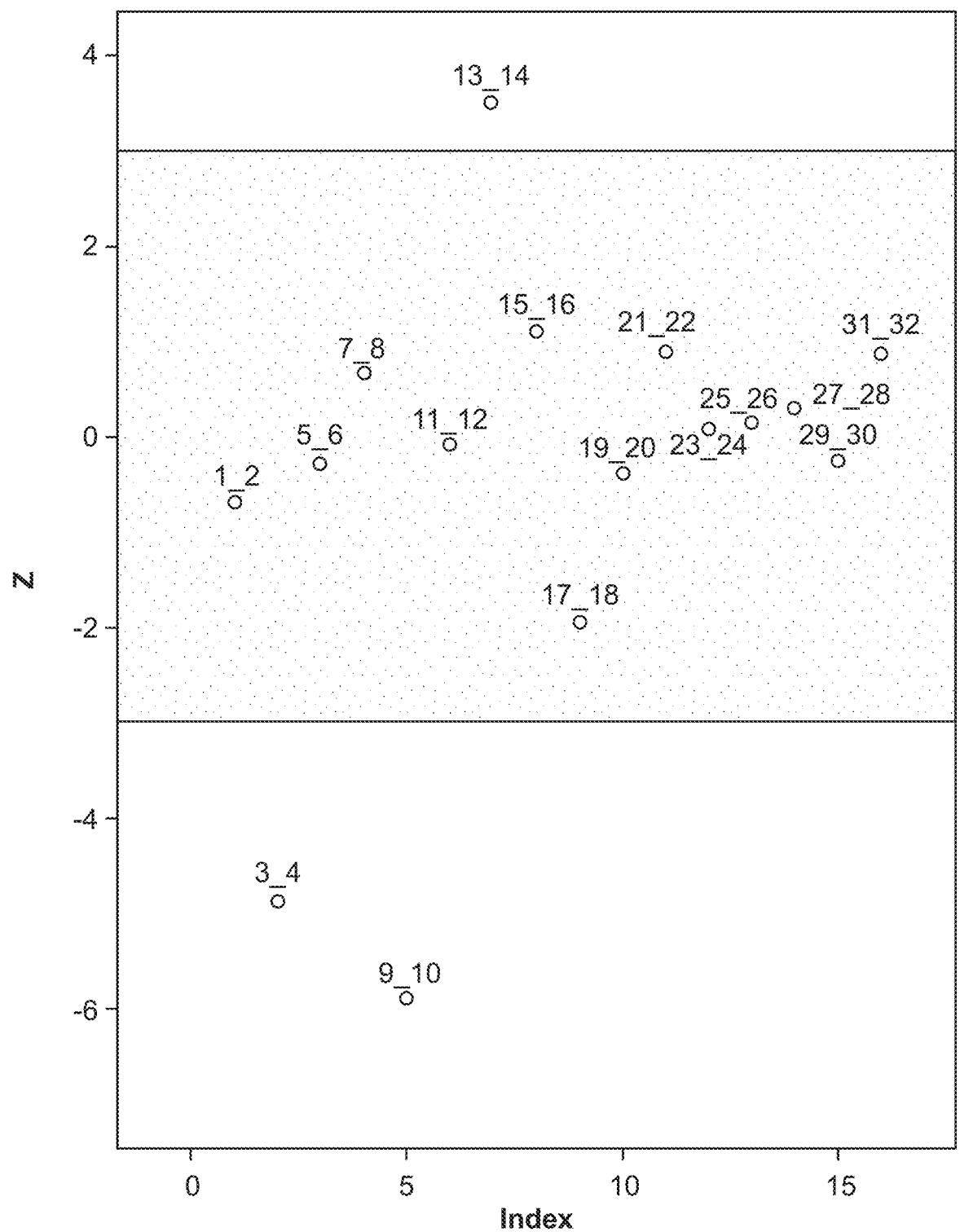
FIG. 14 shows Z-scores for the DiGeorge region. Each data point is derived from a sum of two profiles, obtained from two separate plasma aliquots from each patient. Z-standardization was done based on all 16 patients, including the two affected cases.

In some embodiments a distribution is generated for the level of significance (e.g., Z-scores) determined for all discrete segments generated by a sliding edges process (e.g., see FIGS. 13-14). In certain embodiments a discrete segment is validated or invalidated according to the median, mean or average level of significance and/or a distribution of the level of significance. In some embodiments about 50%, 60%, 70%, 75%, 80%, 85%, 90%, or about 95% or more of a distribution is outside a pre-determined range for the level of significance and a discrete segment is validated. For example, for a predetermined range of Z-scores from 3.0 to −3.0, a validated candidate segment can have a median Z-score and 70% or more of the distribution of Z-scores with an absolute value greater than 3.0.

Leave One Out Validation

In some embodiments a validation comprises a "leave one out" process. A suitable "leave one out" process can be used. In some embodiments a "leave one out" process provides a level of confidence associated with a select set of reference samples. In some embodiments a "leave one out" process provides a level of uncertainty associated with a select set of reference samples. In some embodiments a "leave one out" process validates or invalidates a candidate segment according to a level of confidence and/or level of uncertainty determined according to a select set of reference samples.

In some embodiments a "leave one out" process is performed for a test sample and two or more reference samples (e.g., a set of reference samples, sometimes referred to herein as the original set). In some embodiments the test sample is included as one of the two or more reference samples. In some embodiments the test sample is not included as one of the two or more reference samples. In some embodiments the "leave one out" process comprises removing one of two or more reference samples from the original set of samples thereby providing a subset of reference samples. In certain embodiments the process of removing a reference sample from the original set is repeated for each reference sample in the set. Often, when a reference sample is removed from the original set, the previously removed reference sample, if any, is returned to the original set. In some embodiments only one reference sample is removed from any one subset. The result is often multiple subsets of reference samples (sometimes referred to herein as multiple subsets of samples) where each subset is missing one of the reference samples from the original set.

In certain embodiments the "leave one out" process comprises determining a level of significance according to each subset of the subsets of reference samples. In certain embodiments a mean, average, or median level of significance is then calculated from the level of significance values determined for all of the subsets. In some embodiments a level of uncertainty (e.g., a MAD) is calculated according to the mean, average, or median level of significance. In some embodiments a discrete segment is validated or invalidated according to a median, mean or average level of significance and/or the level of uncertainty generated according to the "leave one out" process.

In certain embodiments of the "leave one out" process, a level of significance is a Z-score or a p-value. In some embodiments a Z-score for the "leave one out" process is calculated according to the following formula:

$$Z_i = (E_i - \text{Med}.E_{(n)})/\text{MAD}$$

where $E_i$ is a quantitative determination of the level of the segment i, $\text{Med}.E_{(n)}$ is the median level for segment i for a subset of reference samples and MAD is the median absolute deviation for $\text{Med}.E_{(n)}$, and $Z_i$ is the resulting Z-score for the segment i. In some embodiments a MAD can be replaced by any suitable measure of uncertainty. In some embodiments $E_i$ is any suitable measure of a level, non-limiting examples of which include a median level, average level, mean level, sum of the counts for the portions, or the like.

In some embodiments a validation comprises a "sliding edges" process and a "leave one out" process. For example, in some embodiments, subsets of reference samples (e.g., generated from the "leave one out" process) are generated from a set of reference samples generated by the "sliding edges process". For example, for a given test sample, a "sliding edge" process may produce 225 segments for a discrete segment identified from a segmentation process and a "leave one out" process is then performed using a set of 10 reference samples. In the above example, a composite median, mean or average level of significance (e.g., a composite median Z-score) and a composite level of uncertainty (e.g., a composite MAD) is calculated from the resulting 2250 Z-scores. In some embodiments a discrete segment identified by a segmentation process is validated or invalidated according to a composite median level of significance (e.g., a composite median Z-score) and/or a composite level of uncertainty (e.g., a composite MAD).

In some embodiments a decision analysis comprises determining the presence or absence of a chromosome aneuploidy, microduplication or microdeletion according to Z-score or composite Z-score for a candidate segment (e.g., a composite candidate segment). In some embodiments a candidate segment is indicative of a trisomy and the candidate segment is for a set of portions representing a whole chromosome. In certain embodiments a candidate segment is indicative of a whole chromosome aneuploidy when the absolute Z-score for a set of portions representing a whole chromosome is greater than or equal to a predetermined value or threshold (e.g., see FIG. 7). In certain embodiments a candidate segment is indicative of a whole chromosome aneuploidy when the absolute Z-score for a set of portions representing a whole chromosome is greater than or equal to a predetermined value of about 2.8, 2.9, 3.0, 3.1, 3.2, 3.3, 3.4, 3.5, 3.6, 3.75, 3.8, 3.85, 3.9, 3.95, 4.0, 4.05, 4.1, 4.15, 4.2, 4.3, 4.4, or about 4.5. In certain embodiments a candidate segment is indicative of a trisomy when the absolute Z-score for a set of portions representing a whole chromosome is greater than or equal to 3.95. In certain embodiments a candidate segment is indicative of a trisomy when the absolute Z-score for a set of portions representing a whole chromosome is greater than or equal to the absolute value of a Z-score determined for (i) a discrete segment identified according to a Haar Wavelet decomposition process or (ii) a discrete segment identified according to a CBS process. In certain embodiments a candidate segment is indicative of a trisomy when the absolute Z-score for a set of portions representing a whole chromosome is greater than or equal to a multiple of the absolute value of a Z-score determined for (i) a discrete segment identified according to a Haar Wavelet decomposition process or (ii) a discrete segment identified according to a CBS process. In some embodiments a multiple of the absolute value of a Z-score is the absolute value of a Z-score multiplied by about 0.4, 0.5, 0.6, 0.7, 0.8 or about 0.9.

In certain embodiments a candidate segment (e.g., a significant candidate segment) is indicative of a trisomy when the absolute Z-score for a set of portions representing a whole chromosome is greater than or equal to 3.95 and is greater than or equal to the absolute value of a Z-score determined for (i) a discrete segment identified according to a Haar Wavelet decomposition process or (ii) a discrete segment identified according to a CBS process. In certain embodiments a candidate segment is indicative of a trisomy when the absolute Z-score for a set of portions representing a whole chromosome is greater than or equal to 3.95 and is greater than or equal to a multiple of the absolute value of a Z-score determined for (i) a discrete segment identified according to a Haar Wavelet decomposition process or (ii) a discrete segment identified according to a CBS process. In some embodiments a multiple of the absolute value of a Z-score is the absolute value of a Z-score multiplied by about 0.4, 0.5, 0.6, 0.7, 0.8 or about 0.9.

In some embodiments a candidate segment is not indicative of a trisomy and the presence of a microdeletion or microduplication is determined when the absolute value of a Z-score determined for (i) the discrete segment identified according to a Haar Wavelet decomposition process and (ii) the discrete segment identified according to a CBS process is greater than or equal to about 2.8, 2.9, 3.0, 3.1, 3.2, 3.3, 3.4, 3.5, 3.6, 3.75, 3.8, 3.85, 3.9, 3.95, 4.0, 4.05, 4.1, 4.15, 4.2, 4.3, 4.4, or about 4.5. In some embodiments a candidate segment is not indicative of a trisomy and the presence of a microdeletion or microduplication is determined. In some embodiments a candidate segment is not indicative of a trisomy and the presence of a microdeletion or microduplication is determined when the absolute value of a Z-score determined for (i) the discrete segment identified according to a Haar Wavelet decomposition process and (ii) the discrete segment identified according to a CBS process is greater than or equal to 3.95. In some embodiments a candidate segment is not indicative of a trisomy and the presence of a microdeletion or microduplication is determined and the discrete segment identified according to a Haar Wavelet decomposition process is substantially the same as the discrete segment identified according to a CBS process.

In some embodiments determining an outcome (e.g., determining the presence or absence of a genetic variation e.g., in a fetus) comprises a decision analysis. In some embodiments a method of determining the presence or absence of a chromosome aneuploidy, microduplication or microdeletion in a fetus with reduced false negative and reduced false positive determinations, comprises a decision analysis. In some embodiments a decision analysis comprises a series of methods or method steps. Non-limiting examples of a decision analysis are shown in FIGS. 6-8 and are described herein.

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by a communication means, a written and/or graphical representation comprising an outcome, which upon review allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by a other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file.

The term "providing an outcome" and grammatical equivalents thereof, as used herein also can refer to a method for obtaining such information, including, without limitation, obtaining the information from a laboratory (e.g., a laboratory file). A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

In some embodiments, an outcome can be provided to a health care professional, physician or qualified individual from a laboratory and the health care professional, physician or qualified individual can make a diagnosis based on the outcome. In some embodiments, an outcome can be provided to a health care professional, physician or qualified individual from a laboratory and the health care professional, physician or qualified individual can make a diagnosis based, in part, on the outcome along with additional data and/or information and other outcomes.

A healthcare professional or qualified individual, can provide a suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Laboratory personnel (e.g., a laboratory manager) can analyze values (e.g., test counts, reference counts, level of deviation) underlying a determination of the presence or absence of a genetic variation (or determination of euploid or non-euploid for a test region). For calls pertaining to presence or absence of a genetic variation that are close or questionable, laboratory personnel can re-order the same test, and/or order a different test (e.g., karyotyping and/or amniocentesis in the case of fetal aneuploidy determinations), that makes use of the same or different sample nucleic acid from a test subject.

Genetic Variations and Medical Conditions

The presence or absence of a genetic variance can be determined using a method or apparatus described herein. In certain embodiments, the presence or absence of one or more genetic variations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy), partial chromosome abnormality or mosaicism, each of which is described in greater detail herein. Non-limiting examples of genetic variations include one or more deletions (e.g., micro-deletions), duplications (e.g., micro-duplications), insertions, mutations, polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 1,000 kilobases (kb) in length (e.g., about 10 bp, 50 bp, 100 bp, 500 bp, 1 kb, 5 kb, 10 kb, 50 kb, 100 kb, 500 kb, or 1000 kb in length).

A genetic variation is sometime a deletion. In certain embodiments a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a segment of a chromosome, an allele, a gene, an intron, an exon, any non-coding region, any coding region, a segment thereof or combination thereof. A deletion can comprise a microdeletion. A deletion can comprise the deletion of a single base.

A genetic variation is sometimes a genetic duplication. In certain embodiments a duplication is a mutation (e.g., a genetic aberration) in which a part of a chromosome or a sequence of DNA is copied and inserted back into the genome. In certain embodiments a genetic duplication (i.e. duplication) is any duplication of a region of DNA. In some embodiments a duplication is a nucleic acid sequence that is repeated, often in tandem, within a genome or chromosome. In some embodiments a duplication can comprise a copy of one or more entire chromosomes, a segment of a chromosome, an allele, a gene, an intron, an exon, any non-coding region, any coding region, segment thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation is sometimes an insertion. An insertion is sometimes the addition of one or more nucleotide base pairs into a nucleic acid sequence. An insertion is sometimes a microinsertion. In certain embodiments an insertion comprises the addition of a segment of a chromosome into a genome, chromosome, or segment thereof. In certain embodiments an insertion comprises the addition of an allele, a gene, an intron, an exon, any non-coding region, any coding region, segment thereof or combination thereof into a genome or segment thereof. In certain embodiments an insertion comprises the addition (i.e., insertion) of nucleic acid of unknown origin into a genome, chromosome, or segment thereof. In certain embodiments an insertion comprises the addition (i.e. insertion) of a single base.

As used herein a "copy number variation" generally is a class or type of genetic variation or chromosomal aberration. A copy number variation can be a deletion (e.g. microdeletion), duplication (e.g., a micro-duplication) or insertion (e.g., a micro-insertion). Often, the prefix "micro" as used herein sometimes is a segment of nucleic acid less than 5 Mb in length. A copy number variation can include one or more deletions (e.g. micro-deletion), duplications and/or insertions (e.g., a micro-duplication, micro-insertion) of a segment of a chromosome. In certain embodiments a duplication comprises an insertion. In certain embodiments an insertion is a duplication. In certain embodiments an insertion is not a duplication. For example, often a duplication of a sequence in a portion increases the counts for a portion in which the duplication is found. Often a duplication of a sequence in a portion increases the level. In certain embodiments, a duplication present in portions making up a first level increases the level relative to a second level where a duplication is absent. In certain embodiments an insertion increases the counts of a portion and a sequence representing the insertion is present (i.e., duplicated) at another location within the same portion. In certain embodiments an insertion does not significantly increase the counts of a portion or level and the sequence that is inserted is not a duplication of a sequence within the same portion. In certain embodiments an insertion is not detected or represented as a duplication and a duplicate sequence representing the insertion is not present in the same portion.

In some embodiments a copy number variation is a fetal copy number variation. Often, a fetal copy number variation is a copy number variation in the genome of a fetus. In some embodiments a copy number variation is a maternal and/or fetal copy number variation. In certain embodiments a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

"Ploidy" is a reference to the number of chromosomes present in a fetus or mother. In certain embodiments "Ploidy" is the same as "chromosome ploidy". In humans, for example, autosomal chromosomes are often present in pairs. For example, in the absence of a genetic variation, most humans have two of each autosomal chromosome (e.g., chromosomes 1-22). The presence of the normal complement of 2 autosomal chromosomes in a human is often referred to as euploid. "Microploidy" is similar in meaning to ploidy. "Microploidy" often refers to the ploidy of a segment of a chromosome. The term "microploidy" sometimes is a reference to the presence or absence of a copy number variation (e.g., a deletion, duplication and/or an insertion) within a chromosome (e.g., a homozygous or heterozygous deletion, duplication, or insertion, the like or absence thereof). "Ploidy" and "microploidy" sometimes are determined after normalization of counts of a level in a profile. Thus, a level representing an autosomal chromosome pair (e.g., a euploid) is often normalized to a ploidy of 1. Similarly, a level within a segment of a chromosome representing the absence of a duplication, deletion or insertion is often normalized to a microploidy of 1. Ploidy and microploidy are often portion-specific (e.g., portion specific) and sample-specific. Ploidy is often defined as integral multiples of ½, with the values of 1, ½, 0, 3/2, and 2 representing euploid (e.g., 2 chromosomes), 1 chromosome present (e.g., a chromosome deletion), no chromosome present, 3 chromosomes (e.g., a trisomy) and 4 chromosomes, respectively. Likewise, microploidy is often defined as integral multiples of ½, with the values of 1, ½, 0, 3/2, and 2 representing euploid (e.g., no copy number variation), a heterozygous deletion, homozygous deletion, heterozygous duplication and homozygous duplication, respectively. Some examples of ploidy values for a fetus are provided in Table 2.

In certain embodiments the microploidy of a fetus matches the microploidy of the mother of the fetus (i.e., the pregnant female subject). In certain embodiments the microploidy of a fetus matches the microploidy of the mother of the fetus and both the mother and fetus carry the same heterozygous copy number variation, homozygous copy number variation or both are euploid. In certain embodiments the microploidy of a fetus is different than the microploidy of the mother of the fetus. For example, sometimes the microploidy of a fetus is heterozygous for a copy number variation, the mother is homozygous for a copy number variation and the microploidy of the fetus does not match (e.g., does not equal) the microploidy of the mother for the specified copy number variation.

A microploidy is often associated with an expected level. For example, sometimes a level (e.g., a level in a profile, sometimes a level that includes substantially no copy number variation) is normalized to a value of 1 (e.g., a ploidy of 1, a microploidy of 1) and the microploidy of a homozygous duplication is 2, a heterozygous duplication is 1.5, a heterozygous deletion is 0.5 and a homozygous deletion is zero.

A genetic variation for which the presence or absence is identified for a subject is associated with a medical condition in certain embodiments. Thus, technology described herein can be used to identify the presence or absence of one or more genetic variations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations, medical conditions and states are described hereafter.

Fetal Gender

In some embodiments, the prediction of a fetal gender or gender related disorder (e.g., sex chromosome aneuploidy) can be determined by a method or apparatus described herein. Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production. Individuals with XX are female and XY are male and non-limiting variations, often referred to as sex chromosome aneuploidies, include X0, XYY, XXX and XXY. In certain embodiments, males have two X chromosomes and one Y chromosome (XXY; Klinefelter's Syndrome), or one X chromosome and two Y chromosomes (XYY syndrome; Jacobs Syndrome), and some females have three X chromosomes (XXX; Triple X Syndrome) or a single X chromosome instead of two (X0; Turner Syndrome). In certain embodiments, only a portion of cells in an individual are affected by a sex chromosome aneuploidy which may be referred to as a mosaicism (e.g., Turner mosaicism). Other cases include those where SRY is damaged (leading to an XY female), or copied to the X (leading to an XX male).

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder. Sex-linked disorders include, without limitation, X-linked and Y-linked disorders. X-linked disorders include X-linked recessive and X-linked dominant disorders. Examples of X-linked recessive disorders include, without limitation, immune disorders (e.g., chronic granulomatous disease (CYBB), Wiskott-Aldrich syndrome, X-linked severe combined immunodeficiency, X-linked agammaglobulinemia, hyper-IgM syndrome type 1, IPEX, X-linked lymphoproliferative disease, Properdin deficiency), hematologic disorders (e.g., Hemophilia A, Hemophilia B, X-linked sideroblastic anemia), endocrine disorders (e.g., androgen insensitivity syndrome/Kennedy disease, KAL1 Kallmann syndrome, X-linked adrenal hypoplasia congenital), metabolic disorders (e.g., ornithine transcarbamylase deficiency, oculocerebrorenal syndrome, adrenoleukodystrophy, glucose-6-phosphate dehydrogenase deficiency, pyruvate dehydrogenase deficiency, Danon disease/glycogen storage disease Type IIb, Fabry's disease, Hunter syndrome, Lesch-Nyhan syndrome, Menkes disease/occipital horn syndrome), nervous system disorders (e.g., Coffin-Lowry syndrome, MASA syndrome, X-linked alpha thalassemia mental retardation syndrome, Siderius X-linked mental retardation syndrome, color blindness, ocular albinism, Norrie disease, choroideremia, Charcot-Marie-Tooth disease (CMTX2-3), Pelizaeus-Merzbacher disease, SMAX2), skin and related tissue disorders (e.g., dyskeratosis congenita, hypohidrotic ectodermal dysplasia (EDA), X-linked ichthyosis, X-linked endothelial corneal dystrophy), neuromuscular disorders (e.g., Becker's muscular dystrophy/Duchenne, centronuclear myopathy (MTM1), Conradi-Hünermann syndrome, Emery-Dreifuss muscular dystrophy 1), urologic disorders (e.g., Alport syndrome, Dent's disease, X-linked nephrogenic diabetes insipidus), bone/tooth disorders (e.g., AMELX Amelogenesis imperfecta), and other disorders (e.g., Barth syndrome, McLeod syndrome, Smith-Fineman-Myers syndrome, Simpson-Golabi-Behmel syndrome, Mohr-Tranebjæg syndrome, Nasodigitoacoustic syndrome). Examples of X-linked dominant disorders include, without limitation, X-linked hypophosphatemia, Focal dermal hypoplasia, Fragile X syndrome, Aicardi syndrome, Incontinentia pigmenti, Rett syndrome, CHILD syndrome, Lujan-Fryns syndrome, and Orofaciodigital syndrome 1. Examples of Y-linked disorders include, without limitation, male infertility, retinitis pigmentosa, and azoospermia.

Chromosome Abnormalities

In some embodiments, the presence or absence of a fetal chromosome abnormality can be determined by using a method or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, translocations, deletions and/or duplications of one or more nucleotide sequences (e.g., one or more genes), including deletions and duplications caused by unbalanced translocations. The term "chromosomal abnormality" or "aneuploidy" as used herein refers to a deviation between the structure of the subject chromosome and a normal homologous chromosome. The term "normal" refers to the predominate karyotype or banding pattern found in healthy individuals of a particular species, for example, a euploid genome (in humans, 46,XX or 46,XY). As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a segment of a chromosome. The term "euploid", in some embodiments, refers a normal complement of chromosomes.

The term "monosomy" as used herein refers to lack of one chromosome of the normal complement. Partial monosomy can occur in unbalanced translocations or deletions, in which only a segment of the chromosome is present in a single copy. Monosomy of sex chromosomes (45, X) causes Turner syndrome, for example. The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47, XYY in Jacobs Syndrome). In some embodiments, a trisomy is a duplication of most or all of an autosome. In certain embodiments a trisomy is a whole chromosome aneuploidy resulting in three instances (e.g., three copies) of a particular type of chromosome (e.g., instead of two instances (i.e., a pair) of a particular type of chromosome for a euploid).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the segment that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Tables 1A and 1B present a non-limiting list of chromosome conditions, syndromes and/or abnormalities that can be potentially identified by methods and apparatus described herein. Table 1B is from the DECIPHER database as of Oct. 6, 2011 (e.g., version 5.1, based on positions mapped to GRCh37; available at uniform resource locator (URL) dechipher.sanger.ac.uk).

TABLE 1A

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphoproliferative disease |
| 1 | 1p (somatic) monosomy trisomy | neuroblastoma |

TABLE 1A-continued

| Chromosome | Abnormality | Disease Association |
|---|---|---|
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobsen Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion | Rubenstein-Taybi |
| 3 | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 1B

| Syndrome | Chromosome | Start | End | Interval (Mb) | Grade |
|---|---|---|---|---|---|
| 12q14 microdeletion syndrome | 12 | 65,071,919 | 68,645,525 | 3.57 | |
| 15q13.3 microdeletion syndrome | 15 | 30,769,995 | 32,701,482 | 1.93 | |
| 15q24 recurrent microdeletion syndrome | 15 | 74,377,174 | 76,162,277 | 1.79 | |
| 15q26 overgrowth syndrome | 15 | 99,357,970 | 102,521,392 | 3.16 | |
| 16p11.2 microduplication syndrome | 16 | 29,501,198 | 30,202,572 | 0.70 | |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |
| 22q11 deletion syndrome (Velocardiofacial / DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |
| 7q11.23 duplication syndrome | 7 | 72,332,743 | 74,616,901 | 2.28 | |
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |

TABLE 1B-continued

| Syndrome | Chromosome | Start | End | Interval (Mb) | Grade |
|---|---|---|---|---|---|
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | 21 | 27,037,956 | 27,548,479 | 0.51 | |
| Familial Adenomatous Polyposis | 5 | 112,101,596 | 112,221,377 | 0.12 | |
| Hereditary Liability to Pressure Palsies (HNPP) | 17 | 13,968,607 | 15,434,038 | 1.47 | 1 |
| Leri-Weill dyschondrostosis (LWD) - SHOX deletion | X | 751,878 | 867,875 | 0.12 | |
| Leri-Weill dyschondrostosis (LWD) - SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population; functional data confirming single gene or multi-gene dosage effect; confirmed or strong candidate genes; clinical management implications defined; known cancer risk with implication for surveillance; multiple sources of information (OMIM, Genereviews, Orphanet, Unique, Wkipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, Genereviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

Preeclampsia

In some embodiments, the presence or absence of preeclampsia is determined by using a method or apparatus described herein. Preeclampsia is a condition in which hypertension arises in pregnancy (i.e. pregnancy-induced hypertension) and is associated with significant amounts of protein in the urine. In certain embodiments, preeclampsia also is associated with elevated levels of extracellular nucleic acid and/or alterations in methylation patterns. For example, a positive correlation between extracellular fetal-derived hypermethylated RASSF1A levels and the severity of pre-eclampsia has been observed. In certain examples, increased DNA methylation is observed for the H19 gene in preeclamptic placentas compared to normal controls.

Preeclampsia is one of the leading causes of maternal and fetal/neonatal mortality and morbidity worldwide. Circulating cell-free nucleic acids in plasma and serum are novel biomarkers with promising clinical applications in different medical fields, including prenatal diagnosis. Quantitative changes of cell-free fetal (cff)DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as measurement of total cell-free DNA or the use of gender-independent fetal epigenetic markers, such as DNA methylation, offer an alternative. Cell-free RNA of placental origin is another alternative biomarker that may be used for screening and diagnosing preeclampsia in clinical practice. Fetal RNA is associated with subcellular placental particles that protect it from degradation. Fetal RNA levels sometimes are ten-fold higher in pregnant females with preeclampsia compared to controls, and therefore is an alternative biomarker that may be used for screening and diagnosing preeclampsia in clinical practice.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g. strain).

Cancers

In some embodiments, the presence or absence of a cell proliferation disorder (e.g., a cancer) is determined by using a method or apparatus described herein. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Thus, it is further contemplated that a method provided herein can be used to identify a particular type of cancer.

Software can be used to perform one or more steps in the processes described herein, including but not limited to; counting, data processing, generating an outcome, and/or providing one or more recommendations based on generated outcomes, as described in greater detail hereafter.

Machines, Software and Interfaces

Certain processes and methods described herein (e.g., quantifying, mapping, normalizing, range setting, adjusting, categorizing, counting and/or determining sequence reads, counts, levels (e.g., levels) and/or profiles) often cannot be performed without a computer, processor, software, module or other apparatus. Methods described herein typically are computer-implemented methods, and one or more portions of a method sometimes are performed by one or more processors (e.g., microprocessors), computers, or microprocessor controlled apparatuses. Embodiments pertaining to methods described in this document generally are applicable to the same or related processes implemented by instructions in systems, apparatus and computer program products described herein. In some embodiments, processes and methods described herein (e.g., quantifying, counting and/or determining sequence reads, counts, levels and/or profiles) are performed by automated methods. In some embodiments one or more steps and a method described herein is carried out by a processor and/or computer, and/or carried out in conjunction with memory. In some embodiments, an automated method is embodied in software, modules, processors, peripherals and/or an apparatus comprising the like, that determine sequence reads, counts, mapping, mapped sequence tags, levels, profiles, normalizations, comparisons, range setting, categorization, adjustments, plotting, outcomes, transformations and identifications. As used herein, software refers to computer readable program instructions that, when executed by a processor, perform computer operations, as described herein.

Sequence reads, counts, levels, and profiles derived from a test subject (e.g., a patient, a pregnant female) and/or from a reference subject can be further analyzed and processed to determine the presence or absence of a genetic variation. Sequence reads, counts, levels and/or profiles sometimes are referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific, portion or portion specific], the like and combinations thereof). In certain embodiments, data or data sets can be organized into a matrix having two or more dimensions based on one or more features or variables. Data organized into matrices can be organized using any suitable features or variables. A non-limiting example of data in a matrix includes data that is organized by maternal age, maternal ploidy, and fetal contribution. In certain embodiments, data sets characterized by one or more features or variables sometimes are processed after counting.

Apparatuses, software and interfaces may be used to conduct methods described herein. Using apparatuses, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by a suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more apparatus. Each apparatus comprises one or more of memory, one or more processors, and instructions. Where a system includes two or more apparatus, some or all of the apparatus may be located at the same location, some or all of the apparatus may be located at different locations, all of the apparatus may be located at one location and/or all of the apparatus may be located at different locations. Where a system includes two or more apparatus, some or all of the apparatus may be located at the same location as a user, some or all of the apparatus may be located at a location different than a user, all of the apparatus may be located at the same location as the user, and/or all of the apparatus may be located at one or more locations different than the user.

A system sometimes comprises a computing apparatus and a sequencing apparatus, where the sequencing apparatus is configured to receive physical nucleic acid and generate sequence reads, and the computing apparatus is configured to process the reads from the sequencing apparatus. The computing apparatus sometimes is configured to determine the presence or absence of a genetic variation (e.g., copy number variation; fetal chromosome aneuploidy) from the sequence reads.

A user may, for example, place a query to software which then may acquire a data set via internet access, and in certain embodiments, a programmable processor may be prompted to acquire a suitable data set based on given parameters. A programmable processor also may prompt a user to select one or more data set options selected by the processor based on given parameters. A programmable processor may prompt a user to select one or more data set options selected by the processor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, apparatuses, or computer programs.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus may serve as data that can be input via an input device. In certain embodiments, mapped sequence reads may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., sequencing module, logic processing module, data display organization module). The term "software" refers to computer readable program instructions that, when executed by a computer, perform computer operations. Instructions executable by the one or more processors sometimes are provided as executable code, that when executed, can cause one or more processors to implement a method described herein. A module described herein can exist as software, and instructions (e.g., processes, routines, subroutines) embodied in the software can be implemented or performed by a processor. For example, a module (e.g., a software module) can be a part of a program that performs a particular process or task. The term "module" refers to a self-contained functional unit that can be used in a larger apparatus or software system. A module can comprise a set of instructions for carrying out a function of the module. A module can transform data and/or information. Data and/or information can be in a suitable form. For example, data and/or information can be digital or analogue. In certain embodiments, data and/or information can be packets, bytes, characters, or bits. In some embodiments, data and/or information can be any gathered, assembled or usable data or information.

Non-limiting examples of data and/or information include a suitable media, pictures, video, sound (e.g. frequencies, audible or non-audible), numbers, constants, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to an apparatus, peripheral, component or another module. A module can perform one or more of the following non-limiting functions: mapping sequence reads, providing counts, assembling portions, providing or determining a level, providing a count profile, normalizing (e.g., normalizing reads, normalizing counts, and the like), providing a normalized count profile or levels of normalized counts, comparing two or more levels, providing uncertainty values, providing or determining expected levels and expected ranges(e.g., expected level ranges, threshold ranges and threshold levels), providing adjustments to levels (e.g., adjusting a first level, adjusting a second level, adjusting a profile of a chromosome or a segment thereof, and/or padding), providing identification (e.g., identifying a copy number variation, genetic variation or aneuploidy), categorizing, plotting, and/or determining an outcome, for example. A processor can, In certain embodiments, carry out the instructions in a module. In some embodiments, one or more processors are required to carry out instructions in a module or group of modules. A module can provide data and/or information to another module, apparatus or source and can receive data and/or information from another module, apparatus or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and processor capable of implementing instructions from a module can be located in an apparatus or in different apparatus. A module and/or processor capable of implementing an instruction for a module can be located in the same location as a user (e.g., local network) or in a different location from a user (e.g., remote network, cloud system). In embodiments in which a method is carried out in conjunction with two or more modules, the modules can be located in the same apparatus, one or more modules can be located in different apparatus in the same physical location, and one or more modules may be located in different apparatus in different physical locations.

An apparatus, in some embodiments, comprises at least one processor for carrying out the instructions in a module. Counts of sequence reads mapped to portions of a reference genome sometimes are accessed by a processor that executes instructions configured to carry out a method described herein. Counts that are accessed by a processor can be within memory of a system, and the counts can be accessed and placed into the memory of the system after they are obtained. In some embodiments, an apparatus includes a processor (e.g., one or more processors) which processor can perform and/or implement one or more instructions (e.g., processes, routines and/or subroutines) from a module. In some embodiments, an apparatus includes multiple processors, such as processors coordinated and working in parallel. In some embodiments, an apparatus operates with one or more external processors (e.g., an internal or external network, server, storage device and/or storage network (e.g., a cloud)). In some embodiments, an apparatus comprises a module. In certain embodiments an apparatus comprises one or more modules. An apparatus comprising a module often can receive and transfer one or more of data and/or information to and from other modules. In certain embodiments, an apparatus comprises peripherals and/or components. In certain embodiments an apparatus can comprise one or more peripherals or components that can transfer data and/or information to and from other modules, peripherals and/or components. In certain embodiments an apparatus interacts with a peripheral and/or component that provides data and/or information. In certain embodiments peripherals and components assist an apparatus in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a processor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like,), the world wide web (www), the internet, a computer and/or another module.

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash drives, RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

In some embodiments, provided are computer program products, such as, for example, a computer program product comprising a computer usable medium having a computer readable program code embodied therein, the computer readable program code adapted to be executed to implement a method comprising: (a) obtaining sequence reads of sample nucleic acid from a test subject; (b) mapping the sequence reads obtained in (a) to a known genome, which known genome has been divided into portions; (c) counting the mapped sequence reads within the portions; (d) generating a sample normalized count profile by normalizing the counts for the portions obtained in (c); and (e) determining the presence or absence of a genetic variation from the sample normalized count profile in (d).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more processors in certain embodiments. A processor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A processor may implement software in a system. In some embodiments, a processor may be programmed to automatically perform a task described herein that a user could perform. Accordingly, a processor, or algorithm conducted by such a processor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

One entity can generate counts of sequence reads, map the sequence reads to portions, count the mapped reads, and utilize the counted mapped reads in a method, system, apparatus or computer program product described herein, in some embodiments. Counts of sequence reads mapped to portions sometimes are transferred by one entity to a second entity for use by the second entity in a method, system, apparatus or computer program product described herein, in certain embodiments.

In some embodiments, one entity generates sequence reads and a second entity maps those sequence reads to portions in a reference genome in some embodiments. The second entity sometimes counts the mapped reads and utilizes the counted mapped reads in a method, system, apparatus or computer program product described herein. In certain embodiments the second entity transfers the mapped reads to a third entity, and the third entity counts the mapped reads and utilizes the mapped reads in a method, system, apparatus or computer program product described herein. In certain embodiments the second entity counts the mapped reads and transfers the counted mapped reads to a third entity, and the third entity utilizes the counted mapped reads in a method, system, apparatus or computer program product described herein. In embodiments involving a third entity, the third entity sometimes is the same as the first entity. That is, the first entity sometimes transfers sequence reads to a second entity, which second entity can map sequence reads to portions in a reference genome and/or count the mapped reads, and the second entity can transfer the mapped and/or counted reads to a third entity. A third entity sometimes can utilize the mapped and/or counted reads in a method, system, apparatus or computer program product described herein, wherein the third entity sometimes is the same as the first entity, and sometimes the third entity is different from the first or second entity.

In some embodiments, one entity obtains blood from a pregnant female, optionally isolates nucleic acid from the blood (e.g., from the plasma or serum), and transfers the blood or nucleic acid to a second entity that generates sequence reads from the nucleic acid.

Figure 30:
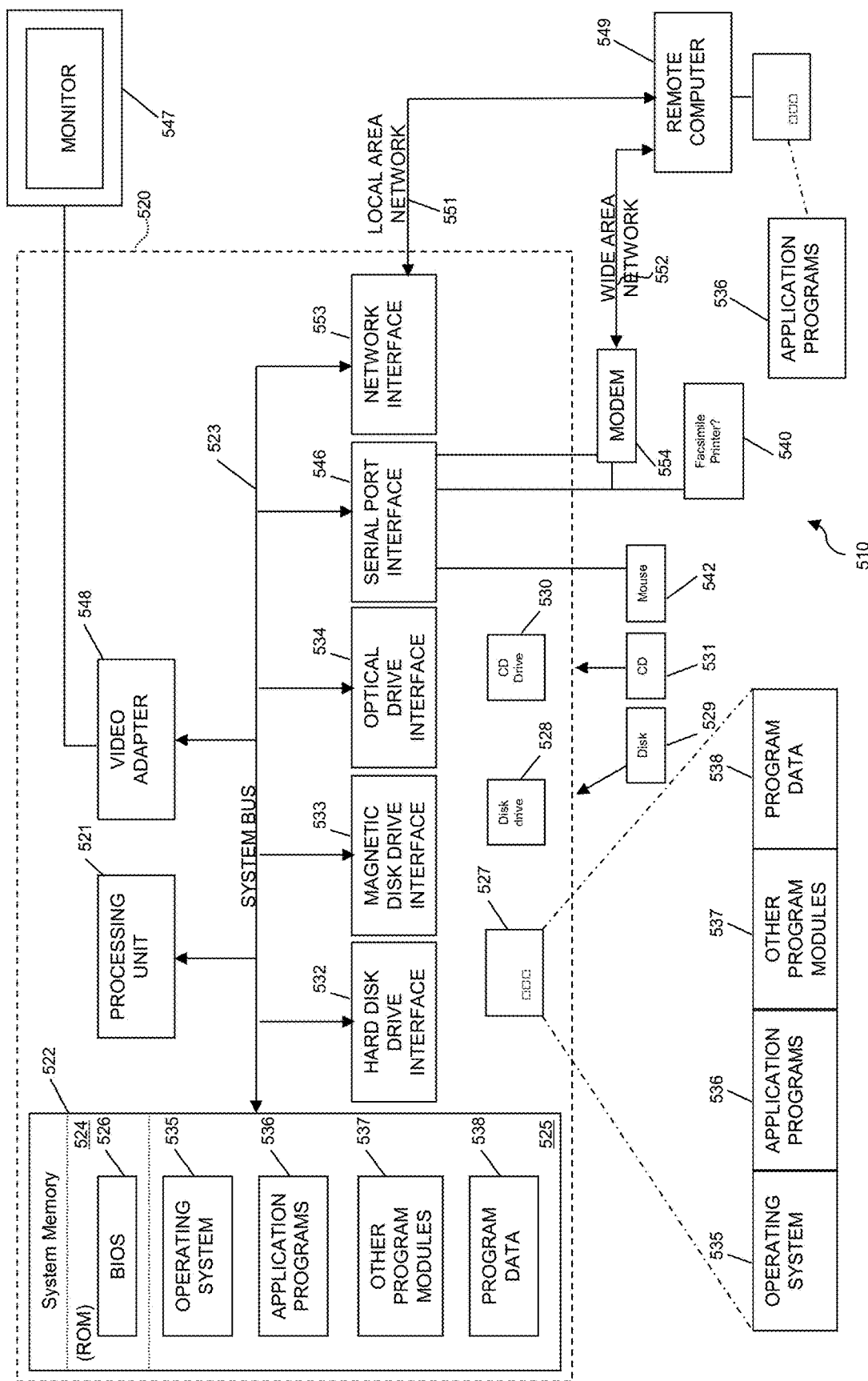
FIG. 30 shows an illustrative embodiment of a system in which certain embodiments of the technology may be implemented.

FIG. 30 illustrates a non-limiting example of a computing environment 510 in which various systems, methods, algorithms, and data structures described herein may be implemented. The computing environment 510 is only one example of a suitable computing environment and is not intended to suggest any limitation as to the scope of use or functionality of the systems, methods, and data structures described herein. Neither should computing environment 510 be interpreted as having any dependency or requirement relating to any one or combination of components illustrated in computing environment 510. A subset of systems, methods, and data structures shown in FIG. 30 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 510 of FIG. 30 includes a general purpose computing device in the form of a computer 520, including a processing unit 521, a system memory 522, and a system bus 523 that operatively couples various system components including the system memory 522 to the processing unit 521. There may be only one or there may be more than one processing unit 521, such that the processor of computer 520 includes a single central-processing unit (CPU), or a plurality of processing units, commonly referred to as a parallel processing environment. The computer 520 may be a conventional computer, a distributed computer, or any other type of computer.

The system bus 523 may be any of several types of bus structures including a memory bus or memory controller, a peripheral bus, and a local bus using any of a variety of bus architectures. The system memory may also be referred to as simply the memory, and includes read only memory (ROM) 524 and random access memory (RAM). A basic input/output system (BIOS) 526, containing the basic routines that help to transfer information between elements within the computer 520, such as during start-up, is stored in ROM 524. The computer 520 may further include a hard disk drive interface 527 for reading from and writing to a hard disk, not shown, a magnetic disk drive 528 for reading from or writing to a removable magnetic disk 529, and an optical disk drive 530 for reading from or writing to a removable optical disk 531 such as a CD ROM or other optical media.

The hard disk drive 527, magnetic disk drive 528, and optical disk drive 530 are connected to the system bus 523 by a hard disk drive interface 532, a magnetic disk drive interface 533, and an optical disk drive interface 534, respectively. The drives and their associated computer-readable media provide nonvolatile storage of computer-readable instructions, data structures, program modules and other data for the computer 520. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 529, optical disk 531, ROM 524, or RAM, including an operating system 535, one or more application programs 536, other program modules 537, and program data 538. A user may enter commands and information into the personal computer 520 through input devices such as a keyboard 540 and pointing device 542. Other input devices (not shown) may include a microphone, joystick, game pad, satellite dish, scanner, or the like. These and other input devices are often connected to the processing unit 521 through a serial port interface 546 that is coupled to the system bus, but may be connected by other interfaces, such as a parallel port, game port, or a universal serial bus (USB). A monitor 547 or other type of display device is also connected to the system bus 523 via an interface, such as a video adapter 548. In addition to the monitor, computers typically include other peripheral output devices (not shown), such as speakers and printers.

The computer 520 may operate in a networked environment using logical connections to one or more remote computers, such as remote computer 549. These logical connections may be achieved by a communication device coupled to or a part of the computer 520, or in other manners. The remote computer 549 may be another computer, a server, a router, a network PC, a client, a peer device or other common network node, and typically includes many or all of the elements described above relative to the computer 520, although only a memory storage device 550 has been illustrated in FIG. 30. The logical connections depicted in FIG. 30 include a local-area network (LAN) 551 and a wide-area network (WAN) 552. Such networking environments are commonplace in office networks, enterprise-wide computer networks, intranets and the Internet, which all are types of networks.

When used in a LAN-networking environment, the computer 520 is connected to the local network 551 through a network interface or adapter 553, which is one type of communications device. When used in a WAN-networking environment, the computer 520 often includes a modem 554, a type of communications device, or any other type of communications device for establishing communications over the wide area network 552. The modem 554, which may be internal or external, is connected to the system bus 523 via the serial port interface 546. In a networked environment, program modules depicted relative to the personal computer 520, or portions thereof, may be stored in the remote memory storage device. It is appreciated that the network connections shown are non-limiting examples and other communications devices for establishing a communications link between computers may be used.

Modules

One or more modules can be utilized in a method described herein, non-limiting examples of which include a logic processing module, sequencing module, mapping module, counting module, filtering module, weighting module, normalization module, GC bias module, level module, comparison module, range setting module, categorization module, plotting module, representation module, relationship module, outcome module and/or data display organization module, the like or combination thereof. Modules are sometimes controlled by a microprocessor. In certain embodiments a module or an apparatus comprising one or more modules, gather, assemble, receive, obtain, access, recover provide and/or transfer data and/or information to or from another module, apparatus, component, peripheral or operator of an apparatus. In some embodiments, data and/or information (e.g., sequencing reads) are provided to a module by an apparatus comprising one or more of the following: one or more flow cells, a camera, a detector (e.g., a photo detector, a photo cell, an electrical detector (e.g., an amplitude modulation detector, a frequency and phase modulation detector, a phase-locked loop detector), a counter, a sensor (e.g., a sensor of pressure, temperature, volume, flow, weight), a fluid handling device, a printer, a display (e.g., an LED, LCT or CRT), the like or combinations thereof. For example, sometimes an operator of an apparatus provides a constant, a threshold value, a formula or a predetermined value to a module. A module is often configured to transfer data and/or information to or from another module or apparatus. A module can receive data and/or information from another module, non-limiting examples of which include a logic processing module, sequencing module, mapping module, counting module, filtering module, weighting module, normalization module, GC bias module, level module, comparison module, range setting module, categorization module, plotting module, representation module, relationship module, outcome module and/or data display organization module, the like or combination thereof. A module can manipulate and/or transform data and/or information. Data and/or information derived from or transformed by a module can be transferred to another suitable apparatus and/or module, non-limiting examples of which include a logic processing module, sequencing module, mapping module, counting module, filtering module, weighting module, normalization module, GC bias module, level module, comparison module, range setting module, categorization module, plotting module, representation module, relationship module, outcome module and/or data display organization module, the like or combination thereof. An apparatus comprising a module can comprise at least one processor. In some embodiments, data and/or information are received by and/or provided by an apparatus comprising a module. An apparatus comprising a module can include a processor (e.g., one or more processors) which processor can perform and/or implement one or more instructions (e.g., processes, routines and/or subroutines) of a module. In some embodiments, a module operates with one or more external processors (e.g., an internal or external network, server, storage device and/or storage network (e.g., a cloud)).

Logic Processing Module

In certain embodiments a logic processing module orchestrates, controls, limits, organizes, orders, distributes, partitions, transforms and/or regulates data and/or information or the transfer of data and/or information to and from one or more other modules, peripherals or devices.

Data Display Organization Module

In certain embodiments a data display organization module processes and/or transforms data and/or information into a suitable visual medium non-limiting examples of which include images, video and/or text (e.g., numbers, letters and symbols). In some embodiments a data display organization module processes, transforms and/or transfers data and/or information for presentation on a suitable display (e.g., a monitor, LED, LCD, CRT, the like or combinations thereof), a printer, a suitable peripheral or device. In some embodiments a data display organization module processes, transforms data and/or information into a visual representation of a fetal or maternal genome, chromosome or part thereof.

Sequencing Module

In some embodiments, a sequence module obtains, generates, gathers, assembles, manipulates, transforms, processes, transforms and/or transfers sequence reads. A "sequence receiving module" as used herein is the same as a "sequencing module". An apparatus comprising a sequencing module can be any apparatus that determines the sequence of a nucleic acid utilizing a sequencing technology known in the art. In some embodiments a sequencing module can align, assemble, fragment, complement, reverse complement, error check, or error correct sequence reads.

Mapping Module

Sequence reads can be mapped by a mapping module or by an apparatus comprising a mapping module, which mapping module generally maps reads to a reference genome or segment thereof. A mapping module can map sequencing reads by a suitable method known in the art. In some embodiments, a mapping module or an apparatus comprising a mapping module is required to provide mapped sequence reads.

Counting Module

Counts can be provided by a counting module or by an apparatus comprising a counting module. In some embodiments a counting module counts sequence reads mapped to a reference genome. In some embodiments a counting module generates, assembles, and/or provides counts according to a counting method known in the art. In some embodiments, a counting module or an apparatus comprising a counting module is required to provide counts.

Filtering Module

Filtering portions (e.g., portions of a reference genome) can be provided by a filtering module (e.g., by an apparatus comprising a filtering module). In some embodiments, a filtering module is required to provide filtered portion data (e.g., filtered portions) and/or to remove portions from consideration. In certain embodiments a filtering module removes counts mapped to a portion from consideration. In certain embodiments a filtering module removes counts mapped to a portion from a determination of a level or a profile. A filtering module can filter data (e.g., counts, counts mapped to portions, portions, portion levels, normalized counts, raw counts, and the like) by one or more filtering methods known in the art or described herein.

Weighting Module

Weighting portions (e.g., portions of a reference genome) can be provided by a weighting module (e.g., by an apparatus comprising a weighting module). In some embodiments, a weighting module is required to weight genomics sections and/or provide weighted portion values. A weighting module can weight portions by one or more weighting methods known in the art or described herein.

Normalization Module

Normalized data (e.g., normalized counts) can be provided by a normalization module (e.g., by an apparatus comprising a normalization module). In some embodiments, a normalization module is required to provide normalized data (e.g., normalized counts) obtained from sequencing reads. A normalization module can normalize data (e.g., counts, filtered counts, raw counts) by one or more normalization methods described herein (e.g., PERUN, ChAI, hybrid normalization, the like or combinations thereof) or known in the art.

GC Bias Module

Determining GC bias (e.g., determining GC bias for each of the portions of a reference genome (e.g., portions, portions of a reference genome)) can be provided by a GC bias module (e.g., by an apparatus comprising a GC bias module). In some embodiments, a GC bias module is required to provide a determination of GC bias. In some embodiments a GC bias module provides a determination of GC bias from a fitted relationship (e.g., a fitted linear relationship) between counts of sequence reads mapped to each of the portions of a reference genome and GC content of each portion. A GC bias module sometimes is part of a normalization module (e.g., PERUN, ChAI normalization module).

Level Module

Determining levels (e.g., levels) and/or calculating genomic section levels for portions of a reference genome can be provided by an level module (e.g., by an apparatus comprising a level module). In some embodiments, a level module is required to provide a level or a calculated genomic section level (e.g., according to Equation A, B, L, M, N, O and/or Q). In some embodiments a level module provides a level from a fitted relationship (e.g., a fitted linear relationship) between a GC bias and counts of sequence reads mapped to each of the portions of a reference genome. In some embodiments a level module calculates a genomic section level as part of PERUN. In some embodiments, a level module provides a genomic section level (i.e., $L_i$) according to equation $L_i=(m_i-G_iS) I^{-1}$ wherein $G_i$ is the GC bias, $m_i$ is measured counts mapped to each portion of a reference genome, i is a sample, and I is the intercept and S is the slope of the a fitted relationship (e.g., a fitted linear relationship) between a GC bias and counts of sequence reads mapped to each of the portions of a reference genome.

Comparison Module

A first level can be identified as significantly different from a second level by a comparison module or by an apparatus comprising a comparison module. In some embodiments, a comparison module or an apparatus comprising a comparison module is required to provide a comparison between two levels.

Range Setting Module

Expected ranges (e.g., expected level ranges) for various copy number variations (e.g., duplications, insertions and/or deletions) or ranges for the absence of a copy number variation can be provided by a range setting module or by an apparatus comprising a range setting module. In certain embodiments, expected levels are provided by a range setting module or by an apparatus comprising a range setting module. In some embodiments, a range setting module or an apparatus comprising a range setting module is required to provide expected levels and/or ranges.

Categorization Module

A copy number variation (e.g., a maternal and/or fetal copy number variation, a fetal copy number variation, a duplication, insertion, deletion) can be categorized by a categorization module or by an apparatus comprising a categorization module. In certain embodiments a copy number variation (e.g., a maternal and/or fetal copy number variation) is categorized by a categorization module. In certain embodiments a level (e.g., a first level) determined to be significantly different from another level (e.g., a second level) is identified as representative of a copy number variation by a categorization module. In certain embodiments the absence of a copy number variation is determined by a categorization module. In some embodiments, a determination of a copy number variation can be determined by an apparatus comprising a categorization module. A categorization module can be specialized for categorizing a maternal and/or fetal copy number variation, a fetal copy number variation, a duplication, deletion or insertion or lack thereof or combination of the foregoing. For example, a categorization module that identifies a maternal deletion can be different than and/or distinct from a categorization module that identifies a fetal duplication. In some embodiments, a categorization module or an apparatus comprising a categorization module is required to identify a copy number variation or an outcome determinative of a copy number variation.

Plotting Module

In some embodiments a plotting module processes and/or transforms data and/or information into a suitable visual medium, non-limiting examples of which include a chart, plot, graph, the like or combinations thereof. In some embodiments a plotting module processes, transforms and/or transfers data and/or information for presentation on a suitable display (e.g., a monitor, LED, LCD, CRT, the like or combinations thereof), a printer, a suitable peripheral or device. In certain embodiments a plotting module provides a visual display of a count, a level, and/or a profile. In some embodiments a data display organization module processes, transforms data and/or information into a visual representation of a fetal or maternal genome, chromosome or part thereof. In some embodiments, a plotting module or an apparatus comprising a plotting module is required to plot a count, a level or a profile.

Relationship Module

In certain embodiments, a relationship module processes and/or transforms data and/or information into a relationship. In certain embodiments, a relationship is generated by and/or transferred from a relationship module.

Outcome Module

The presence or absence of a genetic variation (an aneuploidy, a fetal aneuploidy, a copy number variation) is, in some embodiments, identified by an outcome module or by an apparatus comprising an outcome module. In certain embodiments a genetic variation is identified by an outcome module. Often a determination of the presence or absence of an aneuploidy is identified by an outcome module. In some embodiments, an outcome determinative of a genetic variation (an aneuploidy, a copy number variation) can be identified by an outcome module or by an apparatus comprising an outcome module. An outcome module can be specialized for determining a specific genetic variation (e.g., a trisomy, a trisomy 21, a trisomy 18). For example, an outcome module that identifies a trisomy 21 can be different than and/or distinct from an outcome module that identifies a trisomy 18. In some embodiments, an outcome module or an apparatus comprising an outcome module is required to identify a genetic variation or an outcome determinative of a genetic variation (e.g., an aneuploidy, a copy number variation). A genetic variation or an outcome determinative of a genetic variation identified by methods described herein can be independently verified by further testing (e.g., by targeted sequencing of maternal and/or fetal nucleic acid).

Transformations

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

EXAMPLES

The following examples are provided by way of illustration only and not by way of limitation. Thus, the examples set forth below illustrate certain embodiments and do not limit the technology. Those of skill in the art will readily recognize a variety of non-critical parameters that could be changed or modified to yield essentially the same or similar results.

Example 1: PERUN and General Methods for Detecting Conditions Associated with Genetic Variations The methods and underlying theory described herein can be utilized to detect various conditions associated with genetic variation and provide an outcome determinative of, or determine the presence or absence of a genetic variation.

Removal of Uninformative Portions of a Reference Genome

Multiple attempts to remove uninformative portions of a reference genome have indicated that portion selection has the potential to improve classification.

Equation A:

$$M = LI + GS \qquad (A)$$

The various terms in Eq. A have the following meanings:

M: measured counts, representing the primary information polluted by unwanted variation.

L: chromosomal level—this is the desired output from the data processing procedure. L indicates fetal and/or maternal aberrations from euploid. This is the quantity that is masked both by stochastic errors and by the systematic biases. The chromosomal level L is both sample specific and portion-specific.

G: GC bias coefficient measured using linear model, LOESS, or any equivalent approach. G represents secondary information, extracted from M and from a set of portion-specific GC content values, usually derived from the reference genome (but may be derived from actually observed GC contents as well). G is sample specific and does not vary along the genomic position. It encapsulates a portion of the unwanted variation.

I: Intercept of the linear model. This model parameter is fixed for a given experimental setup, independent on the sample, and portion-specific.

S: Slope of the linear model. This model parameter is fixed for a given experimental setup, independent on the sample, and portion specific.

The quantities M and G are measured. Initially, the portion-specific values/and S are unknown. To evaluate unknown/and S, we must assume that L=1 for all portions of a reference genome in euploid samples. The assumption is not always true, but one can reasonably expect that any samples with deletions/duplications will be overwhelmed by samples with normal chromosomal levels. A linear model applied to the euploid samples extracts the/and S parameter values specific for the selected portion (assuming L=1). The same procedure is applied to all the portions of a reference genome in the human genome, yielding a set of intercepts/ and slopes S for every genomic location. Cross-validation randomly selects a work set containing 90% of all LDTv2CE euploids and uses that subset to train the model. The random selection is repeated 100 times, yielding a set of 100 slopes and 100 intercepts for every portion.

Extraction of Chromosomal Level from Measured Counts

Assuming that the model parameter values/and S are available for every portion, measurements M collected on a new test sample are used to evaluate the chromosomal level according to the following Equation B:

$$L = (M - GS)/I \quad (B)$$

As in Eq. A, the GC bias coefficient G is evaluated as the slope of the regression between the portion-wise measured raw counts M and the GC content of the reference genome. The chromosomal level L is then used for further analyses (Z-values, maternal deletions/duplications, fetal microdeletions/microduplications, fetal gender, sex aneuploidies, and so on). The procedure encapsulated by Eq. B is named Parameterized Error Removal and Unbiased Normalization (PERUN).

Example 2: Examples of Formulas

Provided below are non-limiting examples of mathematical and/or statistical formulas that can be used in methods described herein.

Z-scores and p-values calculated from Z-scores associated with deviations from the expected level of 1 can then be evaluated in light of the estimate for uncertainty in the average level. The p-values are based on a t-distribution whose order is determined by the number of portions of a reference genome in a peak. Depending on the desired level of confidence, a cutoff can suppress noise and allow unequivocal detection of the actual signal.

Equation 1

$$Z = \frac{\Delta_1 - \Delta_2}{\sqrt{\sigma_1^2 \left(\frac{1}{N_1} + \frac{1}{n_1}\right) + \sigma_2^2 \left(\frac{1}{N_2} + \frac{1}{n_2}\right)}} \quad (1)$$

Equation 1 can be used to directly compare peak level from two different samples, where N and n refer to the numbers of portions of a reference genome in the entire chromosome and within the aberration, respectively. The order of the t-test that will yield a p-value measuring the similarity between two samples is determined by the number of portions of a reference genome in the shorter of the two deviant stretches.

Equation 8 can be utilized to incorporate fetal fraction, maternal ploidy, and median reference counts into a classification scheme for determining the presence or absence of a genetic variation with respect to fetal aneuploidy.

Equation 8:

$$y_i = (1-F)Mf_i + FXf_i \quad (8)$$

where $Y_i$ represents the measured counts for a portion in the test sample corresponding to the portion in the median count profile, F represents the fetal fraction, X represents the fetal ploidy, and $M_i$ represents maternal ploidy assigned to each portion. Possible values used for X in equation (8) are: 1 if the fetus is euploid; 3/2, if the fetus is triploid; and, 5/4, if there are twin fetuses and one is affected and one is not. 5/4 is used in the case of twins where one fetus is affected and the other not, because the term F in equation (8) represents total fetal DNA, therefore all fetal DNA must be taken into account. In some embodiments, large deletions and/or duplications in the maternal genome can be accounted for by assigning maternal ploidy, $M_i$, to each portion or portion. Maternal ploidy often is assigned as a multiple of ½, and can be estimated using portion-wise normalization, in some embodiments. Because maternal ploidy often is a multiple of ½, maternal ploidy can be readily accounted for, and therefore will not be included in further equations to simplify derivations.

When evaluating equation (8) at X=1, (e.g., euploid assumption), the fetal fraction is canceled out and the following equation results for the sum of squared residuals.

Equation 9

$$\varphi_E = \sum_{i=1}^{N} \frac{1}{\sigma_i^2}(y_i - f_i)^2 = \sum_{i=1}^{N} \frac{y_i^2}{\sigma_i^2} - 2\sum_{i=1}^{N} \frac{y_i f_i}{\sigma_i^2} + \sum_{i=1}^{N} \frac{f_i^2}{\sigma_i^2} = \Xi_{yy} - 2\Xi_{fy} + \Xi_{ff} \quad (9)$$

To simplify equation (9) and subsequent calculations, the following equations are utilized.

Equation 10

$$\Xi_{yy} = \sum_{i=1}^{N} \frac{y_i^2}{\sigma_i^2} \quad (10)$$

Equation 11

$$\Xi_{ff} = \sum_{i=1}^{N} \frac{f_i^2}{\sigma_i^2} \quad (11)$$

Equation 12

$$\Xi_{fy} = \sum_{i=1}^{N} \frac{y_i f_i}{\sigma_i^2} \quad (12)$$

When evaluating equation (8) at X=3/2 (e.g., triploid assumption), the following equation results for the sum of the squared residuals.

Equation 13

$$\varphi_T = \sum_{i=1}^{N} \frac{1}{\sigma_i^2} \left(y_i - f_i - \frac{1}{2} F f_i\right)^2 = \quad (13)$$

$$\Xi_{yy} - 2\Xi_{fy} + \Xi_{ff} + F(\Xi_{ff} - \Xi_{fy}) + \frac{1}{4} F^2 \Xi_{ff}$$

The difference between equations (9) and (13) forms the functional result (e.g., phi) that can be used to test the null hypothesis (e.g., euploid, X=1) against the alternative hypothesis (e.g., trisomy singleton, X=3/2):

Equation 14

$$\varphi = \varphi_E - \varphi_T = F(\Xi_{fy} - \Xi_{ff}) - \frac{1}{4} F^2 \Xi_{ff} \quad (14)$$

Equation 18

$$\varphi = \sum_{i=1}^{N} \frac{1}{\sigma_i^2} [y_i - (1-F)M_i f_i - FX f_i]^2 = \quad (18)$$

$$\sum_{i=1}^{N} \frac{1}{\sigma_i^2} [y_i^2 - 2(1-F)M_i f_i y_i - 2FX f_i y_i +$$

$$(1-F)^2 M_i^2 f_i^2 + 2F(1-F)XM_i f_i^2 + F^2 X^2 f_i^2]$$

Optimal ploidy value sometimes is given by Equation 20:

$$X = \frac{\sum_{i=1}^{N} \frac{f_i y_i}{\sigma_i^2} - (1-F) \sum_{i=1}^{N} \frac{M_i f_i^2}{\sigma_i^2}}{F \sum_{i=1}^{N} \frac{f_i^2}{\sigma_i^2}} \quad (20)$$

The term for maternal ploidy, $M_i$, can be omitted from some mathematical derivations. The resulting expression for X corresponds to the relatively simple, and often most frequently occurring, special case of when the mother has no deletions or duplications in the chromosome or chromosomes being evaluated.

Equation 21

$$X = \frac{\Xi_{fy} - (1-F)\Xi_{ff}}{F\Xi_{ff}} = \frac{\Xi_{fy}}{F\Xi_{ff}} - \frac{1-F}{F} = 1 + \frac{1}{F}\left(\frac{\Xi_{fy}}{\Xi_{ff}} - 1\right) \quad (21)$$

$Xi_{ff}$ and $Xi_{fy}$ are given by equations (11) and (12), respectively. In embodiments where all experimental errors are negligible, solving equation (21) results in a value of 1 for euploids where $Xi_{ff}=Xi_{fy}$. In certain embodiments where all experimental errors are negligible, solving equation (21) results in a value of 3/2 for triploids (see equation (15) for triploid relationship between $Xi_{ff}$ and $Xi_{fy}$.

TABLE 2

| Pregnancy Status | Fetal Chr21 | Fetal Chr18 | Fetal Chr13 | Fetal ChrX | Fetal ChrY |
|---|---|---|---|---|---|
| Female T21 | $P_{ij}^F = 3/2$ | $P_{ij}^F = 1$ | $P_{ij}^F = 1$ | $P_{ij}^F = 1$ | $P_{ij}^F = 0$ |
| Female T18 | $P_{ij}^F = 1$ | $P_{ij}^F = 3/2$ | $P_{ij}^F = 1$ | $P_{ij}^F = 1$ | $P_{ij}^F = 0$ |
| Female T13 | $P_{ij}^F = 1$ | $P_{ij}^F = 1$ | $P_{ij}^F = 3/2$ | $P_{ij}^F = 1$ | $P_{ij}^F = 0$ |
| Male T21 | $P_{ij}^F = 3/2$ | $P_{ij}^F = 1$ | $P_{ij}^F = 1$ | $P_{ij}^F = 1/2$ | $P_{ij}^F = 1/2$ |
| Male T18 | $P_{ij}^F = 1$ | $P_{ij}^F = 3/2$ | $P_{ij}^F = 1$ | $P_{ij}^F = 1/2$ | $P_{ij}^F = 1/2$ |
| Male T13 | $P_{ij}^F = 1$ | $P_{ij}^F = 1$ | $P_{ij}^F = 3/2$ | $P_{ij}^F = 1/2$ | $P_{ij}^F = 1/2$ |
| Male Euploid | $P_{ij}^F = 1$ | $P_{ij}^F = 1$ | $P_{ij}^F = 1$ | $P_{ij}^F = 1/2$ | $P_{ij}^F = 1/2$ |
| Turner | $P_{ij}^F = 1$ | $P_{ij}^F = 1$ | $P_{ij}^F = 1$ | $P_{ij}^F = 1/2$ | $P_{ij}^F = 0$ |
| Jacobs | $P_{ij}^F = 1$ | $P_{ij}^F = 1$ | $P_{ij}^F = 1$ | $P_{ij}^F = 1/2$ | $P_{ij}^F = 1$ |
| Klinefelter | $P_{ij}^F = 1$ | $P_{ij}^F = 1$ | $P_{ij}^F = 1$ | $P_{ij}^F = 1$ | $P_{ij}^F = 1/2$ |
| TripleX | $P_{ij}^F = 1$ | $P_{ij}^F = 1$ | $P_{ij}^F = 1$ | $P_{ij}^F = 3/2$ | $P_{ij}^F = 0$ |

Example 3. Decision Tree Analysis

A decision tree method was developed that can detect fetal aneuploidies, including unreported or previously unknown aneuploidies, on any chromosomes. In addition, non-uniform coverage events in the genome can be detected after applying a normalization procedure (e.g. PERUN). Non-uniform events, as shown on FIG. 1 (upper left panel), may indicate a microdeletion/duplication. These events can be independently detected.

Methods

Unlike the case for detection of T21, T18 and T13 with predefined genomic coordinates, non-uniform coverage events can occur anywhere in a genome. Detection of a genetic variation at a predefined position only requires determining the significance level at the indicated position. Algorithms described in this Example search for regions with consistently elevated or depressed portion count/coverage and accurately determine the boundaries of such events. Described in this Example is a method that utilizes the power of two orthogonal methods.

Wavelet Decomposition

A first algorithm takes advantage of a wavelet transformation. Wavelet transformation is a mathematical tool that is particularly useful for signal processing purposes. In this modified application, whole genome sequencing data were first aligned, portioned and normalized to remove GC bias. PERUN normalization (described herein) was utilized to reduce GC bias and other GC bias reducing processes can be utilized (e.g., ChAI processes described herein). Subsequently, a wavelet smoothing method was applied to the normalized profile to reduce noise in data, thereby making the microdeletion/microduplication event clearly visible. A schematic plot for a wavelet method is shown on FIG. 1.

Figure 2:
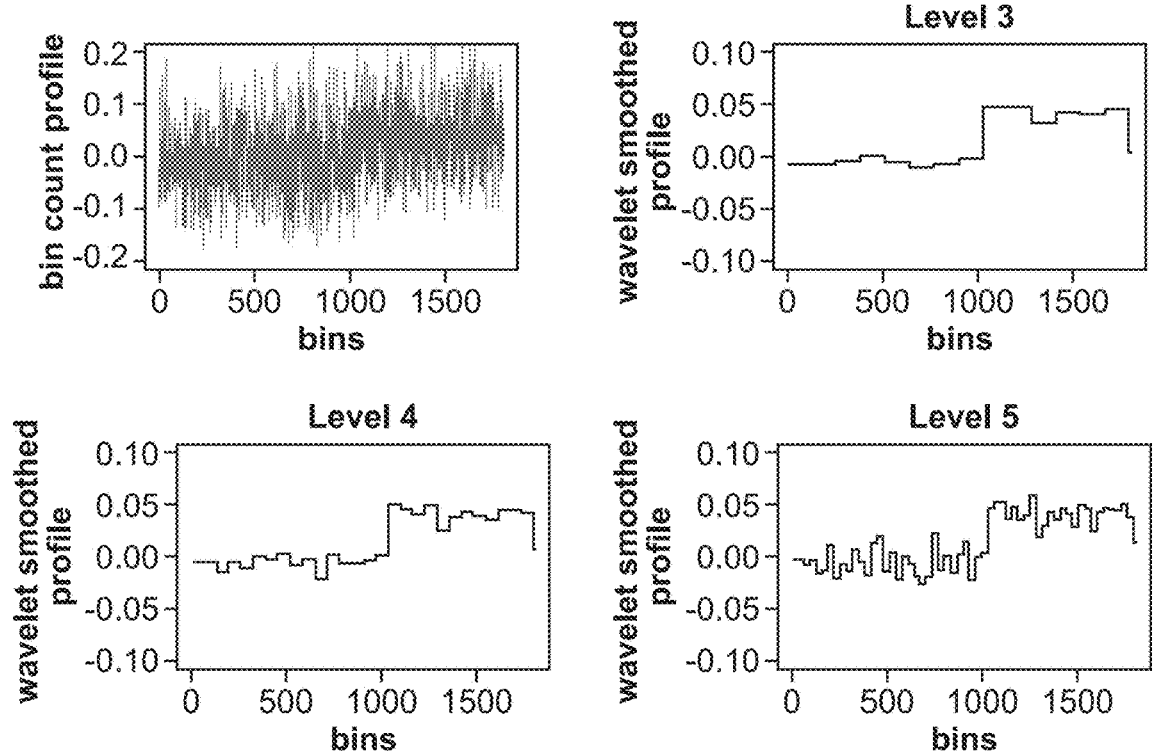
FIG. 2 shows the effect of leveling without thresholding. The optimal level can be determined by the desired size of event.

A standard Haar wavelet was used for wavelet decomposition. In principle more complex wavelet transformations can be used to identify the location of an event after smoothing. To distinguish signals from noise, one needs to determine which wavelet coefficients are indicative of signals and should be retained, and which ones are likely the reflection of noise and should be removed. This step is called thresholding. As is known, large magnitude and low level coefficients preserve the trend of the signal whereas small magnitude and high level coefficients preserve the details of the signal. A "soft" thresholding method was used to remove small and non-significant coefficients [Donoho and Johnstone, (1995) WaveLab and Reproducible Research]. After thresholding, some high level coefficients may remain. These coefficients represent steep changes or large spikes in the original signal and are removed. This step is referred to as "leveling" and FIG. 2 illustrates the effect of leveling without thresholding (e.g., more details are preserved with increased levels). The optimal choice of leveling can depend on many factors, such as the length of the chromosome, the desired event length to detect and the noise level of the normalized profile. Given the length of the chromosome $N_{chr}$ (extended to the nearest number of power of 2) and wavelet decomposition level c, the minimum segment length of wavelet profile is $L=N_{chr}/2^{c+1}$. Therefore, to detect a microdeletion of size $N_{micro}$, the desired decomposition level is $c=\log_2 (N_{chr}/N_{micro})-1$. For example, if $N_{chr}=4096$ portions of a reference genome and the microdeletion has a size of $N_{micro}=128$ portions of a reference genome, then the decomposition level should be c=4. A decomposition level of c±1 also can be utilized.

Circular Binary Segmentation (CBS) Method

Figure 5:
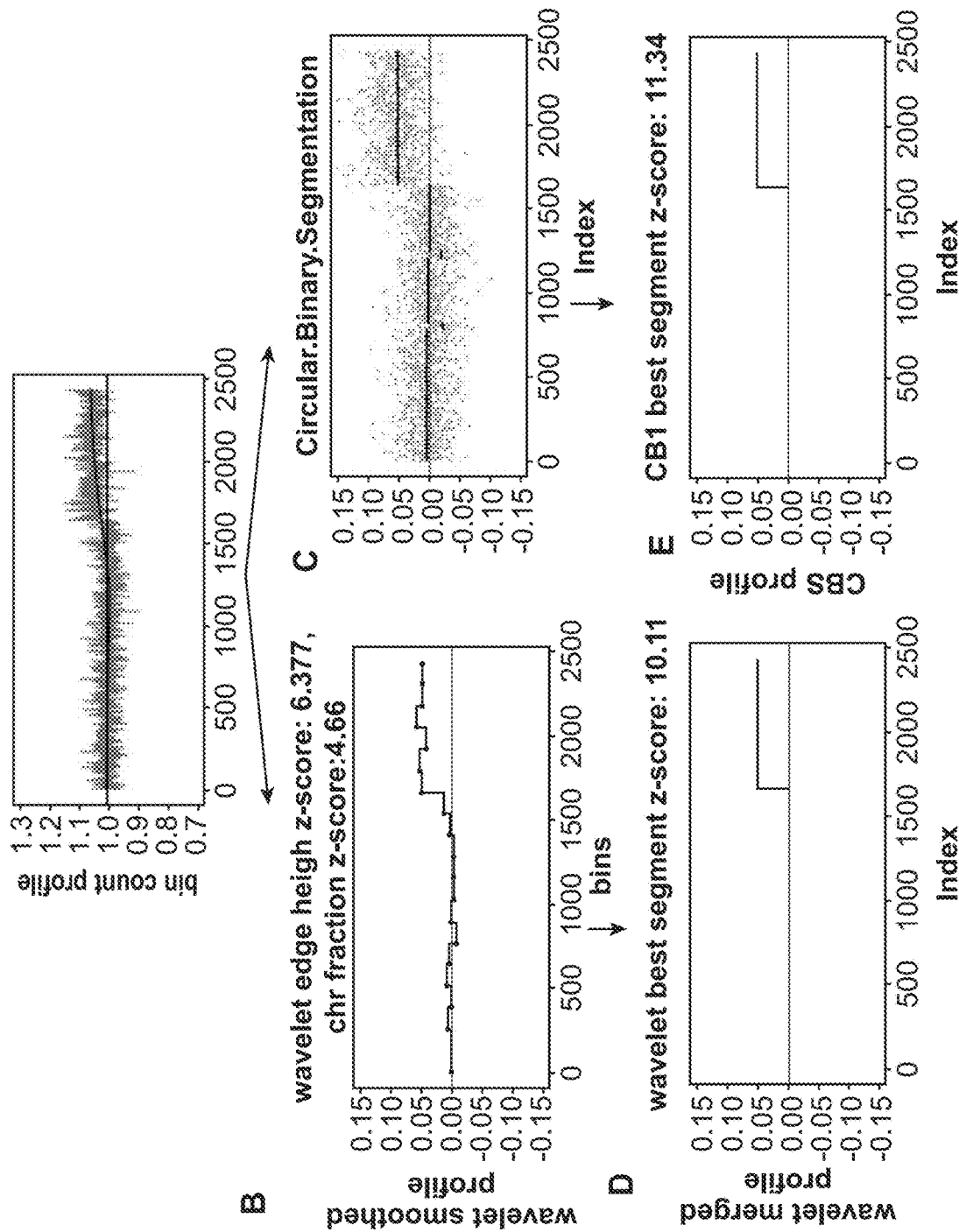
FIG. 5A to FIG. 5E show chromosome profiles that were wavelet smoothed (FIG. 5B), CBS smoothed (FIG. 5C) and segment merged (FIG. 5D and FIG. 5E). The two best segments from the two methods were compared and "cross-confirm" each other.

A wavelet method can identify locations for potential microdeletion/microduplication. However, it alone does not guarantee the existence of true events. When a profile is poorly normalized, the wavelet algorithm could be misled by local fluctuations caused by GC residuals. Moreover, the precision of the detected edge is limited by the wavelet coefficient truncation order. To reduce false positives, an independent method was utilized to validate wavelet findings. Circular Binary Segmentation (CBS) is a method that was originally proposed for copy number variation (CNV) detections using array CGH data. It can pinpoint a change point precisely. CBS works by iteratively partitioning a chromosome into equal copy number regions using the likelihood ratio statistic [Olshen A B, Venkatraman E S, Lucito R, Wgler M. Biostatistics (2004) October; 5(4):557-72]. This works well in general, but tends to over partition the genome when noise is high in the signal [Lai, W R, Johnson, M D, Kucherlapati, R, Park, P J Bioinformatics (2005) 21, 19:3763-70.]. In this Example, it is adapted to work with PERUN-normalized portion count data and used as an independent method to validate wavelet findings. FIG. 5 exemplifies the CBS algorithm.

Merge Segments for Wavelet or CBS Smoothed Profiles

Figure 4:
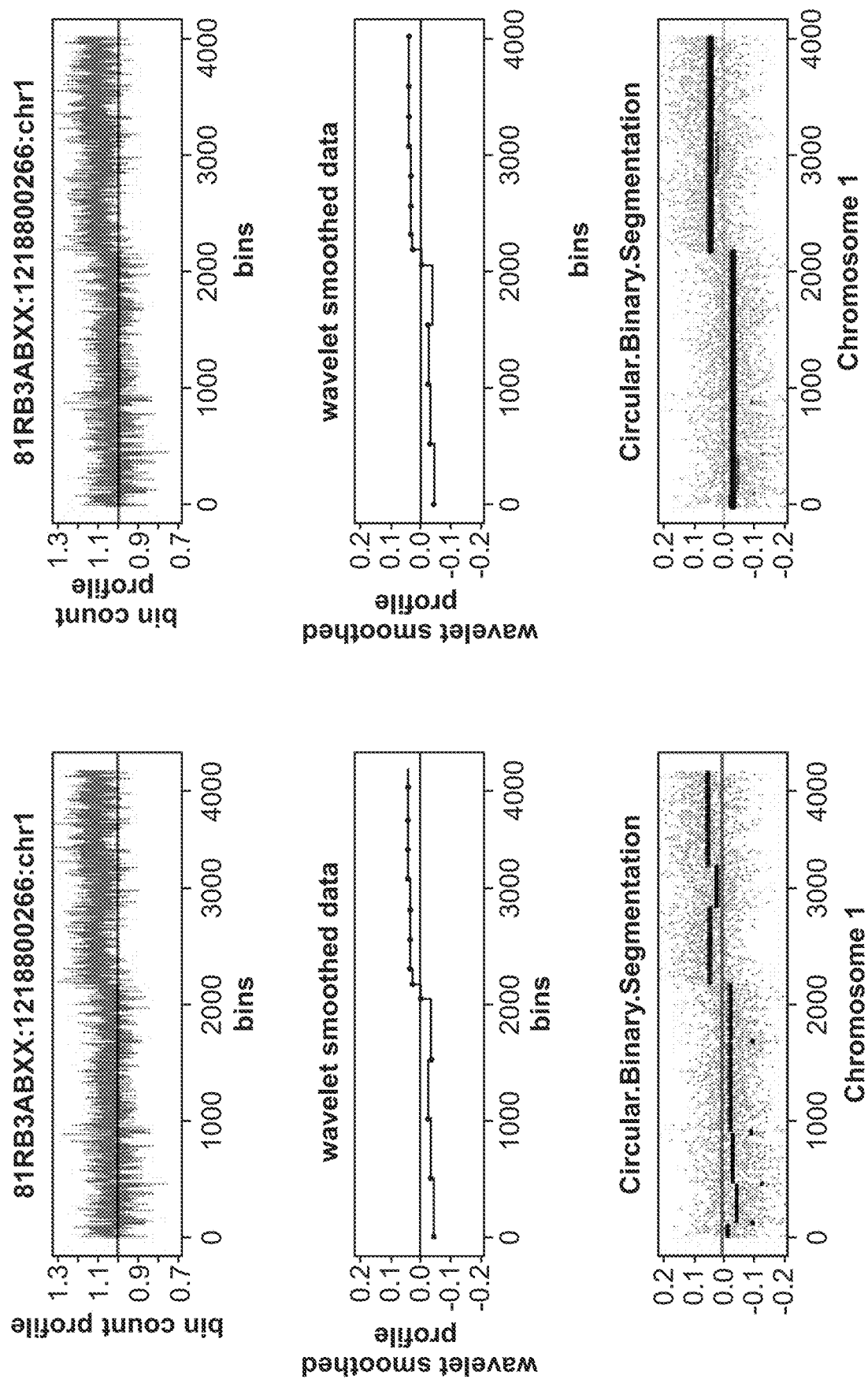
FIG. 4 shows an example of merging segments after wavelet or CBS. Three originally partitioned segments (left panels, right half of chromosome) were merged into a single long stretch (right panel, right half of chromosome), making the microduplications clearly visible.

Wavelet or CBS partitions a chromosome of interest into regions/segments of equal copy numbers. Each segment represents a potential candidate for a CNV. As discussed in previous sections, CBS tends to overly partition a chromosome, and hence a wide span CNV region could be segregated into several smaller pieces. Similar situations can happen for the wavelet method. FIG. 4 illustrates this, where a large duplication was originally portioned into 3 pieces by the CBS method, resulting in underestimate the CNV width (FIG. 4, bottom left panel). To overcome this defect, an algorithm proposed by Willenbrock and Fridlyand (Willenbrock H, Fridlyand J., Bioinformatics (2005) November 15; 21(22):4084-91) was applied to further merge wavelet or CBS smoothed profiles into longer stretches of equal copy number regions. Two segments are merged if the portion counts mapped to those two segments are not significantly different, or if the predicted segment values are closer than a dynamically determined threshold [Willenbrock and Fridlyand 2005]. FIG. 4, bottom right panel, illustrates the effect of merging segments, where a clear microduplication was visible after merging segments.

Statistics Derived from Wavelet and CBS Algorithm

For each chromosome, three key z-score statistics can be inferred from the wavelet/CBS smoothed, segment merged profiles.

(1) The best segment (candidate segment) from the wavelet smoothed profile and its portion count representation z-score ($Z_{wave}$). The sample count representation of the candidate segment is the total normalized counts in the segment divided by the total normalized autosome counts for the test sample. A median count representation for the candidate segment is generated for a euploid sample set, and a MAD is determined for the euploid count representation for the candidate segment. The $Z_{wave}$ statistic for the segment is the test sample count representation minus the euploid median count representation and the subtraction product is divided by the MAD.

(2) The best segment from the CBS smoothed profile and its portion count representation z-score ($Z_{cbs}$). The sample count representation of the candidate segment is the total normalized counts in the segment divided by the total normalized autosome counts for the test sample. A median count representation for the candidate segment is generated for a euploid sample set, and a MAD is determined for the euploid count representation for the candidate segment. The $Z_{cbs}$ statistic for the segment is the test sample count representation minus the euploid median count representation and the subtraction product is divided by the MAD.

(3) The overall chromosomal representation for the entire chromosome ($Z_{chr}$). The sample count representation is the total normalized counts in the chromosome in which the candidate segment resides divided by the total normalized autosome counts for the test sample. A median count representation for the chromosome is generated for a euploid sample set, and a MAD is determined for the euploid count representation. The $Z_{chr}$ statistic for the chromsome is the test sample count representation minus the euploid median count representation and the subtraction product is divided by the MAD.

The best segment is sometimes the segment that has the largest area under the curve (AUC) out of all the segments on that chromosome. Such a segment represents the most significant finding on the chromosome of interest. For example, the bottom right panel of FIG. 4 has two segments, out of which the second one has the largest AUC. FIG. 5 summarizes the wavelet and CBS smoothing for each chromosome and the derived statistics.

Decision Tree for CNV Detection

Once the three key statistics are calculated for each of the chromosomes, they can be used to determine the existence of a trisomy, a microdeletion or microduplication in a given sample. A decision tree is shown below:

1. A chromosome is classified as trisomy or monosomy if:
   a. |Zchr|≥3.95, and
   b. |Zchr|≥min (α|Zwave|, α|Zcbs|)

Figure 9:
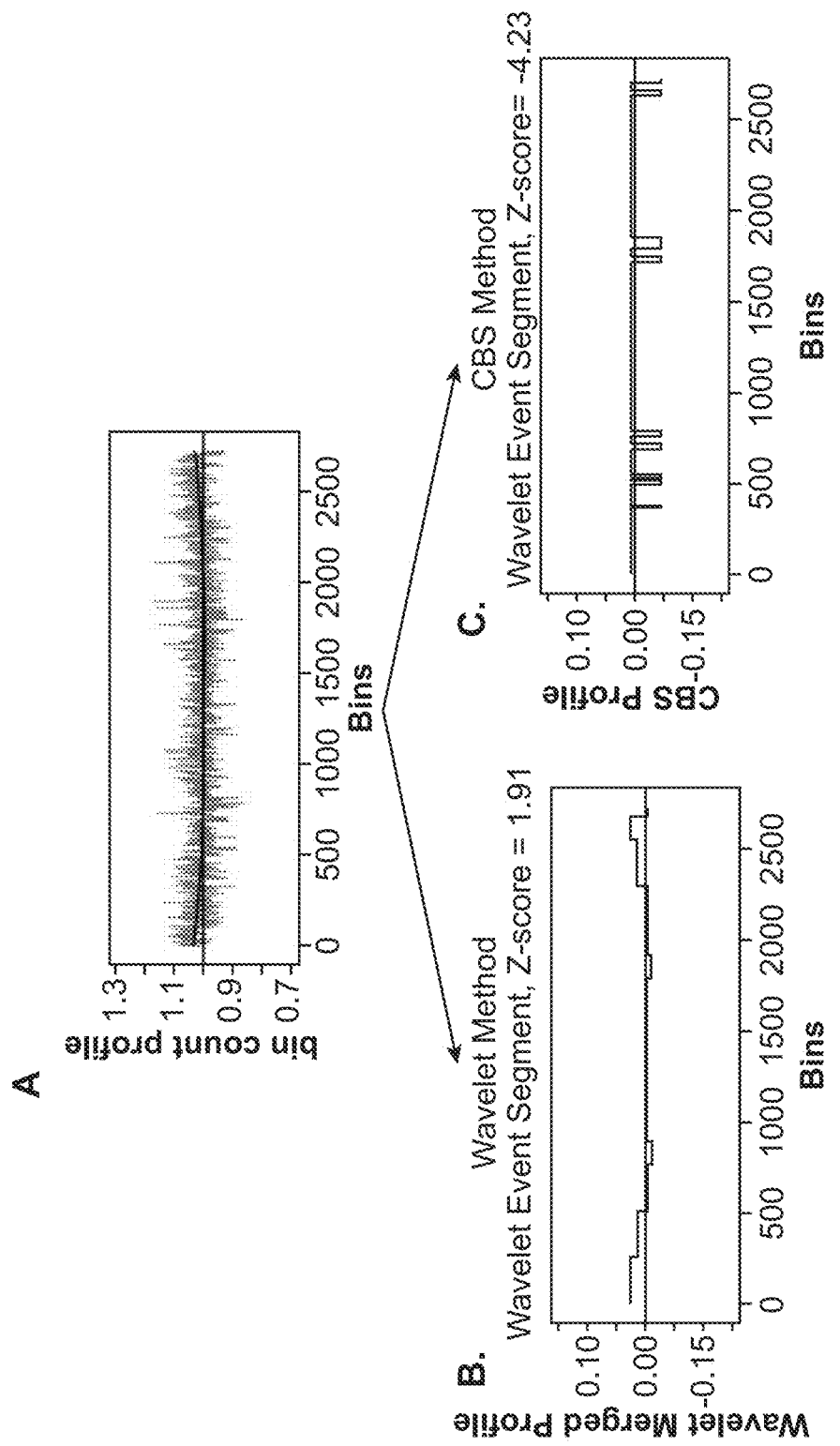
FIG. 9 shows a chromosome profile (A) that is wavelet smoothed and merged (B) and CBS smoothed and merged (C). After comparison, the two best segments from the two methods "cross-reject" each other.

2. A chromosome is classified to have microdeletion/microduplication if:
   a. it is NOT a trisomy or monosomy
   b. $|Z_{wave}| \geq 3.95$, and $|Z_{cbs}| \geq 3.95$
   c. wavelet and CBS best segment overlaps Note that condition 1 essentially requires the overall chromosomal Z-score to be significant and its magnitude should be comparable to best segments of either wavelet or CBS. Condition 2 requires both wavelet and CBS best segment to be significant and requires them to overlap with each other to cross confirm the findings (FIG. 5). In some cases wavelet events identified by CBS and the wavelet method do not overlap (FIG. 9) indicating the absence of a microduplication or microdeletion. In most applications, the Z-score cutoff (e.g., predetermined threshold) of 3.95 can be slightly increased or decreased to achieve a desired sensitivity and specificity. Also, a, a predetermined value, is often set between 0.6-0.8 in most applications shown here.

Results

Figure 10:
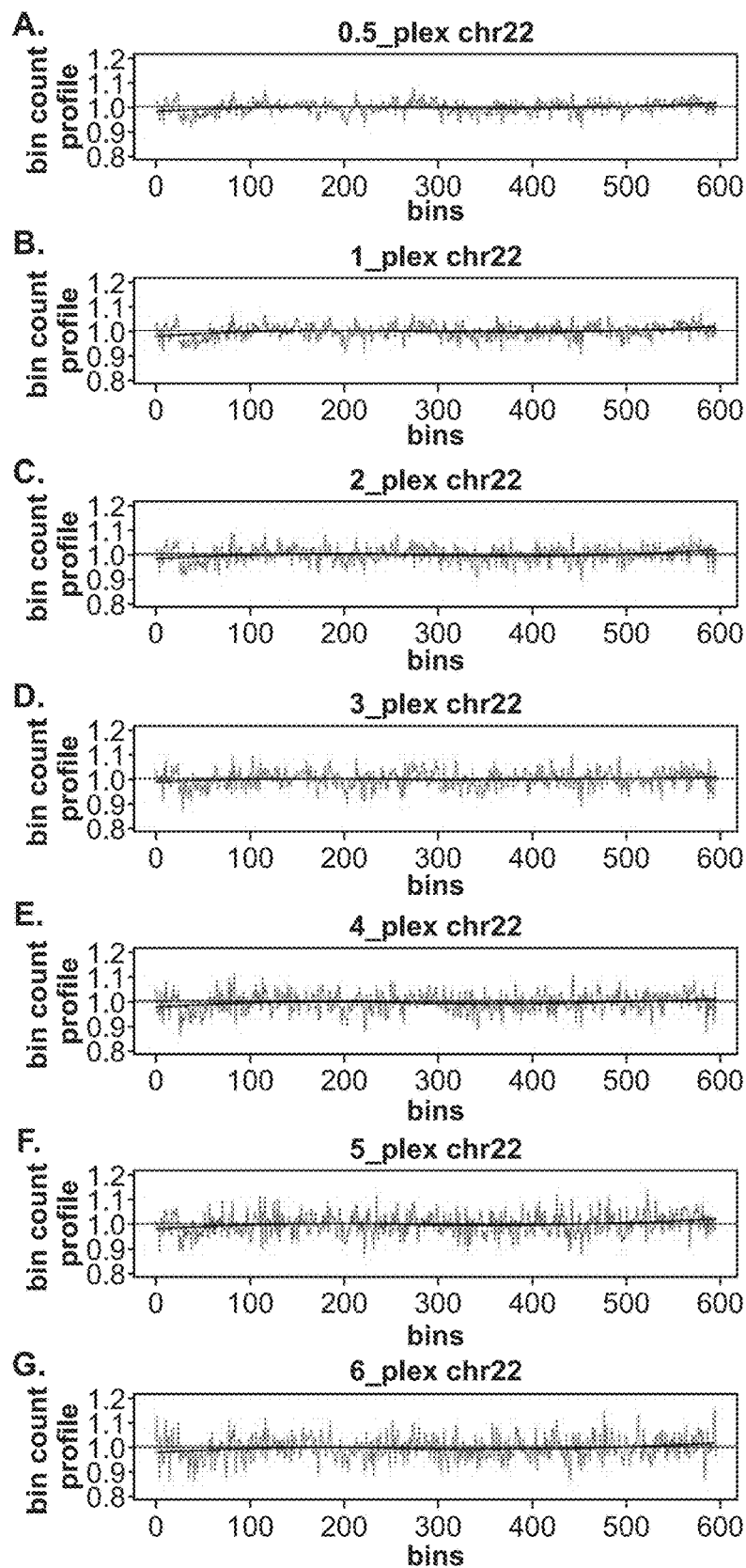
FIG. 10 shows profiles of a segment of Chromosome 22 associated with genetic variations associated with DiGeorge syndrome. Genetic microdeletions and microduplication associated with the DiGeorge syndrome have been mapped to this region. The profiles one the left (panels A-G) were segmented by Haar wavelet and CBS, smoothed, merged and compared. Composite profiles are shown in the right panels (A'-G'). Differences in sample load per flow cell is shown in panels A-A', 0.5-plex; B-B', 1-plex; C-C', 2-plex, D-D', 3-plex; E-E', 4-plex; F-F', 5-plex and G-G', 6-plex. A DiGeorge microdeletion was detected even at a 10-fold decrease in sample read coverage (e.g., see Panel F').
Figure 10:
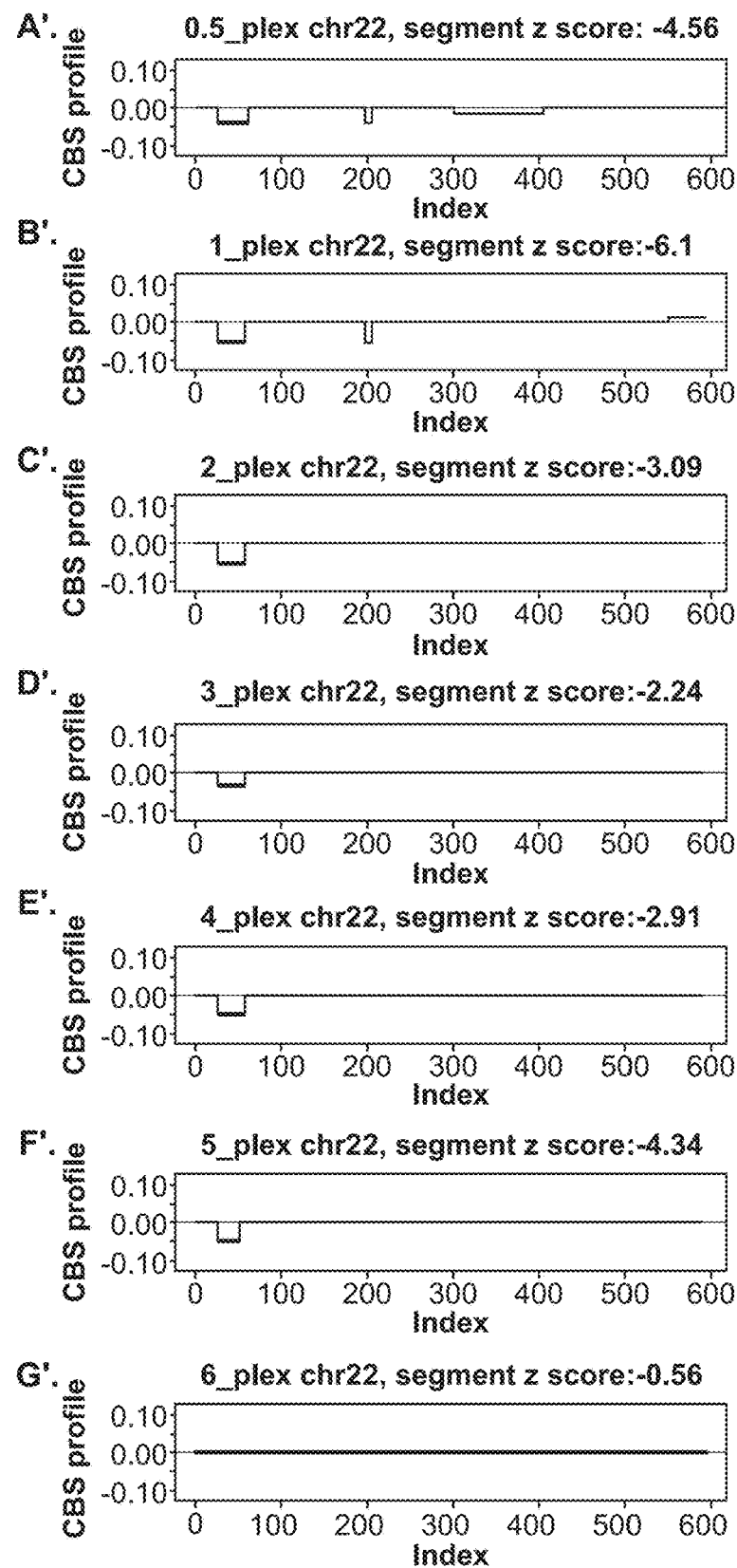

The detection method was applied to 2 cases of a microdeletion 22q11, which extend less than 3 MB on chromosome 22 (FIG. 10). To achieve a 3 MB resolution, the samples were originally sequenced in 0.5-plex. The 22q11 microdeletion was detected even with a ten-fold reduction of the coverage (FIG. 10, F'). The detection result of one sample is shown on FIG. 10, where the highlighted region indicates the microdeletion event (~2.5 MB).

The algorithm was also applied to samples from a different study and 19 putative cases of microdeletions/microduplications were detected. Two of the detected cases are shown on FIGS. 11A and a 11B.

Example 4. Maximum Entropy

Maximum Entropy is an automated algorithm described herein that partitions the genome into segments of uniform levels. This algorithm builds upon a procedure used by Cohen et al. (Cohen N, Dagan T, Stone L, Graur D., (2005) Mol. Biol. Evol., May; 22(5):1260-72) to characterize the GC content distribution of the human genome. The method of Cohen was adapted for the purpose of detecting the location of microdeletion/duplications (e.g., microdeletion/microduplication edges). The modifications included the ability to restrict the segmentation to a minimum length and a t-value based criterion used to terminate the segmentation. The t-value was used to decide whether all the segments identified within a chromosome (e.g., a segment, partition or region) are homogeneous. If the newly identified segments failed the significance test based on the t-value, they were merged back together and the segmentation stops. The code that performed these operations is included below:

```
# PATH: C:\SEQUENOM_PROJECTS\2013\2013_01_10_PARTITIONING_MAX_ENTROPY\
# FILE: PARTITIONING_MAX_ENTROPY.r
# AUTHOR: Zeljko Jovan Dzakula
# See: Cohen et al. (2005): GC Composition of the Human Genome: In Search
of Isochores. Mole Biol. Evol. 22(5):1260-1272.
# DATE: 1/10/2013
rm( list=ls( ) );
shannonEntropy <- function( values ) {
    meanValue <- mean( values, na.rm=TRUE );
    entropy <- -meanValue * log2( meanValue ) -
        ( 1 - meanValue ) * log2( 1 - meanValue );
    return( entropy );
} # shannonEntropy
partitionShannonEntropy <- function( values, edge ) {
    nValues <- length( values );
    if ( edge < 1 | edge >= nValues ) {
      return( NA );
    } # if edge
    overallEntropy <- shannonEntropy( values );
    leftEntropy <- shannonEntropy( values[ 1:edge ] );
    rightEntropy <- shannonEntropy( values[ ( edge +1 ):nValues ] );
    return( overallEntropy - ( leftEntropy * edge + rightEntropy * (
nValues - edge ) ) / nValues );
} # partitionShannonEntropy
findBestEdge <- function( values ) {
    epsilon <- 1e-6;
    bestEdge <- 1;
    bestEntropy <- -1e7;
    values <- values[ !is.na( values ) ];
    minValue <- min( values, na.rm=TRUE ) - epsilon;
    maxValue <- max( values, na.rm=TRUE ) + epsilon;
    values <- ( values - minValue ) / ( maxValue - minValue );
    nValues <- length( values );
    for ( candidateEdge in 1:( nValues - 1 ) ) {
        candidateEntropy <- partitionShannonEntropy( values,
candidateEdge );
        #print( paste(" ", candidateEdge, candidateEntropy ) );
        if ( candidateEntropy > bestEntropy ) {
            bestEdge <- candidateEdge;
            bestEntropy <- candidateEntropy;
        } # if candidateEntropy
    } # for candidateEdge
    return( bestEdge );
```

```
} # findBestEdge
isPartitionHomogeneous <- function( values, edge, cutoff=10 ) {
    nValues <- length( values );
    if ( edge < 1 | edge >= nValues ) {
       print( paste( "Illegal argument: edge=", edge, sep=" ") );
       return( TRUE );
    } # if edge
    leftMean <- median( values[ 1:edge ], na.rm=TRUE );
    leftMAD <- mad( values[ 1:edge ], na.rm=TRUE );
    rightMean <- median( values[ ( edge + 1 ):nValues ], na.rm=TRUE );
    rightMAD <- mad( values[ ( edge + 1 ):nValues ], na.rm=TRUE );
    tValue <- abs( leftMean - rightMean ) / sqrt(
       leftMAD * leftMAD / edge + rightMAD * rightMAD / ( nValues - edge
) );
    print( tValue );
    return( tValue < cutoff );
} # isPartitionHomogeneous
partitionRegions <- function( values, regions, minLength, cutoff=10 ) {
    nValues <- length( values );
    rownames( regions ) <- c( "Start", "End", "Homogeneous",
"MedianLevel", "MAD" );
    finished <- FALSE;
    while ( !finished ) {
       nRegions <- ncol( regions );
       for ( region in 1:nRegions ) {
          if ( regions[ "Homogeneous", region ] == FALSE ) {
             startPoint <- regions[ "Start", region ];
             endPoint <- regions[ "End", region ];
             relativeEdge <- findBestEdge( values[ startPoint:endPoint
] );
             absoluteEdge <- startPoint + relativeEdge - 1;
             homogeneous <- isPartitionHomogeneous(
                values[ startPoint:endPoint ], relativeEdge,
cutoff=cutoff );
             if ( ( homogeneous == TRUE ) |
                  ( edge == endPoint ) |
                  ( relativeEdge < minLength ) |
                  ( endPoint - absoluteEdge ) < minLength ) {
                print( paste( "Homogeneous: ", startPoint, "-",
absoluteEdge, "-", endPoint, sep=" " ) );
                regions[ "Homogeneous", region ]<- TRUE;
             } else {
                print( paste( "Inhomogeneous: ", startPoint, "-",
absoluteEdge, "-", endPoint, sep=" " ) );
                regions[ , region ] <- c( startPoint, absoluteEdge,
FALSE, NA, NA );
                regions <- cbind( regions,
                    c( absoluteEdge + 1, endPoint, FALSE, NA, NA ) );
             } # if homogeneous else
          } # if !homogeneous
       } # for region
       finished <- TRUE;
       nRegions <- ncol( regions );
       for ( region in 1:nRegions ) {
          finished <- finished & regions[ "Homogeneous", region ];
       } # f or region
       if ( finished ) {
          regions <- t( regions );
          nRegions <- nrow( regions );
          rownames( regions ) <- 1:nRegions;
          for ( region in 1:nRegions ) {
             startPoint <- regions[ region, "Start" ];
             endPoint <- regions[ region, "End" ];
             regions[ region, "MedianLevel" ] <-
                median( values[ startPoint:endPoint ], na.rm=TRUE );
             regions[ region, "MAD" ]<-
                mad( values[ startPoint:endPoint ], na.rm=TRUE );
          } # for region
          return( regions );
       } # if done
    } # while TRUE
} # partition
partition <- function( values, minLength, cutoff=10 ) {
  nValues <- length( values );
  regions <- data.frame( "InnitialEdges"=c( 1, nValues, FALSE, NA, NA )
);
```

-continued

```
  #regions <- data.frame( "FirstHalf"=c( 1, floor( nValues / 2 ),
FALSE, NA, NA ) );
  #regions <- cbind( regions, c( floor( nValues / 2 ), nValues, FALSE,
NA, NA ) );
  rownames( regions ) <- c( "Start", "End", "Homogeneous",
"MedianLevel", "MAD" );
  return( partitionRegions( values, regions, minLength, cutoff ) );
} # partition
##########################################################################
#######
##########################################################################
#######
##########################################################################
#######
##########################################################################
#######
##########################################################################
#######
plotRegions <- function( chrProfile, regions, chr=" ", srID=" " ) {
  plot( chrProfile, type="1" );
  for ( region in 1:nrow( regions ) ) {
    abline( v=regions[ region, "Start" ], col="gray" );
    abline( v=regions[ region, "End" ], col="gray" );
    polygon( x=c( regions[ region, "Start" ], regions[ region,
"Start" ],
            regions[ region, "End" ], regions[region, "End" ]
),
          y=c( regions[ region, "MedianLevel" ] - regions[ region,
"MAD" ],
            regions[ region, "MedianLevel" ] + regions[ region,
"MAD" ],
            regions[ region, "MedianLevel" ] + regions[ region,
" MAD" ],
            regions[ region, "MedianLevel"] - regions[ region,
"MAD" ]),
          col="yellow" );
    lines( x=c( regions[ region, "Start" ], regions[region, "End" ]
),
          y=c( regions[ region, "MedianLevel" ], regions[ region,
"MedianLevel" ]),
          lwd=3 );
  } # for region
  par( new=TRUE );
  plot( chrProfile, type="1", lwd=1.5, main=paste( srID, '', "Chr", chr,
sep=" " ) );
} # plotRegions
```

Figure 12:
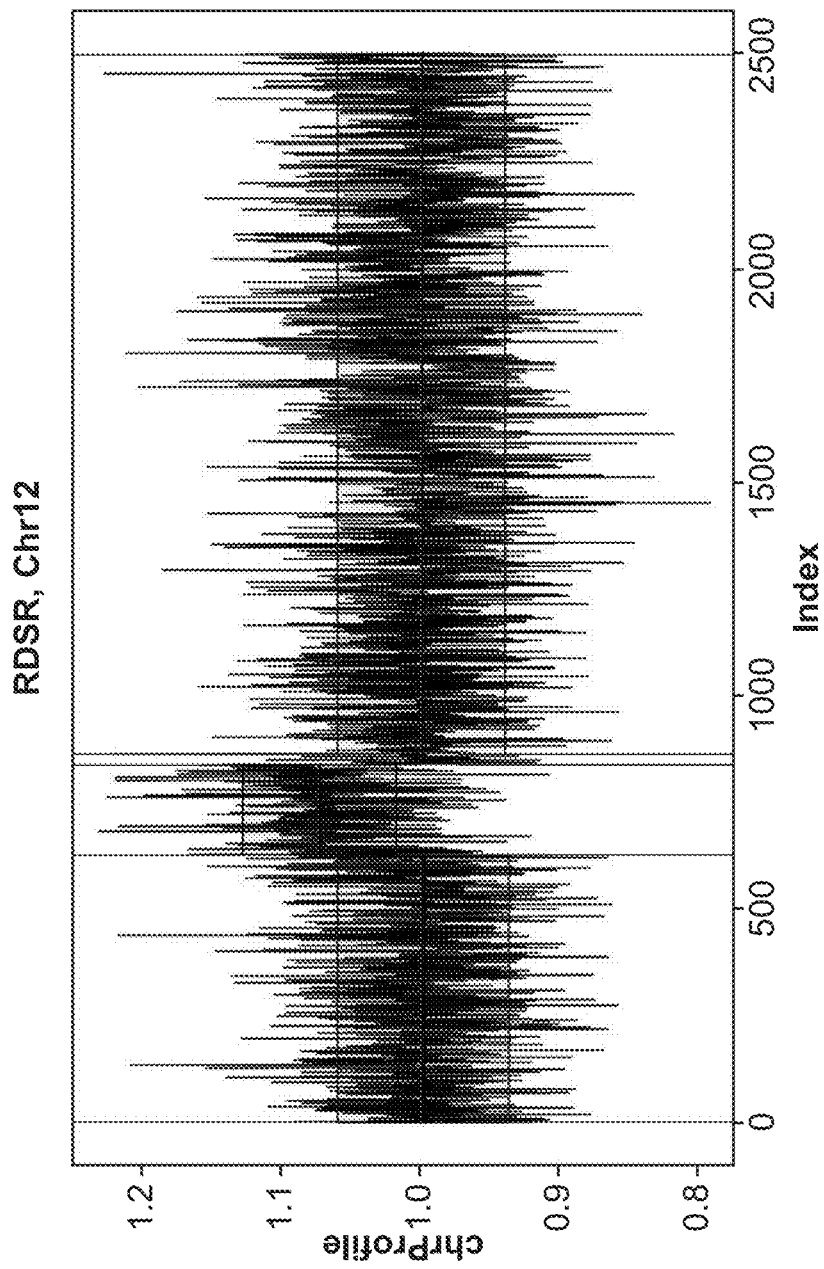
FIG. 12 shows a representative example illustrating the detection of the location of microduplications in Chromosome 12 utilizing the method of maximum entropy.

The above R-script above was used to detect multiple putative microdeletions and microduplications in samples from an OBX study (Table 3 and FIG. 12).

TABLE 3

Microduplication and Microdeletion events detected with maximum entropy method.

| Event Detected | Chromosome |
|---|---|
| Microdeletion | 5 |
| Microduplication | 22 |
| Microdeletion | 22 |
| Microduplication | 10 |
| Microduplication | 21 |
| Microduplication | 12 |
| Microdeletion | 15 |
| Microdeletion | 1 |
| Microduplication | 19 |
| Microduplication | 2 |
| Microdeletion | 7 |
| Microdeletion | 6 |
| Microdeletion | 4 |
| Microduplication | 6 |
| Microduplication | 4 |

Example 5. Validation Methods

Two validation methods termed "leave-one-out" and "sliding edges", were coupled with PERUN, to identify sub-chromosomal abnormalities on chromosome 22, known as Velocardiofacial Syndrome (DiGeorge Syndrome, 22q11), and to evaluate the statistical significance of the observed deviation from the euploid (i.e., "normal") chromosomal level in the 22q11 region. The methodology was applicable both to targeted and untargeted detection of deletions/duplications.

Sixteen pregnant female plasma samples collected, processed, and sequenced as previously described (Jensen T J, Džakula , Deciu C, van den Boom D, Ehrich M. (2012): Detection of microdeletion 22q11.2 in a fetus by next-generation sequencing of maternal plasma. Clin. Chem. 58(7):1148-51). Two samples belong to mothers carrying DiGeorge fetuses, as confirmed by karyotyping. The remaining 14 samples correspond to euploid pregnancies (i.e., "normal fetuses") and serve as references for detection and characterization of 22q11.

The original raw counts for all 16 samples (two data sets per sample) were reprocessed using PERUN portion parameters optimized for ELAND alignments. The parameters were trained on LDT2CE data. and the portion selection was based on cross validation, as previously described. No mappability-based filtering was applied. Secondary LOESS normalization removed any GC bias remaining after PERUN normalization was applied. Since each sample was measured twice, yielding a total of 32 profiles, the paired profiles were combined into a single PERUN profile, resulting in 16 profiles (one per sample). Before combining the profiles, their standard deviations ranged from 0.020 to 0.030. The addition of the matched profiles reduced the variability by a factor of ~1.2 (from 1.14 to 1.27), slightly less than the expected improvement of 1.414 (the square root of 2). The normalized count profiles were significantly improved compared to raw and GCRM profiles, as well as the results of normalization with respect to the median reference profile based on the 14 euploid samples. The improvement is evident from the reduced standard deviation of the profiles and the higher degree of uniformity throughout the genome. While the standard deviations of the 16 raw profiles (scaled with respect to total counts and multiplied by the number of portions of a reference genome) range from 0.55 to 0.64, the standard deviations of the corresponding 16 PERUN profiles range from 0.016 to 0.026. FIG. 13 shows all 16 profiles, with the DiGeorge region (ranging from chr22_368 to chr22_451) depicted with the gray ribbon in the background. Note that the portion filtering based on cross-validation removes many portions of a reference genome from the 22q11 microdeletion, leaving only the following set of portions of a reference genome: chr22_371, chr22_372, chr22_380, chr22_381, chr22_382, chr22_383, chr22_384, chr22_385, chr22_386, chr22_387, chr22_388, chr22_389, chr22_390, chr22_391, chr22_392, chr22_393, chr22_394, chr22_395, chr22_396, chr22_397, chr22_398, chr22_399, chr22_400, chr22_401, chr22_402, chr22_403, chr22_404, chr22_415, chr22_416, chr22_417, chr22_418, chr22_419, chr22_422, chr22_423, chr22_424, chr22_426, chr22_427, chr22_428, chr22_439, chr22_440, chr22_441, chr22_442, chr22_443, chr22_444, chr22_445, and chr22_446.

FIG. 13 shows enlarged PERUN profiles in the DiGeorge region to enable detailed visual inspection. The 22q11 deletions are evident in the affected cases (3_4 and 9_10).

To quantify the confidence in the calls for presence or absence of the 22q11 deletion, Z-scores were evaluated for the canonic DiGeorge region, covering chromosome 22, positions 18,546,349-22,336,469. The PERUN levels for the portions of a reference genome within this region were summed up separately for each sample. Since technical duplicates were measured on all samples, the averages of the two sums were used as representations of the chromosomal material within the DiGeorge region. The median of all representations (including both euploids and affected samples) was subtracted from the individual representations and the difference was divided by the MAD of all representations to yield the Z scores. The results are shown in FIG. 14. The two affected cases 3_4 and 9_10 have Z-scores below −3, confirming the presence of the deletion in those two samples. In addition, the high positive Z-score in one sample (13_14) indicated a possible duplication in the region of interest. Visual inspection of FIG. 13 confirmed that the middle portion of the 13_14 PERUN profile contained an overrepresented section within the DiGeorge region.

The profiles shown in FIG. 13 suggested that the deletion observed in one affected case (3_4) differed from the canonic DiGeorge deletion. The 3_4 profile was only partially depleted, with the right edge of the deletion located close to portion chr22_426, more than 1 Mbp (20 portions of a reference genome) to the left of the expected edge of the aberration. The left edge of the deletion in 3_4 also appeared as shifted to the left from the expected left edge of 22q11. The true extent of the deletion obviously impacted the Z values. The first goal of the present study was to evaluate the confidence in the deletion/duplication calls given the locations of the starting and ending deletion/duplication edges.

Figure 15:
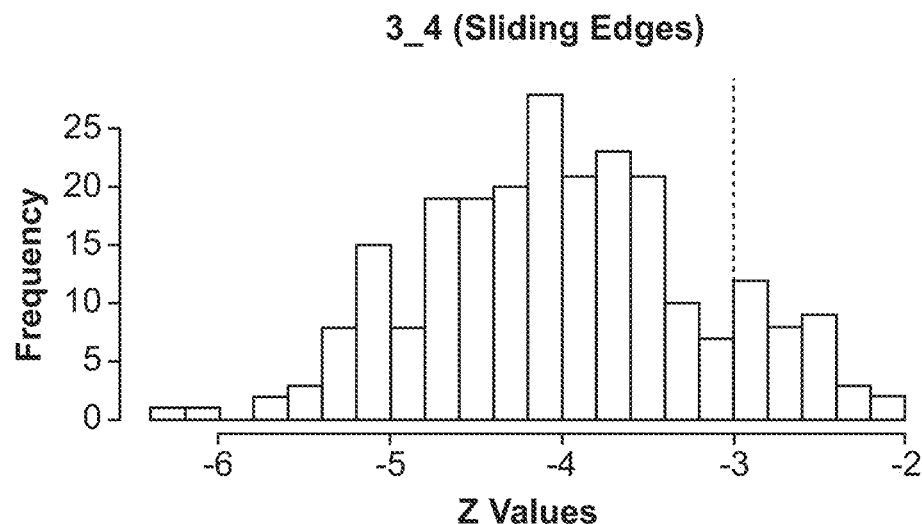
FIGS. 15-16 show representative histograms for samples 3_4 (DiGeorge) and 1_2 (Euploid), respectively. Each histogram shows a distribution of Z-scores obtained on a 15×15 grid of regions contained within the DiGeorge region. The regions were selected by sliding both the left and the right edge of the DiGeorge region by one portion, starting from the outer edges and moving inward. The histograms for samples 3_4 and 9_10 (not shown) consistently showed depletion, with only a few Z-scores for 3_4 exceeding Z=−3. The histogram for sample 13_14 (not shown) consistently suggested overrepresentation, with only a few regions yielding Z-scores below 3. All other samples (e.g., 1_2) remained confined within the [−3, 3] segment of Z-scores.
Figure 16:
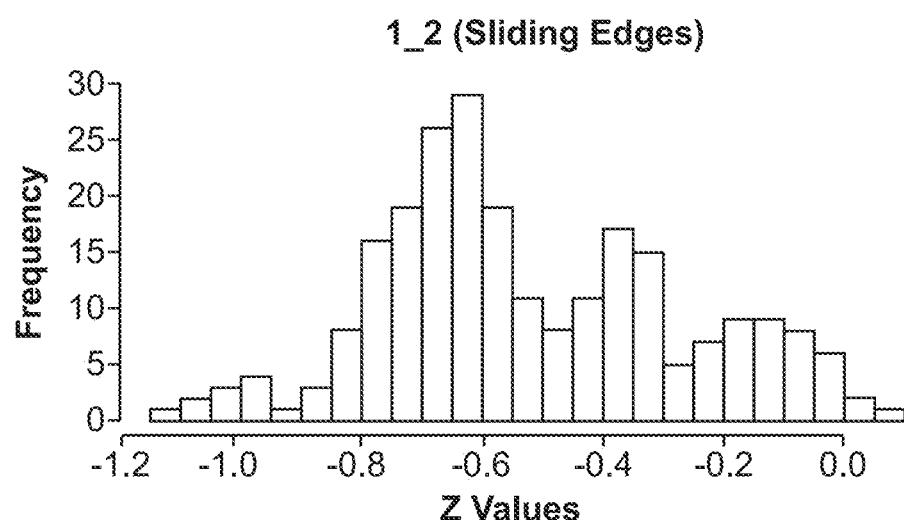

To assess the impact of the location of the deletion edge and to associate confidence intervals with the Z-scores, the evaluation of Z-scores was repeated based on representations of 225 different regions that partially overlap with (or are contained within) the canonic DiGeorge region. The largest of those regions starts at chr22_371 and ends at chr22_446. chr2_447, the last portion in the deletion, was not included in the calculation as being filtered out by PERUN cross-validation. The remaining regions started anywhere between the first and the fifteenth portion from the left edge of the canonic DiGeorge region. Furthermore, the regions ended anywhere between the right edge of the canonic DiGeorge region and the fifteenth portion preceding it. This created a 15×15 grid of region starting/ending points. Representations for all samples were evaluated on this grid and Z-values were obtained for every grid point. All samples contributed to the median and MAD representations used for Z-standardizations. Representative histograms of the resulting Z-values for all 225 possible regions (for samples 3_4 and 1_2) are shown in FIGS. 15-16.

Figure 17:
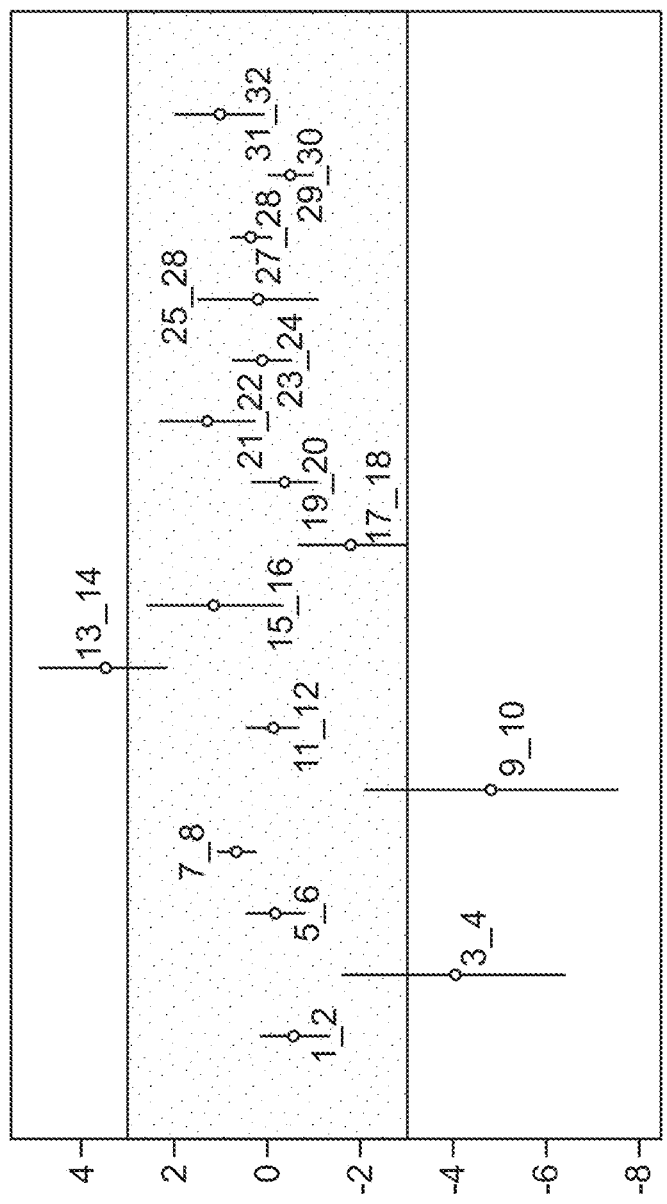
FIG. 17 shows median Z-scores and their ±3 MAD confidence intervals for each of 16 samples. Each median Z-score was determined from a 15×15 grid of regions (225 regions) obtained from sliding edges. The Z-scores for the known DiGeorge samples (3_4 and 9_10) remained below −3 for an overwhelming majority of DiGeorge subregions. The apparent duplication in the sample 13_14 was confirmed by the fact that its Z-scores for the most part exceed 3. The Z-scores of all other samples were always confined within the [−3, 3] segment.

The scatter plot in FIG. 17 summarizes histograms of the resulting Z-values for all 225 possible regions for all samples. FIG. 17 shows only the median Z values per sample and the 3 MAD confidence intervals around those median Z scores. Depending on the choice of deletion edges, sample 13_14 mostly appeared overrepresented (Z >3 for most regions in the 15×15 grid). The 3 MAD confidence intervals for the two affected samples (3_4 and 9_10) partially overlap with the "normal" region (from −3 to 3), but both samples mostly remained below −3.

Figure 18:
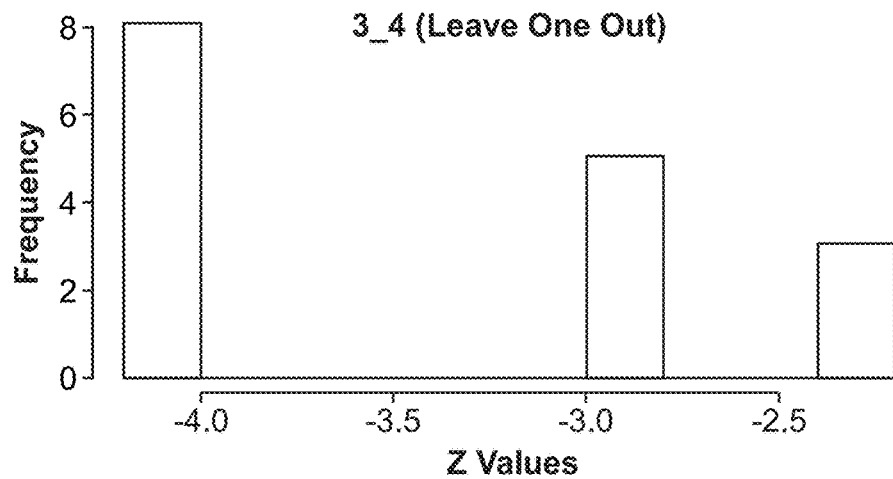
FIGS. 18-19 show representative histograms for samples 3_4 (DiGeorge) and 1_2 (Euploid), respectively. Each histogram shows a distribution of Z-scores obtained for the DiGeorge region. Each Z-score was calculated using 16 different sets of reference samples using the "leave one out" method. The histogram for the sample 9_10 (not shown) confirmed depletion. Depending on the reference set, sample 3_4 was either clearly depleted, or had borderline Z-scores. The histogram for sample 13_14 (not shown) suggested overrepresentation, with a few borderline Z-scores. All other samples, including 1_2, remained confined within the [−3, 3] segment of Z-scores.
Figure 19:
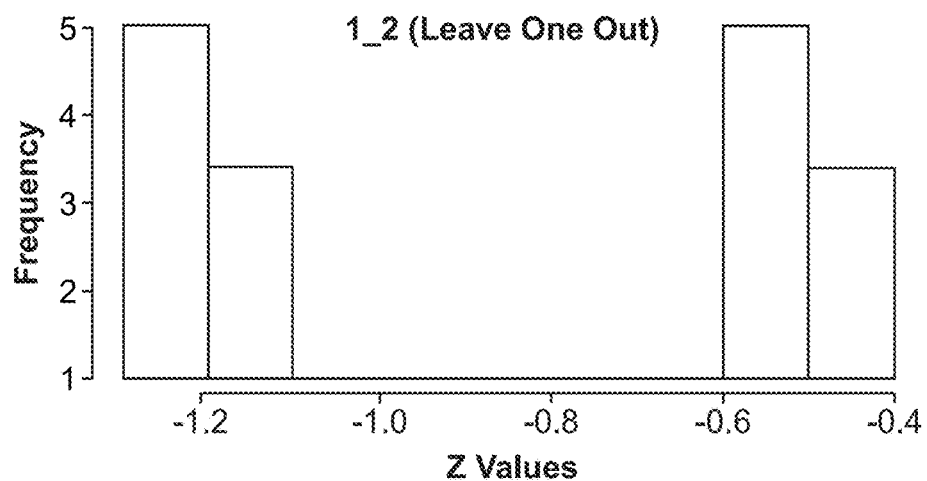
Figure 20:
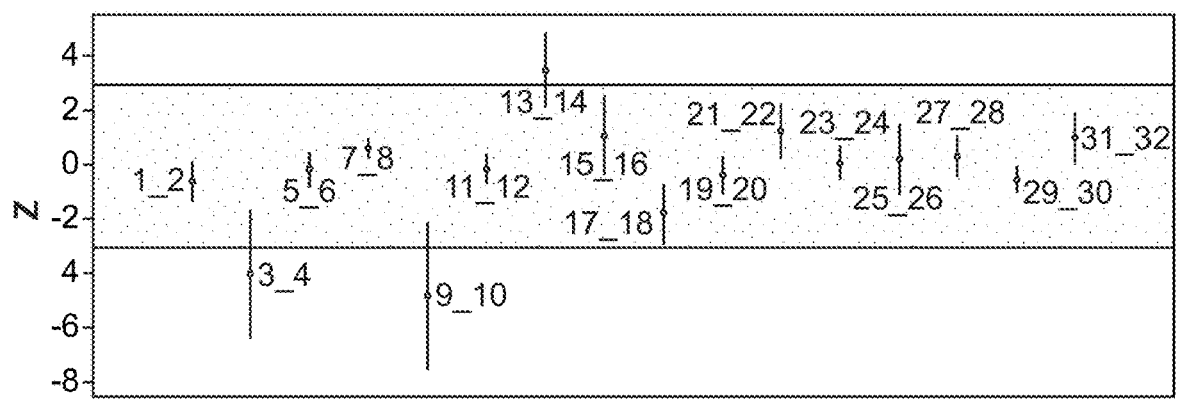
FIG. 20 shows median Z-scores for each sample, representatives of which are shown in FIGS. 18-19. The median Z-scores and their ±3 MAD confidence intervals were calculated from the 16 different sets of reference samples determined using the "leave one out" method. The Z-scores for the known DiGeorge samples (3_4 and 9_10) remained below −3 for an overwhelming majority of subsets of reference samples. The apparent duplication in the sample 13_14 was confirmed by the fact that its Z-scores for the most part exceed 3. The Z-scores of all other samples were always confined within the [−3, 3] segment.

FIG. 20 explored the variability stemming from the choice of microdeletion edges. Another possible source of variability may be the choice of reference samples for Z-score standardization. To asses the contribution of the selection of reference samples to the variability in Z-scores and the resulting confidence (or lack of confidence) in the deletion/duplication calls, a "leave one out" analysis for a single region, as well as the 15×15 grid of regions was performed. When applied to the canonic DiGeorge region alone, the "leave one out" analysis failed to indicate a significant contribution from the choice of reference to the variability in Z-scores (FIGS. 18-20). However, a more comprehensive "leave one out" analysis, performed on a 15×15 grid of regions, confirmed that the choice of the reference samples significantly impacted the variability in Z-scores (FIGS. 21-23).

Figure 21:
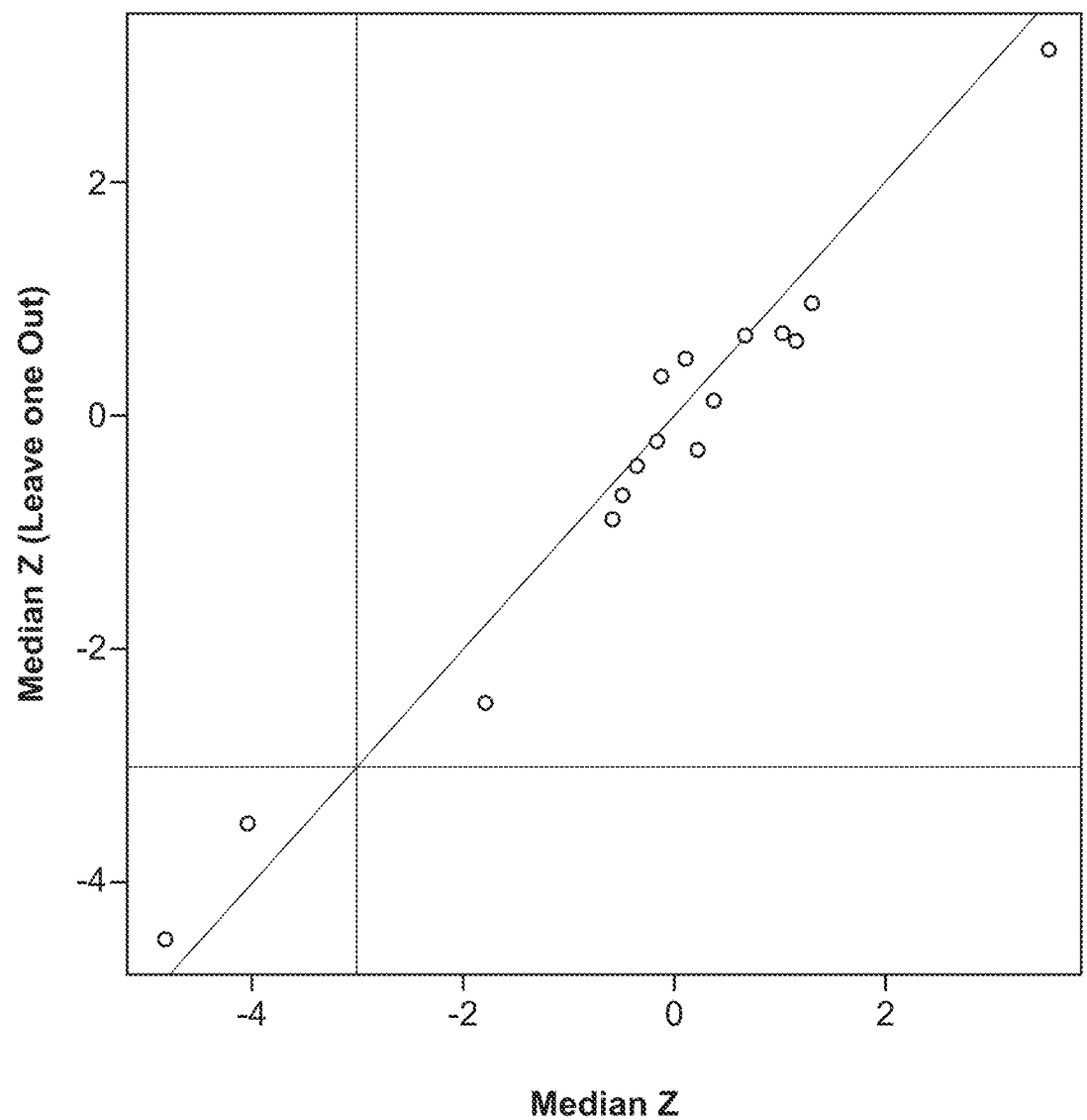
FIG. 21 shows median Z-scores obtained using the 15×15 grid of DiGeorge subregions (x-axis) compared to the median Z-scores generated by the "leave one out" technique (y-axis) for each of the 16 samples. The diagonal represents ideal agreement (slope=1, intercept=0).

FIG. 21 demonstrated the agreement between the median Z values obtained using the 15×15 grid of DiGeorge subregions and the median Z values generated by the "leave one out" technique.

Figure 22:
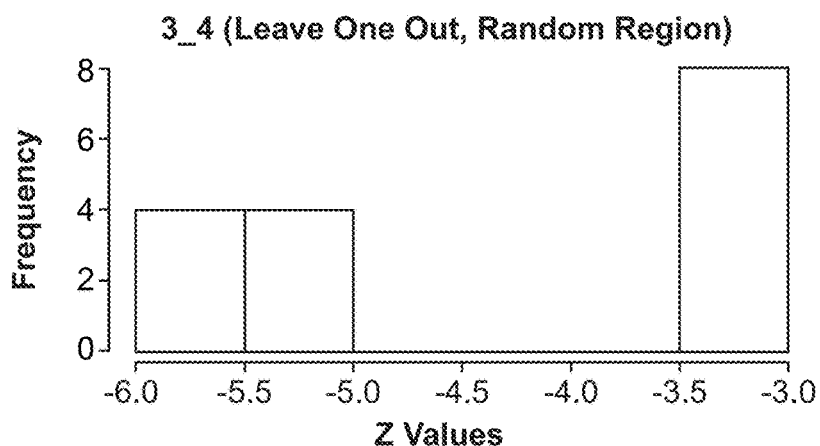
FIGS. 22-23 show representative histograms for samples 3_4 (DiGeorge) and 1_2 (Euploid), respectively. Each histogram shows a distribution of Z-scores obtained for a subregion of the DiGeorge region, using 16 different sets of reference samples. The subregion was randomly chosen from the 15×15 grid of 225 subregions. The "leave one out" analysis confirmed depletion for samples 3_4 (FIG. 37) and 9_10 (not shown). The histogram for the sample 13_14 confirmed overrepresentation (not shown). All other samples, including 1_2, remained confined within the [−3, 3] segment of Z-scores.
Figure 23:
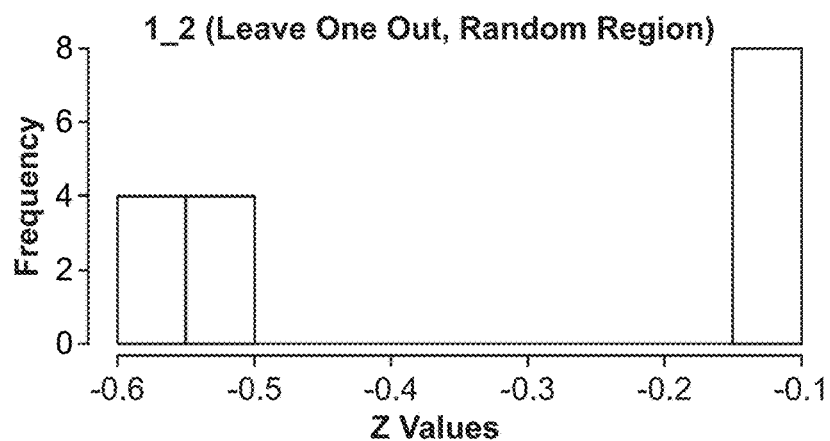
Figure 24:
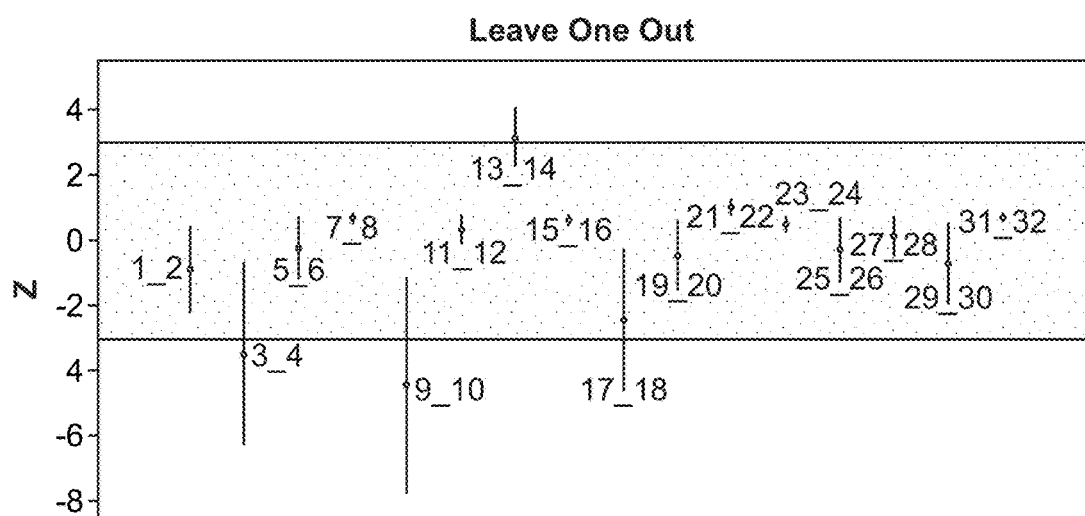
FIG. 24 shows median Z-scores and their ±3 MAD confidence intervals for a randomly chosen subregion of the DiGeorge region for each of 16 samples using the "leave one out" method. The Z-scores for the known DiGeorge samples (3_4 and 9_10) remained below −3 for most reference samples. The apparent duplication in the sample 13_14 was indicated by the fact that its Z-scores for the most part exceed 3. The Z-scores of all other samples were always confined within the [−3, 3] segment, except for the sample 17_18.
Figure 25:
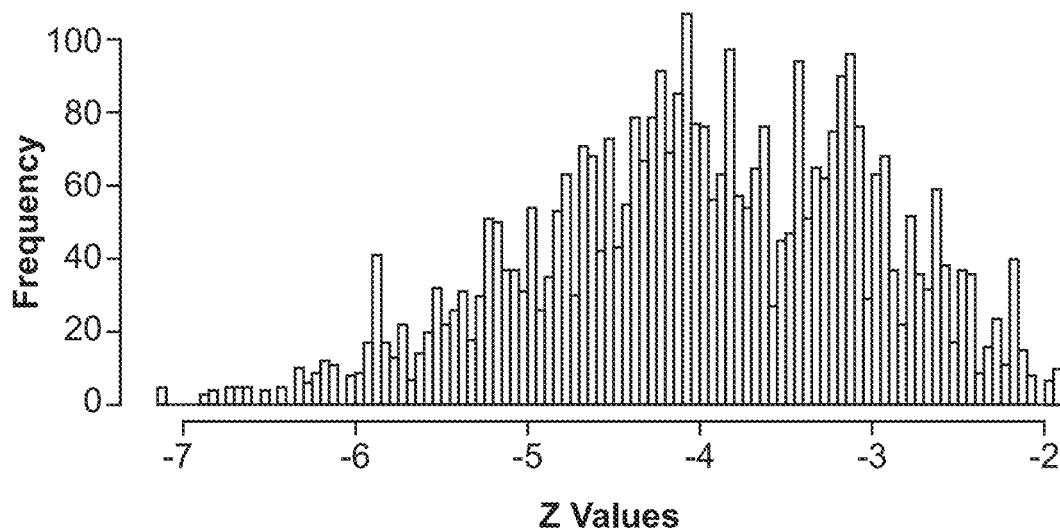
FIGS. 25-26 show representative histograms for samples 3_4 (DiGeorge) and 1_2 (Euploid), respectively, representing distributions of Z-scores obtained for all 225 subregions of the DiGeorge region, using 16 different sets of reference samples. The 225 subregions were generated using a sliding edge method on a 15×15 grid for each sample. The sliding edges were combined with the "leave one out" analysis. The results confirm depletion for both affected samples 3_4 and 9_10 (not shown). The histogram for the sample 13_14 confirmed overrepresentation (not shown). All other samples, including 1_2, remain confined within the [−3, 3] segment of Z-scores, with a sporadic exception in 17_18 (not shown).
Figure 26:
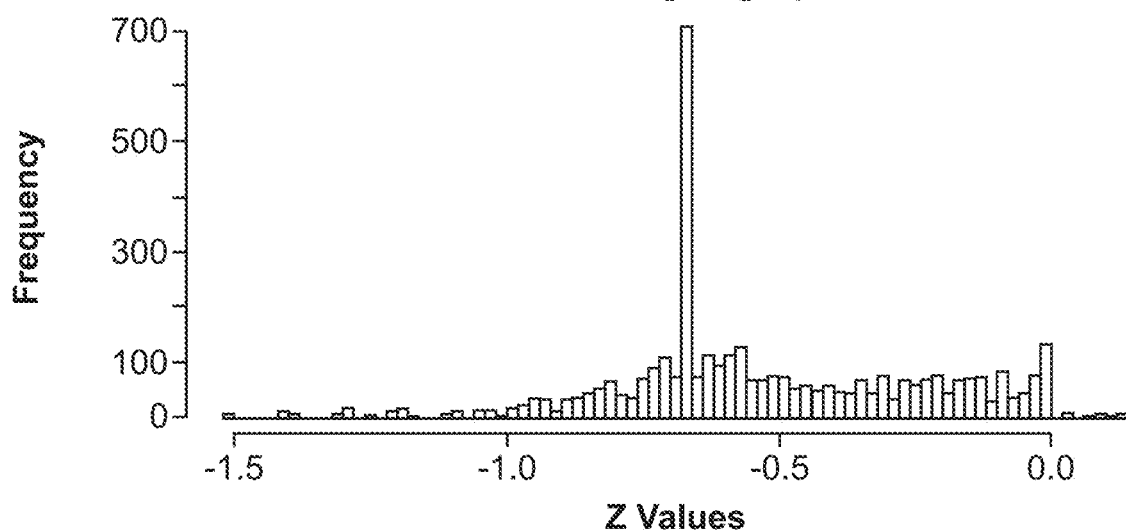
Figure 27:
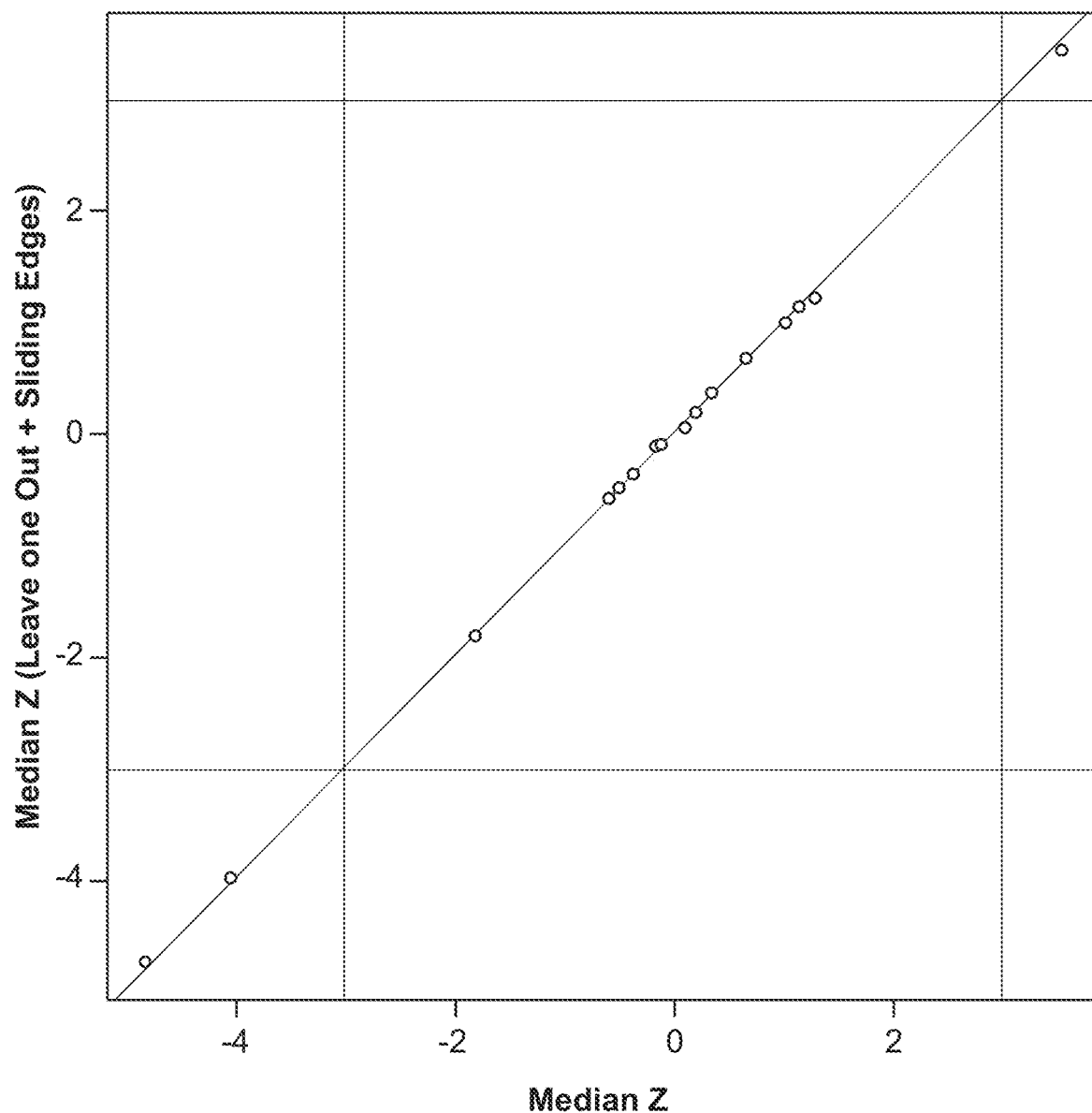
FIG. 27 shows median Z-scores obtained using the 15×15 grid of DiGeorge subregions in combination with the "leave one out" technique compared against the median Z-scores derived from the 15×15 grid alone. The diagonal represents ideal agreement (slope=1, intercept=0).
Figure 28:
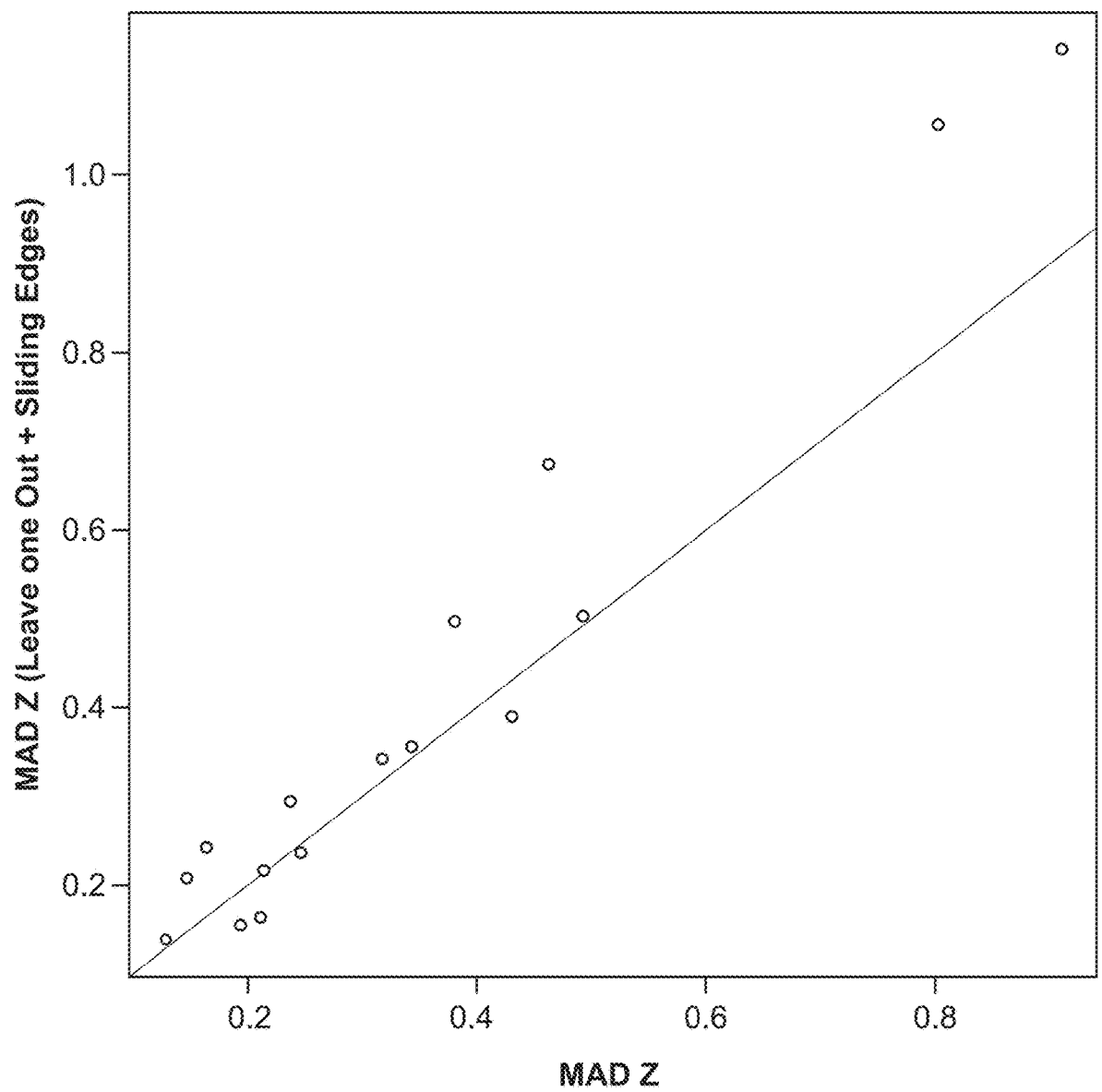
FIG. 28 shows MADs of Z-scores obtained using the 15×15 grid of DiGeorge subregions in combination with the "leave one out" technique were compared against the MADs of Z-scores derived from the 15×15 grid alone. The diagonal represents ideal agreement (slope=1, intercept=0).
Figure 29:
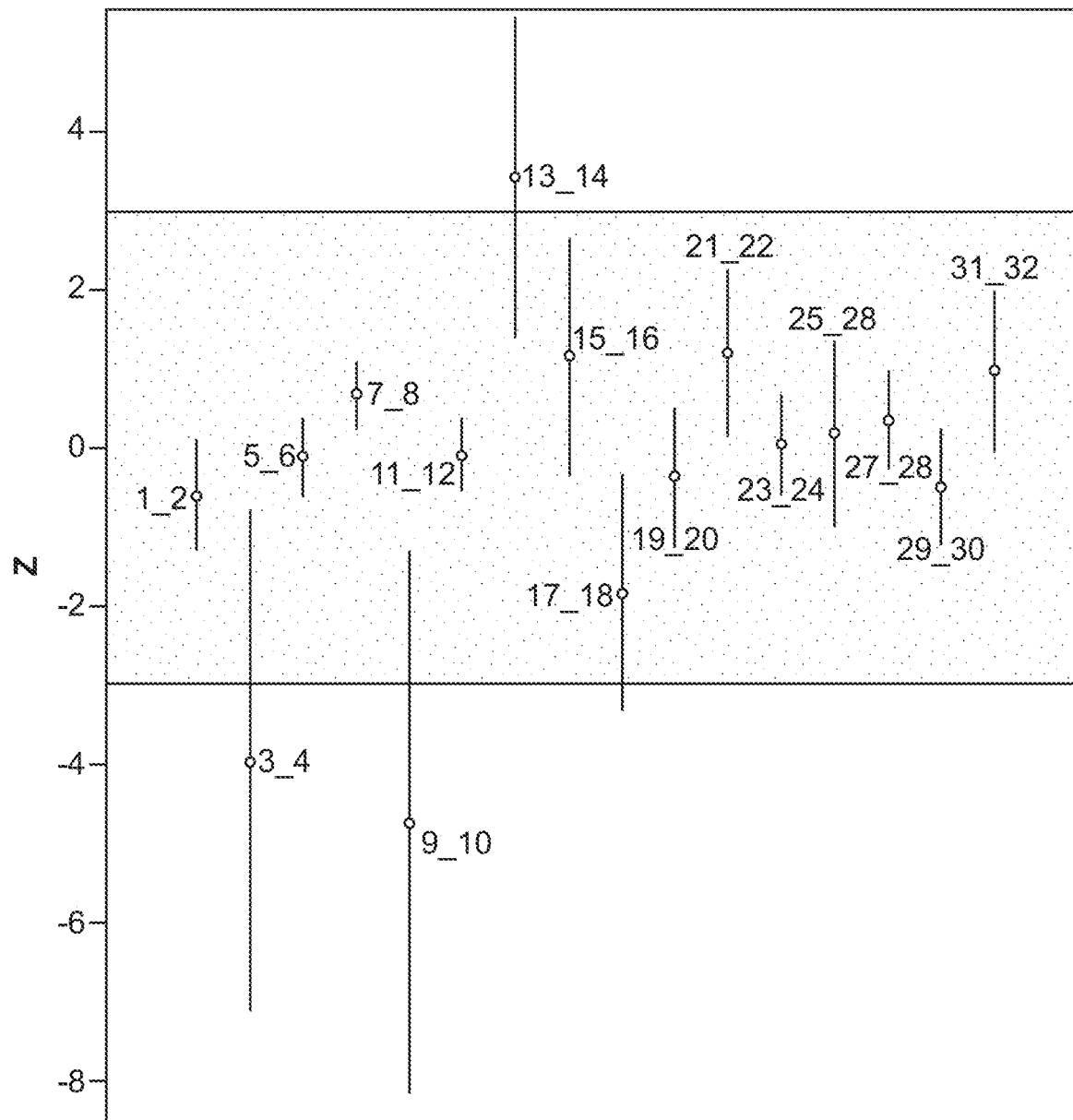
FIG. 29 shows median Z-scores and their ±3 MAD confidence intervals as evaluated on the complete 15×15 grid of subregions of the canonic DiGeorge region in combination with the "leave one out" method. The Z-scores for the known DiGeorge samples (3_4 and 9_10) remained below −3 for most reference samples. The apparent duplication in the sample 13_14 was indicated by the fact that its Z-scores for the most part exceed 3. The Z-scores of all other samples were always confined within the [−3, 3] segment, except for the sample 17_18.

FIGS. 22-24 demonstrated the use of the "leave one out" technique on a DiGeorge subregion randomly picked from the 15×15 grid of subregions. The same conclusions can be drawn as in the case of the canonic DiGeorge region.

FIGS. 25-29 show results of a combination of the "leave one out" technique and the sliding of the region edges. For each of the 15×15 subregions, 16 reference sets generated Z-scores that were combined into a set of 3,600 Z-scores per sample. The distributions shown in representative FIGS. 25-26 generally agreed with the conclusions drawn from FIGS. 14-24, while providing additional detail. The sharp peaks observed in some histograms can be explained by the fact that a subset of samples frequently contribute the median value for Z-score standardization.

The method of "sliding edges" and "leave one out" can be used together or independently to validate a call. The two separate procedures are also combined to yield a more comprehensive picture of the uncertainties in the derived Z-scores. The two techniques were applied here in the context of a targeted deletion/duplication detection, but can in principle be extended to the untargeted "hunt" for previously unknown deletions/duplications throughout the genome. Once an affected area is roughly outlined using wavelets, maximum entropy, circular binary segmentation, convolution with edge detection kernel, or some other appropriate method, a sliding edge technique and the leave one out technique can be applied to ascertain the extent and the reliability of a newly detected deletion/duplication.

The motivation for a sliding edges analysis stems from the observed disagreement between the extent of the 22q11 deletion observed in the patient 3_4 and the canonic DiGeorge deletion. As it turns out, the 2.5 Mb deletions seen in the 3_4 sample was more representative than was known at the time when these calculations were performed. The typical deletion is around 3 Mb, rather than the canonic 8 Mb, according to these two sources:

(C. Carlson, et al., (1997) The American Journal of Human Genetics, Volume 61, Issue 3, 620-629) (Schwinger E, Devriendt K, Rauch A, Philip N. Clinical utility gene card for: DiGeorge syndrome, velocardiofacial syndrome, Shprintzen syndrome, chromosome 22q11.2 deletion syndrome (22q11.2, TBX1). Eur J Hum Genet. 2010 September; 18(9). doi: 10.1038/ejhg.2010.5. Epub 2010 Feb. 3. PubMed PMID: 20125192; PubMed Central PMCID: PMC2987430.)

The DiGeorge deletion has been reported as short as 1.5 Mb in some 7-8% of cases. Such discrepancies between the expected and the actual sizes of chromosomal abnormalities with (high) clinical relevance may be more frequent than current data suggest. For that reason, both the targeted method, tailored for a specific abnormality, and the more general untargeted approach that first discovers an aberration and then queries a database of clinical annotations, will benefit from a sliding edges and the leave one out analyses.

Example 6: Log Odds Ratio Detection of Genetic Variations

Fetal fraction plays a role in non-invasive prenatal testing (NIPT) for genetic variations. It has been observed that samples with high fetal fraction (e.g. 24%) but slightly elevated z-score (e.g. z=3.2) can result in false positive classifications. For such samples, z-scores should be much higher than 3 if they were truly trisomies, for example. A log odds ratio (LOR) process was developed to address this issue and reduce the likelihood of a false positive call.

A LOR can be calculated for a test sample according to the probability of trisomy 21 (T21) versus non-T21 given its observed z-score and fetal fraction in accordance with Equation 22:

$$\log\frac{P(T21\mid Z,\hat{f})}{P(\overline{T21}\mid Z,\hat{f})} = \log\frac{P(Z\mid T21,\hat{f})P(T21,\hat{f})}{P(Z\mid ,\hat{f})P(\overline{T21},\hat{f})} = \log\frac{P(Z\mid T21,\hat{f})P(T21)}{P(\overline{T21},\hat{f})P(\overline{T21})} \quad (22)$$

where $\hat{f}$, also referred to as f herein, is measured fetal fraction (e.g., by chrY for male samples or other fetal fraction determination technique known), $P(T21|Z,\hat{f})$ and $P(\overline{T21}|Z,\hat{f})$ are the posterior probabilities of T21 (having T21) and $\overline{T21}$ (non-T21) respectively, given Z and f as described below, where $P(T21)$ and $P(\overline{T21})$ are the prior probabilities for T21 and non-T21, respectively, and $P(Z|T21,\hat{f})$ and $P(Z|\overline{T21},\hat{f})$ are the conditional probabilities for T21 and non-T21, respectively, which are derived herein.

Conditional probabilities can be determined according to a z-score (Z) and a calculated fetal fraction (f) for a test sample (see right hand portion of equation 22). For an unaffected euploid sample, let X represent the summed bin count for the event region. Due to the inherent randomness in sequencing, X is a random variable with $X\sim f(\mu_X,\sigma_X)$, where $\mu_X$ and $\sigma_X$ are the mean and standard deviation, respectively, and $f(\cdot)$ is a distribution function. Similarly, for an affected trisomy sample, the bin count for the affected region is $Y\sim f(\mu_Y,\sigma_Y)$, where $\mu_Y=\mu_X(1+f/2)$ and f is the fetal fraction. Assuming $\sigma_Y\approx\sigma_X$, the z-score distribution can be written as in Equation 23:

$$Z\sim\text{Normal}\left(\frac{\mu_X}{\sigma_X}\frac{f}{2},1\right) \quad (23)$$

where $\mu_X$ and $\sigma_X$ can be empirically evaluated from a large pool of euploid samples.

For a euploid sample, its z score is independent of fetal fraction, and follows a standard normal distribution.

Figure 32:
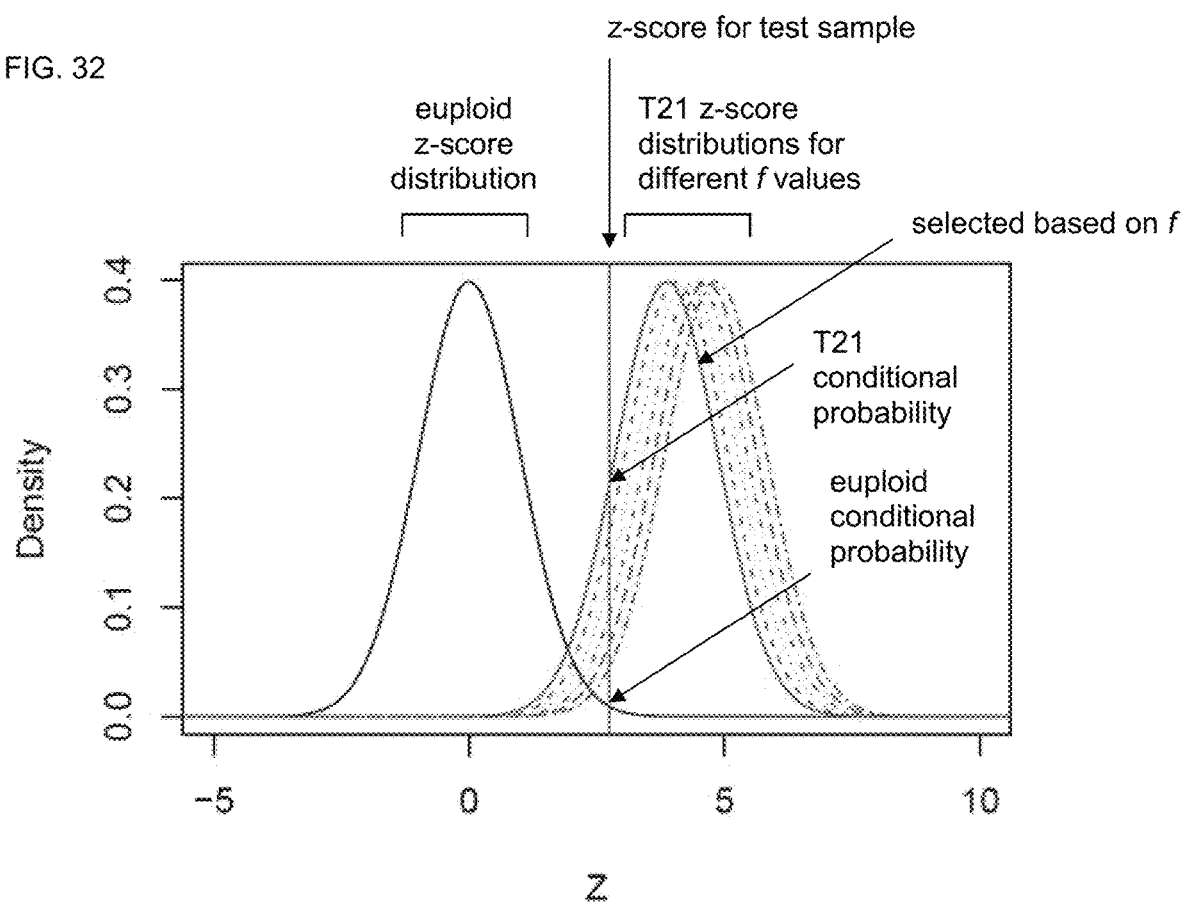
FIG. 32 graphically depicts certain aspects of equation 23 described in Example 6.

Equation 23 is graphically depicted in FIG. 32. A z-score distribution for euploid subjects is centered on zero, and the center of the distribution is not sensitive to fetal fraction. As a graphical depiction of equation 23, discrete z-score distributions for T21 each are centered on a different z-score, where each discrete distribution is for a different fetal fraction. Applying the fetal fraction determined for a test sample determines which z-score distribution for T21 is evaluated. Applying the z-score determined for the test sample identifies the conditional probability for T21. The conditional probability for T21 is at the intersection of the z-score determined for the test sample with the z-score distribution for T21 selected according to the fetal fraction determined for that test sample. Applying the z-score determined for the test sample also identifies the conditional probability for non-T21. The conditional probability for non-T21 is at the intersection of the z-score determined for the test sample with the z-score distribution for non-T21.

Application of the conditional probabilities for T21 and non-T21 to equation 22 provides the LOR calculation for the test sample. Test samples having a z-score greater than 3.95 and a LOR greater than zero are classified as having the presence of a genetic variation (e.g., presence of T21). Test samples having a z-score less than 3.95 and/or a LOR less than zero are classified as having the absence of a genetic variation.

Figure 31:
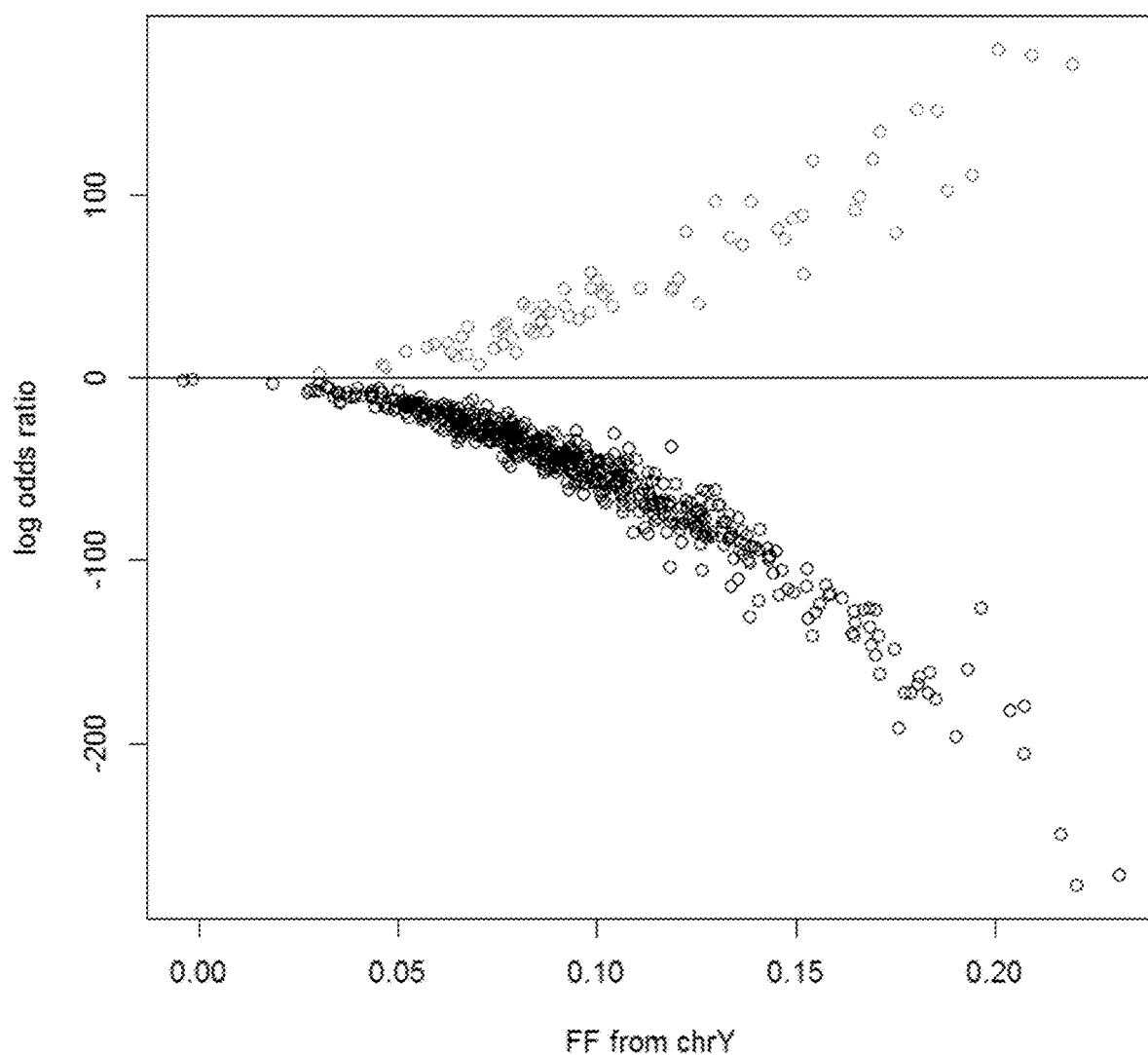
FIG. 31 shows classification results for LDTv2 male samples using the log odds ratio (LOR) method.

FIG. 31 shows classification results for LDTv2 male samples using the LOR method. As can be seen, the LOR diverges quickly as fetal fraction increases. Hence, the borderline samples with high fetal fraction can be and were reliably classified. Specifically, samples designated by open circles having a LOR greater than zero were accurately classified as T21 and samples designated by open circles having a LOR less than zero were accurately classified as non-T21.

Equation 22 assumes the measured fetal fraction is identical to the true fetal fraction, which often is not the case. To compensate measurement uncertainty, an advanced LOR method was developed according to Equation 24:

$$\frac{P(T21 \mid Z, \hat{f})}{P(\overline{T21} \mid Z, \hat{f})} = \frac{P(T21, Z, \hat{f})}{P(\overline{T21}, Z, \hat{f})} = \frac{\sum_f P(T21, Z, f, \hat{f})}{\sum_f P(\overline{T21}, Z, f, \hat{f})} = \quad (24)$$

$$\frac{\sum_f P(Z \mid T21, Z, f, \hat{f}) P(T21 \mid f, \hat{f}) P(f \mid \hat{f}) P(\hat{f})}{\sum_f P(Z \mid \overline{T21}, Z, f, \hat{f}) P(\overline{T21} \mid f, \hat{f}) P(f \mid \hat{f}) P(\hat{f})} =$$

$$\frac{\sum_f P(Z \mid T21, Z, f, \hat{f}) P(f \mid \hat{f}) P(T21)}{\sum_f P(Z \mid \overline{T21}, Z, f, \hat{f}) P(f \mid \hat{f}) P(\overline{T21})} =$$

$$\frac{\sum_f P(Z \mid T21, f,) P(f \mid \hat{f}) P(T21)}{\sum_f P(Z \mid \overline{T21}, f,) P(f \mid \hat{f}) P(\overline{T21})}$$

where f is the true fetal fraction and f^ is the measured fetal fraction. Compared to equation (22), equation (24) averages over the conditional probability of f given f^. The advanced LOR thereby makes use of a weighted average of conditional probabilities, and provides a greater weight to possible fetal fraction values closer to the measured fetal fraction value. Accordingly Based on equation 24, the advanced LOR recovered the true positive samples. The advanced LOR therefore can be used to determine presence or absence of a genetic variation in a test sample.

The LOR method can be applied to determining presence or absence of multiple types of chromosome aneuploidies (e.g., other than T21) and can be applied to determining presence or absence of multiple types of other genetic variations (e.g., aneuploidy of a chromosome other than chromosome 21, microduplication, microdeletion). A positive event (e.g., presence of a chromosome aneuploidy (e.g., monosomy, trisomy); presence of a microduplication, presence of a microdeletion), is determined when a z-score is equal to or greater than 3.95 and a LOR is greater than zero. For determining presence or absence of a microduplication or microdeletion, a $Z_{wave}$ or $Z_{cbs}$ z-score value resulting from a wavelet smoothed decomposition rendering or CBS smoothed decomposition rendering, respectively, can be utilized, for example (see, e.g., Example 3). The relationships shown in FIG. 32 are similar but different for a microdeletion or microduplication event. For a microduplication event, $\mu_X$ and $\mu_{X'}$ for the duplication segment are smaller in value than for a chromosome trisomy, and the microduplication z-score distributions shift to the left closer to the euploid z-score distribution in FIG. 32. The z-score distributions for a microduplication event will remain on the right side of the euploid z-score distribution in FIG. 32. The z-score distributions for a microdeletion event, however, will shift to the left side of the euploid z-score distribution in FIG. 32. For determining presence or absence of a chromosome aneuploidy (e.g., for a chromosome other than chromosome 21), a $Z_{chr}$ z-score value can be utilized, for example (see, e.g., Example 3).

Example 7: ChAI Normalization Processes

Figure 42B:
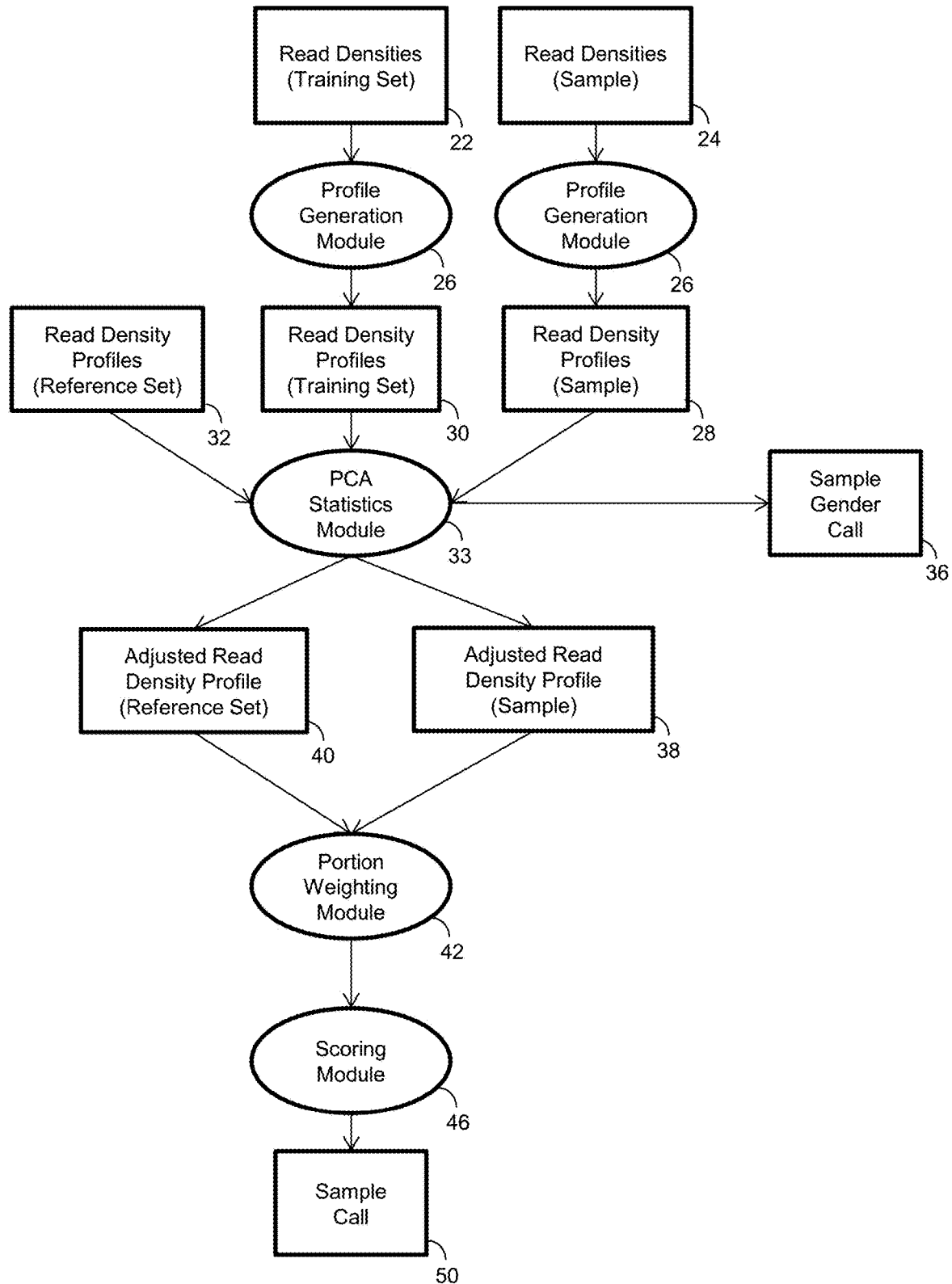

ChAI is a system that can be used for determining the presence or absence of a genetic variation (e.g., aneuploidy, microduplication, microdeletion) in a fetus from sequence reads obtained from a test subject (e.g., a pregnant female). An example of a system flow chart for ChAI is shown in FIG. 42A and 42B. Sequence reads were obtained from a pregnant female test subject and one or more reference subjects sometimes referred to herein as a training set. Pregnant female subjects of the training set had fetuses that were euploid as confirmed by other testing methods.

Sequence reads were first compressed from a SAM or BAM format to a binary-reads format (BReads format) which allowed ChAI to run much more quickly. The BReads format stores the genomic location of each read, including a chromosome and base pair position determined according to a reference genome and discards other information. A BReads file begins with a count of the reads contained. This improves loading times by eliminating the need for memory reallocations. The value was stored on disk as a four-byte array. Reads were then stored using a 5-byte format, one for the chromosome ordinal (zero-index of 1-22, X, Y, M), and four for the chromosome position. BReads files were loaded by first reading the sequence read count from the first four bytes. Each sequence read is then loaded five bytes at a time, with the first byte indicating a chromosome ordinal and the next four converting to the integer position. Random sampling of reads can be performed quickly by using disk-skip commands to specific read indexes.

As an example, the disk usage of different formats is compared to the disk usage of Breads format in Table I for 17,673,732 mapped reads.

TABLE 4

Disk usage for different
formats based on a sample with 17,673,732 reads.

| Format | Space Usage |
|---|---|
| SAM | 4.0 GB |
| Mapped read positions | 247 MB |
| GZip read positions | 97 MB |
| BReads | 85 MB |

The BReads format was roughly 50× smaller than the original SAM file and used about 12% less space than a GZip format. BReads also had the advantage of storing the number of reads at the head for one-time memory allocation, and can be quickly sampled since reads do not have to be read in order. These features were not possible with the other formats.

Modeling GC Bias

GC-bias models were then learned for each sample. Samples which were designated for training were used, in part, to create a portion filter and to learn other genome biases which are not well accounted for by GC bias alone. Finally, the training statistics were used to filter and score test samples.

Figure 33:
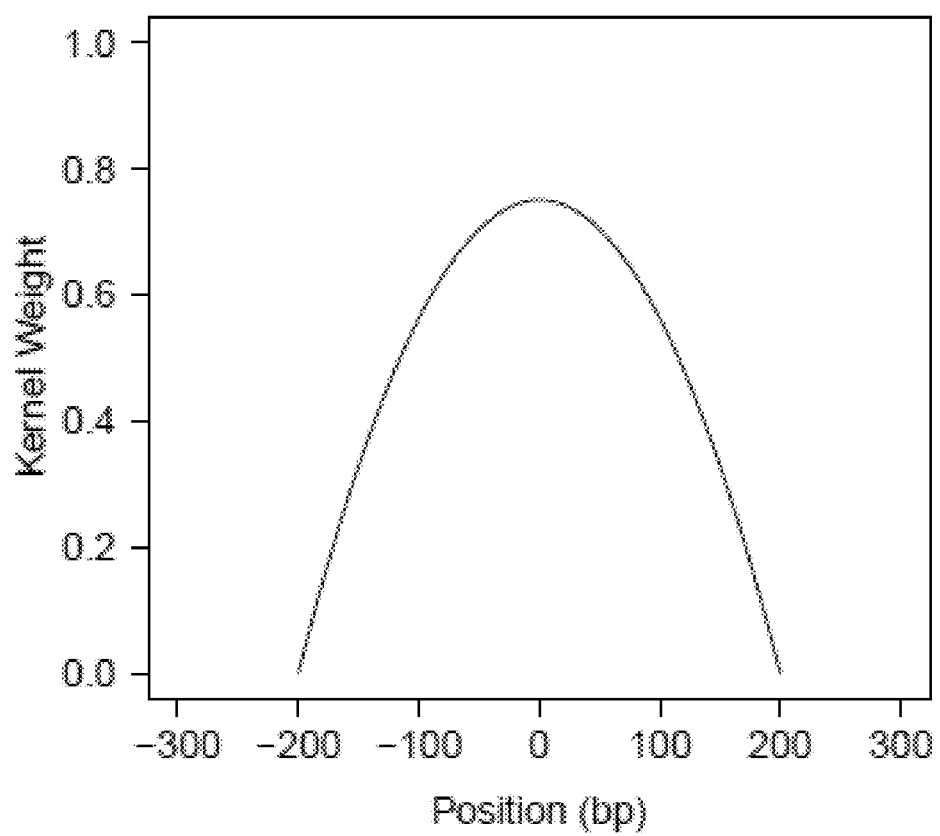
FIG. 33 shows an embodiment of a GC density provided by a Epanechnikov kernel (bandwidth=200 bp).

ChAI modeled GC bias using density estimates of local GC content. GC density was estimated from a reference genome using a kernel function such as the Epanechnikov kernel (FIG. 33). Other kernels are also appropriate, including a Gaussian or a triweight kernel. The bandwidth was selected as 200 bp, however the bandwidth parameter is flexible.

Figure 34:
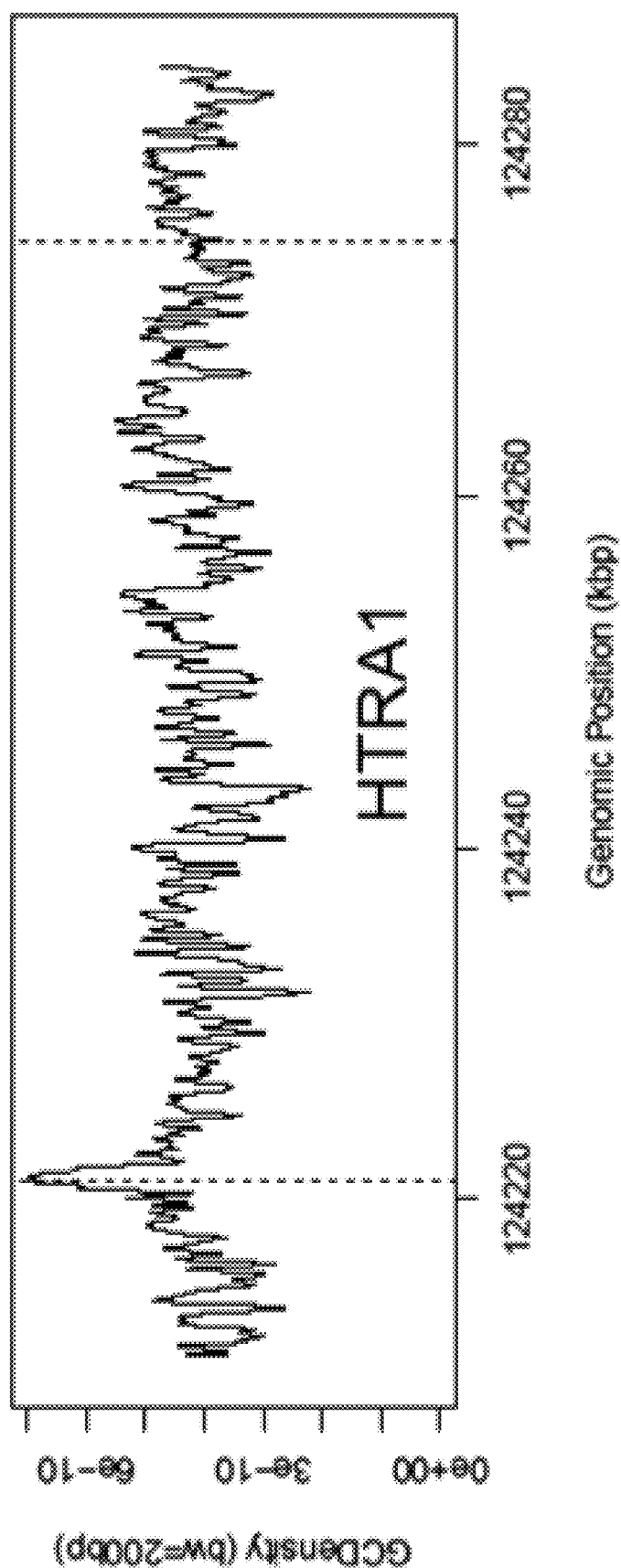
FIG. 34 shows a plot of GC densities (y-axis) for the HTRA1 gene where GC densities are normalized across an entire genome. Genomic positions are shown on the x-axis.
Figure 35:
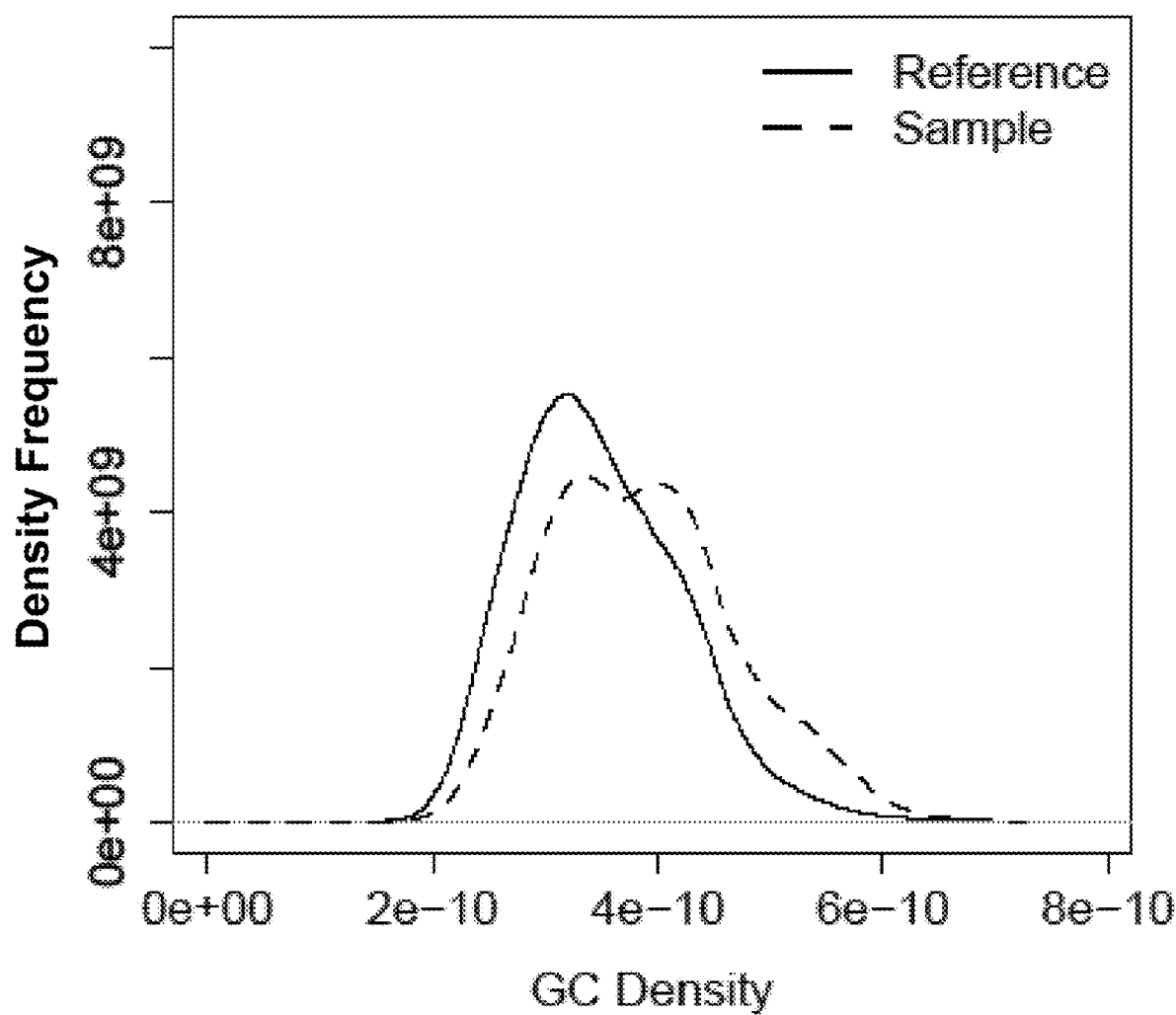
FIG. 35 shows a distribution of local genome bias estimates (e.g., GC Density, x-axis) for a reference genome (solid line) and for sequence reads obtained from a sample (dashed line). Bias frequencies (e.g., Density Frequency) are shown on the y-axis. GC density estimates are normalized across an entire genome. In this example, the sample has more reads with high GC content than would be expected from the reference.

Using a kernel, GC density was estimated at base-pair resolution on a reference genome (e.g., as shown in FIG. 34). Using the GC density estimates of the reference, the local GC content of each read from a sample was determined. The distribution of GC density estimates for the sample was then compared to the distribution across the whole reference genome to determine GC bias (FIG. 35). Reads and reference values which map to AT-rich regions (GC density=0) were discarded. The difference between a sample's GC-density distribution and a reference was modeled using a polynomial, fit on a log-ratio of the density of the reference distribution divided by the density of the sample's distribution (FIG. 36). The model was fit in a weighted fashion, with each weight taken as the sample's distribution-density value for a given GC-density value. This ensured that the tails of the distribution did not excessively drive the fit. Other fitting models, such as a quantile regression model or parameterized distributions can be used as is appropriate for the bias's distribution.

Using the fit GC model, each count of a sequence read for a sample was weighted to adjust for its over- or under-representation as compared to the reference. By incorporating these weights into the estimation of read-density, the ChAl algorithm was able to correct for GC biases.

Multidimensional Bias Correction

GC Bias was only one of several biases affecting read patterns in a genome. Additional biases were sometimes modeled and corrected for using a generalized multivariate model to estimate read weights. This correction was performed as follows:

1. N bias values were estimated for a test sample and a reference genome at each of a subset of genomic positions.

2. Density of the bias values was modeled using an N-dimensional smoothing kernel or an appropriate parametric function.

3. The log-ratio was calculated for a set of density values taken from the reference and test densities.

4. The log-ratio of density was modeled using the chosen points with a multivariate model (e.g., weighted 3rd order polynomial for each dimension).

5. The model was used to estimate the ratio of the frequency of a given read compared to the reference, and the appropriate weight was assigned.

Portion Filtering

Samples were scored for chromosomal abnormalities based on the representation of sequence reads (e.g., counts) on the genome. This representation was determined using a density function, similar to the one used for local GC estimation. The read-density kernel generally has a much larger bandwidth, with the default being 50,000 bp. Each count of a read contributes to the density a value equal to its weight from the GC-bias model. The read-density can be evaluated at any or all base-pairs, but for computational performance only certain locations were used. These positions were termed "portions". Portions can be located wherever it is most important to estimate read-density. For the classification of chromosomal aneuploidies portions were initially (e.g., before filtering) spaced evenly across the genome. Each portion comprised of a 50,000 bp window and, prior to filtering, overlapped the next adjacent portion by 25,000 bp.

Some portions include poorly mapped genomic regions which led to extreme perturbations in read-density from sample to sample. ChAl identified and removed these portions by a filtering process using a training set. Portions which showed large deviations in median (e.g., FIG. 37A) and/or MAD values (e.g., FIG. 37B) were removed from consideration. The threshold of these deviations was taken as any value outside the training population quartiles by more than four times the inter-quartile range (FIG. 37A, 37B). This threshold can be fine-tuned to maximize test performance for a specific set of ChAl parameters.

Training and Scoring

Using only reads which map to filtered portions, each sample's genome read-density profile was calculated. Samples which were part of the training set were then used to estimate training statistics which were used for scoring the test set. These statistics consisted of portion medians, principal-components, and null distributions for the scoring test statistic. The portion medians and principal components were used for modeling genome-wide read biases which may be present from any number of biological and technical artifacts (FIG. 38A-C). To minimize the impact of extreme portion values on the rest of the sample, each value which was outside of 4×IQR across the other portions in a sample was trimmed to 4×IQR.

Test samples were corrected for hidden biases by first subtracting the trained median values from the test portion values. The components of the sample values which correlate with the top trained principal components were also removed. This was done by modeling the portion values using multivariate linear regression based on the principal component terms (FIG. 39A-C). The values predicted by the model were subtracted from the sample values, leaving only the unbiased residuals. The number of principal components used is optional, with the default being eight.

After corrections, samples were scored using a Fisher-exact test. This test compared the number of portions whose values were greater or less than the trained median in the chromosomal region of interest. These counts were evaluated against the rest of the portions in the genome. The scoring statistic was taken as the negative log 10 p-value. Other scoring statistics can be used in this step, such as a Wilcoxon signed-rank test or an F-test.

Figure 40:
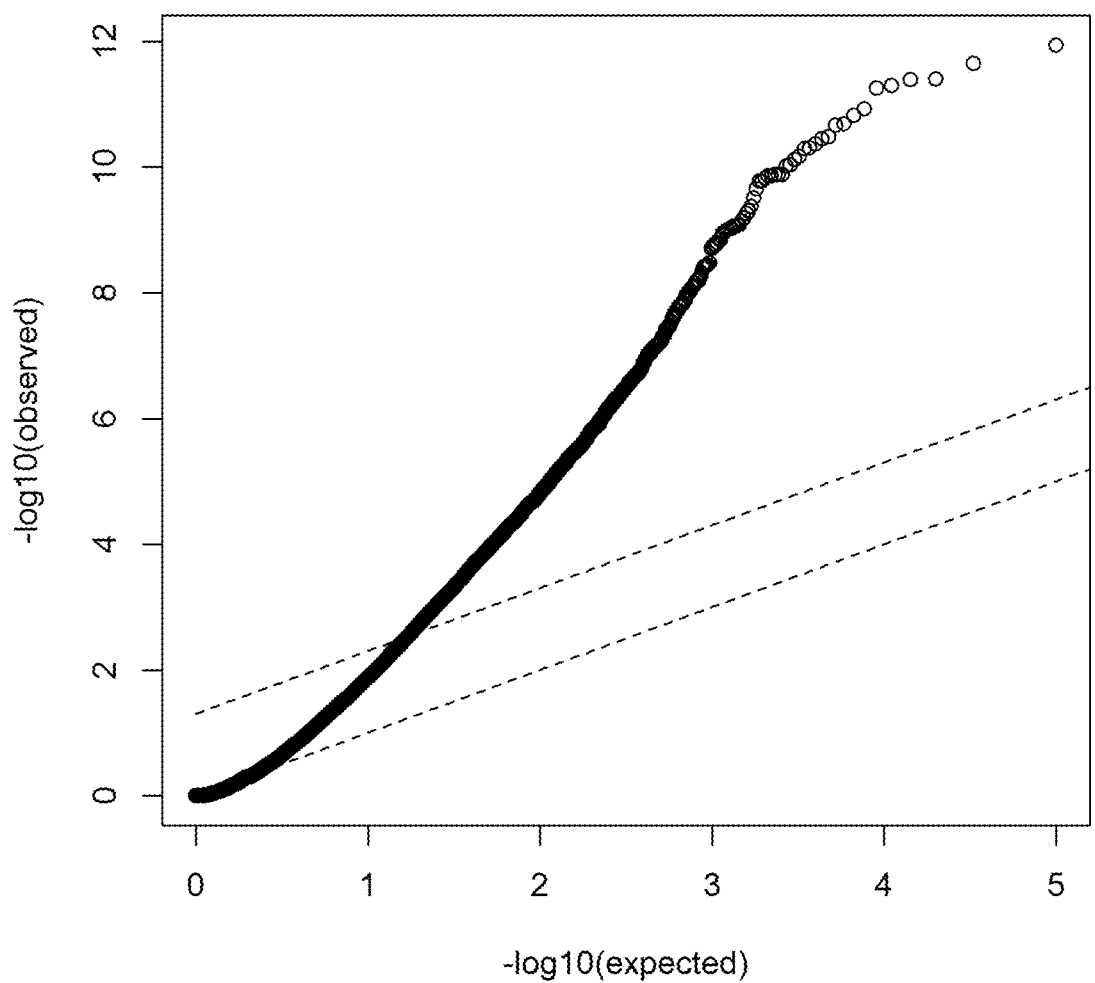
FIG. 40 shows a QQ-plot of test p-values from bootstrapped training samples for a T21 test. A QQ plot generally compares two distributions.

Due to residual correlations between portions, the test statistic was inflated in both the training and test samples. This inflation was estimated from bootstraps of the training set (FIG. 40).

The scores for test samples were corrected using this null distribution as an empirical background. Scores which are much larger than those in the empirical distribution were corrected using a Pareto extrapolation of the tail of the null distribution.

Calling Gender

Figure 41A:
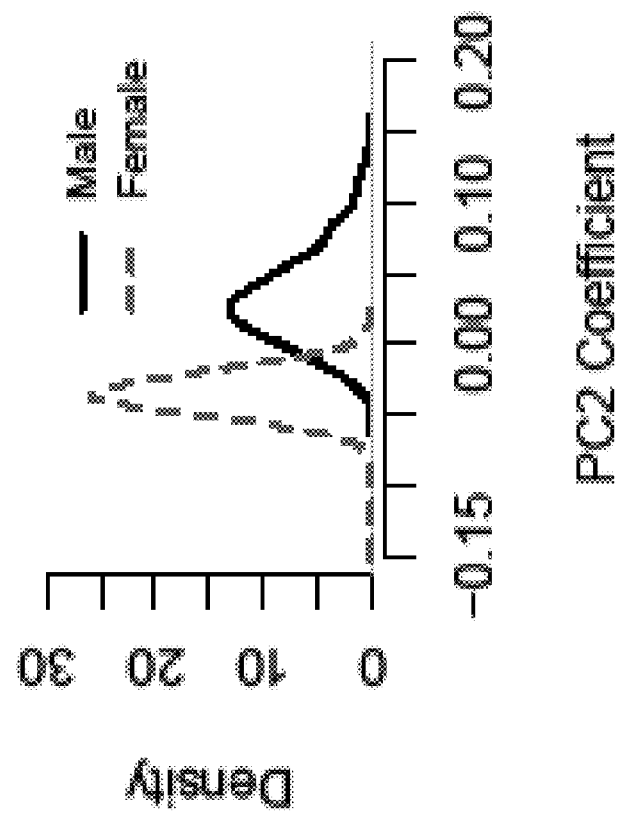
FIG. 41A shows a read density plot showing a difference in PC2 coefficients for men and women in a training set.
Figure 41B:
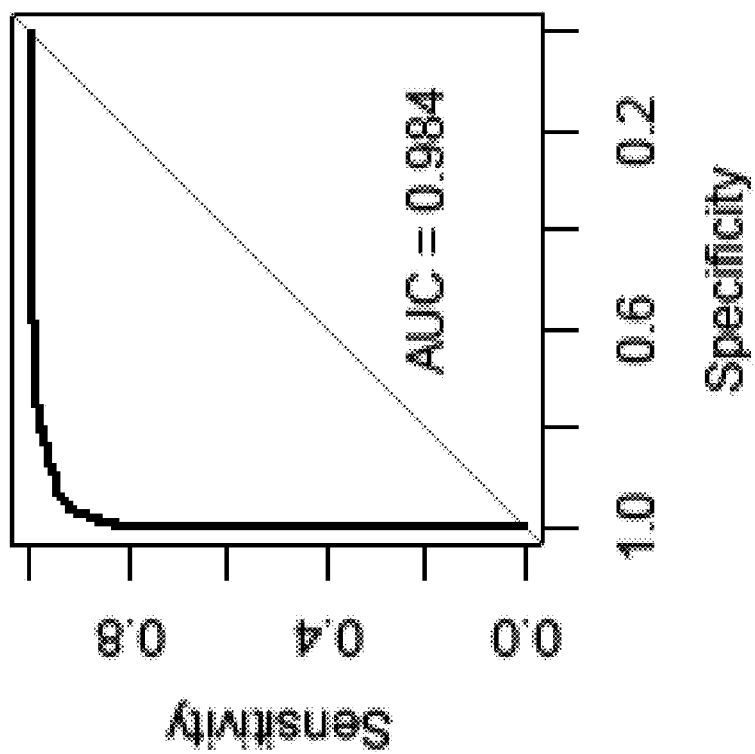
FIG. 41B shows a receiver operating characteristic (ROC) plot for gender calls with a PC2 coefficient. Gender calls performed by sequencing was used for the truth reference.

Gender was determined from a sample's principal component profile. In a training data set, the 2nd principal component (e.g., PC2) was highly correlated with gender. Using a regression coefficient of this component as a test statistic was a highly accurate test of gender (FIG. 41A, 41B).

Removing Portion Dependencies

An additional step was taken during a ChAl run to improve the predictive power of the approach. This involved reducing the amount of correlation structure in the portion-sample matrix, which better supports the test assumption of variable independence and reduced the frequency of significant scores in the null permutations. The approach involved replacing the portions with orthogonal eigen-portions which contain nearly all of the same information, but without correlation structure.

The first step was to learn a transform matrix Meig for a set of training portions M:

1. SVD decomposition: M=U*D*VT

2. Choose the number of independent eigen-portions N: (e.g., Such that the cumulative fraction of the N diagonal elements of D is greater than 95%)

3. Compute the pseudoinverse: Meig=pinv(U[ . . . , 1:N]*D[1:N, 1:N])

Left-multiplication of any subset of the portion matrix M by its corresponding Meig resulted in a dimension-reduced correlation-free representation of that subset. In this way, Meig was derived on a training dataset and applied to test samples without further modification.

Meig was also used to transform the test variable. The test variable was represented as a vector consisting of all zeros, with ones at locations of expected deviations (e.g., Chr 21 portions). This vector was transformed with Meig through left-multiplication to appropriately match the transformed portion data.

This approach can only create as many independent eigen-portions as there are samples in the training set. For an example training set of 50,000 portions and 1,000 samples, the transformed data would contain, at most, 1,000 portions. This was likely an over-correction, reducing the number of portions drastically. The approach can be performed more loosely by computing separate Meig transforms for smaller subsets of the portion data and applying them separately. This was particularly useful for removing local correlation structure from neighboring portions. Other approaches can also be used to reduce portion correlation structure. For example, many clustering methods can be used to group portions and replace them with a smaller set of aggregate portions (e.g., based on group averages or centroids).

Distribution/Profile Generation Module

A script was written in java for generating read density profiles from sequence read data (e.g., BReads). The code below was designed to collect read data for each sequence read and update a density profile at the appropriate read density windows (e.g., individual read densities for a portion), weighted by the distance of a read from the median or middle point of a portion, and according to a sample's GC bias correction. The script below can call or utilize uses weighted and/or normalized counts generated from a relationship module or bias correction module. In some embodiments a distribution module can comprise some or all, or a variation of the java script shown below. In some embodiments a profile generation module can comprise some or all, or a variation of the java script shown below:

```java
package utilities.genome;
import java.util.Iterator;
import utilities.data.VectorUtil;
import utilities.text.DataFormatter;
public class ChromDensScaleRunnable implements Runnable{
   private GenomeScaleBoolean mask;
   private GenomeScaleFloat density;
   private final String modelPath;
   private final String brPath;
   private final int bandwidth;
   private final GenomeFloat gcdens;
   private final int stepSize;
   private final int sampleSize;
   private final int shift;
   private final String report;
   public ChromDensScaleRunnable(String modelPath, String brPath, int bandwidth,
GenomeFloat gcdens, int stepSize, GenomeScaleBoolean mask, String report, int sampleSize, int shift)
   {
      this.modelPath = modelPath;
      this.brPath = brPath;
      this.bandwidth = bandwidth;
      this.gcdens = gcdens;
      this.stepSize = stepSize;
      this.mask = mask;
      this.report = report;
      this.sampleSize = sampleSize;
      this.shift = shift;
   }
   public void run( )
   {
      double[ ] mdat = (gcdens==null) ? null : VectorUtil.loadDoubleFromFile(modelPath, 6);
      //Build density
      density =new GenomeScaleFloat(stepSize);
      double correction = 0;
      try
      {
      Iterator<GenomicPosition> readIterator = (sampleSize==-1) ? GenomeIO.scanBReads(brPath) : new BReadsSampler(brPath, sampleSize,true);
         while (readIterator.hasNext( ))
         {
            GenomicPosition gp = readIterator.next( ).shift(shift);
            int pos = gp.pos;
            int start = Math.max(0, pos-bandwidth);
            int end = Math.min(pos+bandwidth, GenomeUtil.chromosomeSize(gp.chr)-1);
            int cindex = gp.chr.ordinal( );
            double weight;
            if (gcdens!=null)
            {
```

-continued

```
              float gc =gcdens.values[cindex][pos-1];
              if (gc==0) continue;
              weight = modelWeight(mdat, gc);
           }else weight = 1;
           int[ ][ ] gpoints = density.getScalePoints(cindex, start, end, mask);
           if (gpoints[0].length==0 || Double.isNaN(weight)) continue;
           if (weight>2) weight = 2;
           if (weight<.5) weight = .5;
           correction += weight;
           for (int i=0;i<gpoints[0].length;i++)
              density.values[cindex][gpoints[0][i]] += kernel((gpoints[1][i]-
pos)/(double)bandwidth) *weight;
         }
       }catch (Exception e)
       {
          System.out.println("THROW!");
          e.printStackTrace( );
          System.exit(0);
       }
       //System.out.println(GenomeIO.countReadsFromBReads(brPath));
       //System.out.println(correction);
       //Normalize intensity
       for (int i=0;i<density.values.length;i++)
          for (int j=0;j<density.values[i].length;j++)
          {
             float blah = density.values[i][j];
             density.values[i][j]/= correction;
             if (Double.isNaN(density.values[i][j]) ||
Double.isInfinite(density.values[i][j]))
             {
                System.out.println("NA val2: "+modelPath+",
"+density.values[i][j]+", "+blah+", "+correction);
                System.exit(0);
             }
          }
       if (report!=null) System.out.println(report);
    }
    public GenomeScaleFloat density( )
    {
       return density;
    }
    private static double kernel(double x)
    {
       return .75 * (1.0 - x*x);
    }
    public static double modelWeight(double[ ] mdat, double gcdens)
    {
       if (mdat[5]==1) gcdens = Math.log(gcdens);
       double x2 = gcdens *gcdens;
          return Math.pow(2, mdat[0] + mdat[1] * gcdens + mdat[2] * x2 + mdat[3] * x2 *
gcdens);
    }
}
```

Filtering Module

A script was written in R for filtering portions of a read density profile. This code examines a read density profile across all samples and identifies portions that are retained and/or portions that are discarded (e.g., removed from the analysis), based on an inter-quartile range. In some embodiments a filtering module comprises some or all, or a variation of the R script shown below:

```
rcodepath <- "I:/ghannum/Projects/Binless/RCode"
mdistpath <-
"I:/ghannum/Projects/Binless/Reference/MarkerDistribution_LDTv2_200_50000_50000.txt"
outpath <-
"I:/ghannum/Projects/Binless/Reference/LDTv2_200_50000_50000_MarkerMask.txt"
args <- commandArgs(trailingOnly = TRUE)
rcodepath <- args[1]
mdistpath <- args[2]
outpath <- args[3]
source(paste(rcodepath,"/src/utilities/scanmatrix.R",sep=""))
dat <- scanMatrix(mdistpath,rownames=FALSE,colnames=TRUE)
m <- apply(dat,1,median)
v <- apply(dat,1, mad)
qm <- quantile(m,c(.25,.75))
```

```
qv <- quantile(v,c(.25,.75))
scalem <- qm[2]-qm[1]
scalev <- qv[2]-qv[1]
ok <- m > qm[1]-4*scalem & m < qm[2]+4*scalem & v > qv[1]-4*scalev & v < qv[2]+4*scalev
write.table(matrix(as.integer(ok),1),row.names=F,col.names=F,quote=F,file=outpath,sep="")
```

Bias Density Module, Relationship Module, Bias Correction Module & Plotting Module A script was written in R for generating bias densities, generating and comparing a relationship and for correcting bias in sequence reads. This code generally directs a microprocessor to analyze one or more samples and build a bias model (e.g., a relationship and/or a comparison of relationships) based on local genome bias estimations (e.g., GC densities) for each sample and a reference. The script below directs one or more processors, in part, to generate a relationship between (i) guanine and cytosine (GC) densities and (ii) GC density frequencies for sequence reads of a test sample, thereby generating a sample GC density relationship, (b) compare the sample GC density relationship and a reference GC density relationship, thereby generating a comparison, wherein, the reference GC density relationship is between (i) GC densities and (ii) the GC density frequencies for a reference and, with a suitable modification of the script, (c) normalize counts of the sequence reads for the sample according to the comparison determined in (b), where bias in the sequence reads for the sample is reduced. In some embodiments, a bias density module, a relationship module, a bias correction module and/or a plotting module comprises, some, all or a modification of some or all of the script shown below.

```
gcpath <- "I:/ghannum/Projects/Binless/Reference/BiasMaps/DnaseDensity_200_dist.txt"
inpath <- "I:/ghannum/Projects/Binless/Models/LDTv2_DNase-200"
outpath <- "I:/ghannum/Projects/Binless/Models/LDTv2_DNase-200"
makePlots <- TRUE
logTransform <- TRUE
args <- commandArgs(trailingOnly = TRUE)
gcpath <- args[1]
inpath <- args[2]
outpath <- args[3]
makePlots <- args[4]
logTransform <- as.logical(args[5])
paths <- dir(inpath)
paths <- paths[grep(_BiasDistr.txt$,paths)]
gcref <- scan(gcpath,0)
gcref <- gcref[gcref!=0]
if (logTransform) gcref <- log(gcref)
from <- quantile(gcref,.005)
to <- quantile(gcref,.995)
x <- seq(from,to,length.out=100);
d1y <- predict(smooth.spline(density(gcref,from=from,to=to)),x)$y
if (!logTransform) d1y <- sapply(d1y,function(x){max(x,0)})
print(paste("Processing",length(paths),"models.") )
for (f in paths)
{
  distr <- scan(paste(inpath,"/",f,sep=),0)
  distr <- distr[distr!=0]
  if (logTransform) distr <- log(distr)
  d2y <- predict(smooth.spline(density(distr,from=from,to=to)),x)$y
  if (!logTransform) d2y <- sapply(d2y,function(x){max(x,0)})
  pp <- log2(d1y / d2y)
  pp[pp > 2]<- 2; pp[pp < -2]<- -2
  ok <- !is.na(pp)
  mod <- lm(pp[ok]~x+I(x^2)+I(x^3), data=list(x=x[ok]), w=d2y[ok])
  w <- 2^predict(mod,list(x=distr))
  fname <- substr(f,1,nchar(f)-14)
  out <- c(mod$coefficients,mean(w))
  out[out==Inf] <- "Infinity"
  out[out==-Inf] <- "-Infinity"
  write.table(matrix(c(out,as.integer(logTransform)),ncol=1),file=paste(outpath,"/",fname,"_BiasMod.txt",sep=""),row.names=F,col.names=F,quote=F)
  if (make Plots)
  {
    png(units="in",height=4,width=4,res=300,file=paste(outpath,"/",fname,"_BiasMod.png",sep=""))
    if (logTransform)
    {
      plot(x[ok],pp[ok],ylim=c(-4,4),xlab="Bias Density",ylab="Log2 Ratio (Reference / Sample)")
    }else plot(x[ok],pp[ok],ylim=c(-4,4),xlab="Log-Bias Density",ylab="Log2 Ratio (Reference / Sample)")
    abline(h=0,lty=2)
    lines(x[ok],predict(mod),col=3)
    dev.off( )
  }
```

-continued

```
}
##Demo transformation
#load("I:/ghannum/Projects/Binless/2012_11_13_cewi_PERUN_19FCs_AltGCbias_chrFracti
ons.RData")

#d <- dir("I:/ghannum/Projects/Binless/GCDistribution/LDTv2/")
#d <- d[grep("_GCDistr.txt",d)]
#v <- as.numeric(df.cewi.GCbiasTable[,"gcBiasRobust"])[1:length(d)]

#a <-
scan(paste("I:/ghannum/Projects/Binless/GCDistribution/LDTv2/",d[which.min(v)],sep=""),0);
a <- sort(a)
#b <-
scan(paste("I:/ghannum/Projects/Binless/GCDistribution/LDTv2/",d[which.max(v)],sep=""),0);
d <- sort(d)

#r <- scan("I:/ghannum/Projects/Binless/Reference/GCDensity_200_density.txt",0)

#plot(density(r),ylim=c(0,1e10),xlab="GC Density"); lines(density(a),col=3);
lines(density(b),col=2)

#a <- a[a!=0]
#b <- b[b!=0]
#r <- r[r!=0]

#plot(density(r),ylim=c(0,1e10),xlab="GC Density"); lines(density(a),col=3);
lines(density(b),col=2)

#modA <-
as.numeric(scan(paste("I:/ghannum/Projects/Binless/GCDistribution/LDTv2/",substr(d[which.
min(v)],1,nchar(d[which.min(v)])-12),"_GCMod.txt",sep=""),""))
#modB <-
as.numeric(scan(paste("I:/ghannum/Projects/Binless/GCDistribution/LDTv2/",substr(d[which.
max(v)],1,nchar(d[which.max(v)])-12),"_GCMod.txtsep=""),""))

#wa <- sapply(a,function(x){2^sum(c(1,x,x^2,x^3)*modA[1:4])})
#wb <- sapply(b,function(x){2^sum(c(1,x,x^2,x^3)*modB[1:4])})

#wa <- wa/(length(wa)*modA[5])
#wb <- wb/(length(wb)*modB[5])

#plot(density(r),ylim=c(0,1e10),xlab="GC Density"); lines(density(a,weights=wa),col=3);
lines(density(b,weights=wb),col=2)
```

Example 8: Examples of Embodiments

The examples set forth below illustrate certain embodiments and do not limit the technology.

A1. A method of determining the presence or absence of a chromosome aneuploidy, microduplication or microdeletion in a fetus with reduced false negative and reduced false positive determinations, comprising:
 (a) obtaining counts of nucleic acid sequence reads mapped to portions of a reference genome, which sequence reads are reads of circulating cell-free nucleic acid from a pregnant female bearing a fetus;
 (b) normalizing the counts mapped to each portion, thereby providing calculated genomic section levels;
 (c) generating a profile for a segment of a genome according to the calculated genomic section levels;
 (d) segmenting the profile thereby providing two or more decomposition renderings; and
 (e) determining the presence or absence of a chromosome aneuploidy, microduplication or microdeletion with reduced false negative and reduced false positive determinations according to the two or more decomposition renderings.

A2. The method of embodiment A1, wherein the segmenting comprises thresholding.

A3. The method of embodiment A2, wherein the thresholding comprises a soft thresholding.

A4. The method of embodiment A2 or A3, wherein the thresholding comprises a policy.

A5. The method of embodiment A4, wherein the policy is universal.

A6. The method of embodiment A4, wherein the policy is sure.

A7. The method of any one of embodiments A2 to A6, wherein the thresholding is performed by WaveThresh.

A8. The method of any one of embodiments A1 to A7, wherein the segmenting comprises leveling.

A9. The method of embodiment A8, wherein the leveling is performed according to fetal fraction.

A10. The method of embodiment A8 or A9, wherein the leveling is performed according to coverage.

A11. The method of any one of embodiments A8 to A10, wherein the leveling is performed according to a minimum segment length to detect.

A12. The method of any one of embodiments A8 to A11, wherein thresholding and leveling are performed and the thresholding is performed before the leveling.

A13. The method of any one of embodiments A1 to A12, wherein the segmenting in (d) is performed according to two or more different decomposition generation processes.

A14. The method of embodiment A13, wherein each of the two or more different decomposition generation processes are independently chosen from a Haar wavelet segmentation, circular binary segmentation, maximum entropy segmentation, convolution with edge detection kernel, Jensen Shannon Divergence, Binary Recursive Segmentation, and a Fourier transform.

A15. The method of embodiments A13 or A14, wherein one of the two or more different decomposition generation processes is a circular binary segmentation.

A16. The method of any one of embodiments A13 to A15, wherein one of the two or more different decomposition generation processes is a Haar wavelet.

A17. The method of any one of embodiments A13 to A16, wherein the segmenting in (d) comprises a Haar wavelet and a circular binary segmentation.

A18. The method of any one of embodiments A13 to A17, wherein the two or more decomposition generation processes are applied in parallel.

A19. The method of any one of embodiments A13 to A17, wherein the two or more decomposition generation processes are applied in series.

A20. The method of any one of embodiments A1 to A19, comprising polishing one or more of the two or more decomposition renderings thereby providing one or more polished decomposition renderings.

A21. The method of embodiment A20, wherein the polishing comprises merging adjacent fragmented levels in a decomposition rendering.

A22. The method of embodiment A20 or A21, wherein the adjacent fragmented levels are merged according to their genomic section levels.

A23. The method of any one of embodiments A1 to A22, comprising identifying a candidate segment in one or more of the two or more decomposition renderings.

A23.1. The method of embodiment A23, wherein the candidate segment is identified in the one or more polished decomposition renderings.

A24. The method of embodiment A23 or A23.1, comprising determining the edges of the candidate segment.

A25. The method of any one of embodiment A23 to A24, comprising determining a level of the candidate segment.

A26. The method of any one of embodiments A23 or 25, wherein the candidate segment is identified according to a null profile.

A27. The method of anyone of embodiments A1 to A26, wherein the counts in (a) are obtained from a sample obtained from a pregnant female.

A28. The method of embodiment A27, wherein the null profile is generated from the sample.

A29. The method of embodiment A26 or A27, wherein the null profile is generated from a reference sample.

A30. The method of any one of embodiments A23 to A29, wherein the candidate segment is identified according to an area under the curve (AUC) analysis.

A31. The method of any one of embodiments A23 to A30, comprising comparing at least two candidate segments thereby providing a comparison.

A32. The method of embodiment A31, wherein a first candidate segment is from a first decomposition rendering and a second candidate segment is from a second decomposition rendering.

A33. The method of embodiment A31 or A32, wherein the at least two candidate segments are determined as substantially the same according to the comparison.

A33.1. The method of embodiment A31 or A32, wherein the at least two candidate segments are determined as different according to the comparison.

A33.2. The method of any one of embodiments A31 to A33.1, wherein the presence or absence of a chromosome aneuploidy is determined according to the comparison.

A34. The method of any one of embodiments A31 to A33.2, wherein the comparison comprises overlaying the at least two candidate segments.

A34.1. The method of any one of embodiments A31 or A34, comprising determining the presence or absence of a composite candidate segment according to the comparison.

A35. The method of embodiment 34 or 34.1, wherein a first candidate segment substantially overlaps with a second candidate segment and the presence of a composite candidate segment is determined.

A35.1. The method of embodiment 34 or 34.1, wherein a first candidate segment does not substantially overlap with a second candidate segment and the absence of a composite candidate segment is determined.

A36. The method of any one of embodiments A34.1 to A35.1, wherein the presence or absence of a chromosome aneuploidy is determined in (e) according to the presence or absence of a composite candidate segment.

A37. The method of any one of embodiments A23 to A36, comprising validating the candidate segment identified in a decomposition rendering thereby providing a validated candidate segment.

A38. The method of embodiment A37, wherein the validating comprises performing a sliding edges process.

A39. The method of embodiment A37 or A38, wherein the validating comprises performing a leave one out process.

A40. The method of embodiment A39, wherein the validating comprises performing the sliding edges process and the leave one out process.

A41. The method of any one of embodiments A37 to A40, wherein the validating comprises generating a level of significance for the candidate segment.

A42. The method of any one of embodiments A37 to A41, wherein the validating comprises generating a level of significance for the composite candidate segment.

A43. The method of embodiment A41 or A42, wherein the level of significance is a Z-score.

A44. The method of any one of embodiments A41 to A43, wherein a level of uncertainty is associated with the level of significance.

A45. The method of embodiment A44, wherein the presence or absence of a validated candidate segment is determined according to a level of significance and a level of uncertainty for a candidate segment.

A46. The method of embodiment A44 or A45, wherein the presence of a chromosome aneuploidy, microduplication or microdeletion is determined according to a level of significance and a level of uncertainty wherein both the level of significance and the level of uncertainty are generated for the composite candidate segment.

A47. The method of embodiment A46, wherein the presence of a chromosome aneuploidy, microduplication or microdeletion is determined according to a Z-score and a level of uncertainty associated with the Z-score wherein both the Z-score and the level of uncertainty are generated for the composite candidate segment.

A47.1. The method of embodiment A47, wherein the Z-score has an absolute value greater than or equal to about 3.95.

A48. The method of any one of embodiments A1 to A47.1, wherein the presence or absence of a chromosome aneuploidy is determined.

A48.1. The method of any one of embodiments A1 to A48, wherein the chromosome aneuploidy is a trisomy.

A48.2. The method of any one of embodiments A1 to A48.1, wherein the chromosome aneuploidy is a monosomy.

A49. The method of any one of embodiments A1 to A48.3, wherein the presence or absence of a microduplication is determined.

A50. The method of any one of embodiments A1 to A48.3, wherein the presence or absence of a microdeletion is determined.

A51. The method of any one of embodiments A1 to A50, wherein the presence or absence of a microdeletion indicative of a DiGeorge syndrome is determined.

A52. The method of any one of embodiments A1 to A51, wherein one or more or all of (a), (b), (c), (d) and (e) are performed by a processor.

A53. The method of embodiment A52, wherein the processor is a microprocessor.

A54. The method of any one of embodiments A1 to A53, wherein one or more or all of (a), (b), (c), (d) and (e) are performed by a computer.

A55. The method of any one of embodiments A1 to A54, wherein one or more or all of (a), (b), (c), (d) and (e) are performed in conjunction with memory.

A56. The method of any one of embodiments A1 to A55, wherein one or more or all of (a), (b), (c), (d) and (e) are performed by a microprocessor controlled apparatus.

A57. The method of any one of embodiments A1 to A56, comprising, prior to (a), sequencing nucleic acid in a sample obtained from the pregnant female thereby providing the nucleic acid sequencing reads.

A58. The method of any one of embodiments A1 to A57, comprising, prior to (a), mapping the nucleic acid sequence reads to the portions of the reference genome or to an entire reference genome.

B1. A method for determining the presence or absence of a candidate segment with reduced false negative and reduced false positive determinations, comprising:
  (a) obtaining counts of nucleic acid sequence reads mapped to portions of a reference genome, which sequence reads are reads of circulating cell-free nucleic acid from a pregnant female;
  (b) normalizing the counts mapped to each of the portions, thereby providing calculated genomic section levels;
  (c) segmenting a set of portions into multiple subsets of portions;
  (d) determining a level for each of the subsets according to the calculated genomic section levels;
  (e) determining a level of significance for each of the levels; and
  (f) determining the presence or absence of a candidate segment with reduced false negative and reduced false positive determinations according to the level of significance determined for each the levels.

B1.1 The method of embodiment B1, wherein the set of portions is suspected of comprising a candidate segment.

B2. The method of embodiment B1 or B1.1, comprising generating a median level of significance according to the level of significance determined for each of the levels for all of the subsets of portions.

B3. The method of any one of embodiments B1 to B2, comprising generating a distribution of the level of significance determined for each of the levels for all of the subsets of portions.

B4. The method of any one of embodiments B1 to B3, comprising generating an uncertainty value according the level of significance determined for all of the levels for all the subsets of portions.

B5. The method of embodiment B4, wherein the determining in (f) is according to the median level of significance and the uncertainty value.

B6. The method of embodiment B3 or B4, wherein the determining in (f) is according to the median level of significance and the distribution of the level of significance.

B6.1. The method of any one of embodiments B1 to B6, wherein the determining in (f) is according to a pre-determined range determined for the level of significance.

B6.2. The method of embodiment B6.1, wherein the presence of a candidate segment is determined when 75% or more of the distribution of the level of significance generated in B3 is outside of the pre-determined range for the level of significance.

B6.3. The method of embodiments B6.1 or B6.2, wherein the presence of a candidate segment is determined when 75% or more of the uncertainty value generated in embodiment B4 is outside of the pre-determined range for the level of significance.

B7. The method of any one of embodiments B1 to B6.3, wherein the level of significance is a Z-score.

B7.1. The method of embodiment B7, wherein the predetermined range is a Z-score between about 3 and about −3.

B8. The method of any one of embodiments B4 to B7.1, wherein the uncertainty value is a median absolute deviation.

B9. The method of any one of embodiments B1 to B8, wherein the set of portions comprises a first end and a second end and the segmenting in (c) comprises:
  (i) removing one or more portions from the first end of the set of portions by recursive removal thereby providing a subset of portions with each recursive removal;
  (ii) terminating the recursive removal in (i) after n repeats thereby providing n+1 subsets of portions, wherein the set of portions is a subset, and wherein each subset comprises a different number of portions, a first subset end and a second subset end;
  (iii) removing one or more portions from the second subset end of each of the n+1 subsets of portions provided in (ii) by recursive removal; and
  (iv) terminating the recursive removal in (iii) after n repeats, thereby providing multiple subsets of portions.

B10. The method of embodiment B9, wherein the multiple subsets equals $(n+1)2$ subsets.

B11. The method of embodiment B9 or B10, wherein n is equal to an integer between 5 and 30.

B12. The method of any one of embodiments B9 to B11, wherein n is equal to 15.

B13. The method of any one of embodiments B1 to B12, wherein the set of portions is in a chromosome.

B14. The method of embodiment B13, wherein the set of portions comprises a region associated with a known genetic variation or a known genetic disorder.

B14. The method of embodiment B13 or B14, wherein the set of portions comprises a DiGeorge region.

B15. The method of any one of embodiment B1 to B14, wherein (a) through (e) is performed for a test sample and two or more reference samples.

B16. The method of embodiment B15, comprising:
  (i) removing one of the two or more reference samples prior to (a), thereby providing subsets of reference samples;
  (ii) performing (a) through (e) for each of the subsets of reference samples
  (iii) generating a median level of significance according to embodiment B2 for each of the subsets of reference samples;
  (iv) generating a composite median level of significance according to the medians generated in (iii); and (v) generating a composite level of uncertainty for the composite median level of significance in (iv); wherein the determining in (f) is according to the composite median level of significance and the composite level of uncertainty.

B17. The method of embodiment B16, wherein each of the subsets of reference samples comprises a different set of reference samples.

B18. The method of embodiment B16 or B17, wherein each one of the two or more reference samples removed is removed from only one of the subsets.

B19. The method of any one of embodiments B1 to B18, wherein one or more or all of (a), (b), (c), (d), (e) and (f) are performed by a processor.

B20. The method of embodiment B19, wherein the processor is a microprocessor.

B21. The method of any one of embodiments B1 to B20, wherein one or more or all of (a), (b), (c), (d), (e) and (f) are performed by a computer.

B22. The method of any one of embodiments B1 to B21, wherein one or more or all of (a), (b), (c), (d), (e) and (f) are performed in conjunction with memory.

B23. The method of any one of embodiments B1 to B22, wherein one or more or all of (a), (b), (c), (d), (e) and (f) are performed by a micro-processor controlled apparatus.

B24. The method of any one of embodiments B1 to B23, comprising, prior to (a), sequencing nucleic acids in a sample obtained from the pregnant female thereby providing the nucleic acid sequencing reads.

B25. The method of any one of embodiments B1 to B24, comprising, prior to (a), mapping the nucleic acid sequence reads to the portions of the reference genome or to an entire reference genome.

C1. A method of determining the presence or absence of a chromosome aneuploidy, microduplication or microdeletion in a fetus with reduced false negative and reduced false positive determinations, comprising:
  (a) obtaining counts of nucleic acid sequence reads mapped to portions of a reference genome, which sequence reads are reads of circulating cell-free nucleic acid from a pregnant female;
  (b) normalizing the counts mapped to each portion, thereby providing calculated genomic section levels;
  (c) selecting a segment of the genome thereby providing a set of portions;
  (d) partitioning the set of portions recursively thereby providing two or more subsets of portions;
  (e) determining a level for each of the two or more subsets of portions;
  (f) determining the presence or absence of a chromosome aneuploidy, microduplication or microdeletion in a fetus for a sample with reduced false negative and reduced false positive determinations, according to the levels determined in (e).

C2. The method of embodiment C1, comprising determining if the level for each of the two or more subsets of portions determined in (e) are significantly different.

C3. The method of embodiment C1 or C2, wherein the partitioning in (d) comprises a recursive partitioning.

C4. The method of embodiment C3, wherein the recursive partitioning comprises a binary recursive partitioning.

C5. The method of embodiment C3, wherein the recursive partitioning comprises a maximum entropy-based partitioning.

C6. The method of any one of embodiments C2 to C5, comprising partitioning a first and a second subset of portions when the level of the first subset of portions is significantly different than the level of the second subset of portions, and wherein the first and the second subset of portions are adjacent to each other.

C7. The method of any one of embodiments C2 to C6, comprising rejoining a third subset of portions and a fourth subset of portions when the level of the third subset of portions and the fourth subset of portions are not significantly different thereby providing a rejoined subset of portions,
  wherein the third subset of portions and the fourth subset of portions are adjacent to each other, and
  wherein the rejoined portions and not partitioned again.

C8. The method of any one of embodiments C1 to C7, wherein one or more or all of (a), (b), (c), (d), (e) and (f) are performed by a processor.

C9. The method of embodiment C8, wherein the processor is a microprocessor.

C10. The method of any one of embodiments C1 to C9, wherein one or more or all of (a), (b), (c), (d), (e) and (f) are performed by a computer.

C11. The method of any one of embodiments C1 to C10, wherein one or more or all of (a), (b), (c), (d), (e) and (f) are performed in conjunction with memory.

C12. The method of any one of embodiments C1 to C11, wherein one or more or all of (a), (b), (c), (d), (e) and (f) are performed by a micro-processor controlled apparatus.

C13. The method of any one of embodiments C1 to C12, comprising, prior to (a), sequencing nucleic acids in a sample obtained from the pregnant female thereby providing the nucleic acid sequencing reads.

C14. The method of any one of embodiments C1 to C13, comprising, prior to (a), mapping the nucleic acid sequence reads to the portions of the reference genome or to an entire reference genome.

D1. A method for determining the presence or absence of a chromosome aneuploidy, microduplication or microdeletion in a fetus, comprising:
  (a) normalizing counts of nucleic acid sequence reads mapped to portions of a reference genome, which sequence reads are reads of circulating cell-free nucleic acid from a test sample from a pregnant female bearing a fetus, thereby providing normalized counts;
  (b) segmenting the normalized counts of the portions or the normalized counts in a subset of the portions, thereby providing one or more discrete segments;
  (c) identifying a candidate segment among the one or more discrete segments; and
  (d) determining the presence or absence of a chromosome aneuploidy, microduplication or microdeletion according to the candidate segment.

D2. The method of embodiment D1, wherein the segmenting comprises thresholding.

D3. The method of any one of embodiments D1 or D2, wherein the segmenting comprises leveling.

D4. The method of embodiment D3, wherein the leveling is performed according to fetal fraction, coverage, minimum segment length or combination thereof.

D5. The method of any one of embodiments D1 to D4, wherein thresholding and leveling are performed and the thresholding is performed before the leveling.

D5.1. The method of any one of embodiments D1 to D5, wherein the segmenting in (b) is performed on the normalized counts of the portions.

D5.2. The method of any one of embodiments D1 to D5, wherein the segmenting in (b) is performed on the normalized counts in a subset of the portions.

D5.3. The method of embodiment D5.2, wherein the subset of the portions are all portions of a chromosome or a subset of all portions of a chromosome.

D5.4. The method of any one of embodiments D1 to D5.3, wherein the normalized counts are in a profile having levels and the profile is segmented in (b).

D5.5. The method of any one of embodiments D1 to D5.4, wherein the segmenting generates a decomposition rendering comprising the discrete segments.

D5.6. The method of any one of embodiments D1 to D5.5, wherein the normalizing in (a) comprises LOESS normalization of guanine and cytosine (GC) bias (GC-LOESS normalization).

D5.7. The method of any one of embodiments D1 to D5.6, wherein the normalizing in (a) comprises a principal component normalization.

D5.8. The method of any one of embodiments D1 to D5.7, wherein the normalizing in (a) comprises GC-LOESS normalization followed by a principal component normalization.

D5.9. The method of any one of embodiments D1 to D5.8, wherein the normalizing in (a) comprises:
(1) determining a guanine and cytosine (GC) bias coefficient for the test sample based on a fitted relation between (i) the counts of the sequence reads mapped to each of the portions and (ii) GC content for each of the portions, wherein the GC bias coefficient is a slope for a linear fitted relation or a curvature estimation for a non-linear fitted relation; and
(2) calculating, using a microprocessor, a genomic section level for each of the portions based on the counts of (a), the GC bias coefficient of (b) and a fitted relation, for each of the portions, between (i) the GC bias coefficient for each of multiple samples and (ii) the counts of the sequence reads mapped to each of the portions for the multiple samples, thereby providing calculated genomic section levels.

D6. The method of any one of embodiments D1 to D5.9, wherein the segmenting in (b) comprises application of two or more different segmenting processes.

D7. The method of embodiment D6, wherein each of the two or more different segmenting processes are independently chosen from a Haar wavelet segmentation, circular binary segmentation, maximum entropy segmentation, convolution with edge detection kernel, Jensen Shannon Divergence, Binary Recursive Segmentation, and a Fourier transform.

D8. The method of embodiment D6 or D7, wherein one of the two or more different segmenting processes is a circular binary segmentation.

D9. The method of any one of embodiments D6 to D8, wherein one of the two or more different segmenting processes is a Haar wavelet segmentation.

D10. The method of any one of embodiments D6 to D9, wherein the segmenting in (b) comprises a Haar wavelet segmenting process and a circular binary segmenting process.

D11. The method of any one of embodiments D6 to D10, wherein the two or more segmenting processes are performed in parallel.

D12. The method of any one of embodiments D1 to D11, wherein the segmenting comprises a polishing process that comprises merging adjacent fragmented levels in a decomposition rendering.

D13. The method of any one of embodiments D1 to D12, comprising determining one or more edges of the candidate segment.

D14. The method of any one of embodiments D1 to D13, comprising determining the number of portions covered by the candidate segment.

D15. The method of any one of embodiments D1 to D14, comprising determining a level of the candidate segment.

D15.1. The method of any one of embodiments D1 to D15, wherein the candidate segment is identified according to an area under the curve (AUC) analysis.

D16. The method of embodiment D15.1, wherein the AUC analysis is of the number of portions covered by the candidate segment and/or the level for the candidate segment.

D16.1. The method of any one of embodiments D1 to D16, comprising validating the candidate segment thereby providing a validated candidate segment.

D16.2. The method of embodiment D16.1, wherein the validating comprises performing a sliding edges process.

D16.3. The method of embodiment D16.1 or D16.2, wherein the validating comprises performing a leave one out process.

D16.4. The method of embodiment D16.3, wherein the validating comprises performing the sliding edges process and the leave one out process.

D16.5. The method of any one of embodiments D16.1 to D16.4, wherein the validating comprises generating a level of significance for the candidate segment.

D16.6. The method of any one of embodiments D16.1 to D16.5, wherein the validating comprises generating a level of significance for the composite candidate segment.

D16.7. The method of any one of embodiments D1 to D16.6, comprising identifying a first candidate segment form a first segmentation and identifying a second candidate segment from a second segmentation different than the first segmentation.

D16.8. The method of embodiment D16.7, comprising determining whether the first candidate segment and the second candidate segment are substantially the same or substantially different.

D16.9. The method of embodiment D16.7 or D16.8, comprising the absence of a microdeletion or microduplication is determined when the first candidate segment and the second candidate segment are substantially different.

D17. The method of any one of embodiments D1 to D16.9, comprising generating a quantification of the candidate segment or the validated candidate segment.

D18. The method of embodiment D17, wherein the quantification is a count representation for the candidate segment or the validated candidate segment.

D19. The method of embodiment D18, wherein the quantification is a z-score quantification of the count representation for the candidate segment or the validated candidate segment.

D20. The method of embodiment D19, wherein the z-score is a subtraction product of a (i) test sample count representation less a (ii) median of a euploid count representation divided by a (iii) MAD of the euploid count representation, for the candidate segment or the validated candidate segment, wherein: the (i) test sample count representation is a ratio of total counts divided by total autosome counts for the test sample, and the (ii) euploid median count representation is the median of a ratio of total counts divided by total autosome counts for euploid samples.

D21. The method of any one of embodiments D17 to D20, comprising generating a quantification of a chromosome representation of the chromosome in which the candidate segment or the validated candidate segment is located.

D22. The method of embodiment D21, wherein the quantification of the chromosome representation is a z-score quantification.

D23. The method of embodiment D22, wherein the z-score is a subtraction product of a (i) test sample count representation less a (ii) a median of a euploid count representation divided by a (iii) MAD of the euploid count representation, for the chromosome wherein: the (i) test sample count representation is a ratio of total counts in the chromosome in which the candidate segment is located divided by total autosome counts for the test sample, and the (ii) median of the euploid count representation is the median of a ratio of total counts in the chromosome in which the candidate segment is located divided by total autosome counts for euploid samples.

D24. The method of any one of embodiments D17 to D23, wherein the quantification of the candidate segment or the validated candidate segment is compared to the quantification of the chromosome representation.

D25. The method of embodiment D24, wherein: a z-score quantification of a first candidate segment or the first validated candidate segment is generated, a z-score quantification of a second candidate segment or the second validated candidate segment is generated, and the first candidate segment and the second candidate segment are identified from two different types of segmentations.

D26. The method of embodiment D25, comprising determining the minimum of (i) the z-score quantification of the first candidate segment, or the validated first candidate segment, multiplied by a factor less than 1 and (ii) the z-score quantification of the second candidate segment, or the validated second candidate segment, multiplied by the factor.

D27. The method of embodiment D26, comprising determining whether the z-score quantification of the chromosome representation is less than, greater than or equal to the minimum.

D28. The method of embodiment D25, comprising determining whether the z-score quantification of the chromosome representation is less than, greater than or equal to a value of 3.95.

D29. The method of embodiment D28, comprising determining the presence of a chromosome aneuploidy if, for the test sample, (i) the z-score quantification of the chromosome representation is greater than or equal to the value of 3.95, and (ii) the z-score quantification of the chromosome representation is greater than or equal to the minimum.

D30. The method of embodiment D28, comprising determining the absence of a chromosome aneuploidy if, for the test sample, (i) the z-score quantification of the chromosome representation is less than the value of 3.95, and/or (ii) the z-score quantification of the chromosome representation is less than the minimum.

D31. The method of embodiment D29 or D30, wherein the chromosome aneuploidy is a trisomy or monosomy.

D32. The method of embodiment D30, comprising determining whether the z-score quantification of the first candidate segment, or the validated first candidate segment, is less than, greater than or equal to a value of 3.95 and determining whether the z-score quantification of the second candidate segment, or the validated second candidate segment, is less than, greater than or equal to a value of 3.95.

D34. The method of embodiment D32, comprising determining whether the first candidate segment and the second candidate segment, or validated segment thereof, are substantially the same.

D35. The method of embodiment D34, comprising determining the presence of a microdeletion or microinsertion if, for the test sample, (i) the z-score quantification of the first candidate segment, or the validated first candidate segment, is greater than or equal to a value of 3.95 and the z-score quantification of the second candidate segment, or the validated second candidate segment, is greater than or equal to a value of 3.95, and (ii) the first candidate segment and the second candidate segment, or validated segment thereof, are substantially the same.

D36. The method of embodiment D34, comprising determining the absence of a microdeletion or microinsertion if, for the test sample, (i) the z-score quantification of the first candidate segment, or the validated first candidate segment, is less than a value of 3.95 and/or the z-score quantification of the second candidate segment, or the validated second candidate segment, is less than a value of 3.95, and/or (ii) the first candidate segment and the second candidate segment, or validated segment thereof, are not substantially the same.

D37. The method of any one of embodiments D17 to D23, comprising determining a z-score quantification of the count representation for the candidate segment or validated candidate segment and determining whether it is less than, greater than or equal to a value of 3.95.

D37.1. The method of any one of embodiments D17 to D23, comprising determining a z-score quantification of the chromosome representation and determining whether it is less than, greater than or equal to a value of 3.95.

D38. The method of embodiment D37 and/or D37.1, comprising calculating a log odds ratio (LOR), which LOR is the log of the quotient of (i) a first multiplication product of (1) a conditional probability of having a genetic variation and (2) a prior probability of having the genetic variation, and (ii) a second multiplication product of (1) a conditional probability of not having the genetic variation and (2) a prior probability of not having the genetic variation.

D39. The method of embodiment D38, wherein the conditional probability of having the genetic variation is determined according to fetal fraction determined for the test sample, a z-score of the count representation for the segment determined for the test sample, and a distribution for the fetal fraction of z-scores for the count representation for the segment.

D39.1. The method of embodiment D39, wherein the conditional probability of having the genetic variation is determined by the relationship in equation 23:

$$Z \sim \text{Normal}\left(\frac{\mu_X}{\sigma_X} \frac{f}{2}, 1\right) \quad (23)$$

wherein f is fetal fraction, X is the summed portion count for the segment covering the genetic variation, $X \sim f(\mu X, \sigma X)$, where $\mu X$ and $\sigma X$ are the mean and standard deviation of X, respectively, and $f(\bullet)$ is a distribution function.

D40. The method of embodiment D39 or D39.1, wherein the conditional probability of having the genetic variation is the intersection between the z-score for the test sample of the count representation for the segment and a distribution for the fetal fraction of z-scores for the count representation for the segment.

D41. The method of embodiment D38, wherein the conditional probability of not having the genetic variation is the intersection between the z-score of the count representation for the segment determined for the test sample and a distribution of z-scores for the count representation for the segment in euploids.

D42. The method of any one of embodiments D38 to D41, wherein the prior probability of having the genetic variation and the prior probability of not having the genetic variation are determined from multiple samples that do not include the test subject.

D43. The method of any one of embodiments D38 to D42, comprising determining whether the LOR is greater than zero or less than zero.

D44. The method of any one of embodiments D37 to D43, comprising determining the presence of a chromosome aneuploidy if, for the test sample, (i) the z-score quantification of the chromosome representation is greater than or equal to the value of 3.95, and (ii) the LOR is greater than zero.

D45. The method of any one of embodiments D37 to D43, comprising determining the absence of a chromosome aneuploidy if, for the test sample, (i) the z-score quantification of the chromosome representation is less than the value of 3.95, and/or (ii) the LOR is less than zero.

D46. The method of embodiment D44 or D45, wherein the chromosome aneuploidy is a trisomy or monosomy.

D47. The method of any one of embodiments D37 to D43, comprising determining the presence of a microdeletion or microduplication if, for the test sample, (i) the z-score quantification of the count representation for the candidate segment, or validated candidate segment, is greater than or equal to the value of 3.95, and (ii) the LOR is greater than zero.

D48. The method of any one of embodiments D37 to D43, comprising determining the absence of a microdeletion or microduplication if, for the test sample, (i) the z-score quantification of the count representation for the candidate segment, or validated candidate segment, is less than the value of 3.95, and/or (ii) the LOR is less than zero.

D49. The method of embodiment D47 or D48, wherein the microdeletion is associated with DiGeorge Syndrome.

D49.1. The method of any one of embodiments D1 to D49, wherein the count representation is a normalized count representation.

D50. The method of any one of embodiments D1 to D49.1, wherein one or more or all of (a), (b), (c) and (d) are performed by a microprocessor in a system.

D51. The method of any one of embodiments D1 to D50, wherein one or more or all of (a), (b), (c) and (d) are performed by a computer.

D52. The method of any one of embodiments D1 to D51, wherein one or more or all of (a), (b), (c) and (d) are performed in conjunction with memory.

D53. The method of any one of embodiments D1 to D52, comprising, prior to (a), sequencing nucleic acids in a sample obtained from the pregnant female thereby providing the nucleic acid sequence reads.

D54. The method of any one of embodiments D1 to D53, comprising, prior to (a), mapping the nucleic acid sequence reads to the portions of the reference genome.

E1. A method for determining the presence or absence of a chromosome aneuploidy in a fetus, comprising:
  (a) determining a chromosome count representation according to counts of nucleic acid sequence reads mapped to portions of a reference genome, and which sequence reads are reads of circulating cell-free nucleic acid for a test sample from a pregnant female bearing a fetus;
  (b) determining fetal fraction for the test sample;
  (c) calculating a log odds ratio (LOR), which LOR is the log of the quotient of (i) a first multiplication product of (1) a conditional probability of having a chromosome aneuploidy and (2) a prior probability of having the chromosome aneuploidy, and (ii) a second multiplication product of (1) a conditional probability of not having the chromosome aneuploidy and (2) a prior probability of not having the chromosome aneuploidy, wherein: the conditional probability of having the chromosome aneuploidy is determined according to the fetal fraction of (b) and the count representation of (a);
  (d) identifying the presence or absence of a chromosome aneuploidy according to the LOR and the chromsome count representation.

E1.1. The method of embodiment E1, wherein the chromosome count representation is the counts for all portions in the chromosome divided by the counts for all portions in autosomes.

E2. The method of embodiment E1 or E1.1, comprising providing a z-score quantification of the chromosome count representation.

E3. The method of embodiment E2, wherein the z-score is a subtraction product of a (i) test sample chromosome count representation less a (ii) median of a euploid count representation, divided by a (iii) MAD of the euploid count representation, wherein: the (i) test sample chromosome count representation is a ratio of counts in portions in the chromosome divided by counts in portions in the autosomes, and the (ii) median of the euploid count representation is the median of a ratio of counts in portions in the chromosome divided by counts in portions in autosomes for euploids.

E4. The method of any one of embodiments E1 to E3, wherein the conditional probability of having the genetic variation is determined according to fetal fraction determined for the test sample in (b), a z-score for the chromosome count representation for the test sample in (a), and a fetal fraction-specific distribution of z-scores for the chromosome count representation.

E5. The method of embodiment E4, wherein the conditional probability of having the genetic variation is determined by the relationship in equation 23:

$$Z \sim \mathrm{Normal}\left(\frac{\mu_X}{\sigma_X} \frac{f}{2}, 1\right) \tag{23}$$

wherein f is fetal fraction, X is the summed portions for the chromosome, $X \sim f(\mu X, \sigma X)$, where $\mu X$ and $\sigma X$ are the mean and standard deviation of X, respectively, and f(•) is a distribution function.

E6. The method of embodiment E4 or E5, wherein the conditional probability of having the genetic variation is the intersection between the z-score for the test sample chromosome count representation of (a) and a fetal fraction-specific distribution of z-scores for the chromosome count representation.

E7. The method of any one of embodiments E1 to E6, wherein the conditional probability of not having the chromosome aneuploidy is determined according to the chromosome count representation of (a) and count representations for euploids.

E8. The method of embodiment E7, wherein the conditional probability of not having the genetic variation is the intersection between the z-score of the chromosome count representation and a distribution of z-scores for the chromosome count representation in euploids.

E9. The method of any one of embodiments E1 to E8, wherein the prior probability of having the genetic variation and the prior probability of not having the genetic variation are determined from multiple samples that do not include the test subject.

E10. The method of any one of embodiments E1 to E9, comprising determining whether the LOR is greater than or less than zero.

E11. The method of any one of embodiments E1 to E10, wherein the counts of nucleic acid sequence reads mapped to portions of a reference genome are normalized counts.

E12. The method of embodiment E11, wherein the counts are normalized by a normalization comprising GC-LOESS normalization.

E13. The method of embodiment E11 or E12, wherein the counts are normalized by a normalization comprising principal component normalization.

E14. The method of any one of embodiments E11 to E13, wherein counts are normalized by a normalization comprising GC-LOESS normalization followed by a principal component normalization.

E14.1. The method of any one of embodiments E1 to E14, wherein the counts are normalized by a normalization comprising:
(1) determining a guanine and cytosine (GC) bias coefficient for the test sample based on a fitted relation between (i) the counts of the sequence reads mapped to each of the portions and (ii) GC content for each of the portions, wherein the GC bias coefficient is a slope for a linear fitted relation or a curvature estimation for a non-linear fitted relation; and
(2) calculating, using a microprocessor, a genomic section level for each of the portions based on the counts of (a), the GC bias coefficient of (b) and a fitted relation, for each of the portions, between (i) the GC bias coefficient for each of multiple samples and (ii) the counts of the sequence reads mapped to each of the portions for the multiple samples, thereby providing calculated genomic section levels.

E15. The method of any one of embodiments E1 to E14.1, comprising determining a z-score quantification of the chromosome count representation and determining whether it is less than, greater than or equal to a value of 3.95.

E16. The method of E15, comprising determining the presence of a chromosome aneuploidy if, for the test sample, (i) the z-score quantification of the chromosome count representation is greater than or equal to the value of 3.95, and (ii) the LOR is greater than zero.

E17. The method of embodiment E15, comprising determining the absence of a chromosome aneuploidy if, for the test sample, (i) the z-score quantification of the chromosome representation is less than the value of 3.95, and/or (ii) the LOR is less than zero.

E18. The method of embodiment E16 or E17, wherein the chromosome aneuploidy is a trisomy or monosomy.

E18.1. The method of any one of embodiments E1 to E18.1, wherein the count representation is a normalized count representation.

E19. The method of any one of embodiments E1 to E18.1, wherein one or more or all of (a), (b), (c) and (d) are performed by a microprocessor in a system.

E20. The method of any one of embodiments E1 to E19, wherein one or more or all of (a), (b), (c) and (d) are performed by a computer.

E21. The method of any one of embodiments E1 to E20, wherein one or more or all of (a), (b), (c) and (d) are performed in conjunction with memory.

E22. The method of any one of embodiments E1 to E21, comprising, prior to (a), sequencing nucleic acids in a sample obtained from the pregnant female thereby providing the nucleic acid sequence reads.

E23. The method of any one of embodiments E1 to E22, comprising, prior to (a), mapping the nucleic acid sequence reads to the portions of the reference genome.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed can be resorted to by those skilled in the art, and such modifications and variations are considered within the scope of this technology.

Certain embodiments of the technology are set forth in the claim(s) that follow(s).

What is claimed is:

1. A computer-implemented method for determining the presence or absence of a microduplication or microdeletion in a sample, comprising:
(a) receiving input information comprising nucleic acid sequence reads of circulating cell-free nucleic acid from a test sample, wherein the nucleic acid sequence reads are obtained by a non-targeted multiplexed massively parallel sequencing process, and mapping the nucleic acid sequence reads to portions of a reference genome;

(b) normalizing, using a microprocessor, counts of the nucleic acid sequence reads mapped to portions of the reference genome, thereby providing normalized counts;

(c) segmenting, using a microprocessor, the normalized counts of the portions or the normalized counts in a subset of the portions, thereby providing one or more discrete segments;

(d) identifying, using a microprocessor, a candidate segment among the one or more discrete segments;

(e) determining, using a microprocessor, a log odds ratio (LOR) for the candidate segment, wherein the LOR is the loci of the quotient of (i) a first multiplication product of (1) a conditional probability of having a microduplication or microdeletion and (2) a prior probability of having the microduplication or microdeletion, and (ii) a second multiplication product of (1) a conditional probability of not having the microduplication or microdeletion and (2) a prior probability of not having the microduplication or microdeletion; and (f) determining the presence or absence of the microduplication or microdeletion according to the LOR determined for the candidate segment.

2. The method of claim 1, wherein the segmenting in (c) comprises circular binary segmentation.

3. The method of claim 1, wherein the candidate segment is identified as the most significant discrete segment in terms of (i) the number of portions covered by the segment and (ii) the absolute value of a level of normalized counts for the segment.

4. The method of claim 1, comprising generating a quantification of the candidate segment, wherein the quantification is a count representation for the candidate segment.

5. The method of claim 4, wherein the quantification is a z-score quantification of the count representation for the candidate segment, and the z-score is a subtraction product of a (i) test sample count representation less a (ii) median of a euploid count representation divided by a (iii) median absolute deviation (MAD) of the euploid count representation, for the candidate segment, wherein: the (i) test sample count representation is a ratio of total counts divided by total autosome counts for the test sample, and the (ii) euploid median count representation is the median of a ratio of total counts divided by total autosome counts for euploid samples.

6. The method of claim 5, comprising generating a quantification of a chromosome representation of the chromosome in which the candidate segment is located.

7. The method of claim 6, wherein the quantification of the chromosome representation is a z-score quantification, and the z-score is a subtraction product of a (i) test sample count representation less a (ii) median of a euploid count representation divided by a (iii) MAD of the euploid count representation, for the chromosome, wherein the (i) test sample count representation is a ratio of total counts in the chromosome in which the candidate segment is located divided by total autosome counts for the test sample, and the (ii) median of the euploid count representation is the median of a ratio of total counts in the chromosome in which the candidate segment is located divided by total autosome counts for euploid samples.

8. The method of claim 4, wherein the test sample is from a pregnant female bearing a fetus and the conditional probability of having the microduplication or microdeletion is determined according to fetal fraction determined for the test sample, a z-score of the count representation for the candidate segment determined for the test sample, and a distribution for fetal fraction of z-scores for the count representation for the candidate segment.

9. The method of claim 8, wherein the conditional probability of having the microduplication or microdeletion optionally is an intersection between the z-score for the test sample of the count representation for the candidate segment and a distribution for the fetal fraction of z-scores for the count representation for the candidate segment.

10. The method of claim 8, wherein the conditional probability of not having the microduplication or microdeletion is an intersection between a z-score of the count representation for the candidate segment determined for the test sample and a distribution of z-scores for the count representation for the candidate segment in euploids.

11. The method of claim 1, wherein the prior probability of having the microduplication or microdeletion and the prior probability of not having the microduplication or microdeletion are determined from multiple samples that do not include the test subject.

12. The method of claim 5, comprising
determining the presence of a microdeletion or microduplication if, for the test sample, (i) the z-score quantification of the count representation for the candidate segment is greater than or equal to the value of 3.95, and (ii) the LOR is greater than zero, and
determining the absence of a microdeletion or microduplication if, for the test sample, (i) the z-score quantification of the count representation for the candidate segment is less than the value of 3.95, and/or (ii) the LOR is less than zero.

13. The method of claim 1, wherein the candidate segment is less than 5 Mb in length.

14. The method of claim 1, wherein the nucleic acid sequence reads in (a) are obtained by a non-targeted multiplexed massively parallel sequencing process performed with 1-fold coverage or fraction thereof.

15. The method of claim 1, wherein the nucleic acid sequence reads in (a) comprise millions of nucleic acid sequence reads.

16. The method of claim 1, wherein millions of nucleic acid fragments are sequenced by the non-targeted multiplexed massively parallel sequencing process.

* * * * *

UNITED STATES PATENT AND TRADEMARK OFFICE
CERTIFICATE OF CORRECTION

PATENT NO. : 11,462,298 B2
APPLICATION NO. : 16/862324
DATED : October 4, 2022
INVENTOR(S) : Zhao et al.

It is certified that error appears in the above-identified patent and that said Letters Patent is hereby corrected as shown below:

In the Claims

In Column 205, Line 13, in Claim 1, delete "loci" and insert -- log --.

Signed and Sealed this
Twenty-eighth Day of March, 2023

Katherine Kelly Vidal
Director of the United States Patent and Trademark Office